US012606614B2

(12) United States Patent
Hartmann et al.

(10) Patent No.: US 12,606,614 B2
(45) **Date of Patent: \*Apr. 21, 2026**

(54) HUMAN FcRn-BINDING MODIFIED ANTIBODIES AND METHODS OF USE

(71) Applicant: Hoffmann-La Roche Inc., Little Falls, NJ (US)

(72) Inventors: Guido Hartmann, Loerrach (DE); Joerg Regula, Munich (DE); Matthias Rueth, Penzberg (DE); Wolfgang Schaefer, Mannheim (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/373,062

(22) Filed: Jul. 12, 2021

(65) Prior Publication Data

US 2021/0395355 A1     Dec. 23, 2021

Related U.S. Application Data

(63) Continuation of application No. 14/926,844, filed on Oct. 29, 2015, now Pat. No. 11,091,541, which is a continuation of application No. PCT/EP2014/058417, filed on Apr. 25, 2014.

(30) Foreign Application Priority Data

Apr. 29, 2013     (EP) ..................................... 13165744
Jan. 15, 2014     (EP) ..................................... 14151316

(51) Int. Cl.
| C07K 16/22 | (2006.01) |
| A61K 39/00 | (2006.01) |
| C07K 16/28 | (2006.01) |
| C07K 16/46 | (2006.01) |

(52) U.S. Cl.
CPC .......... *C07K 16/22* (2013.01); *C07K 16/2863* (2013.01); *C07K 16/468* (2013.01); *A61K 2039/505* (2013.01); *A61K 2039/54* (2013.01); *C07K 2317/31* (2013.01); *C07K 2317/32* (2013.01); *C07K 2317/52* (2013.01); *C07K 2317/71* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,277,375 | B1 * | 8/2001 | Ward | C07K 16/06 |
| | | | | 530/387.3 |
| 6,737,056 | B1 | 5/2004 | Presta | |
| 6,821,505 | B2 * | 11/2004 | Ward | C07K 16/06 |
| | | | | 424/9.1 |
| 7,572,897 | B2 | 8/2009 | Graus et al. | |
| 7,923,538 | B2 | 4/2011 | Shitara et al. | |
| 8,268,314 | B2 | 9/2012 | Baehner et al. | |
| 9,217,880 | B2 | 12/2015 | Pugh et al. | |
| 9,695,233 | B2 | 7/2017 | Duerr et al. | |
| 10,195,262 | B2 | 2/2019 | Wacker et al. | |
| 10,316,092 | B2 | 6/2019 | Yao et al. | |
| 11,091,541 | B2 | 8/2021 | Hartmann et al. | |
| 11,555,067 | B2 * | 1/2023 | Schlothauer | A61P 27/06 |
| 2006/0067930 | A1 | 3/2006 | Adams et al. | |
| 2007/0219133 | A1 | 9/2007 | Lazar et al. | |
| 2009/0092596 | A1 | 4/2009 | Haley et al. | |
| 2009/0132720 | A1 | 5/2009 | Ruppert et al. | |
| 2009/0136936 | A1 | 5/2009 | Georgiou et al. | |
| 2009/0162360 | A1 | 6/2009 | Klein et al. | |
| 2010/0093979 | A1 | 4/2010 | Lazar | |
| 2010/0111967 | A1 | 5/2010 | Baehner et al. | |
| 2010/0331527 | A1 | 12/2010 | Davis et al. | |
| 2011/0171124 | A1 | 7/2011 | Bugaj et al. | |
| 2011/0236388 | A1 | 9/2011 | Baehner et al. | |
| 2012/0251531 | A1 | 10/2012 | Baehner et al. | |
| 2012/0321627 | A1 | 12/2012 | Baehner et al. | |
| 2013/0039913 | A1 | 2/2013 | Labrijn et al. | |
| 2014/0303356 | A1 * | 10/2014 | Gramer | C07K 16/2887 |
| | | | | 536/23.53 |
| 2015/0175707 | A1 | 6/2015 | De Jong et al. | |
| 2015/0274797 | A1 | 10/2015 | Lo et al. | |
| 2016/0231320 | A1 | 8/2016 | Young et al. | |
| 2019/0016828 | A1 * | 1/2019 | Skolaut | C07K 16/22 |

FOREIGN PATENT DOCUMENTS

| BR | 102016022721 | A2 | 5/2018 |
| CA | 3159061 | A1 | 8/2013 |
| EP | 1601697 | B1 | 5/2007 |
| EP | 2698431 | B1 | 9/2020 |
| WO | 9734631 | A1 | 9/1997 |
| WO | 2005077981 | A2 | 8/2005 |

(Continued)

OTHER PUBLICATIONS

The US Office Action, mailed on Dec. 30, 2022, in the related U.S. Appl. No. 16/590,938.
The US Office Action, mailed on Jan. 12, 2023, in the related U.S. Appl. No. 15/947,377.
DeLano et al., "Convergent Solutions to Binding at a Protein-Protein Interface," Science, 287:1279-1283, Feb. 18, 2000.
Jansson et al., "All individual domains of staphylococcal protein A show Fab binding," FEMS Immunology and Medical Microbiology 20 (1998) 69-78.
The English translation of the Japanese Office Action, mailed on May 16, 2022, in the related Japanese Patent Application No. 2021-092002.

(Continued)

*Primary Examiner* — Phuong Huynh

(57) ABSTRACT

Herein is reported the use of an antibody comprising an Fc-region with abolished FcRn binding for the transport of a soluble receptor ligand from the eye over the blood-ocular-barrier into the blood circulation.

7 Claims, 23 Drawing Sheets

Specification includes a Sequence Listing.

(56)                    References Cited

FOREIGN PATENT DOCUMENTS

| WO |    | 2006053301 | A2 | 5/2006 |
|----|----|-----------|----|--------|
| WO | WO | 2011008517 | A2 | 1/2011 |
| WO |    | 2012069557 | A1 | 5/2012 |
| WO |    | 2012093125 | A1 | 7/2012 |
| WO |    | 2013056233 | A1 | 4/2013 |
| WO |    | 2013063702 | A1 | 5/2013 |
| WO |    | 2013166594 | A1 | 11/2013 |
| WO |    | 2014009465 | A1 | 1/2014 |
| WO |    | 2015057668 | A1 | 4/2015 |

OTHER PUBLICATIONS

The US Office Actions, mailed on Feb. 1, May 5, and May 20, 2022, in the related U.S. Appl. No. 16/590,938.

The US Office Action, mailed on Feb. 24, 2022, in the related U.S. Appl. No. 15/947,424.

Spiekermann et al., "Receptor-mediated Immunoglobulin G Transport Across Mucosal Barriers in Adult Life: Functional Expression of FcRn in the Mammalian Lung," J Exp Med (2002) 196 (3): 303-310.

The Canadian Office Action, mailed on Feb. 17, 2022, in the related Canadian Patent Appl. No. 2,904,805.

The Chinese Office Action, mailed on Feb. 27, 2023, in the related Chinese Patent Appl. No. 201911344011.0.

The English translation of the Chinese Office Action, mailed on Nov. 25, 2022, in the related Chinese Patent Appl. No. 201911266804. 5.

The English translation of the Decision to Grant dated Jul. 26, 2022, in the related Russian Patent Application No. 2020122367/10(038452).

McAuley et al., "Contributions of a disulfide bond to the structure, stability, and dimerization of human IgG1 antibody CH3 domain," Protein Science (2008), 17:95-106.

Yang et al., "Assessment of naturally occurring covalent and total dimer levels in human IgG1 and IgG2," Mol Immunol, Mar. 2014;58(1):108-15.

The extended European Search Report, mailed on May 14, 2021, in the related European Appl. No. 20214926.6.

Canadian Office Action, mailed on Feb. 23, 2021, in the related Canadian Patent Appl. No. 2,932,364.

Korean Office Action, mailed on Jul. 30, 2021, in the related Korean Patent Application No. 10-2016-7018968.

US Office Action, mailed on Mar. 17, 2021, in the related U.S. Appl. No. 14/926,982.

US Office Actions, mailed on May 20 and Aug. 30, 2021, in the related U.S. Appl. No. 15/947,377.

US Office Action, mailed on Jully 6, 2021, in the related U.S. Appl. No. 15/947,424.

US Office Action, mailed on Aug. 4, 2021, in the related U.S. Appl. No. 16/422,147.

US Office Action, mailed on Nov. 30, 2021, in the related U.S. Appl. No. 16/422,147.

The English translation (Google Translate) of the Argentina Office Action, mailed on Dec. 22, 2023, in related Argentina Application No. 20140101718.

US Office Action, mailed on Feb. 16, 2024, in related U.S. Appl. No. 16/590,938.

The Third Party Observations, posted on Dec. 1, 2023, in the related European Patent Appl. No. 15700545.5.

The English translation of the Chinese Office Action, mailed on Jul. 8, 2023, in the related Chinese Patent Appl. No. 201480024044.6.

The US Office Action, mailed on Jul. 5, 2023, in the related U.S. Appl. No. 16/590,938.

The US Office Action, mailed on Aug. 31, 2023, in the related U.S. Appl. No. 17/373,062.

The English translation of the Chinese Office Action, mailed on Aug. 28, 2023, in the related Chinese Patent Appl. No. 202110445639. 0.

The US Office Action, mailed on Sep. 22, 2023, in the related U.S. Appl. No. 15/947,424.

The English translation of the Japanese Office Action, mailed on Aug. 29, 2023, in the related Japanese Patent Appl. No. 2022-010878.

The English translation of the Chinese Office Action, mailed on Jan. 24, 2024, in the related Chinese Patent Appl. No. 202110445639.0.

Tustian et al., "Development of purification processes for fully human bispecific antibodies based upon modification of protein A binding avidity," MAbs May-Jun. 2016;8(4):828-38.

Canadian Office Action, mailed on Feb. 2, 2021, in the related Canadian Patent Appl. No. 2,931,986.

US Office Action, mailed on Sep. 23, 2024, in the related U.S. Appl. No. 15/947,424.

US Office Action, mailed on Oct. 8, 2021, in the related U.S. Appl. No. 16/244,378.

US Office Action, mailed on Oct. 23, 2024, in the related U.S. Appl. No. 18/079,307.

The English translation of the Reexamination Notification, mailed on Apr. 17, 2025, in the related Chinese Appl. No. 201480023252.4.

* cited by examiner

| | Knob | | | | Hole | | |
|---|---|---|---|---|---|---|---|
| | Pos 1 | Pos 2 | Pos 3 | | Pos 1 | Pos 2 | Pos 3 | |
| I253A | H310A | H435A | | I253A | H310A | H435A | No Binding |
| --- | --- | --- | | I253A | H310A | H435A | Binding |
| I253A | H310A | H435A | | --- | H310A | --- | No Binding |
| I253A | H310A | H435A | | --- | --- | H435A | No Binding |

*FIG. 10*

| Sample | Mutation (Hole) | RT (Min) |
|---|---|---|
| anti-VEGF/ANG2 antibody (0096) | - | 51.88 |
| anti-VEGF/ANG2 antibody (0097) | I253A/H310A/H435A | 46.61 |
| anti-VEGF/ANG2 antibody (0098) | H310A/H433A/Y436A | 46.67 |
| anti-VEGF/ANG2 antibody (0099) | L251D/L314AD/L432D | 46.25 |
| anti-VEGF/ANG2 antibody (0100) | M252Y/S254T/T256E | 56.17 |

SEQUENCE LISTING

<160> NUMBER OF SEQ ID NOS: 112

<210> SEQ ID NO 1
<211> LENGTH: 448
<212> TYPE: PRT
<213> ORGANISM: Homo sapiens

<400> SEQUENCE: 1

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

-continued

```
Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 2
<211> LENGTH: 448
<212> TYPE: PRT

<213> ORGANISM: Homo sapiens

<400> SEQUENCE: 2

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
            35                  40                  45

Ala Ile Ile Trp Phe Asp Gly Ser Ser Lys Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 3
<211> LENGTH: 215
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 4
<211> LENGTH: 215
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 5
<211> LENGTH: 118
<212> TYPE: PRT
<213> ORGANISM: Homo sapiens

<400> SEQUENCE: 5

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser
        115

<210> SEQ ID NO 6
<211> LENGTH: 118
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Met
        35                  40                  45

```
Ala Ile Ile Trp Phe Asp Gly Ser Ser Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser
        115

<210> SEQ ID NO 7
<211> LENGTH: 108
<212> TYPE: PRT
<213> ORGANISM: Homo sapiens

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys
            100                 105

<210> SEQ ID NO 9
<211> LENGTH: 107
<212> TYPE: PRT
<213> ORGANISM: Homo sapiens
```

```
<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 10
<211> LENGTH: 106
<212> TYPE: PRT
<213> ORGANISM: Homo sapiens

<400> SEQUENCE: 10

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 11
<211> LENGTH: 1337
<212> TYPE: PRT
<213> ORGANISM: Homo sapiens

<400> SEQUENCE: 11

Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
```

-continued

```
              100                 105                 110

Ile Glu Lys Asn Ala Asp Leu Cys Tyr Leu Ser Thr Val Asp Trp Ser
              115                 120                 125

Leu Ile Leu Asp Ala Val Ser Asn Asn Tyr Ile Val Gly Asn Lys Pro
      130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
                  165                 170                 175

Thr Thr Asn Arg Cys Gln Lys Met Cys Pro Ser Thr Cys Gly Lys Arg
              180                 185                 190

Ala Cys Thr Glu Asn Asn Glu Cys Cys His Pro Glu Cys Leu Gly Ser
      195                 200                 205

Cys Ser Ala Pro Asp Asn Asp Thr Ala Cys Val Ala Cys Arg His Tyr
      210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
                  245                 250                 255

Ser Ala Glu Ser Ser Asp Ser Glu Gly Phe Val Ile His Asp Gly Glu
                  260                 265                 270

Cys Met Gln Glu Cys Pro Ser Gly Phe Ile Arg Asn Gly Ser Gln Ser
              275                 280                 285

Met Tyr Cys Ile Pro Cys Glu Gly Pro Cys Pro Lys Val Cys Glu Glu
      290                 295                 300

Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
                  325                 330                 335

Gly Asn Asn Ile Ala Ser Glu Leu Glu Asn Phe Met Gly Leu Ile Glu
              340                 345                 350

Val Val Thr Gly Tyr Val Lys Ile Arg His Ser His Ala Leu Val Ser
              355                 360                 365

Leu Ser Phe Leu Lys Asn Leu Arg Leu Ile Leu Gly Glu Glu Gln Leu
      370                 375                 380

Glu Gly Asn Tyr Ser Phe Tyr Val Leu Asp Asn Gln Asn Leu Gln Gln
385                 390                 395                 400

Leu Trp Asp Trp Asp His Arg Asn Leu Thr Ile Lys Ala Gly Lys Met
                  405                 410                 415

Tyr Phe Ala Phe Asn Pro Lys Leu Cys Val Ser Glu Ile Tyr Arg Met
                  420                 425                 430

Glu Glu Val Thr Gly Thr Lys Gly Arg Gln Ser Lys Gly Asp Ile Asn
              435                 440                 445

Thr Arg Asn Asn Gly Glu Arg Ala Ser Cys Glu Ser Asp Val Leu His
      450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                  485                 490                 495

Tyr Lys Glu Ala Pro Phe Lys Asn Val Thr Glu Tyr Asp Gly Gln Asp
              500                 505                 510

Ala Cys Gly Ser Asn Ser Trp Asn Met Val Asp Val Asp Leu Pro Pro
              515                 520                 525
```

```
Asn Lys Asp Val Glu Pro Gly Ile Leu Leu His Gly Leu Lys Pro Trp
    530             535             540

Thr Gln Tyr Ala Val Tyr Val Lys Ala Val Thr Leu Thr Met Val Glu
545             550             555             560

Asn Asp His Ile Arg Gly Ala Lys Ser Glu Ile Leu Tyr Ile Arg Thr
                565             570             575

Asn Ala Ser Val Pro Ser Ile Pro Leu Asp Val Leu Ser Ala Ser Asn
            580             585             590

Ser Ser Ser Gln Leu Ile Val Lys Trp Asn Pro Pro Ser Leu Pro Asn
        595             600             605

Gly Asn Leu Ser Tyr Tyr Ile Val Arg Trp Gln Arg Gln Pro Gln Asp
    610             615             620

Gly Tyr Leu Tyr Arg His Asn Tyr Cys Ser Lys Asp Lys Ile Pro Ile
625             630             635             640

Arg Lys Tyr Ala Asp Gly Thr Ile Asp Ile Glu Glu Val Thr Glu Asn
            645             650             655

Pro Lys Thr Glu Val Cys Gly Gly Glu Lys Gly Pro Cys Cys Ala Cys
            660             665             670

Pro Lys Thr Glu Ala Glu Lys Gln Ala Glu Lys Glu Glu Ala Glu Tyr
        675             680             685

Arg Lys Val Phe Glu Asn Phe Leu His Asn Ser Ile Phe Val Pro Arg
    690             695             700

Pro Glu Arg Lys Arg Arg Asp Val Met Gln Val Ala Asn Thr Thr Met
705             710             715             720

Ser Ser Arg Ser Arg Asn Thr Thr Ala Ala Asp Thr Tyr Asn Ile Thr
            725             730             735

Asp Pro Glu Glu Leu Glu Thr Glu Tyr Pro Phe Phe Glu Ser Arg Val
            740             745             750

Asp Asn Lys Glu Arg Thr Val Ile Ser Asn Leu Arg Pro Phe Thr Leu
        755             760             765

Tyr Arg Ile Asp Ile His Ser Cys Asn His Glu Ala Glu Lys Leu Gly
    770             775             780

Cys Ser Ala Ser Asn Phe Val Phe Ala Arg Thr Met Pro Ala Glu Gly
785             790             795             800

Ala Asp Asp Ile Pro Gly Pro Val Thr Trp Glu Pro Arg Pro Glu Asn
            805             810             815

Ser Ile Phe Leu Lys Trp Pro Glu Pro Glu Asn Pro Asn Gly Leu Ile
            820             825             830

Leu Met Tyr Glu Ile Lys Tyr Gly Ser Gln Val Glu Asp Gln Arg Glu
        835             840             845

Cys Val Ser Arg Gln Glu Tyr Arg Lys Tyr Gly Gly Ala Lys Leu Asn
    850             855             860

Arg Leu Asn Pro Gly Asn Tyr Thr Ala Arg Ile Gln Ala Thr Ser Leu
865             870             875             880

Ser Gly Asn Gly Ser Trp Thr Asp Pro Val Phe Phe Tyr Val Gln Ala
            885             890             895

Lys Thr Gly Tyr Glu Asn Phe Ile His Leu Ile Ile Ala Leu Pro Val
            900             905             910

Ala Val Leu Leu Ile Val Gly Gly Leu Val Ile Met Leu Tyr Val Phe
        915             920             925

His Arg Lys Arg Asn Asn Ser Arg Leu Gly Asn Gly Val Leu Tyr Ala
    930             935             940
```

```
Ser Val Asn Pro Glu Tyr Phe Ser Ala Ala Asp Val Tyr Val Pro Asp
945             950             955             960

Glu Trp Glu Val Ala Arg Glu Lys Ile Thr Met Ser Arg Glu Leu Gly
            965             970             975

Gln Gly Ser Phe Gly Met Val Tyr Glu Gly Val Ala Lys Gly Val Val
            980             985             990

Lys Asp Glu Pro Glu Thr Arg Val  Ala Ile Lys Thr Val  Asn Glu Ala
        995             1000            1005

Ala Ser  Met Arg Glu Arg Ile  Glu Phe Leu Asn Glu  Ala Ser Val
    1010            1015            1020

Met Lys  Glu Phe Asn Cys His  His Val Val Arg Leu  Leu Gly Val
    1025            1030            1035

Val Ser  Gln Gly Gln Pro Thr  Leu Val Ile Met Glu  Leu Met Thr
    1040            1045            1050

Arg Gly  Asp Leu Lys Ser Tyr  Leu Arg Ser Leu Arg  Pro Glu Met
    1055            1060            1065

Glu Asn  Asn Pro Val Leu Ala  Pro Pro Ser Leu Ser  Lys Met Ile
    1070            1075            1080

Gln Met  Ala Gly Glu Ile Ala  Asp Gly Met Ala Tyr  Leu Asn Ala
    1085            1090            1095

Asn Lys  Phe Val His Arg Asp  Leu Ala Ala Arg Asn  Cys Met Val
    1100            1105            1110

Ala Glu  Asp Phe Thr Val Lys  Ile Gly Asp Phe Gly  Met Thr Arg
    1115            1120            1125

Asp Ile  Tyr Glu Thr Asp Tyr  Tyr Arg Lys Gly Gly  Lys Gly Leu
    1130            1135            1140

Leu Pro  Val Arg Trp Met Ser  Pro Glu Ser Leu Lys  Asp Gly Val
    1145            1150            1155

Phe Thr  Thr Tyr Ser Asp Val  Trp Ser Phe Gly Val  Val Leu Trp
    1160            1165            1170

Glu Ile  Ala Thr Leu Ala Glu  Gln Pro Tyr Gln Gly  Leu Ser Asn
    1175            1180            1185

Glu Gln  Val Leu Arg Phe Val  Met Glu Gly Gly Leu  Leu Asp Lys
    1190            1195            1200

Pro Asp  Asn Cys Pro Asp Met  Leu Phe Glu Leu Met  Arg Met Cys
    1205            1210            1215

Trp Gln  Tyr Asn Pro Lys Met  Arg Pro Ser Phe Leu  Glu Ile Ile
    1220            1225            1230

Ser Ser  Ile Lys Glu Glu Met  Glu Pro Gly Phe Arg  Glu Val Ser
    1235            1240            1245

Phe Tyr  Tyr Ser Glu Glu Asn  Lys Leu Pro Glu Pro  Glu Glu Leu
    1250            1255            1260

Asp Leu  Glu Pro Glu Asn Met  Glu Ser Val Pro Leu  Asp Pro Ser
    1265            1270            1275

Ala Ser  Ser Ser Ser Leu Pro  Leu Pro Asp Arg His  Ser Gly His
    1280            1285            1290

Lys Ala  Glu Asn Gly Pro Gly  Pro Gly Val Leu Val  Leu Arg Ala
    1295            1300            1305

Ser Phe  Asp Glu Arg Gln Pro  Tyr Ala His Met Asn  Gly Gly Arg
    1310            1315            1320

Lys Asn  Glu Arg Ala Leu Pro  Leu Pro Gln Ser Ser  Thr Cys
    1325            1330            1335
```

```
<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
```

-continued

```
1              5              10             15
Ser Thr Ser Glu Ser Thr Ala Ala Leu Gly Cys Leu Val Lys Asp Tyr
            20             25             30

Phe Pro Glu Pro Val Thr Val Ser Trp Asn Ser Gly Ala Leu Thr Ser
            35             40             45

Gly Val His Thr Phe Pro Ala Val Leu Gln Ser Ser Gly Leu Tyr Ser
      50             55             60

Leu Ser Ser Val Val Thr Val Pro Ser Ser Ser Leu Gly Thr Lys Thr
65             70             75             80

Tyr Thr Cys Asn Val Asp His Lys Pro Ser Asn Thr Lys Val Asp Lys
                85             90             95

Arg Val Glu Ser Lys Tyr Gly Pro Pro Cys Pro Ser Cys Pro Ala Pro
            100            105            110

Glu Phe Leu Gly Gly Pro Ser Val Phe Leu Phe Pro Pro Lys Pro Lys
            115            120            125

Asp Thr Leu Met Ile Ser Arg Thr Pro Glu Val Thr Cys Val Val Val
      130            135            140

Asp Val Ser Gln Glu Asp Pro Glu Val Gln Phe Asn Trp Tyr Val Asp
145            150            155            160

Gly Val Glu Val His Asn Ala Lys Thr Lys Pro Arg Glu Glu Gln Phe
                165            170            175

Asn Ser Thr Tyr Arg Val Val Ser Val Leu Thr Val Leu His Gln Asp
            180            185            190

Trp Leu Asn Gly Lys Glu Tyr Lys Cys Lys Val Ser Asn Lys Gly Leu
            195            200            205

Pro Ser Ser Ile Glu Lys Thr Ile Ser Lys Ala Lys Gly Gln Pro Arg
      210            215            220

Glu Pro Gln Val Tyr Thr Leu Pro Pro Ser Gln Glu Glu Met Thr Lys
225            230            235            240

Asn Gln Val Ser Leu Thr Cys Leu Val Lys Gly Phe Tyr Pro Ser Asp
            245            250            255

Ile Ala Val Glu Trp Glu Ser Asn Gly Gln Pro Glu Asn Asn Tyr Lys
            260            265            270

Thr Thr Pro Pro Val Leu Asp Ser Asp Gly Ser Phe Phe Leu Tyr Ser
      275            280            285

Arg Leu Thr Val Asp Lys Ser Arg Trp Gln Glu Gly Asn Val Phe Ser
      290            295            300

Cys Ser Val Met His Glu Ala Leu His Asn His Tyr Thr Gln Lys Ser
305            310            315            320

Leu Ser Leu Ser Leu Gly Lys
            325
```

```
<210> SEQ ID NO 14
<211> LENGTH: 14
<212> TYPE: PRT
<213> ORGANISM: Artificial
<220> FEATURE:
<223> OTHER INFORMATION: heavy chain CDR3H, <VEGF>ranibizumab

<400> SEQUENCE: 14

Tyr Pro Tyr Tyr Tyr Gly Thr Ser His Trp Tyr Phe Asp Val
1               5               10

<210> SEQ ID NO 15
<211> LENGTH: 17
<212> TYPE: PRT
```

<213> ORGANISM: Artificial
<220> FEATURE:
<223> OTHER INFORMATION: heavy chain CDR2H, <VEGF>ranibizumab

<400> SEQUENCE: 15

Trp Ile Asn Thr Tyr Thr Gly Glu Pro Thr Tyr Ala Ala Asp Phe Lys
1               5                   10                  15

Arg

<210> SEQ ID NO 16
<211> LENGTH: 5
<212> TYPE: PRT
<213> ORGANISM: Artificial
<220> FEATURE:
<223> OTHER INFORMATION: heavy chain CDR1H, <VEGF>ranibizumab

<400> SEQUENCE: 16

His Tyr Gly Met Asn
1               5

<210> SEQ ID NO 17
<211> LENGTH: 9
<212> TYPE: PRT
<213> ORGANISM: Artificial
<220> FEATURE:
<223> OTHER INFORMATION: light chain CDR3L,  <VEGF>ranibizumab

<400> SEQUENCE: 17

Gln Gln Tyr Ser Thr Val Pro Trp Thr
1               5

<210> SEQ ID NO 18
<211> LENGTH: 7
<212> TYPE: PRT
<213> ORGANISM: Artificial
<220> FEATURE:
<223> OTHER INFORMATION: light chain CDR2L,  <VEGF>ranibizumab

<400> SEQUENCE: 18

Phe Thr Ser Ser Leu His Ser
1               5

<210> SEQ ID NO 19
<211> LENGTH: 11
<212> TYPE: PRT
<213> ORGANISM: Artificial
<220> FEATURE:
<223> OTHER INFORMATION: light chain CDR1L,  <VEGF>ranibizumab

<400> SEQUENCE: 19

Ser Ala Ser Gln Asp Ile Ser Asn Tyr Leu Asn
1               5                   10

<210> SEQ ID NO 20
<211> LENGTH: 123
<212> TYPE: PRT
<213> ORGANISM: Artificial
<220> FEATURE:
<223> OTHER INFORMATION: heavy chain variable domain VH,
      <VEGF>ranibizumab

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

-continued

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser
        115                 120
```

```
<210> SEQ ID NO 21
<211> LENGTH: 107
<212> TYPE: PRT
<213> ORGANISM: Artificial
<220> FEATURE:
<223> OTHER INFORMATION: light chain variable domain VL,
      <VEGF>ranibizumab

<400> SEQUENCE: 21
```

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
                100                 105
```

```
<210> SEQ ID NO 22
<211> LENGTH: 20
<212> TYPE: PRT
<213> ORGANISM: Artificial
<220> FEATURE:
<223> OTHER INFORMATION: heavy chain CDR3H, <ANG-2> Ang2i_LC10 variant

<400> SEQUENCE: 22
```

```
Ser Pro Asn Pro Tyr Tyr Tyr Asp Ser Ser Gly Tyr Tyr Tyr Pro Gly
1               5                   10                  15

Ala Phe Asp Ile
            20
```

```
<210> SEQ ID NO 23
<211> LENGTH: 17
<212> TYPE: PRT
<213> ORGANISM: Artificial
<220> FEATURE:
<223> OTHER INFORMATION: heavy chain CDR2H, <ANG-2> Ang2i_LC10 variant

<400> SEQUENCE: 23
```

```
Trp Ile Asn Pro Asn Ser Gly Gly Thr Asn Tyr Ala Gln Lys Phe Gln
1               5                   10                  15
```

-continued

Gly

<210> SEQ ID NO 24
<211> LENGTH: 5
<212> TYPE: PRT
<213> ORGANISM: Artificial
<220> FEATURE:
<223> OTHER INFORMATION: heavy chain CDR1H, <ANG-2> Ang2i_LC10 variant

<400> SEQUENCE: 24

Gly Tyr Tyr Met His
1               5

<210> SEQ ID NO 25
<211> LENGTH: 11
<212> TYPE: PRT
<213> ORGANISM: Artificial
<220> FEATURE:
<223> OTHER INFORMATION: light chain CDR3L, <ANG-2> Ang2i_LC10 variant

<400> SEQUENCE: 25

Gln Val Trp Asp Ser Ser Ser Asp His Trp Val
1               5                   10

<210> SEQ ID NO 26
<211> LENGTH: 7
<212> TYPE: PRT
<213> ORGANISM: Artificial
<220> FEATURE:
<223> OTHER INFORMATION: light chain CDR2L, <ANG-2> Ang2i_LC10 variant

<400> SEQUENCE: 26

Asp Asp Ser Asp Arg Pro Ser
1               5

<210> SEQ ID NO 27
<211> LENGTH: 11
<212> TYPE: PRT
<213> ORGANISM: Artificial
<220> FEATURE:
<223> OTHER INFORMATION: light chain CDR1L, <ANG-2> Ang2i_LC10 variant

<400> SEQUENCE: 27

Gly Gly Asn Asn Ile Gly Ser Lys Ser Val His
1               5                   10

<210> SEQ ID NO 28
<211> LENGTH: 129
<212> TYPE: PRT
<213> ORGANISM: Artificial
<220> FEATURE:
<223> OTHER INFORMATION: heavy chain variable domain VH, <ANG-2>
      Ang2i_LC10 variant

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr

-continued

```
65                    70                    75                    80

Met Glu Leu Ser Arg Leu Arg Ser Asp Asp Thr Ala Val Tyr Tyr Cys
                85                    90                    95

Ala Arg Ser Pro Asn Pro Tyr Tyr Asp Ser Ser Gly Tyr Tyr Tyr
            100                   105                   110

Pro Gly Ala Phe Asp Ile Trp Gly Gln Gly Thr Met Val Thr Val Ser
        115                   120                   125

Ser
```

```
<210> SEQ ID NO 29
<211> LENGTH: 110
<212> TYPE: PRT
<213> ORGANISM: Artificial
<220> FEATURE:
<223> OTHER INFORMATION: light chain variable domain VL, <ANG-2>
      Ang2i_LC10 variant

<400> SEQUENCE: 29
```

```
Ser Tyr Val Leu Thr Gln Pro Pro Ser Val Ser Val Ala Pro Gly Gln
1                     5                     10                    15

Thr Ala Arg Ile Thr Cys Gly Gly Asn Asn Ile Gly Ser Lys Ser Val
                20                    25                    30

His Trp Tyr Gln Gln Lys Pro Gly Gln Ala Pro Val Leu Val Val Tyr
            35                    40                    45

Asp Asp Ser Asp Arg Pro Ser Gly Ile Pro Glu Arg Phe Ser Gly Ser
        50                    55                    60

Asn Ser Gly Asn Thr Ala Thr Leu Thr Ile Ser Arg Val Glu Ala Gly
65                    70                    75                    80

Asp Glu Ala Asp Tyr Tyr Cys Gln Val Trp Asp Ser Ser Ser Asp His
                85                    90                    95

Trp Val Phe Gly Gly Gly Thr Lys Leu Thr Val Leu Gly Gln
            100                   105                   110
```

```
<210> SEQ ID NO 30
<211> LENGTH: 191
<212> TYPE: PRT
<213> ORGANISM: Homo sapiens

<400> SEQUENCE: 30
```

```
Met Asn Phe Leu Leu Ser Trp Val His Trp Ser Leu Ala Leu Leu Leu
1                     5                     10                    15

Tyr Leu His His Ala Lys Trp Ser Gln Ala Ala Pro Met Ala Glu Gly
                20                    25                    30

Gly Gly Gln Asn His His Glu Val Val Lys Phe Met Asp Val Tyr Gln
            35                    40                    45

Arg Ser Tyr Cys His Pro Ile Glu Thr Leu Val Asp Ile Phe Gln Glu
        50                    55                    60

Tyr Pro Asp Glu Ile Glu Tyr Ile Phe Lys Pro Ser Cys Val Pro Leu
65                    70                    75                    80

Met Arg Cys Gly Gly Cys Cys Asn Asp Glu Gly Leu Glu Cys Val Pro
                85                    90                    95

Thr Glu Glu Ser Asn Ile Thr Met Gln Ile Met Arg Ile Lys Pro His
            100                   105                   110

Gln Gly Gln His Ile Gly Glu Met Ser Phe Leu Gln His Asn Lys Cys
        115                   120                   125

Glu Cys Arg Pro Lys Lys Asp Arg Ala Arg Gln Glu Asn Pro Cys Gly
        130                   135                   140
```

-continued

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 31
<211> LENGTH: 496
<212> TYPE: PRT
<213> ORGANISM: Homo sapiens

<400> SEQUENCE: 31

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
        50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
        130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
        210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln

```
              325             330             335

Arg Thr Trp Lys Glu Tyr Lys Val Gly Phe Gly Asn Pro Ser Gly Glu
              340             345             350

Tyr Trp Leu Gly Asn Glu Phe Val Ser Gln Leu Thr Asn Gln Gln Arg
              355             360             365

Tyr Val Leu Lys Ile His Leu Lys Asp Trp Glu Gly Asn Glu Ala Tyr
              370             375             380

Ser Leu Tyr Glu His Phe Tyr Leu Ser Ser Glu Glu Leu Asn Tyr Arg
385             390             395             400

Ile His Leu Lys Gly Leu Thr Gly Thr Ala Gly Lys Ile Ser Ser Ile
              405             410             415

Ser Gln Pro Gly Asn Asp Phe Ser Thr Lys Asp Gly Asp Asn Asp Lys
              420             425             430

Cys Ile Cys Lys Cys Ser Gln Met Leu Thr Gly Gly Trp Trp Phe Asp
              435             440             445

Ala Cys Gly Pro Ser Asn Leu Asn Gly Met Tyr Tyr Pro Gln Arg Gln
              450             455             460

Asn Thr Asn Lys Phe Asn Gly Ile Lys Trp Tyr Tyr Trp Lys Gly Ser
465             470             475             480

Gly Tyr Ser Leu Lys Ala Thr Thr Met Met Ile Arg Pro Ala Asp Phe
              485             490             495

<210> SEQ ID NO 32
<211> LENGTH: 498
<212> TYPE: PRT
<213> ORGANISM: Homo sapiens

<400> SEQUENCE: 32

Met Thr Val Phe Leu Ser Phe Ala Phe Leu Ala Ala Ile Leu Thr His
1               5               10              15

Ile Gly Cys Ser Asn Gln Arg Arg Ser Pro Glu Asn Ser Gly Arg Arg
              20              25              30

Tyr Asn Arg Ile Gln His Gly Gln Cys Ala Tyr Thr Phe Ile Leu Pro
              35              40              45

Glu His Asp Gly Asn Cys Arg Glu Ser Thr Thr Asp Gln Tyr Asn Thr
              50              55              60

Asn Ala Leu Gln Arg Asp Ala Pro His Val Glu Pro Asp Phe Ser Ser
65              70              75              80

Gln Lys Leu Gln His Leu Glu His Val Met Glu Asn Tyr Thr Gln Trp
              85              90              95

Leu Gln Lys Leu Glu Asn Tyr Ile Val Glu Asn Met Lys Ser Glu Met
              100             105             110

Ala Gln Ile Gln Gln Asn Ala Val Gln Asn His Thr Ala Thr Met Leu
              115             120             125

Glu Ile Gly Thr Ser Leu Leu Ser Gln Thr Ala Glu Gln Thr Arg Lys
              130             135             140

Leu Thr Asp Val Glu Thr Gln Val Leu Asn Gln Thr Ser Arg Leu Glu
145             150             155             160

Ile Gln Leu Leu Glu Asn Ser Leu Ser Thr Tyr Lys Leu Glu Lys Gln
              165             170             175

Leu Leu Gln Gln Thr Asn Glu Ile Leu Lys Ile His Glu Lys Asn Ser
              180             185             190

Leu Leu Glu His Lys Ile Leu Glu Met Glu Gly Lys His Lys Glu Glu
              195             200             205
```

```
Leu Asp Thr Leu Lys Glu Glu Lys Glu Asn Leu Gln Gly Leu Val Thr
    210             215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
                260                 265                 270

Lys Gly Gly Lys Arg Glu Glu Glu Lys Pro Phe Arg Asp Cys Ala Asp
                275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
                340                 345                 350

Gly Glu Tyr Trp Leu Gly Asn Glu Phe Ile Phe Ala Ile Thr Ser Gln
                355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
                435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 33
<211> LENGTH: 1124
<212> TYPE: PRT
<213> ORGANISM: Homo sapiens

<400> SEQUENCE: 33

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
                35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80
```

-continued

```
Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
                100                 105                 110

Ile Arg Thr Met Lys Met Arg Gln Gln Ala Ser Phe Leu Pro Ala Thr
                115                 120                 125

Leu Thr Met Thr Val Asp Lys Gly Asp Asn Val Asn Ile Ser Phe Lys
        130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
                180                 185                 190

Tyr Ile Gly Gly Asn Leu Phe Thr Ser Ala Phe Thr Arg Leu Ile Val
                195                 200                 205

Arg Arg Cys Glu Ala Gln Lys Trp Gly Pro Glu Cys Asn His Leu Cys
        210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
                260                 265                 270

Gly Cys Lys Ser Tyr Val Phe Cys Leu Pro Asp Pro Tyr Gly Cys Ser
                275                 280                 285

Cys Ala Thr Gly Trp Lys Gly Leu Gln Cys Asn Glu Ala Cys His Pro
        290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
                340                 345                 350

Val Asp Leu Pro Asp His Ile Glu Val Asn Ser Gly Lys Phe Asn Pro
                355                 360                 365

Ile Cys Lys Ala Ser Gly Trp Pro Leu Pro Thr Asn Glu Glu Met Thr
        370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
                420                 425                 430

Val Glu Lys Pro Phe Asn Ile Ser Val Lys Val Leu Pro Lys Pro Leu
                435                 440                 445

Asn Ala Pro Asn Val Ile Asp Thr Gly His Asn Phe Ala Val Ile Asn
        450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
```

-continued

```
                500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
        530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
                580                 585                 590

Val Pro Gly Asn Leu Thr Ser Val Leu Leu Asn Asn Leu His Pro Arg
                595                 600                 605

Glu Gln Tyr Val Val Arg Ala Arg Val Asn Thr Lys Ala Gln Gly Glu
        610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
        690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
                740                 745                 750

Gly Ser Ala Gly Met Thr Cys Leu Thr Val Leu Leu Ala Phe Leu Ile
        755                 760                 765

Ile Leu Gln Leu Lys Arg Ala Asn Val Gln Arg Arg Met Ala Gln Ala
        770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
                820                 825                 830

Gly Asn Phe Gly Gln Val Leu Lys Ala Arg Ile Lys Lys Asp Gly Leu
        835                 840                 845

Arg Met Asp Ala Ala Ile Lys Arg Met Lys Glu Tyr Ala Ser Lys Asp
        850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
        900                 905                 910

Phe Leu Arg Lys Ser Arg Val Leu Glu Thr Asp Pro Ala Phe Ala Ile
        915                 920                 925
```

-continued

```
Ala Asn Ser Thr Ala Ser Thr Leu Ser Ser Gln Gln Leu Leu His Phe
    930             935         Ser Ser 940

Ala Ala Asp Val Ala Arg Gly Met Asp Tyr Leu Ser Gln Lys Gln Phe
945             950             955             960

Ile His Arg Asp Leu Ala Ala Arg Asn Ile Leu Val Gly Glu Asn Tyr
        965             970             975

Val Ala Lys Ile Ala Asp Phe Gly Leu Ser Arg Gly Gln Glu Val Tyr
        980             985             990

Val Lys Lys Thr Met Gly Arg Leu Pro Val Arg Trp Met Ala Ile Glu
        995             1000            1005

Ser Leu Asn Tyr Ser Val Tyr Thr Thr Asn Ser Asp Val Trp Ser
    1010            1015            1020

Tyr Gly Val Leu Leu Trp Glu Ile Val Ser Leu Gly Gly Thr Pro
    1025            1030            1035

Tyr Cys Gly Met Thr Cys Ala Glu Leu Tyr Glu Lys Leu Pro Gln
    1040            1045            1050

Gly Tyr Arg Leu Glu Lys Pro Leu Asn Cys Asp Asp Glu Val Tyr
    1055            1060            1065

Asp Leu Met Arg Gln Cys Trp Arg Glu Lys Pro Tyr Glu Arg Pro
    1070            1075            1080

Ser Phe Ala Gln Ile Leu Val Ser Leu Asn Arg Met Leu Glu Glu
    1085            1090            1095

Arg Lys Thr Tyr Val Asn Thr Thr Leu Tyr Glu Lys Phe Thr Tyr
    1100            1105            1110

Ala Gly Ile Asp Cys Ser Ala Glu Glu Ala Ala
    1115            1120
```

<210> SEQ ID NO 34
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with AAA mutations (VEGFang2-0012)

<400> SEQUENCE: 34

```
Glu Val Gln Leu Val Glu Ser Gly Gly Gly Leu Val Gln Pro Gly Gly
1               5               10              15

Ser Leu Arg Leu Ser Cys Ala Ala Ser Gly Tyr Asp Phe Thr His Tyr
            20              25              30

Gly Met Asn Trp Val Arg Gln Ala Pro Gly Lys Gly Leu Glu Trp Val
        35              40              45

Gly Trp Ile Asn Thr Tyr Thr Gly Glu Pro Thr Tyr Ala Ala Asp Phe
    50              55              60

Lys Arg Arg Phe Thr Phe Ser Leu Asp Thr Ser Lys Ser Thr Ala Tyr
65              70              75              80

Leu Gln Met Asn Ser Leu Arg Ala Glu Asp Thr Ala Val Tyr Tyr Cys
            85              90              95

Ala Lys Tyr Pro Tyr Tyr Tyr Gly Thr Ser His Trp Tyr Phe Asp Val
            100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
```

-continued

```
145              150              155              160
Thr Val Ser Trp Asn Ser Gly Ala Leu Thr Ser Gly Val His Thr Phe
                165              170              175
Pro Ala Val Leu Gln Ser Ser Gly Leu Tyr Ser Leu Ser Ser Val Val
                180              185              190
Thr Val Pro Ser Ser Ser Leu Gly Thr Gln Thr Tyr Ile Cys Asn Val
                195              200              205
Asn His Lys Pro Ser Asn Thr Lys Val Asp Lys Lys Val Glu Pro Lys
        210              215              220
Ser Cys Asp Lys Thr His Thr Cys Pro Pro Cys Pro Ala Pro Glu Leu
225              230              235              240
Leu Gly Gly Pro Ser Val Phe Leu Phe Pro Pro Lys Pro Lys Asp Thr
                245              250              255
Leu Met Ala Ser Arg Thr Pro Glu Val Thr Cys Val Val Val Asp Val
                260              265              270
Ser His Glu Asp Pro Glu Val Lys Phe Asn Trp Tyr Val Asp Gly Val
        275              280              285
Glu Val His Asn Ala Lys Thr Lys Pro Arg Glu Glu Gln Tyr Asn Ser
        290              295              300
Thr Tyr Arg Val Val Ser Val Leu Thr Val Leu Ala Gln Asp Trp Leu
305              310              315              320
Asn Gly Lys Glu Tyr Lys Cys Lys Val Ser Asn Lys Ala Leu Pro Ala
                325              330              335
Pro Ile Glu Lys Thr Ile Ser Lys Ala Lys Gly Gln Pro Arg Glu Pro
                340              345              350
Gln Val Tyr Thr Leu Pro Pro Cys Arg Asp Glu Leu Thr Lys Asn Gln
                355              360              365
Val Ser Leu Trp Cys Leu Val Lys Gly Phe Tyr Pro Ser Asp Ile Ala
370              375              380
Val Glu Trp Glu Ser Asn Gly Gln Pro Glu Asn Asn Tyr Lys Thr Thr
385              390              395              400
Pro Pro Val Leu Asp Ser Asp Gly Ser Phe Phe Leu Tyr Ser Lys Leu
                405              410              415
Thr Val Asp Lys Ser Arg Trp Gln Gln Gly Asn Val Phe Ser Cys Ser
                420              425              430
Val Met His Glu Ala Leu His Asn Ala Tyr Thr Gln Lys Ser Leu Ser
        435              440              445
Leu Ser Pro Gly Lys
    450
```

<210> SEQ ID NO 35
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations (VEGFang2-0012)

<400> SEQUENCE: 35

```
Gln Val Gln Leu Val Gln Ser Gly Ala Glu Val Lys Lys Pro Gly Ala
1                5              10              15
Ser Val Lys Val Ser Cys Lys Ala Ser Gly Tyr Thr Phe Thr Gly Tyr
                20              25              30
Tyr Met His Trp Val Arg Gln Ala Pro Gly Gln Gly Leu Glu Trp Met
        35              40              45
```

-continued

```
Gly Trp Ile Asn Pro Asn Ser Gly Gly Thr Asn Tyr Ala Gln Lys Phe
    50              55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Asp Ser Ser Gly Tyr Tyr Tyr
            100             105             110

Pro Gly Ala Phe Asp Ile Trp Gly Gln Gly Thr Met Val Thr Val Ser
            115             120             125

Ser Ala Ser Val Ala Ala Pro Ser Val Phe Ile Phe Pro Pro Ser Asp
    130             135             140

Glu Gln Leu Lys Ser Gly Thr Ala Ser Val Val Cys Leu Leu Asn Asn
145             150             155             160

Phe Tyr Pro Arg Glu Ala Lys Val Gln Trp Lys Val Asp Asn Ala Leu
            165             170             175

Gln Ser Gly Asn Ser Gln Glu Ser Val Thr Glu Gln Asp Ser Lys Asp
            180             185             190

Ser Thr Tyr Ser Leu Ser Ser Thr Leu Thr Leu Ser Lys Ala Asp Tyr
            195             200             205

Glu Lys His Lys Val Tyr Ala Cys Glu Val Thr His Gln Gly Leu Ser
    210             215             220

Ser Pro Val Thr Lys Ser Phe Asn Arg Gly Glu Cys Asp Lys Thr His
225             230             235             240

Thr Cys Pro Pro Cys Pro Ala Pro Glu Leu Leu Gly Gly Pro Ser Val
            245             250             255

Phe Leu Phe Pro Pro Lys Pro Lys Asp Thr Leu Met Ala Ser Arg Thr
            260             265             270

Pro Glu Val Thr Cys Val Val Val Asp Val Ser His Glu Asp Pro Glu
            275             280             285

Val Lys Phe Asn Trp Tyr Val Asp Gly Val Glu Val His Asn Ala Lys
    290             295             300

Thr Lys Pro Arg Glu Glu Gln Tyr Asn Ser Thr Tyr Arg Val Val Ser
305             310             315             320

Val Leu Thr Val Leu Ala Gln Asp Trp Leu Asn Gly Lys Glu Tyr Lys
            325             330             335

Cys Lys Val Ser Asn Lys Ala Leu Pro Ala Pro Ile Glu Lys Thr Ile
            340             345             350

Ser Lys Ala Lys Gly Gln Pro Arg Glu Pro Gln Val Cys Thr Leu Pro
            355             360             365

Pro Ser Arg Asp Glu Leu Thr Lys Asn Gln Val Ser Leu Ser Cys Ala
    370             375             380

Val Lys Gly Phe Tyr Pro Ser Asp Ile Ala Val Glu Trp Glu Ser Asn
385             390             395             400

Gly Gln Pro Glu Asn Asn Tyr Lys Thr Thr Pro Pro Val Leu Asp Ser
            405             410             415

Asp Gly Ser Phe Phe Leu Val Ser Lys Leu Thr Val Asp Lys Ser Arg
            420             425             430

Trp Gln Gln Gly Asn Val Phe Ser Cys Ser Val Met His Glu Ala Leu
            435             440             445

His Asn Ala Tyr Thr Gln Lys Ser Leu Ser Leu Ser Pro Gly Lys
    450             455             460
```

```
<210> SEQ ID NO 36
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations (VEGFang2-0012)

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with AAA mutations (VEGF-Ang2-0012)

<400> SEQUENCE: 37

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
```

-continued

```
                          85                        90                        95
Trp Val Phe Gly Gly Gly Thr Lys Leu Thr Val Leu Ser Ser Ala Ser
                          100                       105                       110

Thr Lys Gly Pro Ser Val Phe Pro Leu Ala Pro Ser Ser Lys Ser Thr
              115                       120                       125

Ser Gly Gly Thr Ala Ala Leu Gly Cys Leu Val Lys Asp Tyr Phe Pro
              130                       135                       140

Glu Pro Val Thr Val Ser Trp Asn Ser Gly Ala Leu Thr Ser Gly Val
145                       150                       155                       160

His Thr Phe Pro Ala Val Leu Gln Ser Ser Gly Leu Tyr Ser Leu Ser
                          165                       170                       175

Ser Val Val Thr Val Pro Ser Ser Ser Leu Gly Thr Gln Thr Tyr Ile
                          180                       185                       190

Cys Asn Val Asn His Lys Pro Ser Asn Thr Lys Val Asp Lys Lys Val
                          195                       200                       205

Glu Pro Lys Ser Cys
                          210
```

<210> SEQ ID NO 38
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with AAA mutations and P329G LALA mutations (VEGFang2-0016)

<400> SEQUENCE: 38

```
Glu Val Gln Leu Val Glu Ser Gly Gly Gly Leu Val Gln Pro Gly Gly
1                         5                         10                        15

Ser Leu Arg Leu Ser Cys Ala Ala Ser Gly Tyr Asp Phe Thr His Tyr
                          20                        25                        30

Gly Met Asn Trp Val Arg Gln Ala Pro Gly Lys Gly Leu Glu Trp Val
                          35                        40                        45

Gly Trp Ile Asn Thr Tyr Thr Gly Glu Pro Thr Tyr Ala Ala Asp Phe
              50                        55                        60

Lys Arg Arg Phe Thr Phe Ser Leu Asp Thr Ser Lys Ser Thr Ala Tyr
65                        70                        75                        80

Leu Gln Met Asn Ser Leu Arg Ala Glu Asp Thr Ala Val Tyr Tyr Cys
                          85                        90                        95

Ala Lys Tyr Pro Tyr Tyr Tyr Gly Thr Ser His Trp Tyr Phe Asp Val
                          100                       105                       110

Trp Gly Gln Gly Thr Leu Val Thr Val Ser Ser Ala Ser Thr Lys Gly
              115                       120                       125

Pro Ser Val Phe Pro Leu Ala Pro Ser Ser Lys Ser Thr Ser Gly Gly
              130                       135                       140

Thr Ala Ala Leu Gly Cys Leu Val Lys Asp Tyr Phe Pro Glu Pro Val
145                       150                       155                       160

Thr Val Ser Trp Asn Ser Gly Ala Leu Thr Ser Gly Val His Thr Phe
                          165                       170                       175

Pro Ala Val Leu Gln Ser Ser Gly Leu Tyr Ser Leu Ser Ser Val Val
                          180                       185                       190

Thr Val Pro Ser Ser Ser Leu Gly Thr Gln Thr Tyr Ile Cys Asn Val
                          195                       200                       205

Asn His Lys Pro Ser Asn Thr Lys Val Asp Lys Lys Val Glu Pro Lys
              210                       215                       220
```

-continued

```
Ser Cys Asp Lys Thr His Thr Cys Pro Pro Cys Pro Ala Pro Glu Ala
225             230             235             240

Ala Gly Gly Pro Ser Val Phe Leu Phe Pro Pro Lys Pro Lys Asp Thr
            245             250             255

Leu Met Ala Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
            290             295             300

Thr Tyr Arg Val Val Ser Val Leu Thr Val Leu Ala Gln Asp Trp Leu
305             310             315             320

Asn Gly Lys Glu Tyr Lys Cys Lys Val Ser Asn Lys Ala Leu Gly Ala
            325             330             335

Pro Ile Glu Lys Thr Ile Ser Lys Ala Lys Gly Gln Pro Arg Glu Pro
            340             345             350

Gln Val Tyr Thr Leu Pro Pro Cys Arg Asp Glu Leu Thr Lys Asn Gln
            355             360             365

Val Ser Leu Trp Cys Leu Val Lys Gly Phe Tyr Pro Ser Asp Ile Ala
            370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn Ala Tyr Thr Gln Lys Ser Leu Ser
            435             440             445

Leu Ser Pro Gly Lys
            450
```

```
<210> SEQ ID NO 39
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations and P329G LALA mutations (VEGFang2-0016)

<400> SEQUENCE: 39
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Gly Tyr
            20              25              30

Tyr Met His Trp Val Arg Gln Ala Pro Gly Gln Gly Leu Glu Trp Met
            35              40              45

Gly Trp Ile Asn Pro Asn Ser Gly Gly Thr Asn Tyr Ala Gln Lys Phe
            50              55              60

Gln Gly Arg Val Thr Met Thr Arg Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Arg Ser Pro Asn Pro Tyr Tyr Tyr Asp Ser Ser Gly Tyr Tyr Tyr
            100             105             110

Pro Gly Ala Phe Asp Ile Trp Gly Gln Gly Thr Met Val Thr Val Ser
            115             120             125
```

```
Ser Ala Ser Val Ala Ala Pro Ser Val Phe Ile Phe Pro Pro Ser Asp
    130             135             140

Glu Gln Leu Lys Ser Gly Thr Ala Ser Val Val Cys Leu Leu Asn Asn
145             150             155             160

Phe Tyr Pro Arg Glu Ala Lys Val Gln Trp Lys Val Asp Asn Ala Leu
            165             170             175

Gln Ser Gly Asn Ser Gln Glu Ser Val Thr Glu Gln Asp Ser Lys Asp
            180             185             190

Ser Thr Tyr Ser Leu Ser Ser Thr Leu Thr Leu Ser Lys Ala Asp Tyr
        195             200             205

Glu Lys His Lys Val Tyr Ala Cys Glu Val Thr His Gln Gly Leu Ser
    210             215             220

Ser Pro Val Thr Lys Ser Phe Asn Arg Gly Glu Cys Asp Lys Thr His
225             230             235             240

Thr Cys Pro Pro Cys Pro Ala Pro Glu Ala Ala Gly Gly Pro Ser Val
            245             250             255

Phe Leu Phe Pro Pro Lys Pro Lys Asp Thr Leu Met Ala Ser Arg Thr
            260             265             270

Pro Glu Val Thr Cys Val Val Val Asp Val Ser His Glu Asp Pro Glu
            275             280             285

Val Lys Phe Asn Trp Tyr Val Asp Gly Val Glu Val His Asn Ala Lys
    290             295             300

Thr Lys Pro Arg Glu Glu Gln Tyr Asn Ser Thr Tyr Arg Val Val Ser
305             310             315             320

Val Leu Thr Val Leu Ala Gln Asp Trp Leu Asn Gly Lys Glu Tyr Lys
            325             330             335

Cys Lys Val Ser Asn Lys Ala Leu Gly Ala Pro Ile Glu Lys Thr Ile
            340             345             350

Ser Lys Ala Lys Gly Gln Pro Arg Glu Pro Gln Val Cys Thr Leu Pro
        355             360             365

Pro Ser Arg Asp Glu Leu Thr Lys Asn Gln Val Ser Leu Ser Cys Ala
    370             375             380

Val Lys Gly Phe Tyr Pro Ser Asp Ile Ala Val Glu Trp Glu Ser Asn
385             390             395             400

Gly Gln Pro Glu Asn Asn Tyr Lys Thr Thr Pro Pro Val Leu Asp Ser
            405             410             415

Asp Gly Ser Phe Phe Leu Val Ser Lys Leu Thr Val Asp Lys Ser Arg
            420             425             430

Trp Gln Gln Gly Asn Val Phe Ser Cys Ser Val Met His Glu Ala Leu
            435             440             445

His Asn Ala Tyr Thr Gln Lys Ser Leu Ser Leu Ser Pro Gly Lys
    450             455             460

<210> SEQ ID NO 40
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations and P329G LALA mutations (VEGFang2-0016)

<400> SEQUENCE: 40

Asp Ile Gln Leu Thr Gln Ser Pro Ser Ser Leu Ser Ala Ser Val Gly
1               5               10              15

Asp Arg Val Thr Ile Thr Cys Ser Ala Ser Gln Asp Ile Ser Asn Tyr
```

-continued

```
                20              25              30

Leu Asn Trp Tyr Gln Gln Lys Pro Gly Lys Ala Pro Lys Val Leu Ile
            35              40              45

Tyr Phe Thr Ser Ser Leu His Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Ser Thr Val Pro Trp
                85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
    195             200             205

Phe Asn Arg Gly Glu Cys
    210
```

```
<210> SEQ ID NO 41
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with AAA mutations and P329G LALA mutations (VEGFang2-0016)

<400> SEQUENCE: 41

Ser Tyr Val Leu Thr Gln Pro Pro Ser Val Ser Val Ala Pro Gly Gln
1               5               10              15

Thr Ala Arg Ile Thr Cys Gly Gly Asn Asn Ile Gly Ser Lys Ser Val
            20              25              30

His Trp Tyr Gln Gln Lys Pro Gly Gln Ala Pro Val Leu Val Val Tyr
            35              40              45

Asp Asp Ser Asp Arg Pro Ser Gly Ile Pro Glu Arg Phe Ser Gly Ser
        50              55              60

Asn Ser Gly Asn Thr Ala Thr Leu Thr Ile Ser Arg Val Glu Ala Gly
65              70              75              80

Asp Glu Ala Asp Tyr Tyr Cys Gln Val Trp Asp Ser Ser Ser Asp His
                85              90              95

Trp Val Phe Gly Gly Gly Thr Lys Leu Thr Val Leu Ser Ser Ala Ser
            100             105             110

Thr Lys Gly Pro Ser Val Phe Pro Leu Ala Pro Ser Ser Lys Ser Thr
            115             120             125

Ser Gly Gly Thr Ala Ala Leu Gly Cys Leu Val Lys Asp Tyr Phe Pro
        130             135             140

Glu Pro Val Thr Val Ser Trp Asn Ser Gly Ala Leu Thr Ser Gly Val
145             150             155             160
```

-continued

```
His Thr Phe Pro Ala Val Leu Gln Ser Ser Gly Leu Tyr Ser Leu Ser
             165                 170                 175

Ser Val Val Thr Val Pro Ser Ser Leu Gly Thr Gln Thr Tyr Ile
             180                 185                 190

Cys Asn Val Asn His Lys Pro Ser Asn Thr Lys Val Asp Lys Lys Val
         195                 200                 205

Glu Pro Lys Ser Cys
    210
```

```
<210> SEQ ID NO 42
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 42
```

```
Glu Val Gln Leu Val Glu Ser Gly Gly Gly Leu Val Gln Pro Gly Gly
1                 5                 10                 15

Ser Leu Arg Leu Ser Cys Ala Ala Ser Gly Tyr Asp Phe Thr His Tyr
             20                 25                 30

Gly Met Asn Trp Val Arg Gln Ala Pro Gly Lys Gly Leu Glu Trp Val
         35                 40                 45

Gly Trp Ile Asn Thr Tyr Thr Gly Glu Pro Thr Tyr Ala Ala Asp Phe
    50                 55                 60

Lys Arg Arg Phe Thr Phe Ser Leu Asp Thr Ser Lys Ser Thr Ala Tyr
65                 70                 75                 80

Leu Gln Met Asn Ser Leu Arg Ala Glu Asp Thr Ala Val Tyr Tyr Cys
             85                 90                 95

Ala Lys Tyr Pro Tyr Tyr Tyr Gly Thr Ser His Trp Tyr Phe Asp Val
         100                 105                 110

Trp Gly Gln Gly Thr Leu Val Thr Val Ser Ser Ala Ser Thr Lys Gly
         115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
             165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Lys Thr Tyr Thr Cys Asn Val
         195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
             245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
         275                 280                 285

Asn Ala Lys Thr Lys Pro Arg Glu Glu Gln Phe Asn Ser Thr Tyr Arg
    290                 295                 300
```

```
Val Val Ser Val Leu Thr Val Leu Ala Gln Asp Trp Leu Asn Gly Lys
305             310             315             320

Glu Tyr Lys Cys Lys Val Ser Asn Lys Gly Leu Pro Ser Ser Ile Glu
            325             330             335

Lys Thr Ile Ser Lys Ala Lys Gly Gln Pro Arg Glu Pro Gln Val Cys
            340             345             350

Thr Leu Pro Pro Ser Gln Glu Glu Met Thr Lys Asn Gln Val Ser Leu
        355             360             365

Ser Cys Ala Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Val Ser Arg Leu Thr Val Asp
            405             410             415

Lys Ser Arg Trp Gln Glu Gly Asn Val Phe Ser Cys Ser Val Met His
            420             425             430

Glu Ala Leu His Asn Ala Tyr Thr Gln Lys Ser Leu Ser Leu Ser Leu
        435             440             445

Gly Lys
    450
```

```
<210> SEQ ID NO 43
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 43
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Gly Tyr
            20              25              30

Tyr Met His Trp Val Arg Gln Ala Pro Gly Gln Gly Leu Glu Trp Met
        35              40              45

Gly Trp Ile Asn Pro Asn Ser Gly Gly Thr Asn Tyr Ala Gln Lys Phe
    50              55              60

Gln Gly Arg Val Thr Met Thr Arg Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Arg Ser Pro Asn Pro Tyr Tyr Tyr Asp Ser Ser Gly Tyr Tyr Tyr
            100             105             110

Pro Gly Ala Phe Asp Ile Trp Gly Gln Gly Thr Met Val Thr Val Ser
        115             120             125

Ser Ala Ser Val Ala Ala Pro Ser Val Phe Ile Phe Pro Pro Ser Asp
    130             135             140

Glu Gln Leu Lys Ser Gly Thr Ala Ser Val Val Cys Leu Leu Asn Asn
145             150             155             160

Phe Tyr Pro Arg Glu Ala Lys Val Gln Trp Lys Val Asp Asn Ala Leu
            165             170             175

Gln Ser Gly Asn Ser Gln Glu Ser Val Thr Glu Gln Asp Ser Lys Asp
            180             185             190

Ser Thr Tyr Ser Leu Ser Ser Thr Leu Thr Leu Ser Lys Ala Asp Tyr
```

-continued

```
             195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ala Ser Arg Thr Pro Glu Val
                260                 265                 270

Thr Cys Val Val Val Asp Val Ser Gln Glu Asp Pro Glu Val Gln Phe
                275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu Ala Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
                340                 345                 350

Lys Gly Gln Pro Arg Glu Pro Gln Val Tyr Thr Leu Pro Pro Cys Gln
                355                 360                 365

Glu Glu Met Thr Lys Asn Gln Val Ser Leu Trp Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
                420                 425                 430

Gly Asn Val Phe Ser Cys Ser Val Met His Glu Ala Leu His Asn Ala
                435                 440                 445

Tyr Thr Gln Lys Ser Leu Ser Leu Ser Leu Gly Lys
    450                 455                 460
```

```
<210> SEQ ID NO 44
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG4
      with AAA mutations and with SPLE mutations

<400> SEQUENCE: 44

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
                35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 45
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG4
      with AAA mutations and with SPLE mutations

<400> SEQUENCE: 45
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Cys Ser Arg Ser Thr
            115                 120                 125

Ser Glu Ser Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Lys Thr Tyr Thr
                180                 185                 190

Cys Asn Val Asp His Lys Pro Ser Asn Thr Lys Val Asp Lys Arg Val
            195                 200                 205

Glu Ser Lys Tyr Gly
    210
```

```
<210> SEQ ID NO 46
```

<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with
     AAA mutations

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Cys Thr Leu Pro Pro Ser Arg Asp Glu Leu Thr Lys Asn Gln
                355                 360                 365

Val Ser Leu Ser Cys Ala Val Lys Gly Phe Tyr Pro Ser Asp Ile Ala
```

-continued

```
        370              375              380
Val Glu Trp Glu Ser Asn Gly Gln Pro Glu Asn Asn Tyr Lys Thr Thr
385              390              395              400

Pro Pro Val Leu Asp Ser Asp Gly Ser Phe Phe Leu Val Ser Lys Leu
             405              410              415

Thr Val Asp Lys Ser Arg Trp Gln Gln Gly Asn Val Phe Ser Cys Ser
             420              425              430

Val Met His Glu Ala Leu His Asn Ala Tyr Thr Gln Lys Ser Leu Ser
         435              440              445

Leu Ser Pro Gly Lys
    450
```

```
<210> SEQ ID NO 47
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with
      AAA mutations

<400> SEQUENCE: 47
```

```
Ser Tyr Val Leu Thr Gln Pro Pro Ser Val Ser Val Ala Pro Gly Gln
1               5               10              15

Thr Ala Arg Ile Thr Cys Gly Gly Asn Asn Ile Gly Ser Lys Ser Val
             20              25              30

His Trp Tyr Gln Gln Lys Pro Gly Gln Ala Pro Val Leu Val Val Tyr
         35              40              45

Asp Asp Ser Asp Arg Pro Ser Gly Ile Pro Glu Arg Phe Ser Gly Ser
    50              55              60

Asn Ser Gly Asn Thr Ala Thr Leu Thr Ile Ser Arg Val Glu Ala Gly
65              70              75              80

Asp Glu Ala Asp Tyr Tyr Cys Gln Val Trp Asp Ser Ser Ser Asp His
             85              90              95

Trp Val Phe Gly Gly Gly Thr Lys Leu Thr Val Leu Gly Gln Pro Lys
             100             105             110

Ala Ala Pro Ser Val Thr Leu Phe Pro Pro Ser Ser Glu Glu Leu Gln
         115             120             125

Ala Asn Lys Ala Thr Leu Val Cys Leu Ile Ser Asp Phe Tyr Pro Gly
    130             135             140

Ala Val Thr Val Ala Trp Lys Ala Asp Ser Ser Pro Val Lys Ala Gly
145             150             155             160

Val Glu Thr Thr Thr Pro Ser Lys Gln Ser Asn Asn Lys Tyr Ala Ala
             165             170             175

Ser Ser Tyr Leu Ser Leu Thr Pro Glu Gln Trp Lys Ser His Arg Ser
         180             185             190

Tyr Ser Cys Gln Val Thr His Glu Gly Ser Thr Val Glu Lys Thr Val
         195             200             205

Ala Pro Thr Glu Cys Ser Gly Gly Gly Gly Ser Gly Gly Gly Gly Ser
    210             215             220

Gly Gly Gly Gly Ser Gly Gly Gly Gly Ser Gly Gly Gly Gly Ser Gly
225             230             235             240

Gly Gly Gly Ser Gly Gly Gln Val Gln Leu Val Glu Ser Gly Ala Glu
             245             250             255

Val Lys Lys Pro Gly Ala Ser Val Lys Val Ser Cys Lys Ala Ser Gly
             260             265             270
```

-continued

```
Tyr Thr Phe Thr Gly Tyr Tyr Met His Trp Val Arg Gln Ala Pro Gly
        275             280             285

Gln Gly Leu Glu Trp Met Gly Trp Ile Asn Pro Asn Ser Gly Gly Thr
    290             295             300

Asn Tyr Ala Gln Lys Phe Gln Gly Arg Val Thr Met Thr Arg Asp Thr
305             310             315             320

Ser Ile Ser Thr Ala Tyr Met Glu Leu Ser Arg Leu Arg Ser Asp Asp
                325             330             335

Thr Ala Val Tyr Tyr Cys Ala Arg Ser Pro Asn Pro Tyr Tyr Tyr Asp
            340             345             350

Ser Ser Gly Tyr Tyr Tyr Pro Gly Ala Phe Asp Ile Trp Gly Gln Gly
            355             360             365

Thr Met Val Thr Val Ser Ser Ala Ser Thr Lys Gly Pro Ser Val Phe
    370             375             380

Pro Leu Ala Pro Ser Ser Lys Ser Thr Ser Gly Gly Thr Ala Ala Leu
385             390             395             400

Gly Cys Leu Val Lys Asp Tyr Phe Pro Glu Pro Val Thr Val Ser Trp
                405             410             415

Asn Ser Gly Ala Leu Thr Ser Gly Val His Thr Phe Pro Ala Val Leu
            420             425             430

Gln Ser Ser Gly Leu Tyr Ser Leu Ser Ser Val Val Thr Val Pro Ser
    435             440             445

Ser Ser Leu Gly Thr Gln Thr Tyr Ile Cys Asn Val Asn His Lys Pro
    450             455             460

Ser Asn Thr Lys Val Asp Lys Lys Val Glu Pro Lys Ser Cys Asp Lys
465             470             475             480

Thr His Thr Cys Pro Pro Cys Pro Ala Pro Glu Leu Leu Gly Gly Pro
                485             490             495

Ser Val Phe Leu Phe Pro Pro Lys Pro Lys Asp Thr Leu Met Ala Ser
                500             505             510

Arg Thr Pro Glu Val Thr Cys Val Val Val Asp Val Ser His Glu Asp
            515             520             525

Pro Glu Val Lys Phe Asn Trp Tyr Val Asp Gly Val Glu Val His Asn
    530             535             540

Ala Lys Thr Lys Pro Arg Glu Glu Gln Tyr Asn Ser Thr Tyr Arg Val
545             550             555             560

Val Ser Val Leu Thr Val Leu Ala Gln Asp Trp Leu Asn Gly Lys Glu
            565             570             575

Tyr Lys Cys Lys Val Ser Asn Lys Ala Leu Pro Ala Pro Ile Glu Lys
            580             585             590

Thr Ile Ser Lys Ala Lys Gly Gln Pro Arg Glu Pro Gln Val Tyr Thr
    595             600             605

Leu Pro Pro Cys Arg Asp Glu Leu Thr Lys Asn Gln Val Ser Leu Trp
    610             615             620

Cys Leu Val Lys Gly Phe Tyr Pro Ser Asp Ile Ala Val Glu Trp Glu
625             630             635             640

Ser Asn Gly Gln Pro Glu Asn Asn Tyr Lys Thr Thr Pro Pro Val Leu
                645             650             655

Asp Ser Asp Gly Ser Phe Phe Leu Tyr Ser Lys Leu Thr Val Asp Lys
                660             665             670

Ser Arg Trp Gln Gln Gly Asn Val Phe Ser Cys Ser Val Met His Glu
    675             680             685

Ala Leu His Asn Ala Tyr Thr Gln Lys Ser Leu Ser Leu Ser Pro Gly
```

-continued

```
        690              695              700

Lys
705

<210> SEQ ID NO 48
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG1 with
      AAA mutations

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
      AAA mutations and with SPLE mutations

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
```

-continued

```
        50                        55                        60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn Ala Tyr Thr Gln Lys Ser Leu Ser Leu Ser Leu
            435                 440                 445

Gly Lys
450
```

<210> SEQ ID NO 50

```
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gln Val Gln Leu Val Glu Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
            275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly
            355                 360                 365

Thr Met Val Thr Val Ser Ser Ala Ser Thr Lys Gly Pro Ser Val Phe
```

```
        370             375             380

Pro Leu Ala Pro Cys Ser Arg Ser Thr Ser Glu Ser Thr Ala Ala Leu
385             390             395             400

Gly Cys Leu Val Lys Asp Tyr Phe Pro Glu Pro Val Thr Val Ser Trp
                405             410             415

Asn Ser Gly Ala Leu Thr Ser Gly Val His Thr Phe Pro Ala Val Leu
            420             425             430

Gln Ser Ser Gly Leu Tyr Ser Leu Ser Ser Val Val Thr Val Pro Ser
            435             440             445

Ser Ser Leu Gly Thr Lys Thr Tyr Thr Cys Asn Val Asp His Lys Pro
        450             455             460

Ser Asn Thr Lys Val Asp Lys Arg Val Glu Ser Lys Tyr Gly Pro Pro
465             470             475             480

Cys Pro Pro Cys Pro Ala Pro Glu Phe Glu Gly Gly Pro Ser Val Phe
                485             490             495

Leu Phe Pro Pro Lys Pro Lys Asp Thr Leu Met Ala Ser Arg Thr Pro
            500             505             510

Glu Val Thr Cys Val Val Val Asp Val Ser Gln Glu Asp Pro Glu Val
            515             520             525

Gln Phe Asn Trp Tyr Val Asp Gly Val Glu Val His Asn Ala Lys Thr
        530             535             540

Lys Pro Arg Glu Glu Gln Phe Asn Ser Thr Tyr Arg Val Val Ser Val
545             550             555             560

Leu Thr Val Leu Ala Gln Asp Trp Leu Asn Gly Lys Glu Tyr Lys Cys
            565             570             575

Lys Val Ser Asn Lys Gly Leu Pro Ser Ser Ile Glu Lys Thr Ile Ser
            580             585             590

Lys Ala Lys Gly Gln Pro Arg Glu Pro Gln Val Tyr Thr Leu Pro Pro
            595             600             605

Cys Gln Glu Glu Met Thr Lys Asn Gln Val Ser Leu Trp Cys Leu Val
        610             615             620

Lys Gly Phe Tyr Pro Ser Asp Ile Ala Val Glu Trp Glu Ser Asn Gly
625             630             635             640

Gln Pro Glu Asn Asn Tyr Lys Thr Thr Pro Pro Val Leu Asp Ser Asp
            645             650             655

Gly Ser Phe Phe Leu Tyr Ser Arg Leu Thr Val Asp Lys Ser Arg Trp
            660             665             670

Gln Glu Gly Asn Val Phe Ser Cys Ser Val Met His Glu Ala Leu His
            675             680             685

Asn Ala Tyr Thr Gln Lys Ser Leu Ser Leu Ser Leu Gly Lys
        690             695             700
```

<210> SEQ ID NO 51
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG4 with
      AAA mutations and with SPLE mutations

<400> SEQUENCE: 51

```
Asp Ile Gln Leu Thr Gln Ser Pro Ser Ser Leu Ser Ala Ser Val Gly
1               5               10              15

Asp Arg Val Thr Ile Thr Cys Ser Ala Ser Gln Asp Ile Ser Asn Tyr
            20              25              30
```

```
Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 52
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

-continued

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450
```

```
<210> SEQ ID NO 53
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 53
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
```

-continued

```
65                    70                    75                    80

Met Glu Leu Ser Arg Leu Arg Ser Asp Asp Thr Ala Val Tyr Tyr Cys
                85                    90                    95

Ala Arg Ser Pro Asn Pro Tyr Tyr Asp Ser Ser Gly Tyr Tyr Tyr
                100                   105                   110

Pro Gly Ala Phe Asp Ile Trp Gly Gln Gly Thr Met Val Thr Val Ser
                115                   120                   125

Ser Ala Ser Val Ala Ala Pro Ser Val Phe Ile Phe Pro Pro Ser Asp
        130                   135                   140

Glu Gln Leu Lys Ser Gly Thr Ala Ser Val Val Cys Leu Leu Asn Asn
145                   150                   155                   160

Phe Tyr Pro Arg Glu Ala Lys Val Gln Trp Lys Val Asp Asn Ala Leu
                165                   170                   175

Gln Ser Gly Asn Ser Gln Glu Ser Val Thr Glu Gln Asp Ser Lys Asp
                180                   185                   190

Ser Thr Tyr Ser Leu Ser Ser Thr Leu Thr Leu Ser Lys Ala Asp Tyr
                195                   200                   205

Glu Lys His Lys Val Tyr Ala Cys Glu Val Thr His Gln Gly Leu Ser
        210                   215                   220

Ser Pro Val Thr Lys Ser Phe Asn Arg Gly Glu Cys Asp Lys Thr His
225                   230                   235                   240

Thr Cys Pro Pro Cys Pro Ala Pro Glu Leu Leu Gly Gly Pro Ser Val
                245                   250                   255

Phe Leu Phe Pro Pro Lys Pro Lys Asp Thr Leu Met Ile Ser Arg Thr
                260                   265                   270

Pro Glu Val Thr Cys Val Val Val Asp Val Ser His Glu Asp Pro Glu
                275                   280                   285

Val Lys Phe Asn Trp Tyr Val Asp Gly Val Glu Val His Asn Ala Lys
        290                   295                   300

Thr Lys Pro Arg Glu Glu Gln Tyr Asn Ser Thr Tyr Arg Val Val Ser
305                   310                   315                   320

Val Leu Thr Val Leu His Gln Asp Trp Leu Asn Gly Lys Glu Tyr Lys
                325                   330                   335

Cys Lys Val Ser Asn Lys Ala Leu Pro Ala Pro Ile Glu Lys Thr Ile
                340                   345                   350

Ser Lys Ala Lys Gly Gln Pro Arg Glu Pro Gln Val Cys Thr Leu Pro
                355                   360                   365

Pro Ser Arg Asp Glu Leu Thr Lys Asn Gln Val Ser Leu Ser Cys Ala
        370                   375                   380

Val Lys Gly Phe Tyr Pro Ser Asp Ile Ala Val Glu Trp Glu Ser Asn
385                   390                   395                   400

Gly Gln Pro Glu Asn Asn Tyr Lys Thr Thr Pro Pro Val Leu Asp Ser
                405                   410                   415

Asp Gly Ser Phe Phe Leu Val Ser Lys Leu Thr Val Asp Lys Ser Arg
                420                   425                   430

Trp Gln Gln Gly Asn Val Phe Ser Cys Ser Val Met His Glu Ala Leu
                435                   440                   445

His Asn His Tyr Thr Gln Lys Ser Leu Ser Leu Ser Pro Gly Lys
        450                   455                   460
```

<210> SEQ ID NO 54
<211> LENGTH: 214
<212> TYPE: PRT
<213> ORGANISM: Artificial

-continued

<220> FEATURE:
<223> OTHER INFORMATION: Light chain 1 of <VEGF-ANG-2> CrossMAb IgG1
      wild type (without AAA mutations) (VEGFang2-0201)

<400> SEQUENCE: 54

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      wild type (without AAA mutations) (VEGFang2-0201)

<400> SEQUENCE: 55

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

```
Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190

Cys Asn Val Asn His Lys Pro Ser Asn Thr Lys Val Asp Lys Lys Val
                195                 200                 205

Glu Pro Lys Ser Cys
        210
```

```
<210> SEQ ID NO 56
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with P329G LALA mutations only (without AAA mutations)
      (VEGFang2-0015)

<400> SEQUENCE: 56
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
        20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240
```

-continued

---

Ala Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 57
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with P329G LALA mutations only (without AAA mutations)
      (VEGFang2-0015)

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp

-continued

```
        130              135              140
Glu Gln Leu Lys Ser Gly Thr Ala Ser Val Val Cys Leu Leu Asn Asn
145              150              155              160

Phe Tyr Pro Arg Glu Ala Lys Val Gln Trp Lys Val Asp Asn Ala Leu
                165              170              175

Gln Ser Gly Asn Ser Gln Glu Ser Val Thr Glu Gln Asp Ser Lys Asp
                180              185              190

Ser Thr Tyr Ser Leu Ser Ser Thr Leu Thr Leu Ser Lys Ala Asp Tyr
            195              200              205

Glu Lys His Lys Val Tyr Ala Cys Glu Val Thr His Gln Gly Leu Ser
        210              215              220

Ser Pro Val Thr Lys Ser Phe Asn Arg Gly Glu Cys Asp Lys Thr His
225              230              235              240

Thr Cys Pro Pro Cys Pro Ala Pro Glu Ala Ala Gly Gly Pro Ser Val
                245              250              255

Phe Leu Phe Pro Pro Lys Pro Lys Asp Thr Leu Met Ile Ser Arg Thr
                260              265              270

Pro Glu Val Thr Cys Val Val Val Asp Val Ser His Glu Asp Pro Glu
            275              280              285

Val Lys Phe Asn Trp Tyr Val Asp Gly Val Glu Val His Asn Ala Lys
        290              295              300

Thr Lys Pro Arg Glu Glu Gln Tyr Asn Ser Thr Tyr Arg Val Val Ser
305              310              315              320

Val Leu Thr Val Leu His Gln Asp Trp Leu Asn Gly Lys Glu Tyr Lys
                325              330              335

Cys Lys Val Ser Asn Lys Ala Leu Gly Ala Pro Ile Glu Lys Thr Ile
                340              345              350

Ser Lys Ala Lys Gly Gln Pro Arg Glu Pro Gln Val Cys Thr Leu Pro
                355              360              365

Pro Ser Arg Asp Glu Leu Thr Lys Asn Gln Val Ser Leu Ser Cys Ala
        370              375              380

Val Lys Gly Phe Tyr Pro Ser Asp Ile Ala Val Glu Trp Glu Ser Asn
385              390              395              400

Gly Gln Pro Glu Asn Asn Tyr Lys Thr Thr Pro Pro Val Leu Asp Ser
                405              410              415

Asp Gly Ser Phe Phe Leu Val Ser Lys Leu Thr Val Asp Lys Ser Arg
            420              425              430

Trp Gln Gln Gly Asn Val Phe Ser Cys Ser Val Met His Glu Ala Leu
            435              440              445

His Asn His Tyr Thr Gln Lys Ser Leu Ser Leu Ser Pro Gly Lys
    450              455              460
```

<210> SEQ ID NO 58
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with P329G LALA mutations only (without AAA mutations)
      (VEGFang2-0015)

<400> SEQUENCE: 58

```
Asp Ile Gln Leu Thr Gln Ser Pro Ser Ser Leu Ser Ala Ser Val Gly
1               5               10              15

Asp Arg Val Thr Ile Thr Cys Ser Ala Ser Gln Asp Ile Ser Asn Tyr
            20              25              30
```

```
Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 59
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with P329G LALA mutations only (without AAA mutations)
      (VEGFang2-0015)

<400> SEQUENCE: 59

```
Ser Tyr Val Leu Thr Gln Pro Pro Ser Val Ser Val Ala Pro Gly Gln
1                   5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
                100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160
```

-continued

```
His Thr Phe Pro Ala Val Leu Gln Ser Ser Gly Leu Tyr Ser Leu Ser
             165                 170                 175

Ser Val Val Thr Val Pro Ser Ser Leu Gly Thr Gln Thr Tyr Ile
             180                 185                 190

Cys Asn Val Asn His Lys Pro Ser Asn Thr Lys Val Asp Lys Lys Val
             195                 200                 205

Glu Pro Lys Ser Cys
    210

<210> SEQ ID NO 60
<211> LENGTH: 227
<212> TYPE: PRT
<213> ORGANISM: Homo sapiens

<400> SEQUENCE: 60

Asp Lys Thr His Thr Cys Pro Pro Cys Pro Ala Pro Glu Leu Leu Gly
1                 5                 10                 15

Gly Pro Ser Val Phe Leu Phe Pro Pro Lys Pro Lys Asp Thr Leu Met
             20                 25                 30

Ile Ser Arg Thr Pro Glu Val Thr Cys Val Val Val Asp Val Ser His
             35                 40                 45

Glu Asp Pro Glu Val Lys Phe Asn Trp Tyr Val Asp Gly Val Glu Val
    50                 55                 60

His Asn Ala Lys Thr Lys Pro Arg Glu Glu Gln Tyr Asn Ser Thr Tyr
65                 70                 75                 80

Arg Val Val Ser Val Leu Thr Val Leu His Gln Asp Trp Leu Asn Gly
             85                 90                 95

Lys Glu Tyr Lys Cys Lys Val Ser Asn Lys Ala Leu Pro Ala Pro Ile
             100                105                110

Glu Lys Thr Ile Ser Lys Ala Lys Gly Gln Pro Arg Glu Pro Gln Val
             115                120                125

Tyr Thr Leu Pro Pro Ser Arg Asp Glu Leu Thr Lys Asn Gln Val Ser
    130                135                140

Leu Thr Cys Leu Val Lys Gly Phe Tyr Pro Ser Asp Ile Ala Val Glu
145                150                155                160

Trp Glu Ser Asn Gly Gln Pro Glu Asn Asn Tyr Lys Thr Thr Pro Pro
             165                170                175

Val Leu Asp Ser Asp Gly Ser Phe Phe Leu Tyr Ser Lys Leu Thr Val
             180                185                190

Asp Lys Ser Arg Trp Gln Gln Gly Asn Val Phe Ser Cys Ser Val Met
             195                200                205

His Glu Ala Leu His Asn His Tyr Thr Gln Lys Ser Leu Ser Leu Ser
    210                215                220

Pro Gly Lys
225

<210> SEQ ID NO 61
<211> LENGTH: 223
<212> TYPE: PRT
<213> ORGANISM: Homo sapiens

<400> SEQUENCE: 61

Val Glu Cys Pro Pro Cys Pro Ala Pro Val Ala Gly Pro Ser Val
1                 5                 10                 15

Phe Leu Phe Pro Pro Lys Pro Lys Asp Thr Leu Met Ile Ser Arg Thr
             20                 25                 30
```

-continued

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
                115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 62
<211> LENGTH: 227
<212> TYPE: PRT
<213> ORGANISM: Homo sapiens

<400> SEQUENCE: 62

Asp Thr Pro Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Gln Phe Lys Trp Tyr Val Asp Gly Val Glu Val
        50                  55                  60

His Asn Ala Lys Thr Lys Pro Arg Glu Glu Gln Tyr Asn Ser Thr Phe
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Thr Lys Gly Gln Pro Arg Glu Pro Gln Val
                115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
                180                 185                 190

-continued

```
Asp Lys Ser Arg Trp Gln Gln Gly Asn Ile Phe Ser Cys Ser Val Met
    195                 200                 205

His Glu Ala Leu His Asn Arg Phe Thr Gln Lys Ser Leu Ser Leu Ser
    210                 215                 220

Pro Gly Lys
225

<210> SEQ ID NO 63
<211> LENGTH: 229
<212> TYPE: PRT
<213> ORGANISM: Homo sapiens

<400> SEQUENCE: 63

Glu Ser Lys Tyr Gly Pro Pro Cys Pro Ser Cys Pro Ala Pro Glu Phe
1               5               10                  15

Leu Gly Gly Pro Ser Val Phe Leu Phe Pro Pro Lys Pro Lys Asp Thr
            20              25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50              55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
    195                 200                 205

Val Met His Glu Ala Leu His Asn His Tyr Thr Gln Lys Ser Leu Ser
    210                 215                 220

Leu Ser Leu Gly Lys
225

<210> SEQ ID NO 64
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 64

Asp Lys Thr His Thr Cys Pro Pro Cys Pro Ala Pro Glu Ala Ala Gly
1               5               10                  15

Gly Pro Ser Val Phe Leu Phe Pro Pro Lys Pro Lys Asp Thr Leu Met
            20              25                  30
```

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 65
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 65

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
```

-continued

```
145               150               155               160

Trp Glu Ser Asn Gly Gln Pro Glu Asn Asn Tyr Lys Thr Thr Pro Pro
                165               170               175

Val Leu Asp Ser Asp Gly Ser Phe Phe Leu Val Ser Lys Leu Thr Val
            180               185               190

Asp Lys Ser Arg Trp Gln Gln Gly Asn Val Phe Ser Cys Ser Val Met
        195               200               205

His Glu Ala Leu His Asn His Tyr Thr Gln Lys Ser Leu Ser Leu Ser
    210               215               220

Pro Gly Lys
225

<210> SEQ ID NO 66
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with S354C, T366W mutations

<400> SEQUENCE: 66

Asp Lys Thr His Thr Cys Pro Pro Cys Pro Ala Pro Glu Leu Leu Gly
1               5                 10                15

Gly Pro Ser Val Phe Leu Phe Pro Pro Lys Pro Lys Asp Thr Leu Met
            20                25                30

Ile Ser Arg Thr Pro Glu Val Thr Cys Val Val Val Asp Val Ser His
        35                40                45

Glu Asp Pro Glu Val Lys Phe Asn Trp Tyr Val Asp Gly Val Glu Val
    50                55                60

His Asn Ala Lys Thr Lys Pro Arg Glu Glu Gln Tyr Asn Ser Thr Tyr
65                70                75                80

Arg Val Val Ser Val Leu Thr Val Leu His Gln Asp Trp Leu Asn Gly
            85                90                95

Lys Glu Tyr Lys Cys Lys Val Ser Asn Lys Ala Leu Pro Ala Pro Ile
            100               105               110

Glu Lys Thr Ile Ser Lys Ala Lys Gly Gln Pro Arg Glu Pro Gln Val
            115               120               125

Tyr Thr Leu Pro Pro Cys Arg Asp Glu Leu Thr Lys Asn Gln Val Ser
    130               135               140

Leu Trp Cys Leu Val Lys Gly Phe Tyr Pro Ser Asp Ile Ala Val Glu
145               150               155               160

Trp Glu Ser Asn Gly Gln Pro Glu Asn Asn Tyr Lys Thr Thr Pro Pro
                165               170               175

Val Leu Asp Ser Asp Gly Ser Phe Phe Leu Tyr Ser Lys Leu Thr Val
            180               185               190

Asp Lys Ser Arg Trp Gln Gln Gly Asn Val Phe Ser Cys Ser Val Met
        195               200               205

His Glu Ala Leu His Asn His Tyr Thr Gln Lys Ser Leu Ser Leu Ser
    210               215               220

Pro Gly Lys
225

<210> SEQ ID NO 67
<211> LENGTH: 227
<212> TYPE: PRT
<213> ORGANISM: Artificial Sequence
<220> FEATURE:
```

-continued

<223> OTHER INFORMATION: human IgG1 Fc-region derived Fc-region
      polypeptide with L234A, L235A mutations and Y349C, T366S, L368A,
      Y407V mutations

<400> SEQUENCE: 67

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 68
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a L234A, L235A and S354C, T366W mutations

<400> SEQUENCE: 68

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
        210                 215                 220

Pro Gly Lys
225

<210> SEQ ID NO 69
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 69

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
```

-continued

```
             210                 215                 220

Pro Gly Lys
225

<210> SEQ ID NO 70
<211> LENGTH: 227
<212> TYPE: PRT
<213> ORGANISM: Artificial Sequence
<220> FEATURE:
<223> OTHER INFORMATION: human IgG1 Fc-region derived Fc-region
     polypeptide with L234A, L235A mutations and P329G mutation

<400> SEQUENCE: 70

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 71
<211> LENGTH: 227
<212> TYPE: PRT
<213> ORGANISM: Artificial Sequence
<220> FEATURE:
<223> OTHER INFORMATION: human IgG1 Fc-region derived Fc-region
     polypeptide with a P239G mutation and Y349C, T366S, L368A, Y407V
     mutations

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
    35              40                  45

Glu Asp Pro Glu Val Lys Phe Asn Trp Tyr Val Asp Gly Val Glu Val
    50              55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 72
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50              55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

-continued

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225
```

```
<210> SEQ ID NO 73
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 73
```

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225
```

```
<210> SEQ ID NO 74
<211> LENGTH: 227
<212> TYPE: PRT
<213> ORGANISM: Artificial Sequence
<220> FEATURE:
```

<223> OTHER INFORMATION: human IgG1 Fc-region derived Fc-region
      polypeptide with L234A, L235A, P329G mutations and S354C, T366W
      mutations

<400> SEQUENCE: 74

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 75
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 75

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 76
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 76
```

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
```

-continued

```
                210               215               220

Leu Ser Leu Gly Lys
225

<210> SEQ ID NO 77
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 77

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Cys Gln Glu Glu Met Thr Lys Asn Gln
        130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225

<210> SEQ ID NO 78
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 78

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
```

-continued

```
                35                    40                    45

Ser Gln Glu Asp Pro Glu Val Gln Phe Asn Trp Tyr Val Asp Gly Val
    50                    55                    60

Glu Val His Asn Ala Lys Thr Lys Pro Arg Glu Glu Gln Phe Asn Ser
65                    70                    75                    80

Thr Tyr Arg Val Val Ser Val Leu Thr Val Leu His Gln Asp Trp Leu
                85                    90                    95

Asn Gly Lys Glu Tyr Lys Cys Lys Val Ser Asn Lys Gly Leu Pro Ser
                100                   105                   110

Ser Ile Glu Lys Thr Ile Ser Lys Ala Lys Gly Gln Pro Arg Glu Pro
                115                   120                   125

Gln Val Cys Thr Leu Pro Pro Ser Gln Glu Glu Met Thr Lys Asn Gln
    130                   135                   140

Val Ser Leu Ser Cys Ala Val Lys Gly Phe Tyr Pro Ser Asp Ile Ala
145                   150                   155                   160

Val Glu Trp Glu Ser Asn Gly Gln Pro Glu Asn Asn Tyr Lys Thr Thr
                165                   170                   175

Pro Pro Val Leu Asp Ser Asp Gly Ser Phe Phe Leu Val Ser Arg Leu
                180                   185                   190

Thr Val Asp Lys Ser Arg Trp Gln Glu Gly Asn Val Phe Ser Cys Ser
                195                   200                   205

Val Met His Glu Ala Leu His Asn His Tyr Thr Gln Lys Ser Leu Ser
    210                   215                   220

Leu Ser Leu Gly Lys
225
```

```
<210> SEQ ID NO 79
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 79

Glu Ser Lys Tyr Gly Pro Pro Cys Pro Pro Cys Pro Ala Pro Glu Phe
1                   5                     10                    15

Glu Gly Gly Pro Ser Val Phe Leu Phe Pro Pro Lys Pro Lys Asp Thr
                20                    25                    30

Leu Met Ile Ser Arg Thr Pro Glu Val Thr Cys Val Val Val Asp Val
                35                    40                    45

Ser Gln Glu Asp Pro Glu Val Gln Phe Asn Trp Tyr Val Asp Gly Val
    50                    55                    60

Glu Val His Asn Ala Lys Thr Lys Pro Arg Glu Glu Gln Phe Asn Ser
65                    70                    75                    80

Thr Tyr Arg Val Val Ser Val Leu Thr Val Leu His Gln Asp Trp Leu
                85                    90                    95

Asn Gly Lys Glu Tyr Lys Cys Lys Val Ser Asn Lys Gly Leu Pro Ser
                100                   105                   110

Ser Ile Glu Lys Thr Ile Ser Lys Ala Lys Gly Gln Pro Arg Glu Pro
                115                   120                   125

Gln Val Tyr Thr Leu Pro Pro Cys Gln Glu Glu Met Thr Lys Asn Gln
    130                   135                   140

Val Ser Leu Trp Cys Leu Val Lys Gly Phe Tyr Pro Ser Asp Ile Ala
145                   150                   155                   160
```

```
Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 80
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 80

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 81
<211> LENGTH: 229
<212> TYPE: PRT
<213> ORGANISM: Artificial Sequence
<220> FEATURE:
<223> OTHER INFORMATION: human IgG4 Fc-region derived Fc-region
```

-continued polypeptide with a P329G mutation

<400> SEQUENCE: 81

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 82
<211> LENGTH: 229
<212> TYPE: PRT
<213> ORGANISM: Artificial Sequence
<220> FEATURE:
<223> OTHER INFORMATION: human IgG4 Fc-region derived Fc-region
    polypeptide with a P239G and Y349C, T366S, L368A, Y407V mutations

<400> SEQUENCE: 82

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
```

-continued

```
                    100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225

<210> SEQ ID NO 83
<211> LENGTH: 229
<212> TYPE: PRT
<213> ORGANISM: Artificial Sequence
<220> FEATURE:
<223> OTHER INFORMATION: human IgG4 Fc-region derived Fc-region
     polypeptide with a P329G and S354C, T366W mutations

<400> SEQUENCE: 83

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220
```

-continued

```
Leu Ser Leu Gly Lys
225

<210> SEQ ID NO 84
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and Y349C, T366S, L368A,
      Y407V mutations

<400> SEQUENCE: 84

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 85
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E, P329G and S354C, T366W mutations

<400> SEQUENCE: 85

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

-continued

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220

Leu Ser Leu Gly Lys
225

<210> SEQ ID NO 86
<211> LENGTH: 105
<212> TYPE: PRT
<213> ORGANISM: homo sapiens

<400> SEQUENCE: 86

Gln Pro Lys Ala Ala Pro Ser Val Thr Leu Phe Pro Pro Ser Ser Glu
1                   5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 87
<211> LENGTH: 107
<212> TYPE: PRT
<213> ORGANISM: Homo sapiens

<400> SEQUENCE: 87

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                    40                    45

Ser Gly Asn Ser Gln Glu Ser Val Thr Glu Gln Asp Ser Lys Asp Ser
        50                    55                    60

Thr Tyr Ser Leu Ser Ser Thr Leu Thr Leu Ser Lys Ala Asp Tyr Glu
65                    70                    75                    80

Lys His Lys Val Tyr Ala Cys Glu Val Thr His Gln Gly Leu Ser Ser
                      85                    90                    95

Pro Val Thr Lys Ser Phe Asn Arg Gly Glu Cys
              100                   105

<210> SEQ ID NO 88
<211> LENGTH: 215
<212> TYPE: PRT
<213> ORGANISM: Artificial Sequence
<220> FEATURE:
<223> OTHER INFORMATION: IGF-1R LC

<400> SEQUENCE: 88

Glu Ile Val Leu Thr Gln Ser Pro Ala Thr Leu Ser Leu Ser Pro Gly
1                     5                     10                    15

Glu Arg Ala Thr Leu Ser Cys Arg Ala Ser Gln Ser Val Ser Ser Tyr
              20                    25                    30

Leu Ala Trp Tyr Gln Gln Lys Pro Gly Gln Ala Pro Arg Leu Leu Ile
        35                    40                    45

Tyr Asp Ala Ser Lys Arg Ala Thr Gly Ile Pro Ala Arg Phe Ser Gly
        50                    55                    60

Ser Gly Ser Gly Thr Asp Phe Thr Leu Thr Ile Ser Ser Leu Glu Pro
65                    70                    75                    80

Glu Asp Phe Ala Val Tyr Tyr Cys Gln Gln Arg Ser Lys Trp Pro Pro
                      85                    90                    95

Trp Thr Phe Gly Gln Gly Thr Lys Val Glu Ser Lys Arg Thr Val Ala
              100                   105                   110

Ala Pro Ser Val Phe Ile Phe Pro Pro Ser Asp Glu Gln Leu Lys Ser
        115                   120                   125

Gly Thr Ala Ser Val Val Cys Leu Leu Asn Asn Phe Tyr Pro Arg Glu
        130                   135                   140

Ala Lys Val Gln Trp Lys Val Asp Asn Ala Leu Gln Ser Gly Asn Ser
145                   150                   155                   160

Gln Glu Ser Val Thr Glu Gln Asp Ser Lys Asp Ser Thr Tyr Ser Leu
              165                   170                   175

Ser Ser Thr Leu Thr Leu Ser Lys Ala Asp Tyr Glu Lys His Lys Val
              180                   185                   190

Tyr Ala Cys Glu Val Thr His Gln Gly Leu Ser Ser Pro Val Thr Lys
        195                   200                   205

Ser Phe Asn Arg Gly Glu Cys
        210                   215

<210> SEQ ID NO 89
<211> LENGTH: 447
<212> TYPE: PRT
<213> ORGANISM: Artificial Sequence
<220> FEATURE:
<223> OTHER INFORMATION: IGF-1R wt

<400> SEQUENCE: 89

Gln Val Glu Leu Val Glu Ser Gly Gly Gly Val Val Gln Pro Gly Arg

```
1                    5                    10                   15

Ser Gln Arg Leu Ser Cys Ala Ala Ser Gly Phe Thr Phe Ser Ser Tyr
            20                   25                   30

Gly Met His Trp Val Arg Gln Ala Pro Gly Lys Gly Leu Glu Trp Val
            35                   40                   45

Ala Ile Ile Trp Phe Asp Gly Ser Ser Thr Tyr Tyr Ala Asp Ser Val
            50                   55                   60

Arg Gly Arg Phe Thr Ile Ser Arg Asp Asn Ser Lys Asn Thr Leu Tyr
65                   70                   75                   80

Leu Gln Met Asn Ser Leu Arg Ala Glu Asp Thr Ala Val Tyr Phe Cys
                85                   90                   95

Ala Arg Glu Leu Gly Arg Arg Tyr Phe Asp Leu Trp Gly Arg Gly Thr
            100                  105                  110

Leu Val Ser Val Ser Ser Ala Ser Thr Lys Gly Pro Ser Val Phe Pro
            115                  120                  125

Leu Ala Pro Ser Ser Lys Ser Thr Ser Gly Gly Thr Ala Ala Leu Gly
            130                  135                  140

Cys Leu Val Lys Asp Tyr Phe Pro Glu Pro Val Thr Val Ser Trp Asn
145                  150                  155                  160

Ser Gly Ala Leu Thr Ser Gly Val His Thr Phe Pro Ala Val Leu Gln
                165                  170                  175

Ser Ser Gly Leu Tyr Ser Leu Ser Ser Val Val Thr Val Pro Ser Ser
            180                  185                  190

Ser Leu Gly Thr Gln Thr Tyr Ile Cys Asn Val Asn His Lys Pro Ser
            195                  200                  205

Asn Thr Lys Val Asp Lys Lys Val Glu Pro Lys Ser Cys Asp Lys Thr
            210                  215                  220

His Thr Cys Pro Pro Cys Pro Ala Pro Glu Leu Leu Gly Gly Pro Ser
225                  230                  235                  240

Val Phe Leu Phe Pro Pro Lys Pro Lys Asp Thr Leu Met Ile Ser Arg
                245                  250                  255

Thr Pro Glu Val Thr Cys Val Val Val Asp Val Ser His Glu Asp Pro
            260                  265                  270

Glu Val Lys Phe Asn Trp Tyr Val Asp Gly Val Glu Val His Asn Ala
            275                  280                  285

Lys Thr Lys Pro Arg Glu Glu Gln Tyr Asn Ser Thr Tyr Arg Val Val
            290                  295                  300

Ser Val Leu Thr Val Leu His Gln Asp Trp Leu Asn Gly Lys Glu Tyr
305                  310                  315                  320

Lys Cys Lys Val Ser Asn Lys Ala Leu Pro Ala Pro Ile Glu Lys Thr
                325                  330                  335

Ile Ser Lys Ala Lys Gly Gln Pro Arg Glu Pro Gln Val Tyr Thr Leu
            340                  345                  350

Pro Pro Ser Arg Asp Glu Leu Thr Lys Asn Gln Val Ser Leu Thr Cys
            355                  360                  365

Leu Val Lys Gly Phe Tyr Pro Ser Asp Ile Ala Val Glu Trp Glu Ser
            370                  375                  380

Asn Gly Gln Pro Glu Asn Asn Tyr Lys Thr Thr Pro Pro Val Leu Asp
385                  390                  395                  400

Ser Asp Gly Ser Phe Phe Leu Tyr Ser Lys Leu Thr Val Asp Lys Ser
                405                  410                  415

Arg Trp Gln Gln Gly Asn Val Phe Ser Cys Ser Val Met His Glu Ala
            420                  425                  430
```

```
Leu His Asn His Tyr Thr Gln Lys Ser Leu Ser Leu Ser Pro Gly
        435                 440                 445
```

<210> SEQ ID NO 90
<211> LENGTH: 447
<212> TYPE: PRT
<213> ORGANISM: Artificial Sequence
<220> FEATURE:
<223> OTHER INFORMATION: IGF-1R AAA

<400> SEQUENCE: 90

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Ala Tyr Thr Gln Lys Ser Leu Ser Leu Ser Pro Gly
                435                 440                 445

<210> SEQ ID NO 91
<211> LENGTH: 447
<212> TYPE: PRT
<213> ORGANISM: Artificial Sequence
<220> FEATURE:
<223> OTHER INFORMATION: IGF-1R YTE

<400> SEQUENCE: 91

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
                260                 265                 270
```

```
Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
        340             345             350

Pro Pro Ser Arg Asp Glu Leu Thr Lys Asn Gln Val Ser Leu Thr Cys
        355             360             365

Leu Val Lys Gly Phe Tyr Pro Ser Asp Ile Ala Val Glu Trp Glu Ser
    370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
        420             425             430

Leu His Asn His Tyr Thr Gln Lys Ser Leu Ser Leu Ser Pro Gly
        435             440             445

<210> SEQ ID NO 92
<211> LENGTH: 448
<212> TYPE: PRT
<213> ORGANISM: Artificial Sequence
<220> FEATURE:
<223> OTHER INFORMATION: IgG1 wtKiH

<400> SEQUENCE: 92

Gln Val Glu Leu Val Glu Ser Gly Gly Gly Val Val Gln Pro Gly Arg
1               5               10              15

Ser Gln Arg Leu Ser Cys Ala Ala Ser Gly Phe Thr Phe Ser Ser Tyr
        20              25              30

Gly Met His Trp Val Arg Gln Ala Pro Gly Lys Gly Leu Glu Trp Val
        35              40              45

Ala Ile Ile Trp Phe Asp Gly Ser Ser Thr Tyr Tyr Ala Asp Ser Val
    50              55              60

Arg Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Phe Cys
            85              90              95

Ala Arg Glu Leu Gly Arg Arg Tyr Phe Asp Leu Trp Gly Arg Gly Thr
        100             105             110

Leu Val Ser Val Ser Ser Ala Ser Thr Lys Gly Pro Ser Val Phe Pro
        115             120             125

Leu Ala Pro Ser Ser Lys Ser Thr Ser Gly Gly Thr Ala Ala Leu Gly
        130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
        180             185             190
```

-continued

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 93
<211> LENGTH: 448
<212> TYPE: PRT
<213> ORGANISM: Artificial Sequence
<220> FEATURE:
<223> OTHER INFORMATION: VH-IGG1-FCSSHOLE

<400> SEQUENCE: 93
```

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
        100                 105                 110
```

-continued

```
Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
                340                 345                 350

Pro Pro Ser Arg Asp Glu Leu Thr Lys Asn Gln Val Ser Leu Ser Cys
                355                 360                 365

Ala Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

<210> SEQ ID NO 94
<211> LENGTH: 448
<212> TYPE: PRT
<213> ORGANISM: Artificial Sequence
<220> FEATURE:
<223> OTHER INFORMATION: I253A, H310A, H435A

<400> SEQUENCE: 94

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
        20                  25                  30
```

```
Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Cys Arg Asp Glu Leu Thr Lys Asn Gln Val Ser Leu Trp Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

<210> SEQ ID NO 95
<211> LENGTH: 448
<212> TYPE: PRT
<213> ORGANISM: Artificial Sequence
<220> FEATURE:
<223> OTHER INFORMATION: VH-AK18-IGG1-FCSSHOLE-AAA1

<400> SEQUENCE: 95

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

-continued

```
Ala Val Lys Gly Phe Tyr Pro Ser Asp Ile Ala Val Glu Trp Glu Ser
    370             375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn Ala Tyr Thr Gln Lys Ser Leu Ser Leu Ser Pro Gly Lys
        435                 440                 445
```

<210> SEQ ID NO 96
<211> LENGTH: 448
<212> TYPE: PRT
<213> ORGANISM: Artificial Sequence
<220> FEATURE:
<223> OTHER INFORMATION: H310A, H433A, Y436A

<400> SEQUENCE: 96

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285
```

-continued

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 97
<211> LENGTH: 448
<212> TYPE: PRT
<213> ORGANISM: Artificial Sequence
<220> FEATURE:
<223> OTHER INFORMATION: VH-IGG1-FCSSHOLE-AAA2

<400> SEQUENCE: 97

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
        210             215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290             295                 300

Ser Val Leu Thr Val Leu Ala Gln Asp Trp Leu Asn Gly Lys Glu Tyr
305             310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
        370             375                 380

Asn Gly Gln Pro Glu Asn Asn Tyr Lys Thr Thr Pro Pro Val Leu Asp
385             390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu Ala Asn His Ala Thr Gln Lys Ser Leu Ser Leu Ser Pro Gly Lys
            435                 440                 445
```

<210> SEQ ID NO 98
<211> LENGTH: 448
<212> TYPE: PRT
<213> ORGANISM: Artificial Sequence
<220> FEATURE:
<223> OTHER INFORMATION: M252Y, S254T, T256E

<400> SEQUENCE: 98

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
        50                  55                  60

Arg Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Phe Cys
            85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
            115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Cys Arg Asp Glu Leu Thr Lys Asn Gln Val Ser Leu Trp Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 99
<211> LENGTH: 448
<212> TYPE: PRT
<213> ORGANISM: Artificial Sequence
<220> FEATURE:
<223> OTHER INFORMATION: VH-IGG1-FCSSHOLE-YTE

<400> SEQUENCE: 99

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45
```

-continued

```
Ala Ile Ile Trp Phe Asp Gly Ser Ser Thr Tyr Tyr Ala Asp Ser Val
    50              55                  60

Arg Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Phe Cys
            85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 100
<211> LENGTH: 448
<212> TYPE: PRT

```
<213> ORGANISM: Artificial Sequence
<220> FEATURE:
<223> OTHER INFORMATION: DDD

<400> SEQUENCE: 100

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
```

-continued

```
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 101
<211> LENGTH: 448
<212> TYPE: PRT
<213> ORGANISM: Artificial Sequence
<220> FEATURE:
<223> OTHER INFORMATION: VH-IGG1-FCSSHOLE-DDD

<400> SEQUENCE: 101

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
            50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Asp Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Asp Asn Gly Lys Glu Tyr
```

-continued

```
305                310                315                320

Lys Cys Lys Val Ser Asn Lys Ala Leu Pro Ala Pro Ile Glu Lys Thr
                325                330                335

Ile Ser Lys Ala Lys Gly Gln Pro Arg Glu Pro Gln Val Cys Thr Leu
                340                345                350

Pro Pro Ser Arg Asp Glu Leu Thr Lys Asn Gln Val Ser Leu Ser Cys
                355                360                365

Ala Val Lys Gly Phe Tyr Pro Ser Asp Ile Ala Val Glu Trp Glu Ser
                370                375                380

Asn Gly Gln Pro Glu Asn Asn Tyr Lys Thr Thr Pro Pro Val Leu Asp
385                390                395                400

Ser Asp Gly Ser Phe Phe Leu Val Ser Lys Leu Thr Val Asp Lys Ser
                405                410                415

Arg Trp Gln Gln Gly Asn Val Phe Ser Cys Ser Val Met His Glu Ala
                420                425                430

Asp His Asn His Tyr Thr Gln Lys Ser Leu Ser Leu Ser Pro Gly Lys
                435                440                445

<210> SEQ ID NO 102
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 102

Glu Val Gln Leu Val Glu Ser Gly Gly Gly Leu Val Gln Pro Gly Gly
1                5                10                15

Ser Leu Arg Leu Ser Cys Ala Ala Ser Gly Tyr Asp Phe Thr His Tyr
                20                25                30

Gly Met Asn Trp Val Arg Gln Ala Pro Gly Lys Gly Leu Glu Trp Val
                35                40                45

Gly Trp Ile Asn Thr Tyr Thr Gly Glu Pro Thr Tyr Ala Ala Asp Phe
        50                55                60

Lys Arg Arg Phe Thr Phe Ser Leu Asp Thr Ser Lys Ser Thr Ala Tyr
65                70                75                80

Leu Gln Met Asn Ser Leu Arg Ala Glu Asp Thr Ala Val Tyr Tyr Cys
                85                90                95

Ala Lys Tyr Pro Tyr Tyr Tyr Gly Thr Ser His Trp Tyr Phe Asp Val
                100                105                110

Trp Gly Gln Gly Thr Leu Val Thr Val Ser Ser Ala Ser Thr Lys Gly
                115                120                125

Pro Ser Val Phe Pro Leu Ala Pro Ser Ser Lys Ser Thr Ser Gly Gly
                130                135                140

Thr Ala Ala Leu Gly Cys Leu Val Lys Asp Tyr Phe Pro Glu Pro Val
145                150                155                160

Thr Val Ser Trp Asn Ser Gly Ala Leu Thr Ser Gly Val His Thr Phe
                165                170                175

Pro Ala Val Leu Gln Ser Ser Gly Leu Tyr Ser Leu Ser Ser Val Val
                180                185                190

Thr Val Pro Ser Ser Ser Leu Gly Thr Gln Thr Tyr Ile Cys Asn Val
                195                200                205

Asn His Lys Pro Ser Asn Thr Lys Val Asp Lys Lys Val Glu Pro Lys
        210                215                220
```

-continued

```
Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
            290             295             300

Thr Tyr Arg Val Val Ser Val Leu Thr Val Leu Ala Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Cys Arg Asp Glu Leu Thr Lys Asn Gln
            355             360             365

Val Ser Leu Trp Cys Leu Val Lys Gly Phe Tyr Pro Ser Asp Ile Ala
            370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu Ala Asn His Ala Thr Gln Lys Ser Leu Ser
            435             440             445

Leu Ser Pro Gly Lys
            450
```

```
<210> SEQ ID NO 103
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 103
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Gly Tyr
            20              25              30

Tyr Met His Trp Val Arg Gln Ala Pro Gly Gln Gly Leu Glu Trp Met
            35              40              45

Gly Trp Ile Asn Pro Asn Ser Gly Gly Thr Asn Tyr Ala Gln Lys Phe
    50              55              60

Gln Gly Arg Val Thr Met Thr Arg Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Arg Ser Pro Asn Pro Tyr Tyr Tyr Asp Ser Ser Gly Tyr Tyr Tyr
            100             105             110

Pro Gly Ala Phe Asp Ile Trp Gly Gln Gly Thr Met Val Thr Val Ser
            115             120             125
```

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
                275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
            435                 440                 445

Ala Asn His Ala Thr Gln Lys Ser Leu Ser Leu Ser Pro Gly Lys
    450                 455                 460

<210> SEQ ID NO 104
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr

```
                   20              25              30

Gly Met Asn Trp Val Arg Gln Ala Pro Gly Lys Gly Leu Glu Trp Val
           35              40              45

Gly Trp Ile Asn Thr Tyr Thr Gly Glu Pro Thr Tyr Ala Ala Asp Phe
       50              55              60

Lys Arg Arg Phe Thr Phe Ser Leu Asp Thr Ser Lys Ser Thr Ala Tyr
65              70              75              80

Leu Gln Met Asn Ser Leu Arg Ala Glu Asp Thr Ala Val Tyr Tyr Cys
               85              90              95

Ala Lys Tyr Pro Tyr Tyr Tyr Gly Thr Ser His Trp Tyr Phe Asp Val
           100             105             110

Trp Gly Gln Gly Thr Leu Val Thr Val Ser Ser Ala Ser Thr Lys Gly
       115             120             125

Pro Ser Val Phe Pro Leu Ala Pro Ser Ser Lys Ser Thr Ser Gly Gly
   130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
           165             170             175

Pro Ala Val Leu Gln Ser Ser Gly Leu Tyr Ser Leu Ser Ser Val Val
           180             185             190

Thr Val Pro Ser Ser Ser Leu Gly Thr Gln Thr Tyr Ile Cys Asn Val
           195             200             205

Asn His Lys Pro Ser Asn Thr Lys Val Asp Lys Lys Val Glu Pro Lys
       210             215             220

Ser Cys Asp Lys Thr His Thr Cys Pro Pro Cys Pro Ala Pro Glu Ala
225             230             235             240

Ala Gly Gly Pro Ser Val Phe Leu Phe Pro Pro Lys Pro Lys Asp Thr
           245             250             255

Leu Met Ile Ser Arg Thr Pro Glu Val Thr Cys Val Val Val Asp Val
           260             265             270

Ser His Glu Asp Pro Glu Val Lys Phe Asn Trp Tyr Val Asp Gly Val
           275             280             285

Glu Val His Asn Ala Lys Thr Lys Pro Arg Glu Glu Gln Tyr Asn Ser
       290             295             300

Thr Tyr Arg Val Val Ser Val Leu Thr Val Leu Ala Gln Asp Trp Leu
305             310             315             320

Asn Gly Lys Glu Tyr Lys Cys Lys Val Ser Asn Lys Ala Leu Gly Ala
               325             330             335

Pro Ile Glu Lys Thr Ile Ser Lys Ala Lys Gly Gln Pro Arg Glu Pro
           340             345             350

Gln Val Tyr Thr Leu Pro Pro Cys Arg Asp Glu Leu Thr Lys Asn Gln
           355             360             365

Val Ser Leu Trp Cys Leu Val Lys Gly Phe Tyr Pro Ser Asp Ile Ala
       370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
           405             410             415

Thr Val Asp Lys Ser Arg Trp Gln Gln Gly Asn Val Phe Ser Cys Ser
           420             425             430

Val Met His Glu Ala Leu Ala Asn His Ala Thr Gln Lys Ser Leu Ser
           435             440             445
```

```
Leu Ser Pro Gly Lys
    450

<210> SEQ ID NO 105
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
```

-continued

```
                340                 345                 350
Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
        435                 440                 445

Ala Asn His Ala Thr Gln Lys Ser Leu Ser Leu Ser Pro Gly Lys
    450                 455                 460
```

```
<210> SEQ ID NO 106
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 106
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
        20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240
```

-continued

```
Pro Ser Val Phe Leu Phe Pro Pro Lys Pro Lys Asp Thr Leu Met Ala
            245             250             255

Ser Arg Thr Pro Glu Val Thr Cys Val Val Val Asp Val Ser Gln Glu
            260             265             270

Asp Pro Glu Val Gln Phe Asn Trp Tyr Val Asp Gly Val Glu Val His
            275             280             285

Asn Ala Lys Thr Lys Pro Arg Glu Glu Gln Phe Asn Ser Thr Tyr Arg
    290             295             300

Val Val Ser Val Leu Thr Val Leu Ala Gln Asp Trp Leu Asn Gly Lys
305             310             315             320

Glu Tyr Lys Cys Lys Val Ser Asn Lys Gly Leu Pro Ser Ser Ile Glu
            325             330             335

Lys Thr Ile Ser Lys Ala Lys Gly Gln Pro Arg Glu Pro Gln Val Cys
            340             345             350

Thr Leu Pro Pro Ser Gln Glu Glu Met Thr Lys Asn Gln Val Ser Leu
            355             360             365

Ser Cys Ala Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Val Ser Arg Leu Thr Val Asp
            405             410             415

Lys Ser Arg Trp Gln Glu Gly Asn Val Phe Ser Cys Ser Val Met His
            420             425             430

Glu Ala Leu Ala Asn His Ala Thr Gln Lys Ser Leu Ser Leu Ser Leu
            435             440             445

Gly Lys
    450
```

```
<210> SEQ ID NO 107
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 107
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Gly Tyr
            20              25              30

Tyr Met His Trp Val Arg Gln Ala Pro Gly Gln Gly Leu Glu Trp Met
            35              40              45

Gly Trp Ile Asn Pro Asn Ser Gly Gly Thr Asn Tyr Ala Gln Lys Phe
    50              55              60

Gln Gly Arg Val Thr Met Thr Arg Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Arg Ser Pro Asn Pro Tyr Tyr Tyr Asp Ser Ser Gly Tyr Tyr Tyr
            100             105             110

Pro Gly Ala Phe Asp Ile Trp Gly Gln Gly Thr Met Val Thr Val Ser
            115             120             125

Ser Ala Ser Val Ala Ala Pro Ser Val Phe Ile Phe Pro Pro Ser Asp
    130             135             140
```

-continued

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
            275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu Ala Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Cys Gln
            355                 360                 365

Glu Glu Met Thr Lys Asn Gln Val Ser Leu Trp Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
                420                 425                 430

Gly Asn Val Phe Ser Cys Ser Val Met His Glu Ala Leu Ala Asn His
            435                 440                 445

Ala Thr Gln Lys Ser Leu Ser Leu Ser Leu Gly Lys
    450                 455                 460
```

```
<210> SEQ ID NO 108
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with
      AAA mutations

<400> SEQUENCE: 108
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
                20                  25                  30

Gly Met Asn Trp Val Arg Gln Ala Pro Gly Lys Gly Leu Glu Trp Val
```

-continued

```
                35                    40                    45

Gly Trp Ile Asn Thr Tyr Thr Gly Glu Pro Thr Tyr Ala Ala Asp Phe
    50                    55                    60

Lys Arg Arg Phe Thr Phe Ser Leu Asp Thr Ser Lys Ser Thr Ala Tyr
65                    70                    75                    80

Leu Gln Met Asn Ser Leu Arg Ala Glu Asp Thr Ala Val Tyr Tyr Cys
                85                    90                    95

Ala Lys Tyr Pro Tyr Tyr Tyr Gly Thr Ser His Trp Tyr Phe Asp Val
                100                   105                   110

Trp Gly Gln Gly Thr Leu Val Thr Val Ser Ser Ala Ser Thr Lys Gly
                115                   120                   125

Pro Ser Val Phe Pro Leu Ala Pro Ser Ser Lys Ser Thr Ser Gly Gly
    130                   135                   140

Thr Ala Ala Leu Gly Cys Leu Val Lys Asp Tyr Phe Pro Glu Pro Val
145                   150                   155                   160

Thr Val Ser Trp Asn Ser Gly Ala Leu Thr Ser Gly Val His Thr Phe
                165                   170                   175

Pro Ala Val Leu Gln Ser Ser Gly Leu Tyr Ser Leu Ser Ser Val Val
                180                   185                   190

Thr Val Pro Ser Ser Ser Leu Gly Thr Gln Thr Tyr Ile Cys Asn Val
                195                   200                   205

Asn His Lys Pro Ser Asn Thr Lys Val Asp Lys Lys Val Glu Pro Lys
    210                   215                   220

Ser Cys Asp Lys Thr His Thr Cys Pro Pro Cys Pro Ala Pro Glu Leu
225                   230                   235                   240

Leu Gly Gly Pro Ser Val Phe Leu Phe Pro Pro Lys Pro Lys Asp Thr
                245                   250                   255

Leu Ile Ala Ser Arg Thr Pro Glu Val Thr Cys Val Val Val Asp Val
                260                   265                   270

Ser His Glu Asp Pro Glu Val Lys Phe Asn Trp Tyr Val Asp Gly Val
                275                   280                   285

Glu Val His Asn Ala Lys Thr Lys Pro Arg Glu Glu Gln Tyr Asn Ser
    290                   295                   300

Thr Tyr Arg Val Val Ser Val Leu Thr Val Leu Ala Gln Asp Trp Leu
305                   310                   315                   320

Asn Gly Lys Glu Tyr Lys Cys Lys Val Ser Asn Lys Ala Leu Pro Ala
                325                   330                   335

Pro Ile Glu Lys Thr Ile Ser Lys Ala Lys Gly Gln Pro Arg Glu Pro
                340                   345                   350

Gln Val Cys Thr Leu Pro Pro Ser Arg Asp Glu Leu Thr Lys Asn Gln
                355                   360                   365

Val Ser Leu Ser Cys Ala Val Lys Gly Phe Tyr Pro Ser Asp Ile Ala
    370                   375                   380

Val Glu Trp Glu Ser Asn Gly Gln Pro Glu Asn Asn Tyr Lys Thr Thr
385                   390                   395                   400

Pro Pro Val Leu Asp Ser Asp Gly Ser Phe Phe Leu Val Ser Lys Leu
                405                   410                   415

Thr Val Asp Lys Ser Arg Trp Gln Gln Gly Asn Val Phe Ser Cys Ser
                420                   425                   430

Val Met His Glu Ala Leu Ala Asn His Ala Thr Gln Lys Ser Leu Ser
                435                   440                   445

Leu Ser Pro Gly Lys
    450
```

<210> SEQ ID NO 109
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with
      AAA mutations

<400> SEQUENCE: 109

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gln Val Gln Leu Val Glu Ser Gly Ala Glu
            245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly

```
            355               360               365
Thr Met Val Thr Val Ser Ser Ala Ser Thr Lys Gly Pro Ser Val Phe
    370               375               380

Pro Leu Ala Pro Ser Ser Lys Ser Thr Ser Gly Gly Thr Ala Ala Leu
385               390               395               400

Gly Cys Leu Val Lys Asp Tyr Phe Pro Glu Pro Val Thr Val Ser Trp
                405               410               415

Asn Ser Gly Ala Leu Thr Ser Gly Val His Thr Phe Pro Ala Val Leu
                420               425               430

Gln Ser Ser Gly Leu Tyr Ser Leu Ser Ser Val Val Thr Val Pro Ser
                435               440               445

Ser Ser Leu Gly Thr Gln Thr Tyr Ile Cys Asn Val Asn His Lys Pro
    450               455               460

Ser Asn Thr Lys Val Asp Lys Lys Val Glu Pro Lys Ser Cys Asp Lys
465               470               475               480

Thr His Thr Cys Pro Pro Cys Pro Ala Pro Glu Leu Leu Gly Gly Pro
                485               490               495

Ser Val Phe Leu Phe Pro Pro Lys Pro Lys Asp Thr Leu Met Ile Ser
                500               505               510

Arg Thr Pro Glu Val Thr Cys Val Val Val Asp Val Ser His Glu Asp
    515               520               525

Pro Glu Val Lys Phe Asn Trp Tyr Val Asp Gly Val Glu Val His Asn
    530               535               540

Ala Lys Thr Lys Pro Arg Glu Glu Gln Tyr Asn Ser Thr Tyr Arg Val
545               550               555               560

Val Ser Val Leu Thr Val Leu Ala Gln Asp Trp Leu Asn Gly Lys Glu
                565               570               575

Tyr Lys Cys Lys Val Ser Asn Lys Ala Leu Pro Ala Pro Ile Glu Lys
                580               585               590

Thr Ile Ser Lys Ala Lys Gly Gln Pro Arg Glu Pro Gln Val Tyr Thr
                595               600               605

Leu Pro Pro Cys Arg Asp Glu Leu Thr Lys Asn Gln Val Ser Leu Trp
    610               615               620

Cys Leu Val Lys Gly Phe Tyr Pro Ser Asp Ile Ala Val Glu Trp Glu
625               630               635               640

Ser Asn Gly Gln Pro Glu Asn Asn Tyr Lys Thr Thr Pro Pro Val Leu
                645               650               655

Asp Ser Asp Gly Ser Phe Phe Leu Tyr Ser Lys Leu Thr Val Asp Lys
                660               665               670

Ser Arg Trp Gln Gln Gly Asn Val Phe Ser Cys Ser Val Met His Glu
    675               680               685

Ala Leu Ala Asn His Ala Thr Gln Lys Ser Leu Ser Leu Ser Pro Gly
    690               695               700

Lys
705
```

<210> SEQ ID NO 110
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
      AAA mutations and with SPLE mutations

<400> SEQUENCE: 110

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
            355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
            405                 410                 415

Lys Ser Arg Trp Gln Glu Gly Asn Val Phe Ser Cys Ser Val Met His
```

-continued

```
                420              425              430
Glu Ala Leu Ala Asn His Ala Thr Gln Lys Ser Leu Ser Leu Ser Leu
        435              440              445

Gly Lys
    450
```

<210> SEQ ID NO 111
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 111

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser Gly Gly Gly Ser Gly Gly Gly Gly Ser
        210                 215                 220

Gly Gly Gly Gly Ser Gly Gly Gly Ser Gly Gly Gly Gly Ser Gly
225                 230                 235                 240

Gly Gly Ser Gly Gly Gln Val Gln Leu Val Glu Ser Gly Ala Glu
            245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
            275                 280                 285

Gln Gly Leu Glu Trp Met Gly Trp Ile Asn Pro Asn Ser Gly Gly Thr
        290                 295                 300

Asn Tyr Ala Gln Lys Phe Gln Gly Arg Val Thr Met Thr Arg Asp Thr
305                 310                 315                 320
```

-continued

```
Ser Ile Ser Thr Ala Tyr Met Glu Leu Ser Arg Leu Arg Ser Asp Asp
            325                 330                 335

Thr Ala Val Tyr Tyr Cys Ala Arg Ser Pro Asn Pro Tyr Tyr Tyr Asp
            340             345                 350

Ser Ser Gly Tyr Tyr Pro Gly Ala Phe Asp Ile Trp Gly Gln Gly
            355             360                 365

Thr Met Val Thr Val Ser Ser Ala Ser Thr Lys Gly Pro Ser Val Phe
    370                 375                 380

Pro Leu Ala Pro Cys Ser Arg Ser Thr Ser Glu Ser Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
            435                 440                 445

Ser Ser Leu Gly Thr Lys Thr Tyr Thr Cys Asn Val Asp His Lys Pro
    450                 455                 460

Ser Asn Thr Lys Val Asp Lys Arg Val Glu Ser Lys Tyr Gly Pro Pro
465                 470                 475                 480

Cys Pro Pro Cys Pro Ala Pro Glu Phe Glu Gly Gly Pro Ser Val Phe
                485                 490                 495

Leu Phe Pro Pro Lys Pro Lys Asp Thr Leu Met Ile Ser Arg Thr Pro
                500                 505                 510

Glu Val Thr Cys Val Val Val Asp Val Ser Gln Glu Asp Pro Glu Val
            515                 520                 525

Gln Phe Asn Trp Tyr Val Asp Gly Val Glu Val His Asn Ala Lys Thr
    530                 535                 540

Lys Pro Arg Glu Glu Gln Phe Asn Ser Thr Tyr Arg Val Val Ser Val
545                 550                 555                 560

Leu Thr Val Leu Ala Gln Asp Trp Leu Asn Gly Lys Glu Tyr Lys Cys
                565                 570                 575

Lys Val Ser Asn Lys Gly Leu Pro Ser Ser Ile Glu Lys Thr Ile Ser
            580                 585                 590

Lys Ala Lys Gly Gln Pro Arg Glu Pro Gln Val Tyr Thr Leu Pro Pro
            595                 600                 605

Cys Gln Glu Glu Met Thr Lys Asn Gln Val Ser Leu Trp Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
            645                 650                 655

Gly Ser Phe Phe Leu Tyr Ser Arg Leu Thr Val Asp Lys Ser Arg Trp
            660                 665                 670

Gln Glu Gly Asn Val Phe Ser Cys Ser Val Met His Glu Ala Leu Ala
            675                 680                 685

Asn His Ala Thr Gln Lys Ser Leu Ser Leu Ser Leu Gly Lys
    690                 695                 700
```

<210> SEQ ID NO 112
<211> LENGTH: 447
<212> TYPE: PRT
<213> ORGANISM: Artificial Sequence
<220> FEATURE:
<223> OTHER INFORMATION: IGF-1R wt

<400> SEQUENCE: 112

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
                100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser

-continued

```
                    405              410              415
Arg Trp Gln Gln Gly Asn Val Phe Ser Cys Ser Val Met His Glu Ala
            420              425              430
Leu Ala Asn His Ala Thr Gln Lys Ser Leu Ser Leu Ser Pro Gly
        435              440              445
```

HUMAN FcRn-BINDING MODIFIED ANTIBODIES AND METHODS OF USE

CROSS-REFERENCE TO RELATED APPLICATIONS

This application claims priority to and is a continuation of U.S. patent application Ser. No. 14/926,844, filed Oct. 29, 2015, issued as U.S. patent Ser. No. 11/091,541, which in turn claims priority to National Stage Application of PCT/EP2014/058417, filed Apr. 25, 2014, which in turn claims priority from European Application No. 14151316.8, filed on Jan. 15, 2014 and European Application No. 13165744.7, filed on Apr. 29, 2013. Each of these applications is hereby incorporated by reference herein in its entirety.

INCORPORATION BY REFERENCE OF SEQUENCE LISTING

This application contains references to amino acids and/or nucleic acid sequences that have been filed concurrenly herewith as sequence listing text file "SequenceListing.txt", file size of 300 KB, created on Aug. 23, 2021. The aforementioned sequence listing is hereby incorporated by reference in its entirety pursuant to 37 C.F.R. § 1.52(e)(5).

FIELD OF THE INVENTION

The present invention relates to antibodies and Fc-region fusion polypeptides specifically binding to soluble receptor-ligands that have modified binding affinities with respect to the human neonatal Fc-receptor, methods for their production, pharmaceutical formulations containing these antibodies, and uses thereof.

BACKGROUND

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, in: Pathobiology of ocular disease, A dynamic approach, Garner, A., and Klintworth, G. K. (eds.), 2nd edition, Marcel Dekker, New York (1994), pp. 1625-1710).

Ranibizumab (trade name Lucentis®) is a monoclonal antibody fragment derived from the same parent murine antibody as bevacizumab (Avastin). However, it has been affinity matured to provide stronger binding to VEGF-A (WO 98/45331). It is known that VEGF-A blocking may be related to some systemic toxicities, therefore ranibizumab is missing an Fc-region to reduce the serum half live and consequently systemic toxicities. It is an anti-angiogenic agent that has been approved to treat the "wet" type of age-related macular degeneration (AMD), a common form of age-related vision loss.

Ocular vascular diseases such as age related macular degeneration (AMD) and diabetic retinopathy (DR) are due to abnormal choroidal or retinal neovascularization, respectively. They are the leading causes of visual loss in industrialized nations. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. They affect as many as 1 in 3,500 individuals and are characterized by progressive night blindness, visual field loss, optic nerve atrophy, arteriolar attenuation, and central loss of vision often progressing to complete blindness.

Ischemic retinopathies are characterized by loss or dysfunction of the retinal vasculature which results in a reduction of blood flow and hypoxia. The retina responds to hypoxia by generating signals to grow new blood vessels, but these new vessels are usually fragile and disorganized. It is the growth of these abnormal new vessels that creates most of the threat to vision since they can leak, lead to hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy, an ischemic retinopathy that affects millions, involves destruction of a portion of the retina with a laser in an attempt to stop new vessel growth and preserve central vision. Strategies have been employed to block the function of vascular endothelial growth factor (VEGF), a major promoter of vessel growth. In the short term, anti-VEGF therapy can improve vision, but it does not address the underlying ischemia and in fact may exacerbate this condition as it inhibits all vessel growth, including beneficial collaterals. There is also the serious concern of systemic exposure of these drugs in elderly and/or diabetic patients where new vessel growth may be required in ischemic brains, hearts or limbs.

Typically for ocular diseases via intravitreal application smaller antibody fragments like Fab or $Fab_2$ are often used as they have a low serum half-life and the risk of systemic toxicities is lower. However this smaller fragments typically have also lower intravitreal half-lives (e.g. due to the faster diffusion into serum) and have to be dosed typically more often.

Almost all Fc-receptors bind to the symmetrical Fc-region of antibodies asymmetrically.

For example, the human Fcγ-receptor IIIA interacts with different amino acids residues on the two Fc-region polypeptides. Thus, asymmetrically introduced mutations (e.g. in the lower hinge region at residues 233 to 238) have to be used to either increase or decrease the interaction of the antibody with the human Fcγ receptor IIIA.

But, the interaction between the human neonatal Fc-receptor FcRn is symmetrical: two FcRn molecules can bind to a single IgG with a 2:1 stoichiometry (see. e.g. Huber, A. W., et al., J. Mol. Biol. 230 (1993) 1077-1083). Thus, asymmetrically introduced mutations reduce the binding to/by one FcRn but not to/by both.

Examples of asymmetric IgG-like molecules include but are not limited to those obtained with the following technologies or using in the following formats: Triomab/Quadroma, Knobs-into-Holes, CrossMabs, electrostatically-matched antibodies, LUZ-Y, Strand Exchange Engineered Domain body, Biclonic and DuoBody.

In WO 2012/125850 Fc-containing proteins comprising asymmetric substitutions in their Fc-regions and having increased binding to human Fcγ-receptor IIIA and enhanced ADCC activity are reported.

In WO 2012/58768 isolated heteromultimers comprising a heterodimer Fc-region, wherein the heterodimer Fc-region comprises a variant CH3 domain comprising amino acid mutations to promote heterodimer formation with increased stability, wherein the heterodimer Fc-region further comprises a variant CH2 domain comprising asymmetric amino acid modifications to promote selective binding of an Fcgamma receptor.

In WO 2011/131746 it is reported that by introducing asymmetrical mutations in the CH3 regions of the two monospecific starting proteins, the Fab-arm exchange reaction can be forced to become directional and thereby yield highly stable heterodimeric proteins.

Kim et al. (Kim, H., et al., Invest. Ophthalmol. Vis. Sci. 49 (2008) 2025-2029) report that except for the retinal pigment epithelial and choroid tissue, ocular tissues, including the ciliary body and iris, retina, conjunctiva, cornea, lens, and optic nerve bundle, showed the presence of FcRn transcript at the predicted size. The blood-ocular barrier showed FcRn receptor expression, indicating that IgG transport from ocular tissues to the blood system may use this receptor. Since the inner ocular tissues such as the retina are separated from the blood system by the blood-ocular barrier, one would not expect to detect a full-length antibody in the blood system only a short time after intravitreous injection. However, recent pharmacokinetic data from monkey and humans all indicate that intravitreous bevacizumab appears in the blood within hours after intravitreous injection. Therefore, it may be that the function of the FcRn receptor in the conjunctival lymphatic vessels is to act as an efflux receptor for the efficient elimination of antigen-antibody IgG complexes from the conjunctival space. Despite similar molecular weights, IgG (150 kDa) was detected in the aqueous humor; however, IgA (160 kDa) was not. The discrepancy between IgG and IgA penetration from the serum into the aqueous humor may be explained by the presence of the FcRn receptors, which are selective for IgGs.

Kim et al. further report (Kim, H., et al., Mol. Vis. 15 (2009) 2803-2812) that direct intravitreal injection has become a common approach for delivering therapeutic antibodies to the posterior segment of the eye for retina disorders. Both intravitreally administered bevacizumab (IgG) and chicken IgY overcame the inner limiting membrane barrier and diffused into the deeper retinal structures. After diffusing through the retina bevacizumab crossed the blood-retina barrier and leaked into the systemic circulation. The intraretinal chicken IgY was only localized along the abluminal side of the blood-retina barrier. Furthermore, the choroidal blood vessels were negative for the presence of chicken IgY. Physiologically relevant serum levels of bevacizumab after intravitreal administration, representing up to 30% of the injected dose, were found. This suggests greater risk for systemic side effects than previously recognized. The blood-ocular barrier manifests a specific mechanism for transporting and clearing full-length IgGs into the systemic circulation. Their current study confirms the hypothesis that this mechanism is the neonatal Fc-receptor.

But the binding to FcRn prolongs its half-live in the circulation giving potentially rise to systemic side effects.

There is a need in the art for better means for treating and preventing various ocular vascular diseases such as ischemic retinopathies.

Magdelaine-Beuzelin, C., et al. report for therapeutic antibodies in ophthalmology that old is new again (MABS 2 (2010) 176-180).

Steinbrook, R., report the price of sight—Ranibizumab, Bevacizumab, and the treatment of macular degeneration (New Eng. J. Med. 355 (2006) 1409-1412).

In US 2011/236388 bispecific, bivalent anti-VEGF/anti-ANG-2 antibodies are reported.

Kuo, T. T., et al. report about the neonatal Fc receptor: from immunity to therapeutics (J. Clin. Immunol. 30 (2010) 777-789).

Medesan, C., et al. report the delineation of the amino acid residues involved in transcytosis and catabolism of mouse IgG1 (J. Immunol. 158 (1997) 2211-2217).

Qiao, S.-W., et al. report the dependence of antibody-mediated presentation of antigen on FcRn (Proc. Natl. Acad. Sci. USA 105 (2008) 9337-9342).

Kim, J. K., et al. report the mapping of the site on human IgG for binding of the MHC class I-related receptor, FcRn (Eur. J. Immunol. 29 (1999) 2819-2825).

Kuo, T. T, et al. report about neonatal Fc receptor and IgG-based therapeutics (MABS 3 (2011) 422-438).

SUMMARY

For using an antibody that targets/binds to antigens not only present in the eye but also in the remaining body a short systemic half-live after passage of the blood-ocular-barrier from the eye into the blood is beneficial in order to avoid side effects.

Also for an antibody that specifically binds to a ligand of a receptor and that is effective in the treatment of eye diseases the antibody-antigen complex (=antibody-receptor ligand-complex) has after the removal from the eye and thereafter the antibody (either after dissociation or as complex) has to be removed from the systemic circulation in order to avoid side effects, i.e. the antibody functions as a vehicle for removal of receptor ligands from the eye, thereby inhibits receptor signaling and is cleared fast from the blood circulation in order to avoid systemic side effects.

It has been found that an antibody comprising an Fc-region that does not bind to the human neonatal Fc-receptor can pass the blood-ocular-barrier. This is surprising as the antibody does not bind to human FcRn although binding to FcRn is considered to be required for transport across the blood-ocular-barrier.

One aspect as reported herein is the use of an antibody comprising an Fc-region with abolished FcRn binding for the transport of a soluble receptor ligand from the eye over the blood-ocular-barrier into the blood circulation.

One aspect as reported herein is an antibody comprising an Fc-region with abolished FcRn binding for use as a medicament.

One aspect as reported herein is an antibody comprising an Fc-region with abolished FcRn binding for use in the treatment of an ocular vascular disease.

One aspect as reported herein is the use of an antibody comprising an Fc-region with abolished FcRn binding for the removal of one or more soluble receptor ligands from the eye.

One aspect as reported herein is an antibody comprising an Fc-region with abolished FcRn binding for use in the removal of one or more soluble receptor ligands from the eye.

One aspect as reported herein is the use of an antibody comprising an Fc-region with abolished FcRn binding for the treatment of eye diseases, especially of ocular vascular diseases.

One aspect as reported herein is the use of an antibody comprising an Fc-region with abolished FcRn binding for the transport of one or more soluble receptor ligands from the intravitreal space to the blood circulation.

One aspect as reported herein is an antibody comprising an Fc-region with abolished FcRn binding for use in the transport of one or more soluble receptor ligands from the intravitreal space to the blood circulation.

In one embodiment of all aspects the antibody has no detectable FcRn binding using surface plasmon resonance.

In one embodiment of all aspects the antibody binds to human FcRn with a Kd value of more than 1.7 µM at pH 6, i.e. with low affinity.

In one embodiment of all aspects the antibody has the same or a shorter retention time on an FcRn affinity chromatography column as an antibody comprising an Fc-Region with the mutations I253A/H310A/H435A or H310A/H433A/Y436A or L251D/L314D/L432D or combinations thereof (numbering according to Kabat EU index numbering system).

In one embodiment of all aspects the antibody has a retention time on an FcRn affinity chromatography column of three minutes or less.

In one embodiment the FcRn affinity column has the column dimensions of 50 mm×5 mm, the bed height is 5 cm and the loading is 50 µg antibody. In one embodiment the equilibration buffer is 20 mM MES, with 150 mM NaCl, adjusted to pH 5.5, the elution buffer is 20 mM Tris/HCl, with 150 mM NaCl, adjusted to pH 8.8 and the elution is by applying 7.5 CV equilibration buffer, from 0% to 100% elution buffer in 30 CV, and thereafter 10 CV elution buffer.

In one embodiment of all aspects the antibody binds to human FcRn with about the same or lesser affinity than an antibody comprising an Fc-region with the mutations I253A/H310A/H435A or H310A/H433A/Y436A or L251D/L314D/L432D or combinations thereof (numbering according to Kabat EU index numbering system).

In one embodiment of all aspects the antibody binds to human FcRn with about the same or lesser affinity than an antibody with a heavy chain amino acid sequence of SEQ ID NO: 01 or SEQ ID NO: 02 or SEQ ID NO: 112 and a light chain amino acid sequence of SEQ ID NO: 03.

In one embodiment the antibody binds to human FcRn with about the same or lesser affinity than an antibody comprising an Fc-region with at least one of the mutations L251D, L251S, M252T, I253A, S254W, S254R, H310A, H433A, N434L, H435A, Y436A (numbering according to Kabat EU index numbering system).

In one embodiment the antibody binds to human FcRn with about the same or lesser affinity than an antibody comprising an Fc-region with the mutations I253A/H310A/H435A or H310A/H433A/Y436A or L251D/L314D/L432D or combinations thereof (numbering according to Kabat EU index numbering system).

In one embodiment the antibody binds to human FcRn with about the same or lesser affinity than an antibody with a heavy chain amino acid sequence of SEQ ID NO: 01 or SEQ ID NO: 112 and a light chain amino acid sequence of SEQ ID NO: 03, or than an antibody with a heavy chain amino acid sequence of SEQ ID NO: 02 or SEQ ID NO: 112 and a light chain amino acid sequence of SEQ ID NO: 04.

In one embodiment the antibody has at least one of the mutations L251D, L251S, M252T, I253A, S254W, S254R, H310A, H433A, N434L, H435A, Y436A (numbering according to Kabat EU index numbering system) or a combination thereof.

In one embodiment the antibody has at least one of the mutations L251D, L251S, M252T, I253A, S254W, S254R, H310A, H433A, N434L, H435A, Y436A (numbering according to Kabat EU index numbering system) in the first Fc-region polypeptide and at least one of the mutations L251D, L251S, M252T, I253A, S254W, S254R, H310A, H433A, N434L, H435A, Y436A (numbering according to Kabat EU index numbering system) in the second Fc-region polypeptide.

In one embodiment the antibody has at least the mutations I253A/H310A/H435A or H310A/H433A/Y436A or L251D/L314D/L432D or combinations thereof (numbering according to Kabat EU index numbering system) in both Fc-region polypeptides.

In one embodiment of all aspects the antibody has a heterodimeric Fc-region.

In one embodiment the antibody is a full-length antibody.

In one embodiment the antibody is a monoclonal antibody.

In one embodiment the antibody is a human, humanized or chimeric antibody.

In one embodiment the antibody is a monospecific antibody.

In one embodiment the antibody is a bispecific antibody.

One aspect as reported herein is an antibody comprising an Fc-region with abolished FcRn binding for use in treating an eye disease.

One aspect as reported herein is an antibody comprising an Fc-region with abolished FcRn binding for use in the transport of a soluble receptor ligand from the eye over the blood-ocular-barrier into the blood circulation.

One aspect as reported herein is an antibody comprising an Fc-region with abolished FcRn binding for use in the removal of one or more soluble receptor ligands from the eye.

One aspect as reported herein is an antibody comprising an Fc-region with abolished FcRn binding for use in treating eye diseases, especially ocular vascular diseases.

One aspect as reported herein is an antibody comprising an Fc-region with abolished FcRn binding for use in the transport of one or more soluble receptor ligands from the intravitreal space to the blood circulation.

In one embodiment of all aspects the treatment or application of the antibody is by intravitreal application.

In one embodiment of all aspects the antibody has no detectable FcRn binding using surface plasmon resonance.

In one embodiment of all aspects the antibody binds to human FcRn with a Kd value of more than 1.7 µM at pH 6, i.e. with low affinity.

In one embodiment of all aspects the antibody has the same or a shorter retention time on an FcRn affinity chromatography column as an antibody comprising an Fc-region with the mutations I253A/H310A/H435A or H310A/H433A/Y436A or L251D/L314D/L432D or combinations thereof (numbering according to Kabat EU index numbering system).

In one embodiment of all aspects the antibody has a retention time on an FcRn affinity chromatography column of three minutes or less.

In one embodiment the FcRn affinity column has the column dimensions of 50 mm×5 mm, the bed height is 5 cm and the loading is 50 µg antibody. In one embodiment the equilibration buffer is 20 mM MES, with 150 mM NaCl, adjusted to pH 5.5, the elution buffer is 20 mM Tris/HCl, with 150 mM NaCl, adjusted to pH 8.8 and the elution is by applying 7.5 CV equilibration buffer, from 0% to 100% elution buffer in 30 CV, and thereafter 10 CV elution buffer.

In one embodiment of all aspects the antibody binds to human FcRn with about the same or lesser affinity than an antibody comprising an Fc-Region with the mutations I253A/H310A/H435A or H310A/H433A/Y436A or L251D/L314D/L432D or combinations thereof (numbering according to Kabat EU index numbering system).

In one embodiment of all aspects the antibody binds to human FcRn with about the same or lesser affinity than an antibody with a heavy chain amino acid sequence of SEQ ID NO: 01 or SEQ ID NO: 02 or SEQ ID NO: 112 and a light chain amino acid sequence of SEQ ID NO: 03.

In one embodiment the antibody binds to human FcRn with about the same or lesser affinity than an antibody comprising an Fc-region with at least one of the mutations L251D, L251S, M252T, I253A, S254W, S254R, H310A, H433A, N434L, H435A, Y436A (numbering according to Kabat EU index numbering system).

In one embodiment the antibody binds to human FcRn with about the same or lesser affinity than an antibody comprising an Fc-region with the mutations I253A/H310A/H435A or H310A/H433A/Y436A or L251D/L314D/L432D or combinations thereof (numbering according to Kabat EU index numbering system).

In one embodiment the antibody binds to human FcRn with about the same or lesser affinity than an antibody with a heavy chain amino acid sequence of SEQ ID NO: 01 or SEQ ID NO: 112 and a light chain amino acid sequence of SEQ ID NO: 03, or than an antibody with a heavy chain amino acid sequence of SEQ ID NO: 02 or SEQ ID NO: 112 and a light chain amino acid sequence of SEQ ID NO: 04.

In one embodiment the antibody has at least one of the mutations L251D, L251S, M252T, I253A, S254W, S254R, H310A, H433A, N434L, H435A, Y436A (numbering according to Kabat EU index numbering system) or a combination thereof.

In one embodiment the antibody has at least one of the mutations L251D, L251S, M252T, I253A, S254W, S254R, H310A, H433A, N434L, H435A, Y436A (numbering according to Kabat EU index numbering system) in the first Fc-region polypeptide and at least one of the mutations L251D, L251S, M252T, I253A, S254W, S254R, H310A, H433A, N434L, H435A, Y436A (numbering according to Kabat EU index numbering system) in the second Fc-region polypeptide.

In one embodiment the antibody has at least the mutations I253A/H310A/H435A or H310A/H433A/Y436A or L251D/L314D/L432D or combinations thereof (numbering according to Kabat EU index numbering system) in both Fc-region polypeptides.

In one embodiment of all aspects the antibody has a heterodimeric Fc-region.

In one embodiment the antibody is a full-length antibody.

In one embodiment the antibody is a monoclonal antibody.

In one embodiment the antibody is a human, humanized or chimeric antibody.

In one embodiment the antibody is a monospecific antibody.

In one embodiment the antibody is a bispecific antibody.

One aspect as reported herein is a method of treating an individual having an ocular vascular disease comprising administering to the individual an effective amount of an antibody as reported herein.

One aspect as reported herein is a method for transporting a soluble receptor ligand from the eye over the blood-ocular-barrier into the blood circulation in an individual comprising administering to the individual an effective amount of an antibody as reported herein to transport a soluble receptor ligand from the eye over the blood-ocular-barrier into the blood circulation.

One aspect as reported herein is a method for the removal of one or more soluble receptor ligands from the eye in an individual comprising administering to the individual an effective amount of an antibody as reported herein to remove one or more soluble receptor ligands from the eye.

One aspect as reported herein is a method for the transport of one or more soluble receptor ligands from the intravitreal space to the blood circulation in an individual comprising administering to the individual an effective amount of an antibody as reported herein to transport one or more soluble receptor ligands from the intravitreal space to the blood circulation.

One aspect as reported herein is a method for transporting a soluble receptor ligand from the intravitreal space or the eye over the blood-ocular-barrier into the blood circulation in an individual comprising administering to the individual an effective amount of an antibody as reported herein to transport a soluble receptor ligand from the intravitreal space or the eye over the blood-ocular-barrier into the blood circulation.

In one embodiment of all aspects the antibody comprises a first Fc-region polypeptide and a second Fc-region polypeptide wherein i) the first and the second Fc-region polypeptide comprise the mutation Y436A, or ii) the first and the second Fc-region polypeptide comprise the mutations I253A, H310A and H435A, or iii) the first and the second Fc-region polypeptide comprise the mutations H310A, H433A and Y436A, or iv) the first and the second Fc-region polypeptide comprise the mutations L251D, L314D and L432D, or v) the first Fc-region polypeptide comprises the mutation Y436A and the second Fc-region polypeptide comprises
  a) the mutations I253A, H310A and H435A, or
  b) the mutations H310A, H433A and Y436A, or
  c) the mutations L251D, L314D and L432D,
or vi) the first Fc-region polypeptide comprises the mutations I253A, H310A and H435A and the second Fc-region polypeptide comprises
  a) the mutations H310A, H433A and Y436A, or
  b) the mutations L251D, L314D and L432D,
or vii) the first Fc-region polypeptide comprises the mutations H310A, H433A and Y436A and the second Fc-region polypeptide comprises
  a) the mutations L251D, L314D and L432D.

In one embodiment of all aspects the antibody does not specifically bind to the human FcRn. In one embodiment of all aspects the antibody does not specifically bind to Staphylococcal protein A.

In one embodiment of all aspects the antibody does not specifically bind to the human FcRn. In one embodiment of all aspects the antibody does specifically bind to Staphylococcal protein A.

In one embodiment of all aspects the first Fc-region polypeptide further comprises the mutations Y349C, T366S, L368A and Y407V ("hole") and the second Fc-region polypeptide comprises the mutations S354C and T366W ("knob").

In one embodiment of all aspects the Fc-region polypeptides are of the human IgG1 subclass. In one embodiment the first Fc-region polypeptide and the second Fc-region polypeptide further comprise the mutations L234A and L235A. In one embodiment the first Fc-region polypeptide and the second Fc-region polypeptide further comprise the mutation P329G.

In one embodiment of all aspects the Fc-region polypeptides are of the human IgG4 subclass. In one embodiment the first Fc-region polypeptide and the second Fc-region polypeptide further comprise the mutations S228P and L235E. In one embodiment the first Fc-region polypeptide and the second Fc-region polypeptide further comprise the mutation P329G.

In one embodiment the human IgG class Fc-region is a variant human IgG class heterodimeric Fc-region.

In one embodiment the pairing of the first Fc-region polypeptide and the second Fc-region polypeptide to form an Fc-region results in the formation of a heterodimer.

In one embodiment of all aspects the antibody is not a bispecific, bivalent antibody comprising a first antigen-binding site that specifically binds to human VEGF and a second antigen-binding site that specifically binds to human ANG-2, wherein
   i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and
   ii) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and
   iii) the bispecific antibody comprises a constant heavy chain region of human IgG1 or human IgG4 subclass (derived from human origin) comprising the mutations I253A, H310A and H435A (numbering according to EU Index of Kabat).

In one embodiment of all aspects the antibody is not a bispecific, bivalent antibody comprising a first antigen-binding site that specifically binds to human VEGF and a second antigen-binding site that specifically binds to human ANG-2, wherein
   i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and
   ii) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and
   iii) the bispecific antibody comprises a constant heavy chain region of human IgG1 or human IgG4 subclass (derived from human origin) comprising the mutations I253A, H310A and H435A (numbering according to EU Index of Kabat),
   and wherein the variable domains comprise not more than 3 mutations with respect to SEQ ID NO: 20, 21, 28 and 29.

In one embodiment of all aspects the antibody is not a bispecific, bivalent antibody comprising a first antigen-binding site that specifically binds to human VEGF and a second antigen-binding site that specifically binds to human ANG-2, wherein the bispecific antibody comprises a constant heavy chain region of human IgG1 or human IgG4 subclass (derived from human origin) comprising the mutations I253A, H310A and H435A (numbering according to EU Index of Kabat) in both Fc-region polypeptides.

In one embodiment of all aspects the antibody is not a bispecific, bivalent antibody comprising a first antigen-binding site that specifically binds to human VEGF and a second antigen-binding site that specifically binds to human ANG-2.

BRIEF DESCRIPTION OF THE FIGURES

FIG. 8A) PK data after single i.v. bolus application of 10 mg/kg into huFcRn transgenic male C57BL/6J mice+/−276: AUC data for wild-type IgG as well as YTE and IHH-AAA Fc-modified IgGs; FIG. 8B) BIAcore sensorgram; FIG. 8C) FcRn affinity column elution; wild-type anti-IGF-1R antibody (reference), YTE-mutant of anti-IGF-1R antibody, IHH-AAA-mutant of anti-IGF-1R antibody.

FIG. 10: Change of FcRn-binding depending on asymmetric distribution of mutations introduced into the Fc-region.

DETAILED DESCRIPTION OF EMBODIMENTS OF THE INVENTION

I. Definitions

Figure 1:
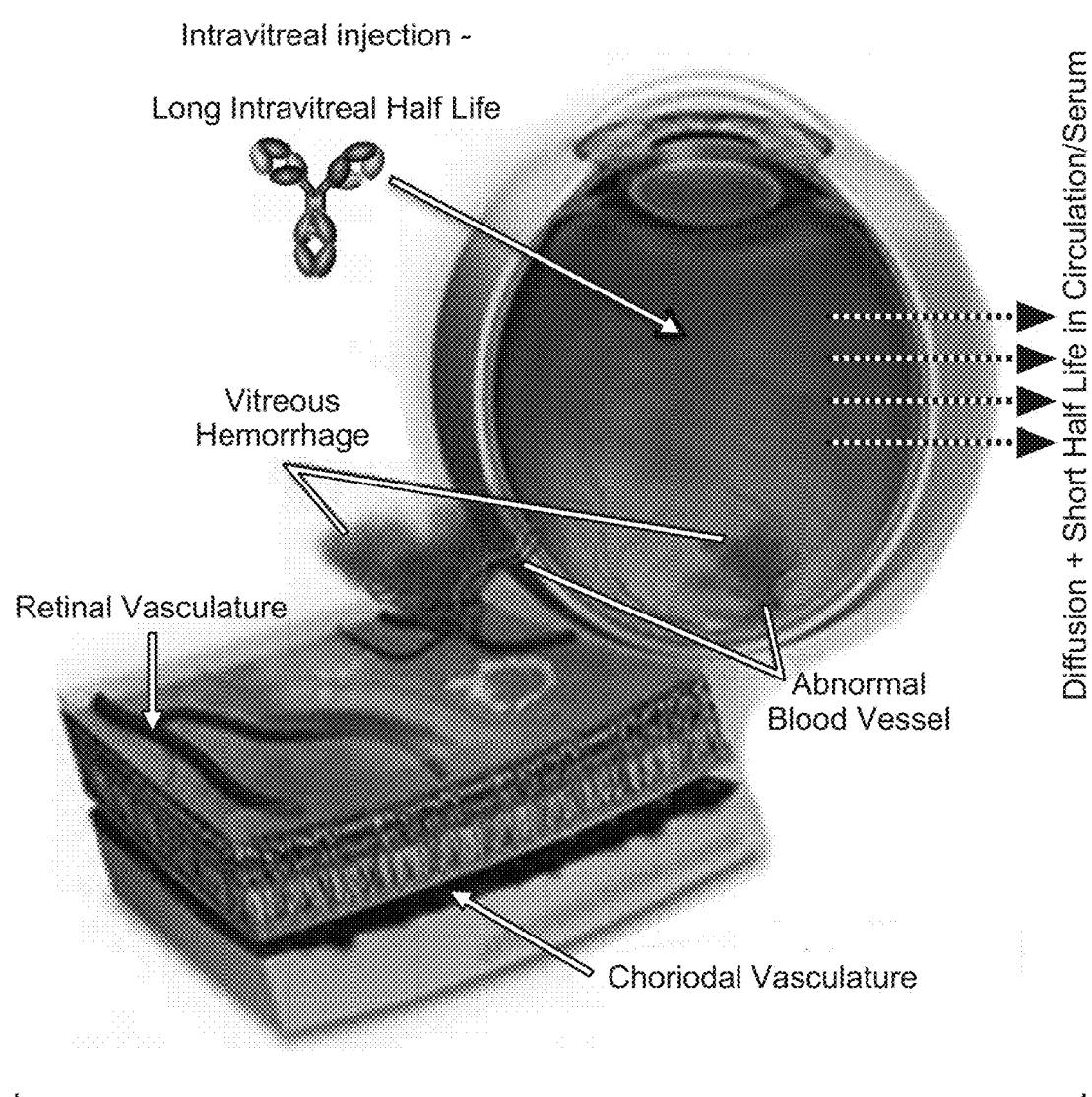
FIG. 1: Scheme of concept and advantages of <VEGF-ANG-2> IgG1 or IgG4 antibodies with IHH-AAA mutation (=combination of mutations I253A, H310A and H435A (numbering according to EU Index of Kabat)).

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence alterations. In some embodiments, the number of amino acid alterations are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alteration" denotes the mutation (substitution), insertion (addition), or deletion of one or more amino acid residues in a parent antibody or fusion polypeptide, e.g. a fusion polypeptide comprising at least an FcRn binding portion of an Fc-region, to obtain a modified antibody or fusion polypeptide. The term "mutation" denotes that the specified amino acid residue is substituted for a different amino acid residue. For example the mutation L234A denotes that the amino acid residue lysine at position 234 in an antibody Fc-region (polypeptide) is substituted by the amino acid residue alanine (substitution of lysine with alanine) (numbering according to the EU index).

The term "amino acid mutation" denotes the substitution of at least one existing amino acid residue with another different amino acid residue (=replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). The replacing amino acid residue may be a "non-naturally occurring amino acid residue". See e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10 (all entirely incorporated by reference herein).

The term "amino acid insertion" denotes the (additional) incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "ANG-2" as used herein refers to human angiopoietin-2 (ANG-2) (alternatively abbreviated with ANGPT2 or ANG2) (SEQ ID NO: 31) which is described e.g. in Maisonpierre, P. C., et al, Science 277 (1997) 55-60 and Cheung, A. H., et al., Genomics 48 (1998) 389-91. The angiopoietins-1 (SEQ ID NO: 32) and -2 were discovered as ligands for the Ties, a family of tyrosine kinases that is selectively expressed within the vascular endothelium (Yancopoulos, G. D., et al., Nature 407 (2000) 242-248). There are now four definitive members of the angiopoietin family. Angiopoietin-3 and -4 (ANG-3 and ANG-4) may represent widely diverged counterparts of the same gene locus in mouse and man (Kim, I., et al., FEBS Let, 443 (1999) 353-356; Kim, I., et al., J. Biol. Chem. 274 (1999) 26523-26528). ANG-1 and ANG-2 were originally identified in tissue culture experiments as agonist and antagonist, respectively (see for ANG-1: Davis, S., et al., Cell 87 (1996) 1161-1169; and for ANG-2: Maisonpierre, P. C., et al., Science 277 (1997) 55-60). All of the known angiopoietins bind primarily to Tie2 (SEQ ID NO: 33), and both ANG-1 and -2 bind to Tie2 with an affinity of 3 nM (Kd) (Maisonpierre, P. C., et al., Science 277 (1997) 55-60).

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen- and/or protein A and/or FcRn-binding activity.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "asymmetric Fc-region" denotes a pair of Fc-region polypeptides that have different amino acid residues at corresponding positions according to the Kabat EU index numbering system.

The term "asymmetric Fc-region with respect to FcRn binding" denotes an Fc-region that consists of two polypeptide chains that have different amino acid residues at corresponding positions, whereby the positions are determined according to the Kabat EU index numbering system, whereby the different positions affect the binding of the Fc-region to the human neonatal Fc-receptor (FcRn). For the purpose herein the differences between the two polypeptide chains of the Fc-region in an "asymmetric Fc-region with respect to FcRn binding" do not include differences that have been introduced to facilitate the formation of heterodimeric Fc-regions, e.g. for the production of bispecific antibodies. These differences can also be asymmetric, i.e. the two chains have differences at non corresponding amino acid residues according to the Kabat EU index numbering system. These differences facilitate heterodimerization and reduce homodimerization. Examples of such differences are the so-called "knobs into holes" substitutions (see, e.g., U.S. Pat. No. 7,695,936 and US 2003/0078385). The following knobs and holes substitutions in the individual polypeptide chains of an Fc-region of an IgG antibody of subclass IgG1 have been found to increase heterodimer formation: 1) Y407T in one chain and T366Y in the other chain; 2) Y407A in one chain and T366W in the other chain; 3) F405A in one chain and T394W in the other chain; 4) F405W in one chain and T394S in the other chain; 5) Y407T in one chain and T366Y in the other chain; 6) T366Y and F405A in one chain and T394W and Y407T in the other chain; 7) T366W and F405W in one chain and T394S and Y407A in the other chain; 8) F405W and Y407A in one chain and T366W and T394S in the other chain; and 9) T366W in one chain and T366S, L368A, and Y407V in the other chain, whereby the last listed is especially suited. In addition, changes creating new disulfide bridges between the two Fc-region polypeptide chains facilitate heterodimer formation (see, e.g., US 2003/0078385). The following substitutions resulting in appropriately spaced apart cysteine residues for the formation of new intra-chain disulfide bonds in the individual polypeptide chains of an Fc-region of an IgG antibody of subclass IgG1 have been found to increase heterodimer formation: Y349C in one chain and S354C in the other; Y349C in one chain and E356C in the other; Y349C in one chain and E357C in the other; L351C in one chain and S354C in the other; T394C in one chain and E397C in the other; or D399C in one chain and K392C in the other. Further examples of heterodimerization facilitating amino acid changes are the so-called "charge pair substitutions" (see, e.g., WO 2009/089004). The following charge pair substitutions in the individual polypeptide chains of an Fc-region of an IgG antibody of subclass IgG1 have been found to increase heterodimer formation: 1) K409D or K409E in one chain and D399K or D399R in the other chain; 2) K392D or K392E in one chain and D399K or D399R in the other chain; 3) K439D or K439E in one chain and E356K or E356R in the other chain; 4) K370D or K370E in one chain and E357K or E357R in the other chain; 5) K409D and K360D in one chain plus D399K and E356K in the other chain; 6) K409D and K370D in one chain plus D399K and E357K in the other chain; 7) K409D and K392D in one chain plus D399K, E356K, and E357K in the other chain; 8) K409D and K392D in one chain and D399K in the other chain; 9) K409D and K392D in one chain and D399K and E356K in the other chain; 10) K409D and K392D in one chain and D399K and D357K in the other chain; 11) K409D and K370D in one chain and D399K and D357K in the other chain; 12) D399K in one chain and K409D and K360D in the other chain; and 13) K409D and K439D in one chain and D399K and E356K on the other.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of $10^{-8}$ M or less, in some embodiments of $10^{-13}$ to $10^{-8}$ M, in some embodiments of $10^{-13}$ to $10^{-9}$ M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

The term "chimeric" antibody refers to an antibody in which a portion of the heavy and/or light chain is derived from a particular source or species, while the remainder of the heavy and/or light chain is derived from a different source or species.

The term "CH2-domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 09: APELLGG PSVFLFPPKP KDTLMISRTP EVTCVWDVS HEDPE-

15

VKFNW YVDGVEVHNA KTKPREEQ E STYRWSVLT VLHQDWLNGK EYKCKVSNKA LPAPIEKTIS KAK.

The term "CH3-domain" denotes the part of an antibody heavy chain polypeptide that extends approximately from EU position 341 to EU position 446. In one embodiment the CH3 domain has the amino acid sequence of SEQ ID NO: 10: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

The term "comparable length" denotes that two polypeptides comprise the identical number of amino acid residues or can be different in length by one or more and up to 10 amino acid residues at most. In one embodiment the Fc-region polypeptides comprise the identical number of amino acid residues or differ by a number of from 1 to 10 amino acid residues. In one embodiment the Fc-region polypeptides comprise the identical number of amino acid residues or differ by a number of from 1 to 5 amino acid residues. In one embodiment the Fc-region polypeptides comprise the identical number of amino acid residues or differ by a number of from 1 to 3 amino acid residues.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

An "effective amount" of an agent, e.g., a pharmaceutical formulation, refers to an amount effective, at dosages and for periods of time necessary, to achieve the desired therapeutic or prophylactic result.

The term "Fc-fusion polypeptide" denotes a fusion of a binding domain (e.g. an antigen binding domain such as a single chain antibody, or a polypeptide such as a ligand of a receptor) with an antibody Fc-region that exhibits the desired target- and/or protein A and/or FcRn-binding activity.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 60. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, MD (1991), NIH Publication 91 3242. The Fc-region is composed of two heavy chain Fc-region polypeptides, which can be covalently linked to each other via the hinge region cysteine residues forming inter-polypeptide disulfide bonds.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein ($\alpha$-FcRn) and a 15 kDa $\beta$2-microglobulin ($\beta$2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245 P, K246, P247, K248, D249, T250, L251, M252, 1253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, 1336, S337, K338, A339, K340, G341, Q342, P343, R344, E345, P346, Q347, V348, C367, V369, F372, Y373, P374, S375, D376, 1377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody having a structure substantially similar to a native antibody structure or having heavy chains that contain an Fc-region as defined herein. A full length antibody may comprise further domains, such as e.g. a scFv or a scFab conjugated to one or more of the chains of the full length antibody. These conjugates are also encompassed by the term full length antibody.

The terms "heterodimer" or "heterodimeric" denote a molecule that comprises two polypeptide chains (e.g. of comparable length), wherein the two polypeptide chains have an amino acid sequence that have at least one different amino acid residue in a corresponding position, whereby corresponding position is determined according to the EU index of Kabat.

The terms "homodimer" and "homodimeric" denote a molecule that comprises two polypeptide chains of comparable length, wherein the two polypeptide chains have an amino acid sequence that is identical in corresponding positions, whereby corresponding positions are determined according to the EU index of Kabat.

An antibody or an Fc-region fusion polypeptide as reported herein can be homodimeric or heterodimeric with respect to its Fc-region which is determined with respect to mutations or properties in focus. For example, with respect to FcRn and/or protein A binding (i.e. the focused on properties) an Fc-region (antibody) is homodimeric (i.e. both heavy chain Fc-region polypeptides comprise these mutations) with respect to the mutations H310A, H433A and Y436A (these mutations are in focus with respect to FcRn and/or protein A binding property of the Fc-region fusion polypeptide or antibody) but at the same time heterodimeric with respect to the mutations Y349C, T366S, L368A and Y407V (these mutations are not in focus as these mutations are directed to the heterodimerization of the heavy chains and not to the FcRn/protein A binding properties) as well as the mutations S354C and T366W, respectively (the first set is comprised only in the first Fc-region polypeptide whereas the second set is comprised only in the second Fc-region polypeptide). Further for example, an Fc-region fusion polypeptide or an antibody as reported herein can be heterodimeric with respect to the mutations I253A, H310A, H433A, H435A and Y436A (i.e. these mutations are directed all to the FcRn and/or protein A binding properties of the dimeric polypeptide), i.e. one Fc-region polypeptide comprises the mutations I253A, H310A and H435A, whereas the other Fc-region polypeptide comprises the mutations H310A, H433A and Y436A.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda MD (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "derived from" denotes that an amino acid sequence is derived from a parent amino acid sequence by introducing alterations at at least one position. Thus a derived amino acid sequence differs from the corresponding parent amino acid sequence at at least one corresponding position (numbering according to Kabat EU index numbering system for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 60, or of a human IgG2 Fc-region polypeptide of SEQ ID NO: 61, or of a human IgG3 Fc-region polypeptide of SEQ ID NO: 62, or of a human IgG4 Fc-region polypeptide of SEQ ID NO: 63. In one embodiment the Fc-region polypeptide is derived from an Fc-region polypeptide of SEQ ID NO: 60, or 61, or 62, or 63 and has at least one amino acid mutation compared to the Fc-region polypeptide of SEQ ID NO: 60, or 61, or 62, or 63. In one embodiment the Fc-region polypeptide comprises/has from about one to about ten amino acid mutations, and in one embodiment from about one to about five amino acid mutations. In one embodiment the Fc-region polypeptide has at least about 80% homology with a human Fc-region polypeptide of SEQ ID NO: 60, or 61, or 62, or 63. In one embodiment the Fc-region polypeptide has least about 90% homology with a human Fc-region polypeptide of SEQ ID NO: 60, or 61, or 62, or 63. In one embodiment the Fc-region polypeptide has at least about 95% homology with a human Fc-region polypeptide of SEQ ID NO: 60, or 61, or 62, or 63.

The Fc-region polypeptide derived from a human Fc-region polypeptide of SEQ ID NO: 60, or 61, or 62, or 63 is defined by the amino acid alterations that are contained. Thus, for example, the term P329G denotes an Fc-region polypeptide derived human Fc-region polypeptide with the mutation of proline to glycine at amino acid position 329 relative to the human Fc-region polypeptide of SEQ ID NO: 60, or 61, or 62, or 63.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype and the Kabat EU index numbering system (see pages 661-723) is used for the constant heavy chain domains (CH1, Hinge, CH2 and CH3).

A human IgG1 Fc-region polypeptide has the following amino acid sequence:

```
                                    (SEQ ID NO: 60)
DKTHTCPPCPAPELLGGPSVFLFPPKPKDTLMISRTPE

VTCVVVDVSHEDPEVKFNWYVDGVEVHNAKTKPREEQY

NSTYRVVSVLTVLHQDWLNGKEYKCKVSNKALPAPIEK

TISKAKGQPREPQVYTLPPSRDELTKNQVSLTCLVKGF

YPSDIAVEWESNGQPENNYKTTPPVLDSDGSFFLYSKL

TVDKSRWQQGNVFSCSVMHEALHNHYTQKSLSLSPGK.
```

A human IgG1 Fc-region derived Fc-region polypeptide with the mutations L234A, L235A has the following amino acid sequence:

```
                                    (SEQ ID NO: 64)
DKTHTCPPCPAPEAAGGPSVFLFPPKPKDTLMISRTP

EVTCVVVDVSHEDPEVKFNWYVDGVEVHNAKTKPREE

QYNSTYRVVSVLTVLHQDWLNGKEYKCKVSNKALPAP

IEKTISKAKGQPREPQVYTLPPSRDELTKNQVSLTCL

VKGFYPSDIAVEWESNGQPENNYKTTPPVLDSDGSFF

LYSKLTVDKSRWQQGNVFSCSVMHEALHNHYTQKSLS

LSPGK.
```

A human IgG1 Fc-region derived Fc-region polypeptide with Y349C, T366S, L368A and Y407V mutations has the following amino acid sequence:

```
                                    (SEQ ID NO: 65)
DKTHTCPPCPAPELLGGPSVFLFPPKPKDTLMISRT

PEVTCVVVDVSHEDPEVKFNWYVDGVEVHNAKTKPR

EEQYNSTYRVVSVLTVLHQDWLNGKEYKCKVSNKAL

PAPIEKTISKAKGQPREPQVCTLPPSRDELTKNQVS

LSCAVKGFYPSDIAVEWESNGQPENNYKTTPPVLDS

DGSFFLVSKLTVDKSRWQQGNVFSCSVMHEALHNHY

TQKSLSLSPGK.
```

A human IgG1 Fc-region derived Fc-region polypeptide with S354C, T366W mutations has the following amino acid sequence:

```
                                    (SEQ ID NO: 66)
DKTHTCPPCPAPELLGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN
```

```
-continued
KALPAPIEKTISKAKGQPREPQVYTLPPCRDELTK

NQVSLWCLVKGFYPSDIAVEWESNGQPENNYKTTP

PVLDSDGSFFLYSKLTVDKSRWQQGNVFSCSVMHE

ALHNHYTQKSLSLSPGK.
```

A human IgG1 Fc-region derived Fc-region polypeptide with L234A, L235A mutations and Y349C, T366S, L368A, Y407V mutations has the following amino acid sequence:

```
                                    (SEQ ID NO: 67)
DKTHTCPPCPAPEAAGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALPAPIEKTISKAKGQPREPQVCTLPPSRDELTK

NQVSLSCAVKGFYPSDIAVEWESNGQPENNYKTTP

PVLDSDGSFFLVSKLTVDKSRWQQGNVFSCSVMHE

ALHNHYTQKSLSLSPGK.
```

A human IgG1 Fc-region derived Fc-region polypeptide with a L234A, L235A and S354C, T366W mutations has the following amino acid sequence:

```
                                    (SEQ ID NO: 68)
DKTHTCPPCPAPEAAGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALPAPIEKTISKAKGQPREPQVYTLPPCRDELTK

NQVSLWCLVKGFYPSDIAVEWESNGQPENNYKTTP

PVLDSDGSFFLYSKLTVDKSRWQQGNVFSCSVMHE

ALHNHYTQKSLSLSPGK.
```

A human IgG1 Fc-region derived Fc-region polypeptide with a P329G mutation has the following amino acid sequence:

```
                                    (SEQ ID NO: 69)
DKTHTCPPCPAPELLGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALGAPIEKTISKAKGQPREPQVYTLPPSRDELTK

NQVSLTCLVKGFYPSDIAVEWESNGQPENNYKTTP

PVLDSDGSFFLYSKLTVDKSRWQQGNVFSCSVMHE

ALHNHYTQKSLSLSPGK.
```

A human IgG1 Fc-region derived Fc-region polypeptide with L234A, L235A mutations and P329G mutation has the following amino acid sequence:

```
                                    (SEQ ID NO: 70)
DKTHTCPPCPAPEAAGGPSVFLFPPKPKDTLMISR

TPEVTCVVVDVSHEDPEVKFNWYVDGVEVHNAKTK
```

-continued

```
PREEQYNSTYRVVSVLTVLHQDWLNGKEYKCKVSN

KALGAPIEKTISKAKGQPREPQVYTLPPSRDELTK

NQVSLTCLVKGFYPSDIAVEWESNGQPENNYKTTP

PVLDSDGSFFLYSKLTVDKSRWQQGNVFSCSVMHE

ALHNHYTQKSLSLSPGK.
```

A human IgG1 Fc-region derived Fc-region polypeptide with a P329G mutation and Y349C, T366S, L368A, Y407V mutations has the following amino acid sequence:

```
                                      (SEQ ID NO: 71)
DKTHTCPPCPAPELLGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALGAPIEKTISKAKGQPREPQVCTLPPSRDELTK

NQVSLSCAVKGFYPSDIAVEWESNGQPENNYKTTP

PVLDSDGSFFLVSKLTVDKSRWQQGNVFSCSVMHE

ALHNHYTQKSLSLSPGK.
```

A human IgG1 Fc-region derived Fc-region polypeptide with a P329G mutation and S354C, T366W mutation has the following amino acid sequence:

```
                                      (SEQ ID NO: 72)
DKTHTCPPCPAPELLGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALGAPIEKTISKAKGQPREPQVYTLPPCRDELTK

NQVSLWCLVKGFYPSDIAVEWESNGQPENNYKTTP

PVLDSDGSFFLYSKLTVDKSRWQQGNVFSCSVMHE

ALHNHYTQKSLSLSPGK.
```

A human IgG1 Fc-region derived Fc-region polypeptide with L234A, L235A, P329G and Y349C, T366S, L368A, Y407V mutations has the following amino acid sequence:

```
                                              (SEQ ID NO: 73)
DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALGAPIEKTISKAKGQPREPQVCTLPPSRDELTKNQVSLSC

AVKGFYPSDIAVEWESNGQPENNYKTTPPVLDSDGSFFLVSKLTVDKSR

WQQGNVFSCSVMHEALHNHYTQKSLSLSPGK.
```

A human IgG1 Fc-region derived Fc-region polypeptide with L234A, L235A, P329G mutations and S354C, T366W mutations has the following amino acid sequence:

```
                                              (SEQ ID NO: 74)
DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE
```

-continued

```
YKCKVSNKALGAPIEKTISKAKGQPREPQVYTLPPCRDELTKNQVSLWC

LVKGFYPSDIAVEWESNGQPENNYKTTPPVLDSDGSFFLYSKLTVDKSR

WQQGNVFSCSVMHEALHNHYTQKSLSLSPGK.
```

A human IgG4 Fc-region polypeptide has the following amino acid sequence:

```
                                      (SEQ ID NO: 63)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with S228P and L235E mutations has the following amino acid sequence:

```
                                      (SEQ ID NO: 75)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with S228P, L235E mutations and P329G mutation has the following amino acid sequence:

```
                                      (SEQ ID NO: 76)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with S354C, T366W mutations has the following amino acid sequence:

```
                                      (SEQ ID NO: 77)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPCQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with Y349C, T366S, L368A, Y407V mutations has the following amino acid sequence:

```
                                        (SEQ ID NO: 78)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVCTLPPSQEEMTKNQVSL

SCAVKGFYPSDIAVEWESNGQPENNYKTTPPVLDSDGSFFLVSRLTVDK

SRWQEGNVFSCSVMHEALHNHYTQKSLSLSLGK.
```

A human IgG4 Fc-region derived Fc-region polypeptide with a S228P, L235E and S354C, T366W mutations has the following amino acid sequence:

```
                                        (SEQ ID NO: 79)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with a S228P, L235E and Y349C, T366S, L368A, Y407V mutations has the following amino acid sequence:

```
                                        (SEQ ID NO: 80)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVCTLPPSQEEMTKNQVSL

SCAVKGFYPSDIAVEWESNGQPENNYKTTPPVLDSDGSFFLVSRLTVDK

SRWQEGNVFSCSVMHEALHNHYTQKSLSLSLGK.
```

A human IgG4 Fc-region derived Fc-region polypeptide with a P329G mutation has the following amino acid sequence:

```
                                        (SEQ ID NO: 81)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with a P329G and Y349C, T366S, L368A, Y407V mutations has the following amino acid sequence:

```
                                        (SEQ ID NO: 82)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVCTLPPSQEEMTKNQVSL
```

-continued
```
SCAVKGFYPSDIAVEWESNGQPENNYKTTPPVLDSDGSFFLVSRLTVDK

SRWQEGNVFSCSVMHEALHNHYTQKSLSLSLGK.
```

A human IgG4 Fc-region derived Fc-region polypeptide with a P329G and S354C, T366W mutations has the following amino acid sequence:

```
                                        (SEQ ID NO: 83)
ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVYTLPPCQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLGK.
```

A human IgG4 Fc-region derived Fc-region polypeptide with a S228P, L235E, P329G and Y349C, T366S, L368A, Y407V mutations has the following amino acid sequence:

```
                                        (SEQ ID NO: 84)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVCTLPPSQEEMTKNQVSL

SCAVKGFYPSDIAVEWESNGQPENNYKTTPPVLDSDGSFFLVSRLTVDK

SRWQEGNVFSCSVMHEALHNHYTQKSLSLSLGK.
```

A human IgG4 Fc-region derived Fc-region polypeptide with a S228P, L235E, P329G and S354C, T366W mutations has the following amino acid sequence:

```
                                        (SEQ ID NO: 85)
ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLGSSIEKTISKAKGQPREPQVYTLPPCQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLGK.
```

An alignment of the different human Fc-regions is shown below (EU numbering):

```
     2          2
     3          5
     0          0
IGG1 DKTHTCPPCP APELLGGPSV FLFPPKPKDT LMISRTPEVT
CVVVDVSHED
IGG2 ...VECPPCP APP.VAGPSV FLFPPKPKDT LMISRTPEVT
CVVVDVSHED
IGG3 DTPPPCPRCP APELLGGPSV FLFPPKPKDT LMISRTPEVT
CVVVDVSHED
IGG4 ...PPCPSCP APEFLGGPSV FLFPPKPKDT LMISRTPEVT
CVVVDVSQED
    --HINGE-|--CH2------------------

3
                0
                0
IGG1 PEVKFNWYVD GVEVHNAKTK PREEQYNSTY RVVSVLTVLF
QDWLNGKEYK
IGG2 PEVQFNWYVD GVEVHNAKTK PREEQFNSTF RVVSVLTVVH
QDWLNGKEYK
```

-continued

```
IGG3 PEVQFKWYVD GVEVHNAKTK PREEQYNSTF RVVSVLTVLH
QDWLNGKEYK
IGG4 PEVQFNWYVD GVEVHNAKTK PREEQFNSTY RVVSVLTVLH
QDWLNGKEYK
    --CH2------------------------

3
                    5
                    0

IGG1 CKVSNKALPA PIEKTISKAK GQPREPQVYT LPPSRDELTK
NQVSLTCLVK
IGG2 CKVSNKGLPA PIEKTISKTK GQPREPQVYT LPPSREEMTK
NQVSLTCLVK
IGG3 CKVSNKALPA PIEKTISKTK GQPREPQVYT LPPSREEMTK
NQVSLTCLVK
IGG4 CKVSNKGLPS SIEKTISKAK GQPREPQVYT LPPSQEEMTK
NQVSLTCLVK
    --CH2---CH2--|--CH3--------------

4
                    0
                    0

IGG1 GFYPSDIAVE WESNGQPENN YKTTPPVLDS DGSFFLYSKL
TVDKSRWQQG
IGG2 GFYPSDISVE WESNGQPENN YKTTPPMLDS DGSFFLYSKL
TVDKSRWQQG
IGG3 GFYPSDIAVE WESSGQPENN YNTTPPMLDS DGSFFLYSKL
TVDKSRWQQG
IGG4 GFYPSDIAVE WESNGQPENN YKTTPPVLDS DGSFFLYSRL
TVDKSRWQEG
    --CH3------------------------

4
                    4
                    7

IGG1 NVFSCSVMHE ALHNHYTQKS LSLSPGK
IGG2 NVFSCSVMHE ALHNHYTQKS LSLSPGK
IGG3 NIFSCSVMHE ALHNRFTQKS LSLSPGK
IGG4 NVFSCSVMHE ALHNHYTQKS LSLSLGK
    --CH3-----------|
```

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified elsewhere in the specification.

Unless otherwise indicated, HVR residues and other residues in the variable domain (e.g., FR residues) are numbered herein according to the Kabat EU index numbering system (Kabat et al., supra).

The term "IGF-1R" as used herein, refers to any native IGF-1R from any vertebrate source, including mammals such as primates (e.g. humans) and rodents (e.g., mice and rats), unless otherwise indicated. The term encompasses "full-length", unprocessed IGF-1R as well as any form of IGF-1R that results from processing in the cell. The term also encompasses naturally occurring variants of IGF-1R, e.g., splice variants or allelic variants. The amino acid sequence of human IGF-1R is shown in SEQ ID NO: 11.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IGF-1R antibody" refers to one or more nucleic acid molecules encoding antibody heavy and light chains (or fragments thereof), including such nucleic acid molecule(s) in a single plasmid or separate plasmids, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immuno-globulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, con-traindications and/or warnings concerning the use of such therapeutic products.

"Percent (%) amino acid sequence identity" with respect to a reference polypeptide sequence is defined as the per-centage of amino acid residues in a candidate sequence that are identical with the amino acid residues in the reference polypeptide sequence, after aligning the sequences and introducing gaps, if necessary, to achieve the maximum percent sequence identity, and not considering any conser-vative substitutions as part of the sequence identity. Align-ment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 com-puter program.

The term "pharmaceutical formulation" refers to a prepa-ration which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A phar-maceutically acceptable carrier includes, but is not limited to, a buffer, excipient, stabilizer, or preservative.

The term "peptidic linker" as used herein denotes a peptide with amino acid sequences, which is in one embodi-ment of synthetic origin. The peptidic linker is in one embodiment a peptide with an amino acid sequence with a length of at least 30 amino acids, in one embodiment with a length of 32 to 50 amino acids. In one embodiment the peptidic linker is a peptide with an amino acid sequence with a length of 32 to 40 amino acids. In one embodiment the peptidic linker is $(G_xS)n$ with G=glycine, S=serine, (x=3, n=8, 9 or 10) or (x=4 and n=6, 7 or 8), in one embodiment with x=4, n=6 or 7, in one embodiment with x=4, n=7. In one embodiment the peptidic linker is $(G_4S)_6G_2$.

The term "recombinant antibody", as used herein, denotes all antibodies (chimeric, humanized and human) that are prepared, expressed, created or isolated by recombinant means. This includes antibodies isolated from a host cell such as a NS0 or CHO cell or from an animal (e.g. a mouse) that is transgenic for human immunoglobulin genes or antibodies expressed using a recombinant expression plas-mid transfected into a host cell. Such recombinant antibod-ies have variable and constant regions in a rearranged form. The recombinant antibodies as reported herein can be sub-jected to in vivo somatic hypermutation. Thus, the amino acid sequences of the VH and VL regions of the recombinant antibodies are sequences that, while derived from and related to human germ line VH and VL sequences, may not naturally exist within the human antibody germ line reper-toire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect patho-logical consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A., Vascular diseases, In: Pathobiology of ocular disease, A dynamic approach, Garner, A., and Klintworth, G. K., (eds.), 2nd edition, Marcel Dekker, New York (1994), pp. 1625-1710).

The term "plasmid", as used herein, refers to a nucleic acid molecule capable of propagating another nucleic acid to which it is linked. The term includes the plasmid as a self-replicating nucleic acid structure as well as the plasmid incorporated into the genome of a host cell into which it has been introduced. Certain plasmids are capable of directing the expression of nucleic acids to which they are operatively linked. Such plasmids are referred to herein as "expression plasmid".

The term "VEGF" as used herein refers to human vascular endothelial growth factor (VEGF/VEGF-A) the 165-amino acid human vascular endothelial cell growth factor (amino acid 27-191 of precursor sequence of human VEGF165: SEQ ID NO: 30; amino acids 1-26 represent the signal peptide), and related 121, 189, and 206 vascular endothelial cell growth factor isoforms, as described by Leung, D. W., et al., Science 246 (1989) 1306-1309; Houck et al., Mol. Endocrin. 5 (1991) 1806-1814; Keck, P. J., et al., Science 246 (1989) 1309-1312 and Connolly, D. T., et al., J. Biol. Chem. 264 (1989) 20017-20024; together with the naturally occurring allelic and processed forms of those growth factors. VEGF is involved in the regulation of normal and abnormal angiogenesis and neovascularization associated with tumors and intraocular disorders (Ferrara, N., et al., Endocrin. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources and includes several isoforms. VEGF shows highly specific mitogenic activity for endothelial cells.

The term "with (the) mutation IHH-AAA" as used herein refers to the combination of the mutations I253A (Ile253Ala), H310A (His310Ala), and H435A (His435Ala) and the term "with (the) mutation HHY-AAA" as used herein refers to the combination of the mutations H310A (His310Ala), H433A (His433Ala), and Y436A (Tyr436Ala) and the term "with (the) mutation YTE" as used herein refers to the combination of mutations M252Y (Met252Tyr), S254T (Ser254Thr), and T256E (Thr256Glu) in the constant heavy chain region of IgG1 or IgG4 subclass, wherein the numbering is according to the EU Index of Kabat.

The term "with (the) mutations P329G LALA" as used herein refers to the combination of the mutations L234A (Leu234Ala), L235A (Leu235Ala) and P329G (Pro329Gly) in the constant heavy chain region of IgG1 subclass, wherein the numbering is according to the EU Index of Kabat. The term "with (the) mutation SPLE" as used herein refers to the combination of the mutations S228P (Ser228Pro) and L235E (Leu235Glu) in the constant heavy chain region of IgG4 subclass, wherein the numbering is according to the EU Index of Kabat. The term "with (the) mutation SPLE and P329G" as used herein refers to the combination of the mutations S228P (Ser228Pro), L235E (Leu235Glu) and P329G (Pro329Gly) in the constant heavy chain region of IgG4 subclass, wherein the numbering is according to the EU Index of Kabat.

II. Compositions and Methods

The invention is based, at least in part, on the finding that antibodies for intravitreal application are beneficial that do not have FcRn-binding as these antibodies do not have substantially changed half-lives compared to antibodies with FcRn-binding in the eye but are cleared rapidly from the systemic blood circulation resulting in no or very limited systemic side effects outside the eye. Antibodies as reported herein are useful, e.g., for the diagnosis or treatment of ocular vascular diseases.

The invention is based, at least in part, on the finding that specific mutations or combinations of mutations which influence the binding of an immunoglobulin Fc-region to the neonatal Fc-receptor (FcRn), i.e. which reduce or even eliminate the binding of the Fc-region to the FcRn, do not simultaneously eliminate the binding of the Fc-region to Staphylococcal protein A. This has a profound effect on the purification process that can be employed as e.g. no specific and species limited affinity chromatography materials, such as e.g. KappaSelect™, which only binds to antibodies comprising a kappa light chain, are required. Thus, with the mutations as reported herein it is possible at the same time to reduce or even eliminate the binding to FcRn while maintaining the binding to protein A.

The invention is based, at least in part, on the finding that by using different mutations in each of the Fc-region polypeptides of an Fc-region a heterodimeric molecule, such as e.g. a bispecific antibody, can be provided that has tailor-made FcRn-binding and therewith antibodies can be provided that have a tailor-made systemic half-life.

The invention is based, at least in part, on the finding that by using different mutations in each of the Fc-region polypeptides of an Fc-region a heterodimeric molecule, such as e.g. a bispecific antibody, can be provided that on the one hand has a reduced or even eliminated binding to FcRn but on the other hand maintains the ability to bind to Staphylococcal protein A. This binding to protein A can be used to separate the heterodimeric antibody from homodimeric by-products. For example by combining the mutations I253A, H310A and H435A in one Fc-region polypeptide with the mutations H310A, H433A and Y436A in the other Fc-region polypeptide using the knobs-into-hole approach a heterodimeric Fc-region can be obtained that on the one hand does not bind to FcRn (both sets of mutations are silent with respect to human FcRn) but maintains binding to Staphylococcal protein A (the Fc-region polypeptide with the mutations I253A, H310A and H435A does not bind to FcRn and does not bind to protein A, whereas the Fc-region polypeptide with the mutations H310A, H433A and Y436A does not bind to FcRn but does still bind to protein A). Thus, the standard protein A affinity chromatography can be used to remove the homodimeric hole-hole by-product as this no longer binds to protein A. Thus, by combining the knobs-into-holes approach with the mutations I253A, H310A and H435A in the hole chain and the mutations H310A, H433A and Y436A in the knobs chain the purification/separation of the heterodimeric knobs-into-holes product from the homodimeric hole-hole by-product can be facilitated.

The combination of mutations I253A, H310A, H435A, or L251D, L314D, L432D, or L251S, L314S, L432S result in a loss of the binding to protein A, whereas the combination of mutations I253A, H310A, H435A, or H310A, H433A, Y436A, or L251D, L314D, L432D result in a loss of the binding to the human neonatal Fc receptor.

The following table presents an exemplary overview of the amino acid residues in an Fc-region that are involved in interactions or have been changed to modify interactions.

| residue | interaction with | | KiH | | protein A | effect of mutations on |
| | protein A | FcRn | knob | hole | binding | FcRn binding |
| --- | --- | --- | --- | --- | --- | --- |
| Pro238 | | | | | | P238A increase |
| Thr250 | | | | | | T250Q/M428L increase |
| Leu251 | main-chain contact | | | | | |
| Met252 | hydrophobic packing | | | | | M252W increase; M252Y increase; M252Y/T256Q increase; M252F/T256D increase; M252Y/S254T/T256E increase |
| Ile253 | main-chain contact; hydrogen bonding; significant binding reduction if mutated to Ala | interaction | | | | I253A reduction |
| Ser254 | polar interaction; hydrogen bonding | | | | | S254A reduction; M252Y/S254T/T256E increase |
| Arg255 | salt-bridge | | | | | R255A reduction |
| Thr256 | | | | | | T256A increase; T256Q increase; T256P increase; M252Y/T256Q reduction; M252F/T256D reduction; M252Y/S254T/T256E increase |
| Pro257 | | | | | | P257I/Q311I increase; P257I/N434H increase |
| Glu272 | | | | | | E272A increase |
| Asp280 | | | | | | D280K increase |
| His285 | | | | | | reduction |
| Lys288 | | | | | | K288A reduction; K288A/N434A increase |
| Val305 | | | | | | V305A increase |
| Thr307 | | | | | | T307A increase; T307A/E380A/N434A increase; T307Q/N434A increase; T307Q/N434S increase; T307Q/E380A/N434A increase |

-continued

| residue | interaction with | | KiH | | protein A | effect of mutations on |
|---|---|---|---|---|---|---|
| | protein A | FcRn | knob | hole | binding | FcRn binding |
| Val308 | | | | | | V308P/N434A increase |
| Leu309 | | | | | | L309A reduction |
| His310 | | interaction | | | | H310A reduction; H310Q/H433N reduction |
| Gln311 | polar or charged interaction | | | | | Q311A increase; P257I/Q311I increase |
| Asp312 | | | | | | D312A increase |
| Leu314 | hydrophobic interaction | | | | | |
| Lys317 | | | | | | K317A increase |
| Ala339 | | | | | | A339T increase |
| Tyr349 | | | | Y349C | | |
| Ser354 | | | S354C | | | |
| Thr366 | | | T366W | T366S | | |
| Leu368 | | | | L368A | | |
| Asp376 | | | | | | D376A increase; D376V/N434H increase |
| Ala378 | | | | | | A378Q increase |
| Glu380 | salt-bridge | | | | | E380A increase E380A/N434A increase; T307A/E380A/N434A increase; T307Q/E380A/N434A increase |
| Glu382 | | | | | | E382A increase |
| Gly385 | | | | | | G385H increase; G385A/Q386P/N389S increase |
| Gln386 | | | | | | G385A/Q386P/N389S increase |
| Asn389 | | | | | | G385A/Q386P/N389S increase |
| Tyr407 | | | | Y407V | | |
| Ser415 | | | | | | S415A reduction |
| Ser424 | | | | | | S424A increase |
| Met428 | | | | | | M428L increase; T250Q/M428L increase |
| Leu432 | polar or charged interaction | | | | | |
| His433 | polar or charged interaction; salt-bridge | interaction | | | | H433A reduction; H310Q/H433N reduction; H433K/N434F/Y436H increase; H433R/N434Y/Y436 Hincrease; H433K/N434F increase |
| Asn434 | hydrogen bonding; significant binding reduction if replaced by Ala | interaction | | | | N434W/Y/F/A/H increase; K288A/N434A increase; E380A/N434A increase; T307A/E380A/N434A increase; N434F/Y436H increase; H433K/N434F/Y436H increase; H433R/N434Y/Y436 Hincrease; H433K/N434F increase; P257I/N434H increase; D376V/N434H increase; |

-continued

| residue | interaction with | | KiH | | protein A binding | effect of mutations on FcRn binding |
|---|---|---|---|---|---|---|
| | protein A | FcRn | knob | hole | | |
| | | | | | | T307Q/N434A increase; T307Q/N434S increase; V308P/N434A increase; T307Q/E380A/N434A increase |
| His435 | hydrophobic packing; significant binding reduction if mutated to Ala | interaction | | | H435R/Y436F eliminates binding to protein A | H435A reduction; H435R reduction |
| Tyr436 | hydrophobic packing; significant binding reduction if replaced by Ala | interaction | | | H435R/Y436F eliminates binding to protein A | Y436A reduction; N434F/Y436H increase; H433K/N434F/Y436H increase; H433R/N434Y/ 6Y43H increase |

The modifications/mutations as reported herein alter the binding specificity for one or more Fc receptors such as the human FcRn. At the same time some of the mutations which alter the binding to human FcRn do not alter the binding to protein A.

In specific embodiments the mutations do alter or do substantially alter the serum half-life of the antibody as compared with a corresponding antibody that lacks these mutations.

In further specific embodiments the mutations further do not alter or do not substantially alter the binding of the antibody to protein A as compared with a corresponding antibody that lacks these mutations.

A. The neonatal Fc-Receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein ($\alpha$-FcRn) and a 15 kDa $\beta$2-microglobulin ($\beta$2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically the following amino acid residues according to the EU numbering of Kabat are involved in the interaction between the Fc-region and the FcRn: F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J. K., et al., Eur. J. Immunol. 29 (1999) 2819-2825; Raghavan, M., et al., Biochem. 34 (1995) 14649-146579; Medesan, C., et al., J Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases antibodies with reduced half-life in the blood circulation are desired. For example, drugs for intravitreal application should have a long half-live in the eye and a short half-life in the circulation of the patient. Such antibodies also have the advantage of increased exposure to a disease site, e.g. in the eye.

Different mutations that influence the FcRn binding and therewith the half-life in the blood circulation are known. Fc-region residues critical to the mouse Fc-mouse FcRn interaction have been identified by site-directed mutagenesis (see e.g. Dall'Acqua, W. F., et al. J. Immunol 169 (2002)

5171-5180). Residues I253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues 1253, H310, and H435 were found to be critical for the interaction of human Fc with murine FcRn (Kim, J. K., et al., Eur. J. Immunol. 29 (1999) 2819-2825). Residues M252Y, S254T, T256E have been described by Dall'Acqua et al. to improve FcRn binding by protein-protein interaction studies (Dall'Acqua, W. F., et al. J. Biol.

Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined. Exemplary mutations and their effect on FcRn binding are listed in the following Table.

TABLE

| mutation | effect on FcRn binding | half-live in the circulation | reference |
|---|---|---|---|
| H285 H310Q/H433N (murine IgG1) | reduced (murine) | reduced (in mouse) | Kim, J.K., Scand. J. Immunol. 40 (1994) 457-465 |
| I253A H310A H435A H436A (murine IgG1) | reduced (murine) | reduced (in mouse) | Ghetie, V. and Ward, E.S., Immunol. Today 18 (1997) 592-598 |
| T252L/T254S/T256F T252A/T254S/T256A (murine IgG1) | increased (murine) | increased (in mouse) | Ghetie, V. and Ward, E.S., Immunol. Today 18 (1997) 592-598 |
| I253A H310A H435A H436A H433A/N434Q (murine IgG1) | reduced (murine) | reduced (in mouse) | Medesan, C., et al., J. Immunol. 158 (1997) 2211-2217 |
| I253A H310A H435A H435R (human IgG1) | reduced H310A: <0.1 rel. binding to muFcRn (murine) | reduced (in mouse) | Kim, J.K., Eur. J. Immunol. 29 (1999) 2819-2825 |
| H433A (human IgG1) | 1.1 rel. binding to muFcRn, 0.4 rel. binding hu FcRn (murine) | | Kim, J.K., Eur. J. Immunol. 29 (1999) 2819-2825 |
| I253A S254A H435A Y436A (human IgG1) | reduced <0.1 relative binding to huFcRn | reduced | Shields, R.L., et al., J. Biol. Chem. 276 (2001) 6591-6604 |
| R255A K288A L309A S415A H433A (human IgG1) | reduced (human) | reduced | Shields, R.L., et al., J. Biol. Chem. 276 (2001) 6591-6604 |
| P238A T256A E272A V305A T307A Q311A D312A K317A D376A A378Q E380A E382A S424A N434A K288A/N434A E380A/N434A T307A/E380A/N434A (human IgG1) | increased (human) | increased | Shields, R.L., et al., J. Biol. Chem. 276 (2001) 6591-6604 |
| H435A (humanized IgG1) | reduced <0.1 rel. binding to huFcRn | reduced | Firan, M., et al., Int. Immunol. 13 (2001) 993-1002 |
| I253A (no binding) M252W M252Y | increased (murine and human) | reduced (in mouse) | Dall'Acqua, J. Immunol. 169 (2002) 5171-5180 |

TABLE-continued

| mutation | effect on FcRn binding | half-live in the circulation | reference |
|---|---|---|---|
| M252Y/T256Q<br>M252F/T256D<br>N434F/Y436H<br>M252Y/S254T/T256E<br>G385A/Q386P/N389S<br>H433K/N434F/Y436H<br>H433R/N434Y/Y436H<br>G385R/Q386T/P387R/N389P<br>M252Y/S254T/T256E/H433K/<br>N434F/Y436H<br>M252Y/S254T/T256E/G385R/<br>Q386T/P387R/N389P<br>(human IgG1) | | | |
| M428L<br>T250Q/M428L<br>(human IgG2) | increased<br>(human) | increased<br>(in monkey) | Hinton, P.R.,<br>et al., J. Biol.<br>Chem. 279<br>(2004) 6213-6216 |
| M252Y/S254T/T256E +<br>H433K/N434F<br>(human IgG) | increased<br>(human) | increased<br>(in mouse) | Vaccaro, C., et<br>al., Nat.<br>Biotechnol. 23<br>(2005) 1283-1288 |
| T307A/E380A/N434A<br>(chimeric IgG1) | increased | increased in<br>transgenic mouse | Pop, L.M., et<br>al., Int.<br>Immunopharm<br>acol. 5 (2005)<br>1279-1290 |
| T250Q<br>E380A<br>M428L<br>N434A<br>K288A/N434A<br>E380A/N434A<br>T307A/E380A/N434A<br>(human IgG1) | increased<br>(human) | increased in<br>transgenic mouse | Petkova, S.B.,<br>et al., Int.<br>Immunol 18<br>(2006) 1759-1769 |
| I253A<br>(human IgG1) | reduced<br>(human) | reduced in<br>transgenic mouse | Petkova, S.B.,<br>et al., Int.<br>Immunol 18<br>(2006) 1759-1769 |
| S239D/A330L/I332E<br>M252Y/S254T/T256E<br>(humanized) | increased<br>(human and<br>Cynomolgus) | increased in<br>Cynomolgus | Dall'Acqua,<br>W.F., et al., J.<br>Biol. Chem.<br>281 (2006)<br>23514-23524 |
| T250Q<br>M428L<br>T250Q/M428L<br>(human IgG1) | increased<br>(human) | increased in Rhesus<br>apes | Hinton, P.R.,<br>et al., J.<br>Immunol. 176<br>(2006) 346-356 |
| T250Q/M428L<br>P257I/Q311I<br>(humanized IgG1) | increased<br>(mouse and<br>Cynomolgus) | no change in<br>Cynomolgus<br>increased in mouse | Datta-<br>Mannan, A., et<br>al., J. Biol.<br>Chem. 282<br>(2007) 1709-1717 |
| P257I/Q311I<br>P257I/N434H<br>D376V/N434H<br>(humanized IgG1) | increased<br>at pH 6<br>(human,<br>Cynomolgus,<br>mouse) | reduced in mice<br>P257I/N434H<br>reduced in<br>Cynomolgus | Datta-<br>Mannan, A., et<br>al., Drug<br>Metab.<br>Dispos. 35<br>(2007) 86-94 |
| abrogate FcRn binding:<br>I253<br>H310<br>H433<br>H435<br>reduce FcRn binding:<br>Y436<br>increased FcRn binding:<br>T250<br>N252<br>S254<br>T256<br>T307<br>M428<br>N434 | increased and<br>reduced | reducing the<br>binding ability of<br>IgG for FcRn<br>reduces its serum<br>persistence; a<br>higher-affinity<br>FcRn-IgG<br>interaction prolongs<br>the half-lives of IgG<br>and Fc-coupled<br>drugs in the serum | Ropeenian,<br>D.C. and<br>Akilesh, S.,<br>Nat. Rev.<br>Immunol. 7<br>(2007) 715-725 |

TABLE-continued

| mutation | effect on FcRn binding | half-live in the circulation | reference |
|---|---|---|---|
| N434A T307Q/N434A T307Q/N434S V308P/N434A T307Q/E380A/N434A (human IgG1) | increased (Cynomolgus monkey) | increased in Cynomolgus monkey | Yeung, Y.A., et al., Cancer Res. 70 (2010) 3269-3277 |
| 256P 280K 339T 385H 428L 434W/Y/F/A/H (human IgG) | increased at neutral pH | | WO 2011/ 122011 |

It has been found that one mutation one-sided in one Fc-region polypeptide is sufficient to weaken the binding to FcRn significantly. The more mutations are introduced into the Fc-region the weaker the binding to the FcRn becomes. But one-sided asymmetric mutations are not sufficient to completely inhibit FcRn binding. Mutations on both sides are necessary to completely inhibit FcRn binding.

The results of a symmetric engineering of an IgG1 Fc-region to influence FcRn binding is shown in the following table (alignment of mutations and retention time on an FcRn-affinity chromatography column).

TABLE

| effector function influencing mutations | FcRn-binding influencing mutation 1 | FcRn-binding influencing mutation 2 | FcRn-binding influencing mutation 3 | FcRn-affinity column retention time [min] |
|---|---|---|---|---|
| L234A/L235A/P329G | — | — | — | 45.3 |
| L234A/L235A/P329G | I253A | H310A | H435A | 2.3 |
| L234A/L235A/P329G | I253A | — | — | 2.7 |
| L234A/L235A/P329G | — | H310A | — | 2.4 |
| L234A/L235A/P329G | — | — | H435A | 2.7 |
| L234A/L235A/P329G | I253A | H310A | — | 2.3 |
| L234A/L235A/P329G | I253A | — | H435A | 2.3 |
| L234A/L235A/P329G | — | H310A | H435A | 2.4 |
| L234A/L235A/P329G | — | H310A | Y436A | 2.3 |
| L234A/L235A/P329G | H310A | H433A | Y436A | 2.4 |
| L234A/L235A/P329G | — | — | Y436A | 41.3 |

Retention times below 3 minutes correspond to no binding as the substance is in the flow-through (void peak).

The single mutation H310A is the most silent symmetrical mutation to delete any FcRn-binding.

The symmetric single mutation I253A and H435A result in a relative shift of retention time of 0.3-0.4 min. This can be generally regarded as a non-detectable binding.

The single mutation Y436A results in detectable interaction strength to the FcRn affinity column. Without being bound by this theory this mutation could have an FcRn mediated half-life which can be differentiated from a zero interaction such as the combination of the mutations I253A, H310A and H435A (IHH-AAA mutation).

The results obtained with a symmetrically modified anti-HER2 antibody are presented in the following table (see WO 2006/031370 for reference).

TABLE

| mutation | retention time [min] |
|---|---|
| I253H | no binding |
| M252D | no binding |
| S254D | no binding |
| R255D | 41.4 |
| M252H | 43.6 |
| K288E | 45.2 |
| L309H | 45.5 |
| E258H | 45.6 |
| T256H | 46.0 |
| K290H | 46.2 |
| D98E | 46.2 |

TABLE-continued

| mutation | retention time [min] |
|---|---|
| wild-type | 46.3 |
| K317H | 46.3 |
| Q311H | 46.3 |
| E430H | 46.4 |
| T307H | 47.0 |
| N434H | 52.0 |

Figure 9:
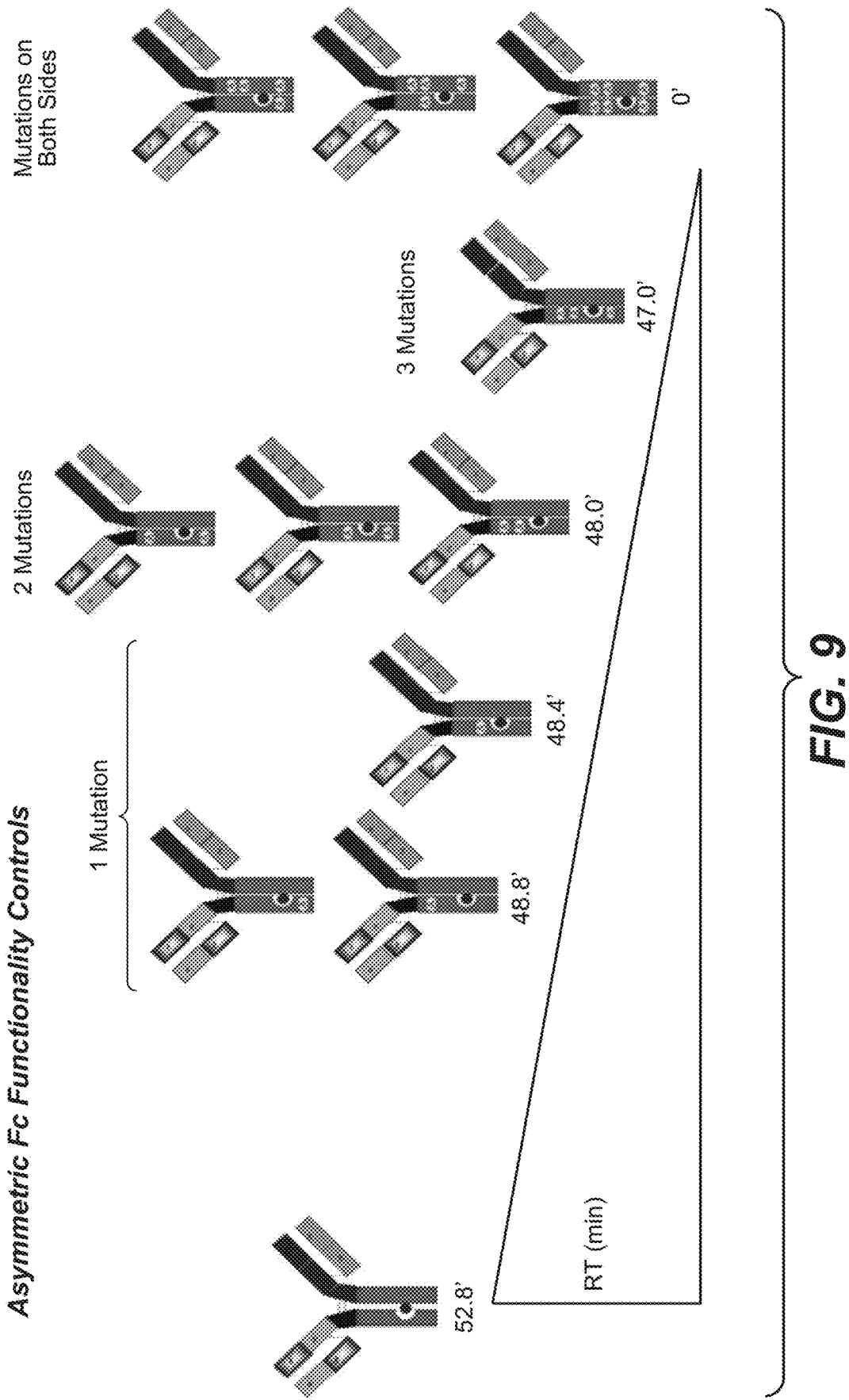
FIG. 9: Change of retention time in an FcRn affinity chromatography depending on the number of mutations introduced into the Fc-Region.
Figure 11:
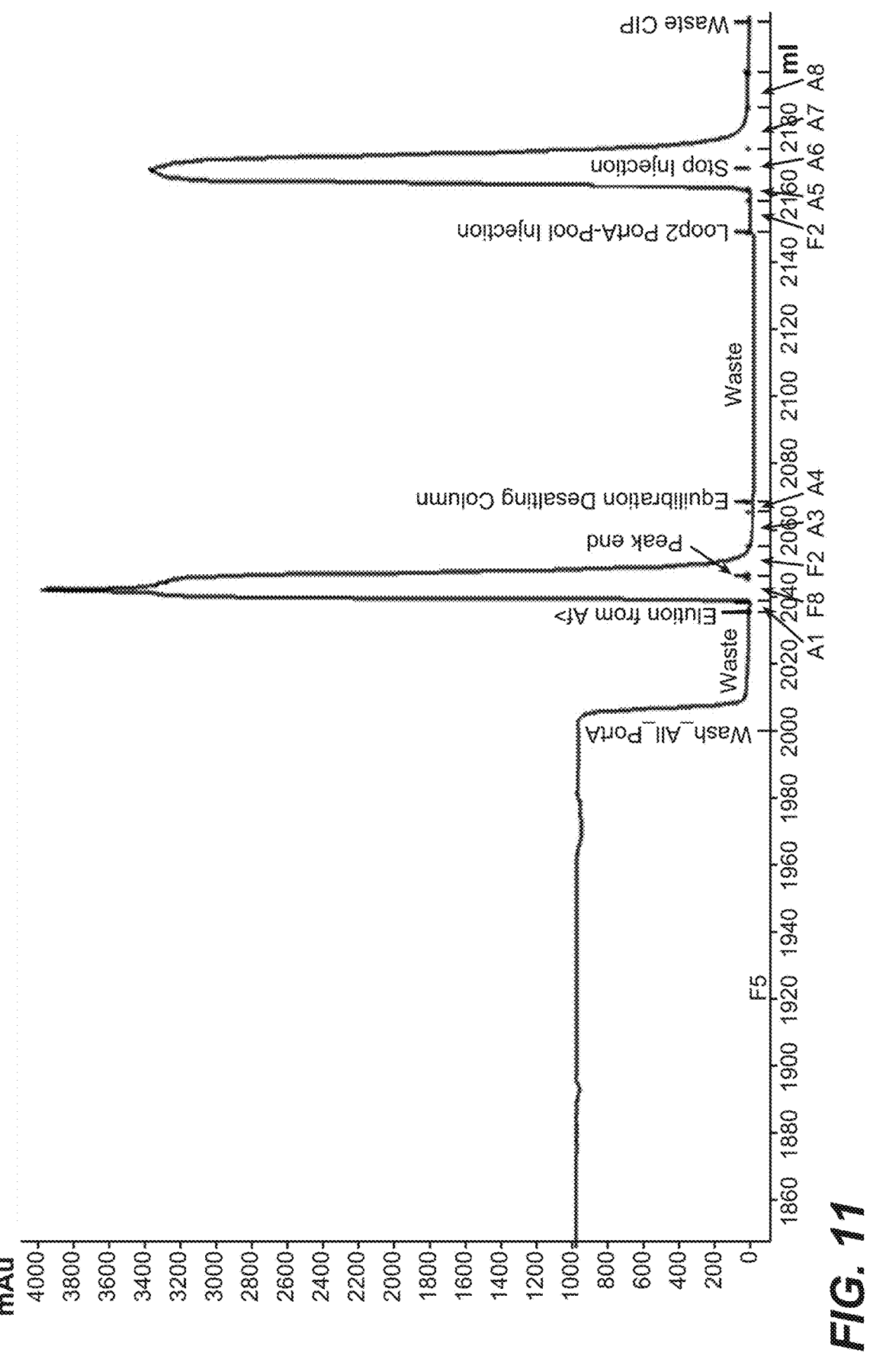
FIG. 11: Elution chromatogram of a bispecific <VEGF-ANG-2> antibody (VEGF/ANG2-0121) with the mutations H310A, H433A and Y436A in both heavy chains from two consecutive protein A affinity chromatography columns.
Figure 12:
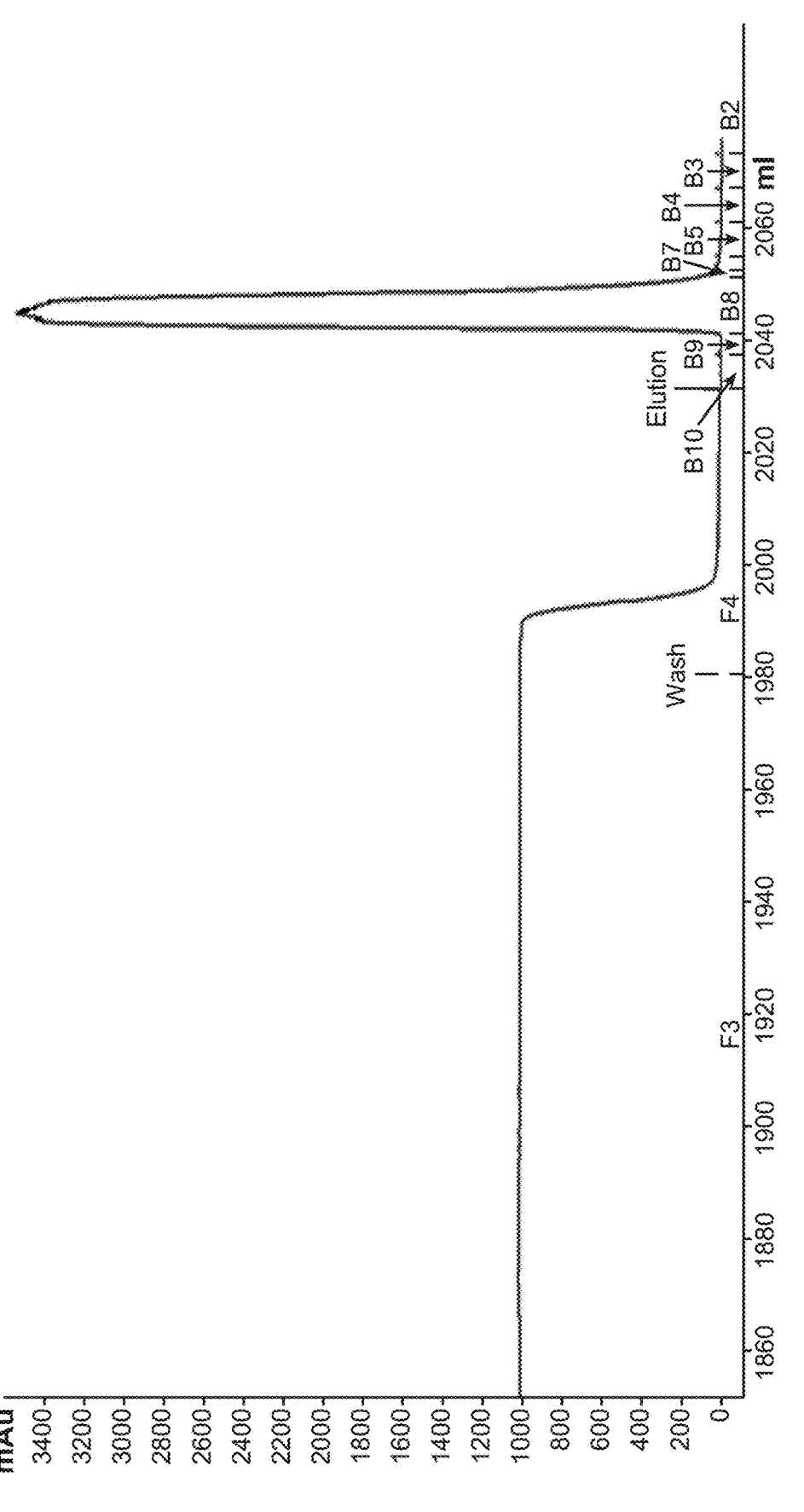
FIG. 12: Elution chromatogram of an anti-IGF-1R antibody (IGF-1R-0045) with the mutations H310A, H433A and Y436A in both heavy chains from a protein A affinity chromatography column.
Figure 13:
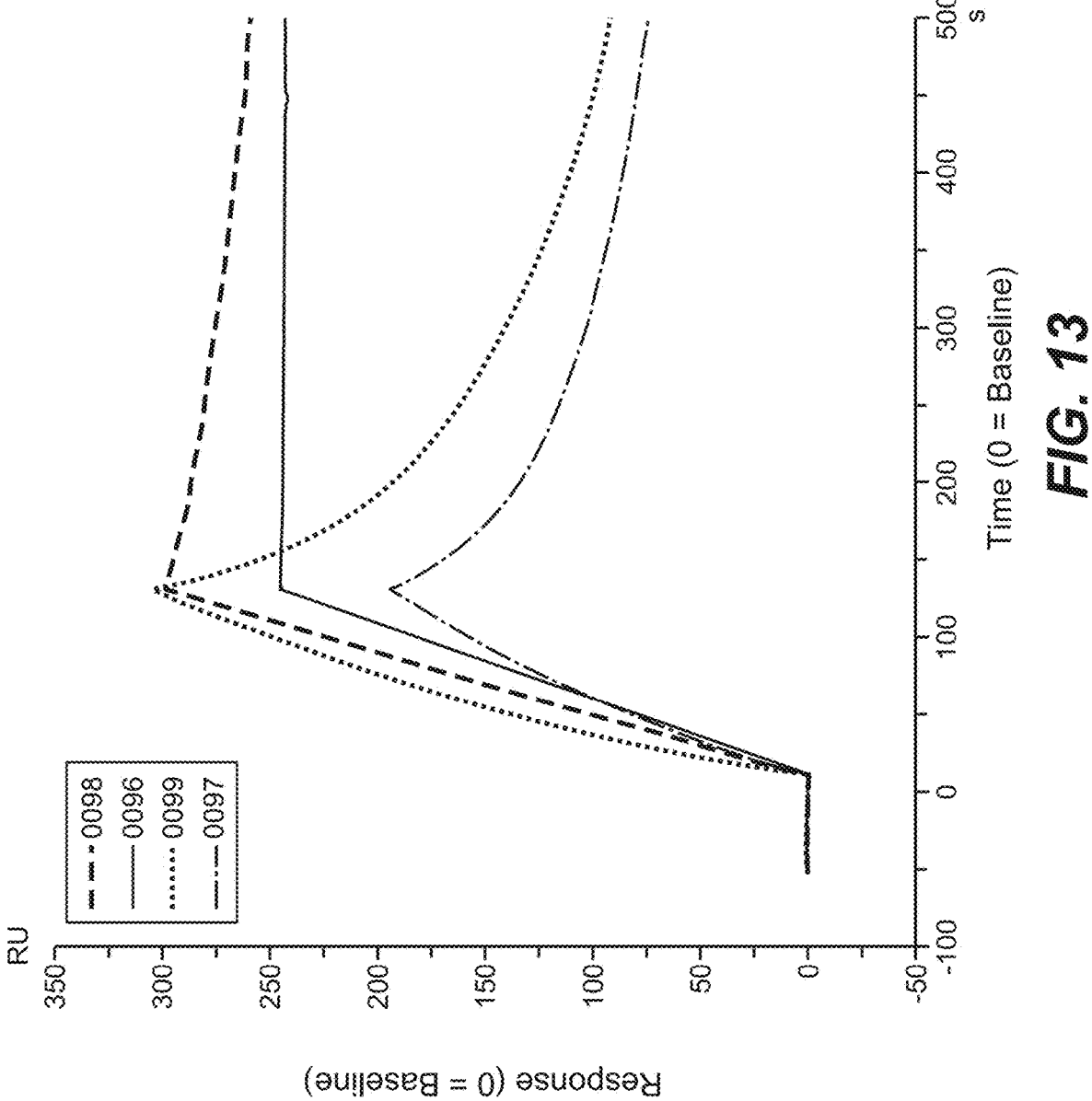
FIG. 13: Binding of IgG Fc-region modified <VEGF-ANG-2> antibodies to immobilized protein A on a CM5 chip.
Figure 14:
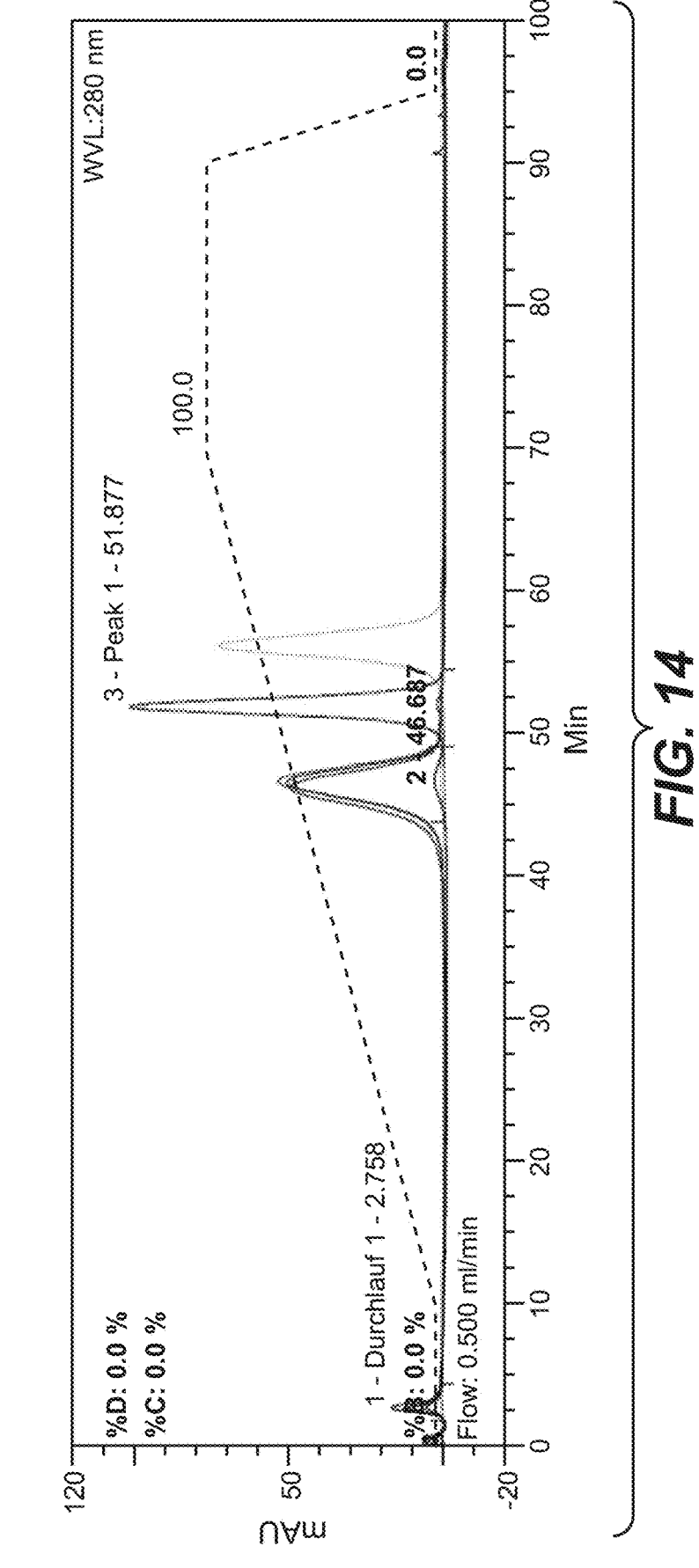
FIG. 14: Elution chromatogram of different <VEGF-ANG-2> antibodies on an FcRn affinity column.
Figure 15:
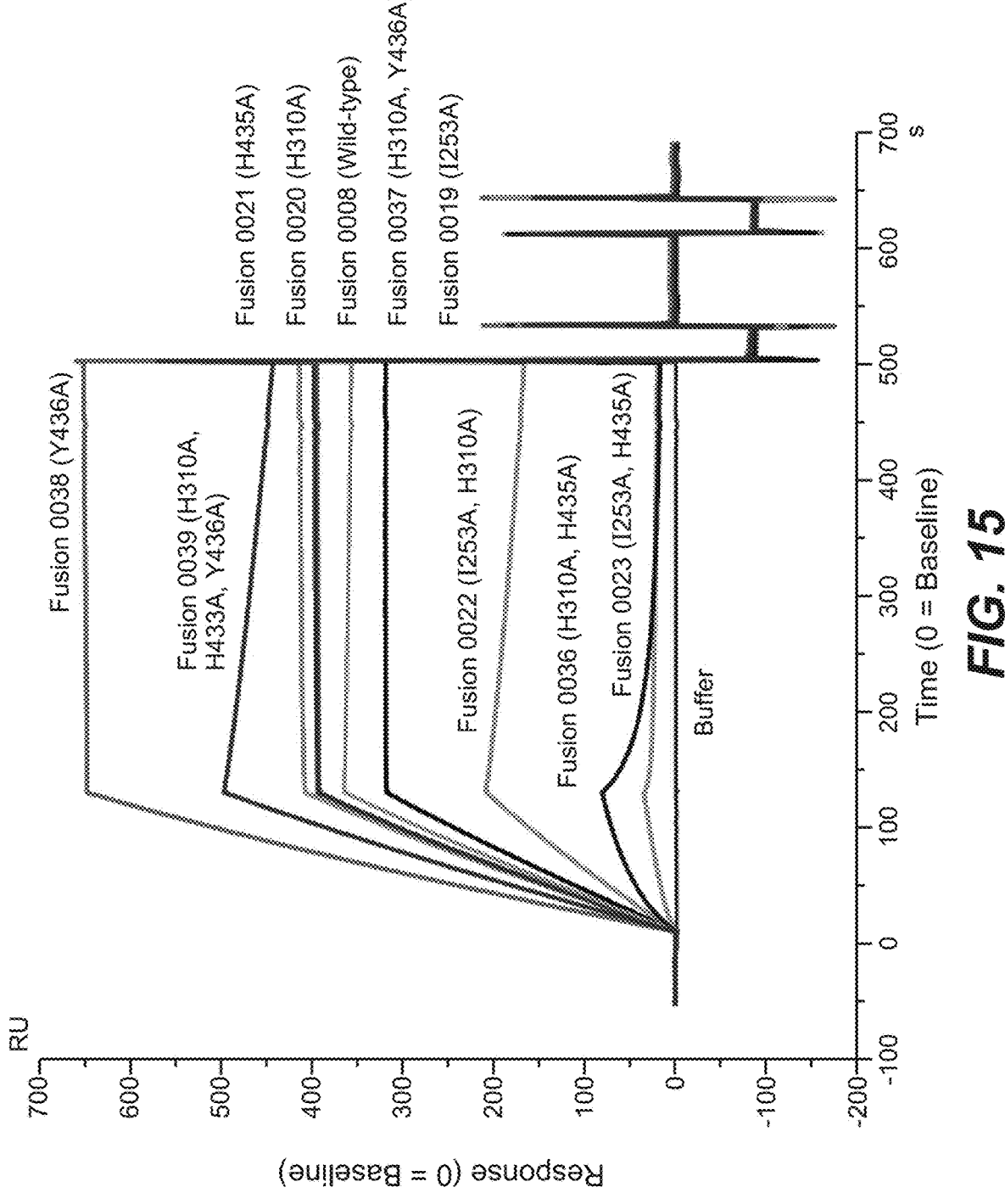
FIG. 15: Binding of different fusion polypeptides to Staphylococcal protein A (SPR).
Figure 16:
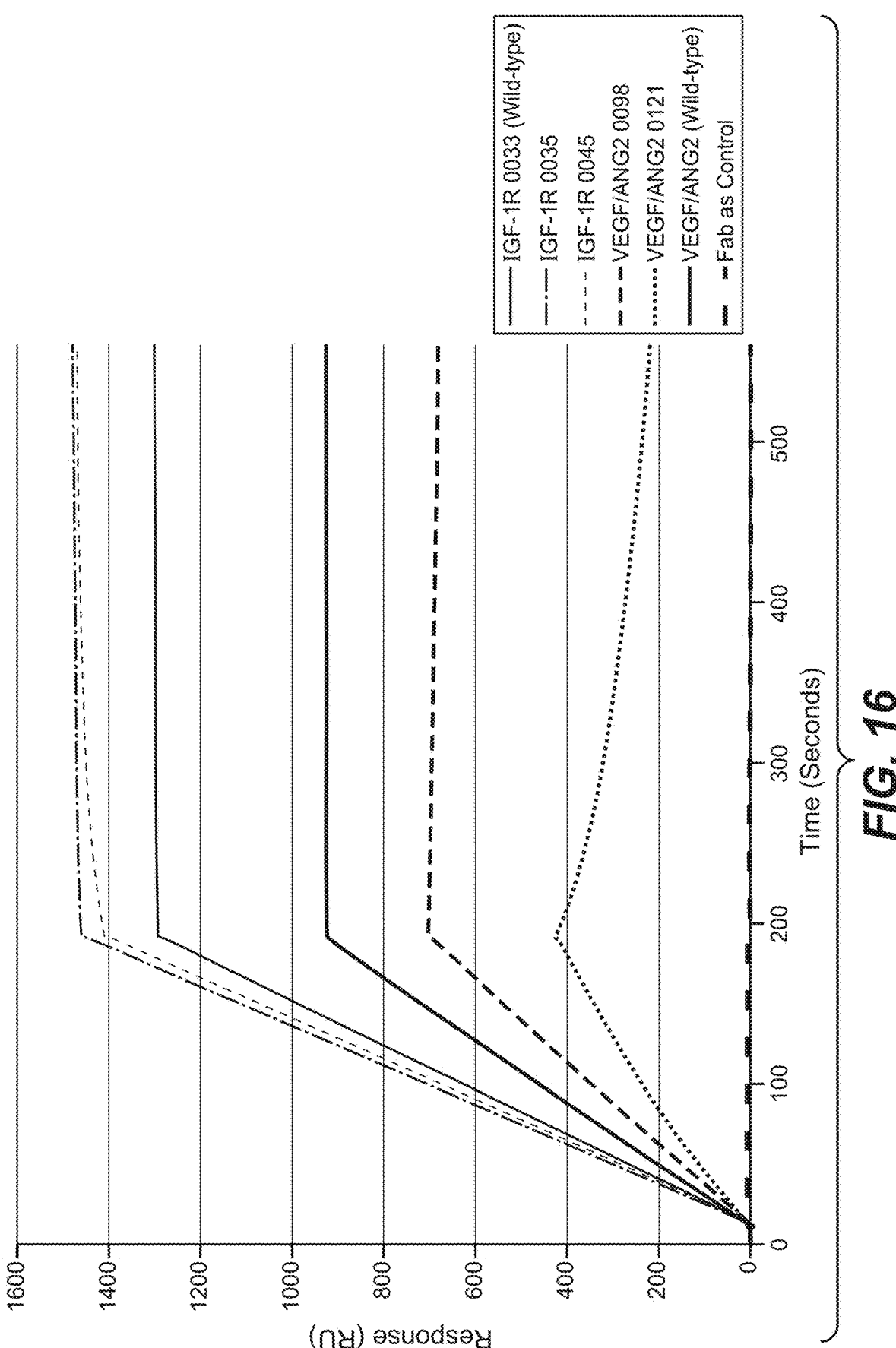
FIG. 16: Binding of different <VEGF-ANG-2> antibody and anti-IGF-1R antibody mutants to immobilized protein A (SPR).

The effect of the introduction of asymmetric FcRn-binding affecting mutations in the Fc-region has been exemplified with a bispecific anti-VEGF/ANG-2 antibody assembled using the knobs-into-holes technology (see e.g. U.S. Pat. No. 7,695,936, US 2003/0078385; "hole chain" mutations: S354C/T366W, "knob chain" mutations: Y349C/ T366S/L368A/Y407V). The effect of the introduced mutations on FcRn-binding can easily be determined using an FcRn affinity chromatography method (see FIG. 9 and the following Table). Antibodies that have a later elution from the FcRn affinity column, i.e. that have a longer retention time on the FcRn affinity column, have a longer half-life in vivo, and vice versa.

TABLE

| FcRn affecting mutation | retention time on FcRn affinity column |
|---|---|
| one chain with M252Y/S254T/T256E | 56.2 min. |
| none | 51.8 min. |
| one chain with I253A or H435A | 48.8 min. |
| one chain with H310A | 48.4 min. |
| one chain with I253A/H435A or I253A/H310A or H310A/H435A | 48.0 min. |
| one chain with H310A/H433A/Y436A | 46.7 min. |
| one chain with I253A/H310A/H435A | 46.6 min. |
| one chain with L251D/L314D/L432D | 46.3 min. |
| first chain with I253A/H310A/H435A and second chain with H310A or H435A or I253A/H310A/H435A | no binding |

The effect of the introduction of asymmetric FcRn-binding affecting mutations in the Fc-region has further been exemplified with a monospecific anti-IGF-1R antibody assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the introduced mutations on FcRn-binding can easily be determined using an FcRn affinity chromatography method (see the following Table). Antibodies that have a later elution from the FcRn affinity column, i.e. that have a longer retention time on the FcRn affinity column, have a longer half-life in vivo, and vice versa.

TABLE

| FcRn affecting mutation | retention time on FcRn affinity column |
|---|---|
| one chain with M252Y/S254T/T256E | 57.6 min. |
| none | 53.0 min. |
| one chain with H310A/H433A/Y436A | 42.4 min. |
| one chain with I253A/H310A/H435A | 42.0 min. |
| one chain with L251D/L314D/L432D | 40.9 min. |
| first chain with I253A/H310A/H435A and second chain with H310A or H435A or I253A/H310A/H435A | no binding |

The asymmetric IHH-AAA- and LLL-DDD-mutations (LLL-DDD-mutation=L251D, L314D and L432D) show weaker binding than the corresponding parent or wild-type antibody.

The symmetric HHY-AAA mutation (=combination of the mutations H310A, H433A and Y436A) results in an Fc-region that does no longer bind to the human FcRn whereas the binding to protein A is maintained (see FIGS. 11, 12, 13 and 14).

The effect of the introduction of asymmetric FcRn-binding affecting mutations in the Fc-region has further been exemplified with a monospecific anti-IGF-1R antibody (IGF-1R), a bispecific anti-VEGF/ANG-2 antibody (VEGF/ANG2), and a full length antibody with fusions to the C-terminus of both heavy chains (fusion) assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the introduced mutations on FcRn-binding and protein A binding can easily be determined using an FcRn affinity chromatography method, a protein A affinity chromatography method and SPR-based methods (see the following Table).

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| VEGF/ANG2 0096 | none | none | L234A L235A P329G | yes | yes | stable binding | yes |
| VEGF/ANG2 0097 | none | I253A H310A H435A | L234A L235A P329G | yes | yes | fast off-rate | yes |
| VEGF/ANG2 0098 | none | H310A H433A Y436A | L234A L235A P329G | yes | yes | stable binding | yes |
| VEGF/ANG2 0099 | none | L251D L314D L432D | L234A L235A P329G | reduced | reduced | fast off-rate | yes |
| VEGF/ANG2 0100 | none | M252Y S254T T256E | L234A L235A P329G | increased | increased | increased | yes |
| VEGFang2 0016 | I253A H310A H435A | I253A H310A H435A | L234A L235A P329G | no | no | n.d. | no |
| VEGF/ANG2 0121 | H310A H433A Y436A | H310A H433A Y436A | L234A L235A P329G | no | n.d. | yes | yes |
| IGF-1R 0033 | none | none | none | yes | yes | n.d. | yes |

-continued

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| IGF-1R 0034 | none | I253A H310A H435A | L234A L235A P329G | n.d. | yes | n.d. | yes |
| IGF-1R 0035 | none | H310A H433A Y436A | none | reduced | reduced | n.d. | yes |
| IGF-1R 0037 | none | L251D L314D L432D | L234A L235A P329G | n.d. | yes | n.d. | yes |
| IGF-1R 0036 | none | M252Y S254T T256E | L234A L235A P329G | n.d. | yes | n.d. | yes |
| IGF-1R 0045 | H310A H433A Y436A | H310A H433A Y436A | none | n.d. | n.d. | n.d. | yes |
| fusion 0008 | none | none | L234A L235A P329G | yes | yes | n.d. | n.d. |
| fusion 0019 | I253A | I253A | L234A L235A P329G | no | no | n.d. | n.d. |
| fusion 0020 | H310A | H310A | L234A L235A P329G | no | no | n.d. | n.d. |
| fusion 0021 | H435A | H435A | L234A L235A P329G | no | no | n.d. | n.d. |
| fusion 0038 | Y436A | Y436A | L234A L235A P329G | reduced | reduced | yes | n.d. |
| fusion 0022 | I253A H310A | I253A H310A | L234A L235A P329G | no | no | n.d. | n.d. |
| fusion 0023 | I253A H435A | I253A H435A | L234A L235A P329G | no | no | n.d. | n.d. |
| fusion 0036 | H310A H435A | H310A H435A | L234A L235A P329G | no | no | n.d. | n.d. |
| fusion 0037 | H310A Y436A | H310A Y436A | L234A L235A P329G | no | no | n.d. | n.d. |
| fusion 0018 | I253A H310A H435A | I253A H310A H435A | L234A L235A P329G | no | no | n.d. | n.d. |
| fusion 0039 | H310A H433A Y436A | H310A H433A Y436A | L234A L235A P329G | no | no | yes | n.d. |

One aspect as reported herein is an antibody comprising the variant human IgG class Fc-region as reported herein.

The Fc-region polypeptide confers the above described characteristics to the antibody or its fusion partner.

The fusion partner can be any molecules having a biological activity whose in vivo half-live shall be reduced or increased, i.e. whose in vivo half-life shall be clearly defined and tailor-made for its intended application.

Fc-region fusion polypeptides may comprise e.g. a variant (human) IgG class Fc-region as reported herein and a receptor protein that binds to a target including a ligand, such as, for example, TNFR-Fc-region fusion polypeptide (TNFR=human tumor necrosis factor receptor), or IL-1R-Fc-region fusion polypeptide (IL-1R=human interleukin-1 receptor), or VEGFR-Fc-region fusion polypeptides (VEGFR=human vascular endothelial growth factor receptor), or ANG2R-Fc-region fusion polypeptides (ANG2R=human angiopoietin 2 receptor).

Fc-region fusion polypeptides may comprise e.g. a variant (human) IgG class Fc-region as reported herein and an antibody fragment that binds to a target including, such as, for example, an antibody Fab fragment, scFvs (see e.g. Nat. Biotechnol. 23 (2005) 1126-1136), or domain antibodies (dAbs) (see e.g. WO 2004/058821, and WO 2003/002609).

Fc-region fusion polypeptides may comprise e.g. a variant (human) IgG class Fc-region as reported herein and a receptor ligand (either naturally occurring or artificial).

B. Ocular Vascular Diseases

Ocular vascular diseases are any pathological condition characterized by altered or unregulated proliferation and invasion of new blood vessels into the structures of ocular tissues such as the retina or cornea.

In one embodiment the ocular vascular disease is selected from the group consisting of wet age-related macular degeneration (wet AMD), dry age-related macular degeneration (dry AMD), diabetic macular edema (DME), cystoid macular edema (CME), non-proliferative diabetic retinopathy (NPDR), proliferative diabetic retinopathy (PDR), cystoid macular edema, vasculitis (e.g. central retinal vein occlusion), papilloedema, retinitis, conjunctivitis, uveitis, choroiditis, multifocal choroiditis, ocular histoplasmosis, blepharitis, dry eye (Sjogren's disease) and other ophthalmic diseases wherein the eye disease or disorder is associated with ocular neovascularization, vascular leakage, and/or retinal edema.

The antibody as reported herein is useful in the prevention and treatment of wet AMD, dry AMD, CME, DME, NPDR, PDR, blepharitis, dry eye and uveitis, also in one preferred embodiment wet AMD, dry AMD, blepharitis, and dry eye, also in one preferred embodiment CME, DME, NPDR and PDR, also in one preferred embodiment blepharitis, and dry eye, in particular wet AMD and dry AMD, and also particularly wet AMD.

In some embodiments, the ocular vascular disease is selected from the group consisting of wet age-related macular degeneration (wet AMD), macular edema, retinal vein occlusions, retinopathy of prematurity, and diabetic retinopathy.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, Sjogren's disease, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegener's sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Retinopathy of prematurity (ROP) is a disease of the eye that affects prematurely born babies. It is thought to be caused by disorganized growth of retinal blood vessels which may result in scarring and retinal detachment. ROP can be mild and may resolve spontaneously, but may lead to blindness in serious cases. As such, all preterm babies are at risk for ROP, and very low birth weight is an additional risk factor. Both oxygen toxicity and relative hypoxia can contribute to the development of ROP.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula (central area of the retina which provides detailed central vision, called fovea) called drusen between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula. Large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case. RP is a type of hereditary retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Macular edema occurs when fluid and protein deposits collect on or under the macula of the eye, a yellow central area of the retina, causing it to thicken and swell. The swelling may distort a person's central vision, as the macula is near the center of the retina at the back of the eyeball. This area holds tightly packed cones that provide sharp, clear central vision to enable a person to see form, color, and detail that is directly in the line of sight. Cystoid macular edema is a type of macular edema that includes cyst formation.

C. Exemplary Antibodies

In one aspect, the invention provides isolated antibodies that have abolished FcRn-binding, i.e. these antibodies bind to human FcRn with an affinity comparable to or less than an antibody having the mutations I253A/H310A/H435A or H310A/H433A/Y436A or L251D/L314D/L432D or combinations thereof in the Fc-region, i.e. in both Fc-region polypeptides (numbering according to Kabat EU index numbering system).

One exemplary antibody as reported herein is an antibody that has abolished FcRn-binding and comprises a first Fc-region polypeptide and a second Fc-region polypeptide wherein i) the first and the second Fc-region polypeptide comprise the mutations I253A, H310A and H435A, or ii) the first and the second Fc-region polypeptide comprise the mutations H310A, H433A and Y436A, or iii) the first and the second Fc-region polypeptide comprise the mutations L251D, L314D and L432D, or iv) the first Fc-region polypeptide comprises the mutations I253A, H310A and H435A and the second Fc-region polypeptide comprises a) the mutations H310A, H433A and Y436A, or b) the mutations L251D, L314D and L432D, or vi) the first Fc-region polypeptide comprises the mutations H310A, H433A and Y436A and the second Fc-region polypeptide comprises a) the mutations L251D, L314D and L432D.

In one embodiment of all aspects the antibody does not specifically bind to the human FcRn. In one embodiment of all aspects the antibody does not specifically bind to Staphylococcal protein A.

In one embodiment of all aspects the antibody does not specifically bind to the human FcRn. In one embodiment of all aspects the antibody does specifically bind to Staphylococcal protein A.

In one embodiment of all aspects the second Fc-region polypeptide further comprises the mutations Y349C, T366S, L368A and Y407V ("hole") and the first Fc-region polypeptide further comprises the mutations S354C and T366W ("knob").

In one embodiment of all aspects the Fc-region polypeptides are of the human IgG1 subclass. In one embodiment the first Fc-region polypeptide and the second Fc-region polypeptide further comprise the mutations L234A and L235A. In one embodiment the first Fc-region polypeptide and the second Fc-region polypeptide further comprise the mutation P329G.

In one embodiment of all aspects the Fc-region polypeptides are of the human IgG4 subclass. In one embodiment the first Fc-region polypeptide and the second Fc-region polypeptide further comprise the mutations S228P and L235E. In one embodiment the first Fc-region polypeptide and the second Fc-region polypeptide further comprise the mutation P329G.

In one embodiment the antibody is a bispecific antibody. In one embodiment the bispecific antibody has one binding specificity that specifically binds to human ANG-2 and one binding specificity that specifically binds to human VEGF.

One exemplary antibody as reported herein and also one aspect of the current invention is a bispecific, bivalent antibody with abolished FcRn binding comprising a first antigen-binding site that specifically binds to human VEGF and a second antigen-binding site that specifically binds to human ANG-2, wherein i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and ii) second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and wherein iii) the bispecific antibody comprises an IgG class Fc-region comprising a first and a second Fc-region polypeptide both of human IgG1 or human IgG4 subclass (derived from human origin) which comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the IgG class Fc-region.

In one embodiment of all aspects the IgG class Fc-region is a variant (human) IgG class Fc-region. In one embodiment the variant (human) IgG class Fc-region is an IgG class heterodimeric Fc-region.

In one embodiment of all aspects the pairing of the first Fc-region polypeptide and the second Fc-region polypeptide to form a (functional) IgG class Fc-region results in the formation of a heterodimer.

In one embodiment the human Fc-region polypeptide is a human Fc-region polypeptide of the IgG1 subclass or of the IgG4 subclass.

In one embodiment the human Fc-region polypeptide is a human Fc-region polypeptide of the IgG1 subclass with the mutation L234A, L235A and P329G.

In one embodiment the human Fc-region polypeptide is a human Fc-region polypeptide of the IgG4 subclass with the mutation S228P and L235E.

In one embodiment the first Fc-region polypeptide further comprises the mutations S354C and T366W and the second Fc-region polypeptide further comprises the mutations Y349C, T366S, L368A and Y407V.

In one embodiment the bispecific antibody is characterized in that i) the first antigen-binding site specifically binding to VEGF comprises as heavy chain variable domain VH an amino acid sequence of SEQ ID NO: 20 and as light chain variable domain VL an amino acid sequence of SEQ ID NO: 21, and ii) the second antigen-binding site specifically binding to ANG-2 comprises as heavy chain variable domain VH an amino acid sequence of SEQ ID NO: 28 and as light chain variable domain VL an amino acid sequence of SEQ ID NO: 29.

In one embodiment the bispecific antibody is characterized in that the Fc-region of iii) is of human IgG1 subclass. In one embodiment the bispecific antibody is characterized in that the Fc-region of human IgG1 subclass further comprises the mutations L234A, L235A and P329G (numbering according to EU Index of Kabat). In one embodiment the first Fc-region polypeptide further comprises the mutations S354C and T366W and the second Fc-region polypeptide further comprises the mutations Y349C, T366S, L368A and Y407V. In one embodiment the first Fc-region polypeptide further comprises the mutations Y349C and T366W and the second Fc-region polypeptide further comprises the mutations S354C, T366S, L368A and Y407V.

In one embodiment the bispecific antibody is characterized in that the Fc-region of iii) is of human IgG4 subclass. In one embodiment the bispecific antibody is characterized in that the Fc-region of human IgG4 subclass further comprises the mutations S228P and L235E (numbering according to EU Index of Kabat). In one embodiment the bispecific antibody is characterized in that the Fc-region of human IgG4 subclass further comprises the mutations S228P, L235E and P329G (numbering according to EU Index of Kabat). In one embodiment the first Fc-region polypeptide further comprises the mutations S354C and T366W and the second Fc-region polypeptide further comprises the mutations Y349C, T366S, L368A and Y407V. In one embodiment the first Fc-region polypeptide further comprises the mutations Y349C and T366W and the second Fc-region polypeptide further comprises the mutations S354C, T366S, L368A and Y407V.

In one embodiment the bispecific antibody comprises an Fc-region comprising a first and a second Fc-region polypeptide both of human IgG1 or human IgG4 subclass (i.e. derived from human origin), which comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region.

In one embodiment the bispecific antibody comprises an Fc-region comprising a first and a second Fc-region polypeptide both of human IgG1 or human IgG4 subclass (i.e. derived from human origin), which comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region.

Still further aspects as reported herein are a pharmaceutical formulation comprising the bispecific antibody, the pharmaceutical formulation for use in the treatment of ocular vascular diseases, the use of the bispecific antibody for the manufacture of a medicament for the treatment of ocular vascular diseases, a method of treatment of patient suffering from ocular vascular diseases by administering the bispecific antibody to a patient in the need of such treatment. In one embodiment the bispecific antibody or the pharmaceutical formulation comprising the bispecific antibody is administered via intravitreal application.

A further aspect according to the current invention is a nucleic acid molecule encoding a heavy and/or light chain of a bispecific antibody as reported herein.

The invention further provides expression plasmids containing the nucleic acid as reported herein capable of expressing the nucleic acid in a prokaryotic or eukaryotic host cell, and host cells containing such plasmids for the recombinant production of a bispecific antibody as reported herein.

The invention further comprises a prokaryotic or eukaryotic host cell comprising a plasmid as reported herein.

The invention further comprises a method for the production of a bispecific antibody as reported herein, characterized by expressing a nucleic acid as reported herein in a prokaryotic or eukaryotic host cell and recovering the bispecific antibody from the cell or the cell culture supernatant. One embodiment is a method for the preparation of a bispecific antibody as reported herein comprising the steps of a) transforming a host cell with plasmids comprising nucleic acid molecules encoding the antibody, b) culturing the host cell under conditions that allow synthesis of the antibody, and c) recovering the antibody from the culture.

The invention further comprises the antibody obtained by such method for the production of a bispecific antibody.

Figure 4:
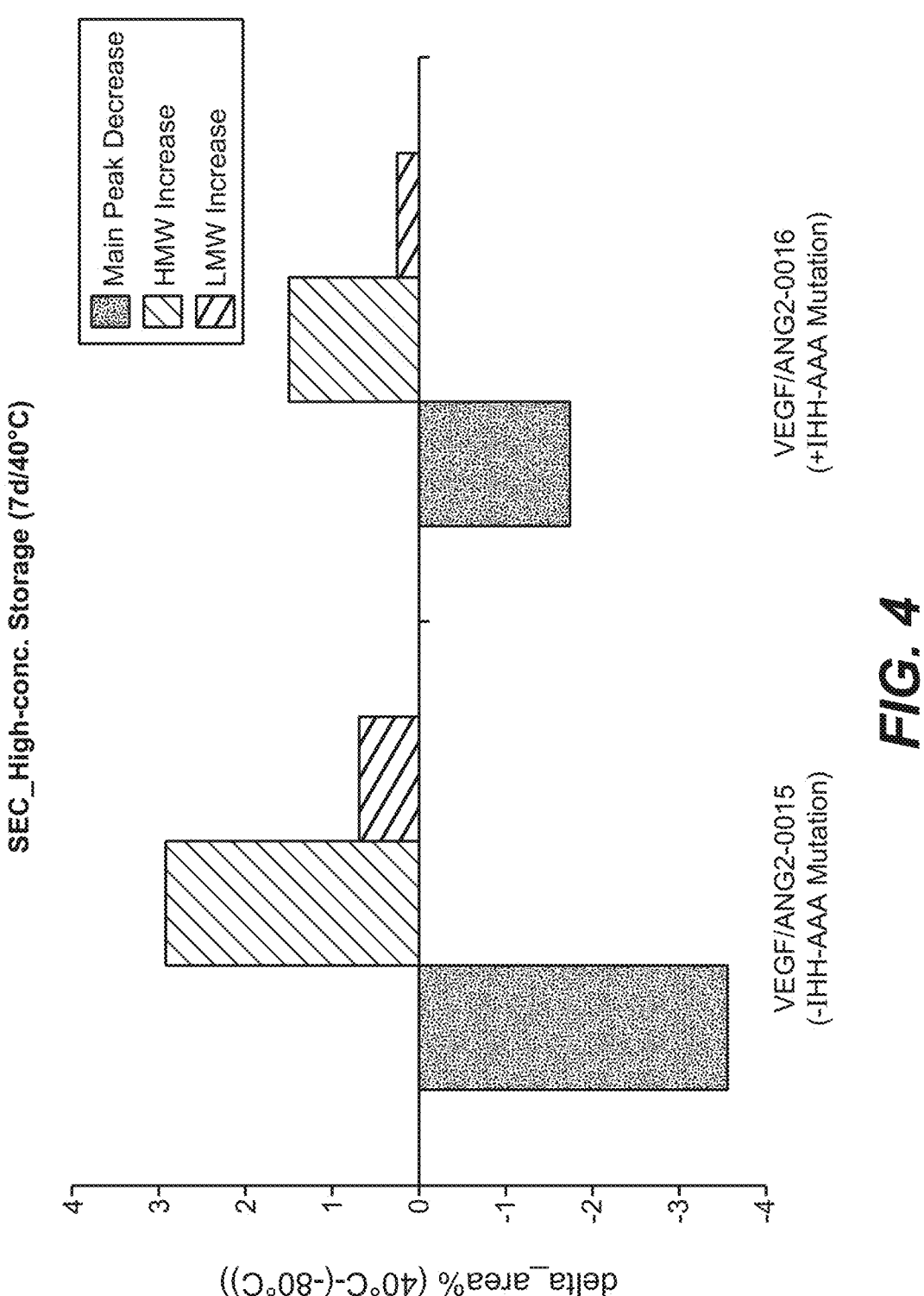
FIG. 4: Seven day storage at 40° C. at 100 mg/mL (decrease of Main Peak and High Molecular Weight (HMW) increase) (comparison of <VEGF-ANG-2> antibodies as reported herein VEGFang2-0016 (with IHH-AAA mutation) which showed a lower aggregation with a reference antibody VEGFang2-0015 (without such IHH-AAA mutation)).

The antibodies as reported herein have highly valuable properties due to their specific modifications in the Fc-region causing a benefit for a patient suffering from ocular vascular diseases. They show high stability in the intravitreal environment and slow diffusion from the eye (compared to smaller antibody fragments without a constant heavy chain region), where the actual disease is located and treated (so treatment schedule may potentially be improved compared to non-full length IgG-like antibodies like e.g. Fab and (Fab)2 fragments. The antibodies as reported herein are cleared on the other hand quite rapidly from serum (which is highly desired to reduce potential side effects arising from systemic exposure). Surprisingly they also show lower viscosity (see FIG. 2) (compared to versions without the mutations I253A, H310A and H435A in the constant region) and are therefore especially useful for intravitreal application through thin needles during the treatment of eye diseases (for such application typically thin needles are used and high viscosity makes an appropriate application rather difficult). The lower viscosity also allows higher concentration formulations. Also surprisingly the antibodies as reported herein show a lower aggregation tendency (see FIG. 4) during storage (compared to versions without the mutations I253A, H310A and H435A in the Fc-region) which is critical for intravitreal application in the eye (as an aggregation in the eye can lead to complications during such treatment). The bispecific antibodies as reported herein show good efficacy in inhibition of vascular diseases. In certain embodiments, the bispecific antibodies as reported herein due to their specific modifications in the constant region (e.g. P329G LALA) show valuable properties like no binding to/of Fcgamma receptors which reduces the risk of side effects like thrombosis and/or unwanted cell death (due to e.g. ADCC).

In one embodiment as reported herein the bispecific antibody as reported herein is bivalent.

In one aspect according to the invention such bispecific, bivalent antibody as reported herein is characterized in comprising a) the heavy chain and the light chain of a first full length antibody that specifically binds to VEGF, and b) the modified heavy chain and modified light chain of a second full length antibody that specifically binds to ANG-2, in which the constant domains CL and CH1 are replaced by each other.

This bispecific, bivalent antibody format for the bispecific antibody specifically binding to human vascular endothelial growth factor (VEGF) and human angiopoietin-2 (ANG-2)

is described in WO 2009/080253 (including knobs-into-holes modified CH3 domains). The antibodies based on this bispecific, bivalent antibody format are named CrossMabs.

In one embodiment such bispecific, bivalent antibody is characterized in comprising
   a) as heavy chain of the first full length antibody the amino acid sequence of SEQ ID NO: 102 and as light chain of the first full length antibody the amino acid sequence of SEQ ID NO: 36, and
   b) as modified heavy chain of the second full length antibody the amino acid sequence of SEQ ID NO: 103 and as modified light chain of the second full length antibody the amino acid sequence of SEQ ID NO: 37.

In one embodiment such bispecific, bivalent antibody is characterized in comprising
   a) as heavy chain of the first full length antibody the amino acid sequence of SEQ ID NO: 104 and as light chain of the first full length antibody the amino acid sequence of SEQ ID NO: 40, and
   b) as modified heavy chain of the second full length antibody the amino acid sequence of SEQ ID NO: 105 and as modified light chain of the second full length antibody the amino acid sequence of SEQ ID NO: 41.

In one embodiment such bispecific, bivalent antibody is characterized in comprising
   a) as heavy chain of the first full length antibody the amino acid sequence of SEQ ID NO: 106 and as light chain of the first full length antibody the amino acid sequence of SEQ ID NO: 44, and
   b) as modified heavy chain of the second full length antibody the amino acid sequence of SEQ ID NO: 107 and as modified light chain of the second full length antibody the amino acid sequence of SEQ ID NO: 45.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 102, of SEQ ID NO: 103, of SEQ ID NO: 36, and of SEQ ID NO: 37.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 104, of SEQ ID NO: 105, of SEQ ID NO: 40, and of SEQ ID NO: 41.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 106, of SEQ ID NO: 107, of SEQ ID NO: 44, and of SEQ ID NO: 45.

In another aspect as reported herein the bispecific antibody as reported herein is characterized in comprising
   a) the heavy chain and the light chain of a first full length antibody that specifically binds to VEGF, and
   b) the heavy chain and the light chain of a second full length antibody that specifically binds to ANG-2, wherein the N-terminus of the heavy chain is connected to the C-terminus of the light chain via a peptidic linker.

This bispecific, bivalent antibody format for this bispecific antibody specifically binding to human vascular endothelial growth factor (VEGF) and human angiopoietin-2 (ANG-2) is described in WO 2011/117330 (including knobs-into-holes modified CH3 domains). The antibodies based on this bispecific, bivalent antibody format are named one-armed single chain Fabs (OAscFabs).

In one embodiment such bispecific, bivalent antibody is characterized in comprising
   a) as heavy chain of the first full length antibody the amino acid sequence of SEQ ID NO: 108 and as light chain of the first full length antibody the amino acid sequence of SEQ ID NO: 48, and
   b) as heavy chain of the second full length antibody connected to the light chain of the second full length antibody via a peptidic linker the amino acid sequence of SEQ ID NO: 109.

In one embodiment such bispecific, bivalent antibody is characterized in comprising
   a) as heavy chain of the first full length antibody the amino acid sequence of SEQ ID NO: 110 and as light chain of the first full length antibody the amino acid sequence of SEQ ID NO: 51, and
   b) as heavy chain of the second full length antibody connected to the light chain of the second full length antibody via a peptidic linker the amino acid sequence of SEQ ID NO: 111.

In one embodiment the antibody heavy chain variable domain (VH) and the antibody light chain variable domain (VL) of the heavy and light chain of the second full length antibody are further stabilized by introduction of a disulfide bond between the following positions: heavy chain variable domain position 44 and light chain variable domain position 100 (numbering according to EU index of Kabat (Kabat, E. A., et al., Sequences of Proteins of Immunological Interest, 5th ed., Public Health Service, National Institutes of Health, Bethesda, MD (1991)). Techniques to introduce disulfide bridges for stabilization are described e.g. in WO 94/029350, Rajagopal, V., et al, Prot. Eng. 10 (1997) 1453-1459, Kobayashi et al., Nuclear Medicine & Biology 25 (1998) 387-393, and Schmidt, M., et al., Oncogene 18 (1999) 1711-1721.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 108, of SEQ ID NO: 109, and of SEQ ID NO: 48.

Accordingly one aspect as reported herein is a bispecific, bivalent antibody comprising a first antigen-binding site that specifically binds to human VEGF and a second antigen-binding site that specifically binds to human ANG-2, characterized in comprising the amino acid sequences of SEQ ID NO: 110, of SEQ ID NO: 111, and of SEQ ID NO: 51.

In one embodiment the CH3 domains of the bispecific, bivalent antibody as reported herein are altered by the "knob-into-holes" technology which is described in detail with several examples e.g. in WO 96/027011, Ridgway J. B., et al., Protein Eng. 9 (1996) 617-621, and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob" while the other is the "hole". The introduction of a disulfide bridge further stabilizes the heterodimers (Merchant, A. M, et al., Nature Biotech. 16 (1998) 677-681, Atwell, S., et al. J. Mol. Biol. 270 (1997) 26-35) and increases the yield.

In one preferred embodiment of all aspects as reported herein the bispecific antibodies is characterized in that the CH3 domain of one heavy chain and the CH3 domain of the other heavy chain each meet at an interface which comprises an original interface between the antibody CH3 domains, wherein the interface is altered to promote the formation of the bispecific antibody, wherein the alteration is characterized in that:

a) the CH3 domain of one heavy chain is altered, so that within the original interface the CH3 domain of one heavy chain that meets the original interface of the CH3 domain of the other heavy chain within the bispecific antibody an amino acid residue is replaced with an amino acid residue having a larger side chain volume, thereby generating a protuberance within the interface of the CH3 domain of one heavy chain which is positionable in a cavity within the interface of the CH3 domain of the other heavy chain, and b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

Thus, the antibody according to invention is in one preferred embodiment characterized in that the CH3 domain of the heavy chain of the full length antibody of a) and the CH3 domain of the heavy chain of the full length antibody of b) each meet at an interface which comprises an alteration in the original interface between the antibody's CH3 domains, wherein i) in the CH3 domain of one heavy chain an amino acid residue is replaced with an amino acid residue having a larger side chain volume, thereby generating a protuberance within the interface of the CH3 domain of one heavy chain which is positionable in a cavity within the interface of the CH3 domain of the other heavy chain, and wherein ii) in the CH3 domain of the other heavy chain an amino acid residue is replaced with an amino acid residue having a smaller side chain volume, thereby generating a cavity within the interface of the second CH3 domain within which a protuberance within the interface of the first CH3 domain is positionable.

In one preferred embodiment the amino acid residue having a larger side chain volume is selected from the group consisting of arginine (R), phenylalanine (F), tyrosine (Y), tryptophan (W).

In one preferred embodiment the amino acid residue having a smaller side chain volume is selected from the group consisting of alanine (A), serine (S), threonine (T), valine (V).

In one embodiment both CH3 domains are further altered by the introduction of a cysteine residue (C) in the corresponding positions of each CH3 domain such that a disulfide bridge between both CH3 domains can be formed.

In one embodiment, the bispecific antibody comprises a T366W mutation in the CH3 domain of the "knobs chain" and the T366S, L368A and Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C or S354C mutation into the CH3 domain of the "knobs chain" and a Y349C or E356C or S354C mutation into the CH3 domain of the "hole chain".

In one embodiment the bispecific antibody as reported herein comprises the mutation Y349C or S354C and the mutation T366W in one of the two CH3 domains and the mutation S354C or E356C or Y349C and the mutations T366S, L368A and Y407V in the other of the two CH3 domains. In one preferred embodiment the bispecific antibody comprises the Y349C, T366W mutations in one of the two CH3 domains and the S354C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, MD (1991)). In one preferred embodiment the bispecific antibody comprises the S354C, T366W mutations in one of the two CH3 domains and the Y349C, T366S, L368A, Y407V mutations in the other of the two CH3 domains (the additional Y349C mutation in one CH3 domain and the additional S354C mutation in the other CH3 domain forming a interchain disulfide bridge) (numbering according to EU index of Kabat (Kabat, E. A., et al., Sequences of Proteins of Immunological Interest, 5th ed., Public Health Service, National Institutes of Health, Bethesda, MD (1991)).

But also other knobs-in-holes technologies as described by EP 1 870 459 A1, can be used alternatively or additionally. Thus another example for the bispecific antibody are the R409D and K370E mutations in the CH3 domain of the "knobs chain" and the D399K and E357K mutations in the CH3 domain of the "hole chain" (numbering according to EU index of Kabat (Kabat, E. A., et al., Sequences of Proteins of Immunological Interest, 5th ed., Public Health Service, National Institutes of Health, Bethesda, MD (1991)).

In another embodiment the bispecific antibody comprises a T366W mutation in the CH3 domain of the "knobs chain" and the T366S, L368A and Y407V mutations in the CH3 domain of the "hole chain" and additionally the R409D, K370E mutations in the CH3 domain of the "knobs chain" and the D399K, E357K mutations in the CH3 domain of the "hole chain".

In one embodiment the bispecific antibody comprises the Y349C, T366W mutations in one of the two CH3 domains and the S354C, T366S, L368A and Y407V mutations in the other of the two CH3 domains, or the bispecific antibody comprises the Y349C, T366W mutations in one of the two CH3 domains and the S354C, T366S, L368A and Y407V mutations in the other of the two CH3 domains and additionally the R409D, K370E mutations in the CH3 domain of the "knobs chain" and the D399K, E357K mutations in the CH3 domain of the "hole chain".

In one embodiment the bispecific antibody comprises the S354C, T366W mutations in one of the two CH3 domains and the Y349C, T366S, L368A, Y407V mutations in the other of the two CH3 domains, or the bispecific antibody comprises the S354C, T366W mutations in one of the two CH3 domains and the Y349C, T366S, L368A and Y407V mutations in the other of the two CH3 domains and additionally the R409D, K370E mutations in the CH3 domain of the "knobs chain" and the D399K, E357K mutations in the CH3 domain of the "hole chain".

In one embodiment as reported herein the bispecific antibody as reported herein is characterized in having one or more of the following properties:

shows a lower serum concentration compared to corresponding bispecific antibody without the mutations described under iii) (96 hours after intravitreal application in mice, which are mouse FcRn deficient, but hemizygous transgenic for human FcRn) (determined in assays as described in Example 6), and/or shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye) (determined in assays as described in Example 6), and has abolished binding to the human FcRn, and/or has no binding to Staphylococcal protein A (determined by SPR), and/or has maintained binding to Staphylococcal protein A (determined by SPR).

In one embodiment the bispecific, bivalent antibody is characterized in comprising a first antigen-binding site that specifically binds to human VEGF and a second antigen-binding site that specifically binds to human ANG-2, characterized in that i) the first antigen-binding site comprises as heavy chain variable domain (VH) the SEQ ID NO: 20 and as light chain variable domain (VL) the SEQ ID NO: 21; and ii) the second antigen-binding site comprises as heavy chain variable domain (VH) the SEQ ID NO: 28 and as light chain variable domain (VL) the SEQ ID NO: 29, and iii) the bispecific antibody comprises α) an IgG class Fc-region comprising a first and a second Fc-region polypeptide both of human IgG1 or human IgG4 subclass (derived from human origin) which comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region, or β) an IgG class Fc-region comprising a first and a second Fc-region polypeptide both of human IgG1 or human IgG4 subclass (i.e. derived from human origin), which both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region, or γ) an IgG class Fc-region comprising a first and a second Fc-region polypeptide both of human IgG1 or human IgG4 subclass (i.e. derived from human origin), which comprise the mutations I253A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system), and having one or more of the following properties:

shows a lower serum concentration compared to corresponding bispecific antibody without the mutations described under iii) (96 hours after intravitreal application in mice, which are mouse FcRn deficient, but hemizygous transgenic for human FcRn) (determined in assays as described in Example 6), and/or shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye) (determined in assays as described in Example 6), and/or has abolished binding to the human FcRn, and/or has no binding to Staphylococcal protein A (determined by SPR), and/or has maintained binding to Staphylococcal protein A (determined by SPR).

In one embodiment the bispecific antibody is characterized in comprising a first antigen-binding site that specifically binds to human VEGF and a second antigen-binding site that specifically binds to human ANG-2, characterized in that i) the first antigen-binding site comprises as heavy chain variable domain (VH) the SEQ ID NO: 20 with 1, 2 or 3 amino acid residue substitutions, and as light chain variable domain (VL) the SEQ ID NO: 21 with 1, 2 or 3 amino acid residue substitutions; and ii) the second antigen-binding site comprises as heavy chain variable domain (VH) the SEQ ID NO: 28 with 1, 2 or 3 amino acid residue substitutions, and as light chain variable domain (VL) the SEQ ID NO: with 1, 2 or 3 amino acid residue substitutions; and iii) the bispecific antibody comprises α) an IgG class Fc-region comprising a first and a second Fc-region polypeptide both of human IgG1 or human IgG4 subclass (derived from human origin) which comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region, or β) an IgG class Fc-region comprising a first and a second Fc-region polypeptide both of human IgG1 or human IgG4 subclass (i.e. derived from human origin), which both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region, or γ) an IgG class Fc-region comprising a first and a second Fc-region polypeptide both of human IgG1 or human IgG4 subclass (i.e. derived from human origin), which comprise the mutations I253A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system), and having one or more of the following properties:

shows a lower serum concentration compared to corresponding bispecific antibody without the mutations described under iii) (96 hours after intravitreal application in mice, which are mouse FcRn deficient, but hemizygous transgenic for human FcRn) (determined in assays as described in Example 6), and/or shows a similar (factor 0.8 to 1.2) concentration in whole right eye lysates compared to corresponding bispecific antibody without the mutations described under iii) (in mice, which are mouse FcRn deficient, but hemizygous transgenic for human FcRn, 96 hours after intravitreal application in the right eye) (determined in assays as described in Example 6), and/or has abolished binding to the human FcRn, and/or has no binding to Staphylococcal protein A (determined by SPR), and/or has maintained binding to Staphylococcal protein A (determined by SPR).

An antigen-binding sites of the bispecific antibody as reported herein contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

The antibody as reported herein is produced by recombinant means. Thus, one aspect of the current invention is a nucleic acid encoding the antibody as reported herein and a further aspect is a cell comprising the nucleic acid encoding an antibody as reported herein. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective (modified) light and heavy chains are inserted into expression plasmids by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (cultivation supernatant or cells after lysis). General methods for recombinant production of antibodies are well-known in the state of the art and described, for example, in the review articles of Makrides, S. C., Protein Expr. Purif. 17 (1999) 183-202, Geisse, S., et al., Protein Expr. Purif. 8 (1996) 271-282, Kaufman, R. J., Mol. Biotechnol. 16 (2000) 151-160, and Werner, R. G., Drug Res. 48 (1998) 870-880.

Accordingly one aspect as reported herein is a method for the preparation of a bispecific antibody as reported herein, comprising the steps of a) transforming a host cell with plasmids comprising nucleic acid molecules encoding the antibody, b) culturing the host cell under conditions that allow synthesis of the antibody, and c) recovering the antibody from the culture.

In one embodiment the recovering step under c) includes the use of a light chain constant domain specific capture reagent (which e.g. specific for the kappa or the lambda constant light chain, depending on whether a kappa or a lambda light chain is used in the bispecific antibody). In one embodiment the light chain specific capture reagent is used in in a bind-and-elute-mode. Examples of such light chain constant domain specific capture reagents are e.g. KappaSelect™ and LambdaFabSelect™ (available from GE Healthcare/BAC), which are based on a highly rigid agarose base matrix that allows high flow rates and low back pressure at large scale. These materials contain a ligand that binds to the constant region of the kappa or the lambda light chain, respectively (i.e. fragments lacking the constant region of the light chain will not bind; FIG. 1). Both are therefore capable of binding other target molecules containing the constant region of the light chain, for example, IgG, IgA and IgM. The ligands are attached to the matrix via a long hydrophilic spacer arm to make them easily available for binding to the target molecule. They are based on a single-chain antibody fragment that is screened for either human Ig kappa or lambda.

In one embodiment the recovering step under c) includes the use of an Fc-region specific capture reagent. In one embodiment the Fc-region specific capture reagent is used in a bind-and-elute-mode. Examples of such Fc-region specific capture reagents are e.g. Staphylococcus protein A-based affinity chromatography materials.

The bispecific antibodies are suitably separated from the culture medium by conventional immunoglobulin purification procedures such as, for example, affinity chromatography (protein A-Sepharose, KappaSelect™, LambdaFabSelect™), hydroxylapatite chromatography, gel electrophoresis, or dialysis.

DNA and RNA encoding the monoclonal antibodies is readily isolated and sequenced using conventional procedures. B-cells or hybridoma cells can serve as a source of such DNA and RNA. Once isolated, the DNA may be inserted into expression plasmids, which are then transfected into host cells such as HEK 293 cells, CHO cells, or myeloma cells that do not otherwise produce immunoglobulin protein, to obtain the synthesis of recombinant mono-clonal antibodies in the host cells.

Some of the (bispecific) antibody as reported herein provide ease of isolation/purification by comprising Fc-regions that are differentially modified, wherein at least one of the modifications results in i) a differential affinity of the (bispecific) antibody for protein A, and ii) a differential affinity of the (bispecific) antibody for the human FcRn, and the (bispecific) antibody is isolable from a disrupted cell, from medium, or from a mixture of antibodies based on its affinity for protein A.

Purification of antibodies is performed in order to elimi-nate cellular components or other contaminants, e.g. other cellular nucleic acids or proteins, by standard techniques, including alkaline/SDS treatment, CsCl banding, column chromatography, agarose gel electrophoresis, and others well known in the art (see e.g. Ausubel, F., et al., ed. Current Protocols in Molecular Biology, Greene Publishing and Wiley Interscience, New York (1987)). Different methods are well established and widespread used for protein puri-fication, such as affinity chromatography with microbial proteins (e.g. protein A or protein G affinity chromatogra-phy), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-amino-phenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The bivalent bispecific antibody against human VEGF and human ANG-2 as reported herein may have a valuable efficacy/safety profile and may provide benefits for a patient in the need of an anti-VEGF and anti-ANG-2 therapy.

One aspect as reported herein is a pharmaceutical formu-lation comprising an antibody as reported herein. Another aspect as reported herein is the use of an antibody as reported herein for the manufacture of a pharmaceutical formulation. A further aspect as reported herein is a method for the manufacture of a pharmaceutical formulation com-prising an antibody as reported herein. In another aspect, a formulation is provided, e.g. a pharmaceutical formulation, containing an antibody as reported herein, formulated together with a pharmaceutical carrier.

A formulation as reported herein can be administered by a variety of methods known in the art. As will be appreciated by the skilled artisan, the route and/or mode of administra-tion will vary depending upon the desired results. To admin-ister a compound as reported herein by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically accept-able diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical applica-tion. In one embodiment the application is intraocular and includes, but it's not limited to, subconjunctival injection, intracanieral injection, injection into the anterior chamber via the termporai limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but it's not limited to eye drops to the cornea.

In one embodiment the bispecific antibody or pharma-ceutical formulation as reported herein is administered via intravitreal application, e.g. via intravitreal injection. This can be performed in accordance with standard procedures known in the art (see, e.g., Ritter et al., J. Clin. Invest. 116 (2006) 3266-3276, Russelakis-Carneiro et al., Neuropathol. Appl. Neurobiol. 25 (1999) 196-206, and Wray et al., Arch. Neurol. 33 (1976) 183-185).

In some embodiments, therapeutic kits as reported herein can contain one or more doses of a (bispecific) antibody present in a pharmaceutical formulation described herein, a suitable device for intravitreal injection of the pharmaceu-tical formulation, and an instruction detailing suitable sub-jects and protocols for carrying out the injection. In these embodiments, the formulations are typically administered to the subject in need of treatment via intravitreal injection. This can be performed in accordance with standard proce-dures known in the art (see, e.g., Ritter et al., J. Clin. Invest. 116 (2006) 3266-3276, Russelakis-Carneiro et al., Neu-ropathol. Appl. Neurobiol. 25 (1999) 196-206, and Wray et al., Arch. Neurol. 33 (1976) 183-185).

The formulations may also contain adjuvants such as preservatives, wetting agents, emulsifying agents and dis-persing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the inject-able pharmaceutical form may be brought about by the inclusion of agents which delay absorption such as alumi-num monostearate and gelatin.

Regardless of the route of administration selected, the compounds as reported herein, which may be used in a suitable hydrated form, and/or the pharmaceutical formula-tions as reported herein, are formulated into pharmaceuti-cally acceptable dosage forms by conventional methods known to those of skill in the art.

Actual dosage levels of the active ingredients in the pharmaceutical formulations of as reported herein may be varied so as to obtain an amount of the active ingredient which is effective to achieve the desired therapeutic response for a particular patient, formulation, and mode of administration, without being toxic to the patient. The selected dosage level will depend upon a variety of phar-macokinetic factors including the activity of the particular formulations as reported herein employed, the route of administration, the time of administration, the rate of excre-tion of the particular compound being employed, the dura-tion of the treatment, other drugs, compounds and/or mate-rials used in combination with the particular formulations employed, the age, sex, weight, condition, general health and prior medical history of the patient being treated, and like factors well known in the medical arts.

The formulation must be sterile and fluid to the extent that the formulation is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the formulation.

The formulation can comprise an ophthalmic depot formulation comprising an active agent for subconjunctival administration. The ophthalmic depot formulation comprises microparticles of essentially pure active agent, e.g., the bispecific antibody as reported herein. The microparticles comprising the bispecific antibody as reported herein can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect as reported herein is the bispecific antibody as reported herein for use in the treatment of ocular vascular diseases.

One embodiment as reported herein is the bispecific antibody as reported herein for use in the treatment of ocular vascular diseases.

Another aspect as reported herein is the pharmaceutical formulation as reported herein for use in the treatment of ocular vascular diseases.

Another aspect as reported herein is the use of an antibody as reported herein for the manufacture of a medicament for the treatment of ocular vascular disease.

Another aspect as reported herein is method of treatment of patient suffering from ocular vascular diseases by administering an antibody as reported herein to a patient in the need of such treatment.

It is herewith expressly stated that the term "comprising" as used herein comprises the term "consisting of". Thus, all aspects and embodiments that contain the term "comprising" are likewise disclosed with the term "consisting of".

D. Modifications

In a further aspect, an antibody according to any of the above embodiments may incorporate any of the features, singly or in combination, as described in Sections 1-6 below:

1. Antibody Affinity

In certain embodiments, an antibody provided herein has a dissociation constant (Kd) of $\leq 100$ nM, $\leq 10$ nM (e.g. $10^{-7}$ M or less, e.g. from $10^{-7}$ M to $10^{-13}$ M, e.g., from $10^{-8}$ M to $10^{-13}$ M).

In one embodiment, Kd is measured using a BIACORE® surface plasmon resonance assay. For example, an assay using a BIACORE®-2000 or a BIACORE®-3000 (GE Healthcare Inc., Piscataway, NJ) is performed at 25° C. with immobilized antigen CMS chips at ~10 response units (RU). In one embodiment, carboxymethylated dextran biosensor chips (CMS, GE Healthcare Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/mL (~0.2 µM) before injection at a flow rate of 5 µL/minute to achieve approximately 10 response units (RU) of coupled protein. Following the injection of antigen, 1 M ethanolamine is injected to block non-reacted groups. For kinetics measurements, two-fold serial dilutions (e.g. of Fab) (0.78 nM to 500 nM) are injected in PBS with 0.05% polysorbate 20 (TWEEN-20™) surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Antibodies

In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F., et al., Methods 36 (2005) 43-60 (describing "FR shuffling"); Osbourn, J., et al., Methods 36 (2005) 61-68; and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol.5 (2001) 368-374 and Lonberg, N., Curr. Opin. Immunol. 20 (2008) 450-459.

Human antibodies maybe prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125 (see also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J., et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies may also be used to localize cytotoxic agents to cells which express at least one of the antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No.

4,676,980, and Brennan, M. et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tuft, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |

TABLE-continued

| Original Residue | Exemplary Substitutions | Preferred Substitutions |
|---|---|---|
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or down-stream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more further amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution/mutation) at one or more amino acid positions.

In certain embodiments, the invention contemplates an antibody variant that possesses some but not all effector functions, which make it a desirable candidate for applications in which the half-life of the antibody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express Fc☐RI, Fc☐RII and Fc☐RIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest are described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Antibodies with reduced effector function include those with substitution of one or more of Fc-region residues 238, 265, 269, 270, 297, 327 and 329 (U.S. Pat. No. 6,737,056). Such Fc-region variants include Fc-regions with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

f) Heterodimerization

There exist several approaches for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the multispecific antibodies according to the invention which reduce light chain mispairing an Bence-Jones type side products.

In one preferred embodiment of the invention (in case the multispecific antibody comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO 98/050431(In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one embodiment of the invention said multispecific antibody (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains.

wherein said interface is altered to promote the formation of the multispecific antibody, wherein the alteration is characterized in that:

i) the CH3 domain of one heavy chain is altered, so that within the original interface of the CH3 domain of one heavy chain that meets the original interface of the CH3 domain of the other heavy chain within the multispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the multispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said multispecific antibody comprises a amino acid T366W mutation in the first CH3 domain of the "knobs chain" and amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681) e.g. by introducing an amino acid Y349C mutation into the CH3 domain of the "hole chain" and an amino acid E356C mutation or an amino acid S354C mutation into the CH3 domain of the "knobs chain".

In one preferred embodiment, said multispecific antibody (which comprises a CH3 domain in each heavy chain) comprises amino acid S354C, T366W mutations in one of the two CH3 domains and amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459A1, can be used alternatively. This approach is based on the by the introduction of substitutions/mutations of charged amino acids with the opposite charge at specific amino acid positions of the in the CH3/CH3 domain interface between both heavy chains. One preferred embodiment for said multispecific antibody are amino acid R409D; K370E mutations in the first CH3 domain of the (of the multispecific antibody) and amino acid D399K; E357K mutations in the seconds CH3 domain of the multispecific antibody (numbering according to Kabat).

In another embodiment said multispecific antibody comprises a amino acid T366W mutation in the CH3 domain of the "knobs chain" and amino acid T366S, L368A, Y407V mutations in the CH3 domain of the "hole chain" and additionally amino acid R409D; K370E mutations in the CH3 domain of the "knobs chain" and amino acid D399K; E357K mutations in the CH3 domain of the "hole chain".

In another embodiment said multispecific antibody comprises amino acid S354C, T366W mutations in one of the two CH3 domains and amino acid Y349C, T366S, L368A, Y407V mutations in the other of the two CH3 domains or said multispecific antibody comprises amino acid Y349C, T366W mutations in one of the two CH3 domains and amino acid S354C, T366S, L368A, Y407V mutations in the other of the two CH3 domains and additionally amino acid R409D; K370E mutations in the CH3 domain of the "knobs chain" and amino acid D399K; E357K mutations in the CH3 domain of the "hole chain".

In one embodiment the heterodimerization approach described in WO2013/157953 can be used alternatively. In one embodiment a first CH3 domain comprises amino acid T366K mutation and a second CH3 domain polypeptide comprises amino acid L351D mutation. In a further embodiment the first CH3 domain comprises further amino acid L351K mutation. In a further embodiment the second CH3 domain comprises further amino acid mutation selected from Y349E, Y349D and L368E (preferably L368E).

In one embodiment the heterodimerization approach described in WO2012/058768 can be used alternatively. In one embodiment a first CH3 domain comprises amino acid L351Y, Y407A mutations and a second CH3 domain comprises amino acid T366A, K409F mutations. In a further embodiment the second CH3 domain comprises a further amino acid mutation at position T411, D399, 5400, F405, N390, or K392 e.g. selected from a) T411 N, T411R, T411Q, T411 K, T411D, T411E or T411W, b) D399R, D399W, D399Y or D399K, c S400E, S400D, S400R, or S400K F4051, F405M, F405T, F405S, F405V or F405W N390R, N390K or N390D K392V, K392M, K392R, K392L, K392F or K392E. In a further embodiment a first CH3 domain comprises amino acid L351Y, Y407A mutations and a second CH3 domain comprises amino acid T366V, K409F mutations. In a further embodiment a first CH3 domain comprises amino acid Y407A mutations and a second CH3 domain comprises amino acid T366A, K409F mutations. In a further embodiment the second CH3 domain comprises a further amino acid K392E, T411E, D399R and S400R mutations.

In one embodiment the heterodimerization approach described in WO2011/143545 can be used alternatively e.g. with the amino acid modification at a position selected from the group consisting of 368 and 409.

In one embodiment the heterodimerization approach described in WO2011/090762 which also uses the knobs-into-holes technology described above can be used alternatively. In one embodiment a first CH3 domain comprises amino acid T366W mutations and a second CH3 domain comprises amino acid Y407A mutations. In one embodiment a first CH3 domain comprises amino acid T366Y mutations and a second CH3 domain comprises amino acid Y407T mutations.

In one embodiment the multispecific antibody is of IgG2 isotype and the heterodimerization approach described in WO2010/129304 can be used alternatively.

In one embodiment the heterodimerization approach described in WO2009/089004 can be used alternatively. In one embodiment a first CH3 domain comprises amino acid substitution of K392 or N392 with a negative-charged amino acid (e.g. glutamic acid (E), or aspartic acid (D), preferably K392D or N392D) and a second CH3 domain comprises amino acid substitution of D399, E356, D356, or E357 with a positive-charged amino acid (e.g. Lysine (K) or arginine (R), preferably D399K, E356K, D356K, or E357K and more preferably D399K and E356K. In a further embodiment the first CH3 domain further comprises amino acid substitution of K409 or R409 with a negative-charged amino acid (e.g. glutamic acid (E), or aspartic acid (D), preferably K409D or R409D). In a further embodiment the first CH3 domain further or alternatively comprises amino acid substitution of K439 and/or K370 with a negative-charged amino acid (e.g. glutamic acid (E), or aspartic acid (D)).

In one embodiment the heterodimerization approach described in WO2007/147901 can be used alternatively. In one embodiment a first CH3 domain comprises amino acid K253E, D282K, and K322D mutations and a second CH3 domain comprises amino acid D239K, E240K, and K292D mutations.

In one embodiment the heterodimerization approach described in WO2007/110205 can be used alternatively.

E. Recombinant Methods and Compositions

Antibodies may be produced using recombinant methods and compositions, e.g., as described in U.S. Pat. No. 4,816, 567. In one embodiment, isolated nucleic acid(s) encoding an antibody as reported herein is(are) provided. Such nucleic acid may encode an amino acid sequence comprising the VL and/or an amino acid sequence comprising the VH of the antibody (e.g., the light and/or heavy chains of the antibody). In a further embodiment, one or more plasmids (e.g., expression plasmids) comprising such nucleic acid are provided. In a further embodiment, a host cell comprising such nucleic acid is provided. In one such embodiment, a host cell comprises (e.g., has been transformed with): (1) a plasmid comprising a nucleic acid that encodes an amino acid sequence comprising the VL of the antibody and an amino acid sequence comprising the VH of the antibody, or (2) a first plasmid comprising a nucleic acid that encodes an amino acid sequence comprising the VL of the antibody and a second plasmid comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody as reported herein, nucleic acid encoding an antibody, e.g., as described above, is isolated and inserted into one or more plasmids for further cloning and/or expression in a host cell. Such nucleic acid may be readily isolated and sequenced using conventional procedures (e.g., by using oligonucleotide probes that are capable of binding specifically to genes encoding the variant Fc-region polypeptide or the heavy and light chains of the antibody).

Suitable host cells for cloning or expression of antibody-encoding plasmids include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, NJ (2003), pp. 245-254, describing expression of antibody fragments in *E. coli.*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding plasmids, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK)p; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

F. Combination Treatment

In certain embodiments the antibody or pharmaceutical formulation as reported herein is administered alone (without an additional therapeutic agent) for the treatment of one or more ocular vascular diseases described herein.

In other embodiments the antibody or pharmaceutical formulation as reported herein is administered in combination with one or more additional therapeutic agents or methods for the treatment of one or more vascular eye diseases described herein.

In other embodiments, the antibody or pharmaceutical formulation as reported herein is formulated in combination with one or more additional therapeutic agents and administered for the treatment of one or more vascular eye diseases described herein.

In certain embodiments, the combination treatments provided herein include that the antibody or pharmaceutical formulation as reported herein is administered sequentially with one or more additional therapeutic agents for the treatment of one or more ocular vascular diseases described herein.

The additional therapeutic agents include, but are not limited to, Tryptophanyl-tRNA synthetase (TrpRS), EyeOOl (anti-VEGF PEGylated aptamer), squalamine, RETAANE™ (anecortave acetate for depot suspension; Alcon, Inc.), Combretastatin A4 Prodrug (CA4P), MACU-GEN™, MIFEPREX™ (mifepristone-ru486), subtenon triamcinolone acetonide, intravitreal crystalline triamcinolone acetonide, Prinomastat (AG3340-synthetic matrix metalloproteinase inhibitor, Pfizer), fluocinolone acetonide (including fluocinolone intraocular implant, Bausch & Lomb/Control Delivery Systems), VEGFR inhibitors (Sugen), VEGF-Trap (Regeneron/Aventis), VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin v.beta.3 function and angiostatin.

Other pharmaceutical therapies that can be used in combination with the antibody or pharmaceutical formulation as reported herein, including, but are not limited to, VISU-DYNE™ with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sima Therapeutics, Inc.), pegaptanib (NeXstar Pharmaceuticals/Gilead Sciences), neurotrophins (including, by way of example only, NT-4/5, Genentech), Candy (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group pic), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, Timited retinal translocation, photodynamic therapy, (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Any anti-angiogenic agent can be used in combination with the antibody or pharmaceutical formulation as reported herein, including, but not limited to, those listed by Carmeliet and Jain, Nature 407 (2000) 249-257. In certain embodiments, the anti-angiogenic agent is another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof and these include anti-VEGF aptamers (e.g. Pegaptanib), soluble recombinant decoy receptors (e.g. VEGF Trap). In certain embodiments, the anti-angiogenic agent is include corticosteroids, angiostatic steroids, anecortave acetate, angiostatin, endostatin, small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-I antibodies. Small molecule RTK inhibitors targeting VEGF receptors including PTK787 can also be used. Agents that have activity against neovascularization that are not necessarily anti-VEGF compounds can also be used and include anti-inflammatory drugs, m-Tor inhibitors, rapamycin, everolismus, temsirolismus, cyclospohne, anti-TNF agents, anti-complement agents, and non-steroidal anti-inflammatory agents. Agents that are neuroprotective and can potentially reduce the progression of dry macular degeneration can also be used, such as the class of drugs called the "neurosteroids". These include drugs such as dehydroepiandrosterone (DHEA) (Brand names: Prastera® and Fidelin®), dehydroepiandrosterone sulfate, and pregnenolone sulfate. Any AMD (age-related macular degeneration) therapeutic agent can be used in combination with the bispecific antibody or pharmaceutical formulation as reported herein, including but not limited to verteporfin in combination with PDT, pegaptanib sodium, zinc, or an antioxidant(s), alone or in any combination.

G. Pharmaceutical Formulations

Pharmaceutical formulations of an antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the antibodies provided herein may be used in therapeutic methods.

In one aspect, an antibody as reported herein for use as a medicament is provided. In further aspects, an antibody for use in treating ocular vascular diseases is provided. In certain embodiments, an antibody for use in a method of treatment is provided. In certain embodiments, the antibody for use in a method of treating an individual having an ocular vascular disease comprising administering to the individual an effective amount of the antibody is provided. In one such embodiment, the method further comprises administering to the individual an effective amount of at least one additional therapeutic agent, e.g., as described above in section D. In further embodiments, the invention provides an antibody for use in inhibiting angiogenesis in the eye. In certain embodiments, the invention provides an antibody for use in a method of inhibiting angiogenesis in an individual comprising administering to the individual an effective of the antibody to inhibit angiogenesis. An "individual" according to any of the above embodiments is in one preferred embodiment a human.

In a further aspect, the invention provides for the use of an antibody in the manufacture or preparation of a medicament. In one embodiment, the medicament is for treatment of an ocular vascular disease. In a further embodiment, the medicament is for use in a method of treating an ocular vascular disease comprising administering to an individual having an ocular vascular disease an effective amount of the medicament. In one such embodiment, the method further comprises administering to the individual an effective amount of at least one additional therapeutic agent, e.g., as described above. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating a vascular eye disease. In one embodiment, the method comprises administering to an individual having such a vascular eye disease an effective amount of an antibody as reported herein. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in the eye in an individual. In one embodiment, the method comprises administering to the individual an effective amount of an antibody as reported herein to inhibit angiogenesis. In one embodiment, an "individual" is a human.

In a further aspect, the invention provides pharmaceutical formulations comprising any of the antibodies provided herein, e.g., for use in any of the above therapeutic methods. In one embodiment, a pharmaceutical formulation comprises any of the antibodies provided herein and a pharmaceutically acceptable carrier. In another embodiment, a pharmaceutical formulation comprises any of the antibodies provided herein and at least one additional therapeutic agent, e.g., as described below.

Antibodies as reported herein can be used either alone or in combination with other agents in a therapy. For instance, an antibody as reported herein may be co-administered with at least one additional therapeutic agent An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

III. Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a formulation which is by itself or combined with another formulation effective for treating, preventing and/or diagnosing the condition and may have a sterile access port (for example the container may be an intravenous solution bag or a vial having a stopper pierceable by a hypodermic injection needle). At least one active agent in the formulation is an antibody as reported herein. The label or package insert indicates that the formulation is used for treating the condition of choice. Moreover, the article of manufacture may comprise (a) a first container with a formulation contained therein, wherein the formulation comprises an antibody as reported herein; and (b) a second container with a formulation contained therein, wherein the formulation comprises a further cytotoxic or otherwise therapeutic agent. The article of manufacture in this embodiment as reported herein may further comprise a package insert indicating that the formulations can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to an antibody as reported herein.

IV. Specific Embodiments

1. An antibody comprising a first Fc-region polypeptide and a second Fc-region polypeptide, whereby the antibody comprises the combination of mutations
   i) I253A, H310A, and H435A, or
   ii) H310A, H433A, and Y436A, or
   iii) L251D, L314D, and L432D, or
   iv) combinations of i) to iii)
   in the first Fc-region polypeptide and in the second Fc-region polypeptide.
2. An antibody comprising a first Fc-region polypeptide and a second Fc-region polypeptide, whereby the antibody specifically binds to human FcRn with an affinity comparable to or less than an antibody that has the mutations
   i) I253A, H310A, and H435A, or
   ii) H310A, H433A, and Y436A, or
   iii) L251D, L314D, and L432D, or
   iv) combinations of i) to iii)

in the first Fc-region polypeptide and in the second Fc-region polypeptide.

3. An antibody comprising a first Fc-region polypeptide and a second Fc-region polypeptide, wherein
   i) the first and the second Fc-region polypeptide comprise the mutations I253A, H310A and H435A, or
   ii) the first and the second Fc-region polypeptide comprise the mutations H310A, H433A and Y436A, or
   iii) the first and the second Fc-region polypeptide comprise the mutations L251D, L314D and L432D, or
   iv) the first Fc-region polypeptide comprises the mutations I253A, H310A and H435A and the second Fc-region polypeptide comprises
      a) the mutations H310A, H433A and Y436A, or
      b) the mutations L251D, L314D and L432D,
   or
   v) the first Fc-region polypeptide comprises the mutations H310A, H433A and Y436A and the second Fc-region polypeptide comprises
      a) the mutations L251D, L314D and L432D.

4. An antibody comprising a first Fc-region polypeptide and a second Fc-region polypeptide, wherein
   α) the first and a second Fc-region polypeptide are both of human IgG1 or human IgG4 subclass (derived from human origin) and comprise one or two of the mutations selected from i) the group I253A, H310A and H435A, or ii) the group H310A, H433A and Y436A, or iii) the group L251D, L314D and L432D (numbering according to Kabat EU index numbering system) in the first Fc-region polypeptide and one or two of the mutations selected from the group comprising the mutations L251D, I253A, H310A, L314D, L432D, H433A, H435A and Y436A (numbering according to Kabat EU index numbering system) in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the variant (human) IgG class Fc-region, or
   β) the first and a second Fc-region polypeptide both of human IgG1 or human IgG4 subclass (i.e. derived from human origin) and both comprise the mutations I253A/H310A/H435A or H310A/H433A/Y436A or L251D/L314D/L432D or combinations thereof in the Fc-region (numbering according to Kabat EU index numbering system), whereby either all mutations are in the first or the second Fc-region polypeptide, or one or two mutations are in the first Fc-region polypeptide and one or two mutations are in the second Fc-region polypeptide so that all of the mutations in the first and the second Fc-region polypeptide when taken together result in that the mutations i) I253A, H310A and H435A, or ii) H310A, H433A and Y436A, or iii) L251D, L314D and L432D are comprised in the Fc-region, or
   γ) the first and a second Fc-region polypeptide both of human IgG1 or human IgG4 subclass (i.e. derived from human origin) and comprise the mutations I253A/H310A/H435A or H310A/H433A/Y436A or L251D/L314D/L432D in the first as well as in the second Fc-region polypeptide (numbering according to Kabat EU index numbering system), or comprises the combinations of the mutations I253A/H310A/H435A in the first Fc-region polypeptide and the combination of the mutations H310A/H433A/Y436A in the second Fc-region polypeptide (numbering according to Kabat EU index numbering system).

5. The antibody according to any one of embodiments 1 to 4, wherein the antibody is a bispecific antibody.

6. The antibody according to any one of embodiments 1 to 5, wherein the antibody is a bivalent antibody.

7. The antibody according to any one of embodiments 1 to 6, wherein
   i) the first Fc-region polypeptide is selected from the group comprising
      human IgG1 Fc-region polypeptide,
      human IgG2 Fc-region polypeptide,
      human IgG3 Fc-region polypeptide,
      human IgG4 Fc-region polypeptide,
      human IgG1 Fc-region polypeptide with the mutations L234A, L235A,
      human IgG1 Fc-region polypeptide with the mutations Y349C, T366S, L368A, Y407V,
      human IgG1 Fc-region polypeptide with the mutations S354C, T366S, L368A, Y407V,
      human IgG1 Fc-region polypeptide with the mutations L234A, L235A, Y349C, T366S, L368A, Y407V,
      human IgG1 Fc-region polypeptide with the mutations L234A, L235A, S354C, T366S, L368A, Y407V,
      human IgG1 Fc-region polypeptide with the mutations P329G,
      human IgG1 Fc-region polypeptide with the mutations L234A, L235A, P329G,
      human IgG1 Fc-region polypeptide with the mutations P329G, Y349C, T366S, L368A, Y407V,
      human IgG1 Fc-region polypeptide with the mutations P329G, S354C, T366S, L368A, Y407V,
      human IgG1 Fc-region polypeptide with the mutations L234A, L235A, P329G, Y349C, T366S, L368A, Y407V,
      human IgG1 Fc-region polypeptide with the mutations L234A, L235A, P329G, S354C, T366S, L368A, Y407V,
      human IgG4 Fc-region polypeptide with the mutations S228P, L235E,
      human IgG4 Fc-region polypeptide with the mutations S228P, L235E, P329G,
      human IgG4 Fc-region polypeptide with the mutations Y349C, T366S, L368A, Y407V,
      human IgG4 Fc-region polypeptide with the mutations S354C, T366S, L368A, Y407V,
      human IgG4 Fc-region polypeptide with the mutations S228P, L235E, Y349C, T366S, L368A, Y407V,
      human IgG4 Fc-region polypeptide with the mutations S228P, L235E, S354C, T366S, L368A, Y407V,
      human IgG4 Fc-region polypeptide with the mutations P329G,
      human IgG4 Fc-region polypeptide with the mutations P329G, Y349C, T366S, L368A, Y407V,
      human IgG4 Fc-region polypeptide with the mutations P329G, S354C, T366S, L368A, Y407V,
      human IgG4 Fc-region polypeptide with the mutations S228P, L235E, P329G, Y349C, T366S, L368A, Y407V,
      human IgG4 Fc-region polypeptide with the mutations S228P, L235E, P329G, S354C, T366S, L368A, Y407V, human IgG1, IgG2 or IgG4 with the mutations K392D, and human IgG3 with the mutation N392D, and ii) the second Fc-region polypeptide is selected from the group comprising
human IgG1 Fc-region polypeptide,
human IgG2 Fc-region polypeptide,
human IgG3 Fc-region polypeptide,
human IgG4 Fc-region polypeptide,
human IgG1 Fc-region polypeptide with the mutations L234A, L235A,
human IgG1 Fc-region polypeptide with the mutations S354C, T366W,
human IgG1 Fc-region polypeptide with the mutations Y349C, T366W,
human IgG1 Fc-region polypeptide with the mutations L234A, L235A, S354C, T366W,
human IgG1 Fc-region polypeptide with the mutations L234A, L235A, Y349C, T366W,
human IgG1 Fc-region polypeptide with the mutations P329G,
human IgG1 Fc-region polypeptide with the mutations L234A, L235A, P329G,
human IgG1 Fc-region polypeptide with the mutations P329G, S354C, T366W,
human IgG1 Fc-region polypeptide with the mutations P329G, Y349C, T366W,
human IgG1 Fc-region polypeptide with the mutations L234A, L235A, P329G, S354C, T366W,
human IgG1 Fc-region polypeptide with the mutations L234A, L235A, P329G, Y349C, T366W,
human IgG4 Fc-region polypeptide with the mutations S228P, L235E,
human IgG4 Fc-region polypeptide with the mutations S228P, L235E, P329G,
human IgG4 Fc-region polypeptide with the mutations S354C, T366W,
human IgG4 Fc-region polypeptide with the mutations Y349C, T366W,
human IgG4 Fc-region polypeptide with the mutations S228P, L235E, S354C, T366W,
human IgG4 Fc-region polypeptide with the mutations S228P, L235E, Y349C, T366W,
human IgG4 Fc-region polypeptide with the mutations P329G,
human IgG4 Fc-region polypeptide with the mutations P329G, S354C, T366W,
human IgG4 Fc-region polypeptide with the mutations P329G, Y349C, T366W,
human IgG4 Fc-region polypeptide with the mutations S228P, L235E, P329G, S354C, T366W,
human IgG4 Fc-region polypeptide with the mutations S228P, L235E, P329G, Y349C, T366W,
human IgG1 with the mutations D399K, D356K, and/ or E357K, and
human IgG2, IgG3 or IgG4 with the mutations D399K, E356K, and/or E357K.

8. The antibody according to any one of embodiments 1 to 6, wherein
i) the first Fc-region polypeptide has an amino acid sequence selected from the group comprising SEQ ID NO: 60, 61, 62, 63, 64, 65, 67, 69, 70, 71, 73, 75, 76, 78, 80, 81, 82, and 84, and ii) the second Fc-region polypeptide has an amino acid sequence selected from the group comprising SEQ ID NO: 60, 61, 62, 63, 64, 66, 68, 69, 70, 72, 74, 75, 76, 77, 79, 81, 83, and 85.

9. The antibody according to any one of embodiments 1 to 6, wherein
i) the first Fc-region polypeptide is a human IgG1 Fc-region polypeptide and the second Fc-region polypeptide is a human IgG1 Fc-region polypeptide, or
ii) the first Fc-region polypeptide is a human IgG1 Fc-region polypeptide with the mutations L234A, L235A and the second Fc-region polypeptide is a human IgG1 Fc-region polypeptide with the mutations L234A, L235A, or
iii) the first Fc-region polypeptide is a human IgG1 Fc-region polypeptide with the mutations L234A, L235A, P329G and the second Fc-region polypeptide is a human IgG1 Fc-region polypeptide with the mutations L234A, L235A, P329G, or
iv) the first Fc-region polypeptide is a human IgG1 Fc-region polypeptide with the mutations L234A, L235A, S354C, T366W and the second Fc-region polypeptide is a human IgG1 Fc-region polypeptide with the mutations L234A, L235A, Y349C, T366S, L368A, Y407V, or
v) the first Fc-region polypeptide is a human IgG1 Fc-region polypeptide with the mutations L234A, L235A, P329G, S354C, T366W and the second Fc-region polypeptide is a human IgG1 Fc-region polypeptide with the mutations L234A, L235A, P329G, Y349C, T366S, L368A, Y407V, or
vi) the first Fc-region polypeptide is a human IgG4 Fc-region polypeptide and the second Fc-region polypeptide is a human IgG4 Fc-region polypeptide, or
vii) the first Fc-region polypeptide is a human IgG4 Fc-region polypeptide with the mutations S228P, L235E and the second Fc-region polypeptide is a human IgG4 Fc-region polypeptide with the mutations S228P, L235E, or
viii) the first Fc-region polypeptide is a human IgG4 Fc-region polypeptide with the mutations S228P, L235E, P329G and the second Fc-region polypeptide is a human IgG4 Fc-region polypeptide with the mutations S228P, L235E, P329G, or
ix) the first Fc-region polypeptide is a human IgG4 Fc-region polypeptide with the mutations S228P, L235E, S354C, T366W and the second Fc-region polypeptide is a human IgG4 Fc-region polypeptide with the mutations S228P, L235E, Y349C, T366S, L368A, Y407V, or
x) the first Fc-region polypeptide is a human IgG4 Fc-region polypeptide with the mutations S228P, L235E, P329G, S354C, T366W and the second Fc-region polypeptide is a human IgG4 Fc-region polypeptide with the mutations S228P, L235E, P329G, Y349C, T366S, L368A, Y407V.

10. The antibody according to any one of embodiments 1 to 6, wherein
i) the first Fc-region polypeptide has the amino acid sequence of SEQ ID NO: 60 and the second Fc-region polypeptide has the amino acid sequence of SEQ ID NO: 60, or
ii) the first Fc-region polypeptide has the amino acid sequence of SEQ ID NO: 64 and the second Fc-region polypeptide has the amino acid sequence of SEQ ID NO: 64, or iii) the first Fc-region polypeptide has the amino acid sequence of SEQ ID NO: 70 and the second Fc-region polypeptide has the amino acid sequence of SEQ ID NO: 70, or iv) the first Fc-region polypeptide has the amino acid sequence of SEQ ID NO: 68 and the second Fc-region polypeptide has the amino acid sequence of SEQ ID NO: 67, or v) the first Fc-region polypeptide has the amino acid sequence of SEQ ID NO: 74 and the second Fc-region polypeptide has the amino acid sequence of SEQ ID NO: 73, or vi) the first Fc-region polypeptide has the amino acid sequence of SEQ ID NO: 63 and the second Fc-region polypeptide has the amino acid sequence of SEQ ID NO: 63, or vii) the first Fc-region polypeptide has the amino acid sequence of SEQ ID NO: 75 and the second Fc-region polypeptide has the amino acid sequence of SEQ ID NO: 75, or viii) the first Fc-region polypeptide has the amino acid sequence of SEQ ID NO: 76 and the second Fc-region polypeptide has the amino acid sequence of SEQ ID NO: 76, or ix) the first Fc-region polypeptide is has the amino acid sequence of SEQ ID NO: 79 and the second Fc-region polypeptide has the amino acid sequence of SEQ ID NO: 80, or x) the first Fc-region polypeptide has the amino acid sequence of SEQ ID NO: 85 and the second Fc-region polypeptide has the amino acid sequence of SEQ ID NO: 84.

11. The antibody according to any one of embodiments 5 to 10, wherein the bispecific antibody has one binding specificity that specifically binds to human ANG-2 and one binding specificity that specifically binds to human VEGF.

12. The antibody according to any one of embodiments 5 to 11, wherein the antibody comprises a first antigen-binding site that specifically binds to human VEGF and a second antigen-binding site that specifically binds to human ANG-2, wherein i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and ii) second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27.

13. The antibody according to any one of embodiments 5 to 12, wherein the antibody comprises a first antigen-binding site that specifically binds to human VEGF and a second antigen-binding site that specifically binds to human ANG-2, wherein i) the first antigen-binding site specifically binding to VEGF comprises as heavy chain variable domain VH an amino acid sequence of SEQ ID NO: 20 and as light chain variable domain VL an amino acid sequence of SEQ ID NO: 21, and ii) the second antigen-binding site specifically binding to ANG-2 comprises as heavy chain variable domain VH an amino acid sequence of SEQ ID NO: 28 and as light chain variable domain VL an amino acid sequence of SEQ ID NO: 29.

14. The antibody according to any one of embodiments 5 to 13, comprising a) the heavy chain and the light chain of a first full length antibody that specifically binds to VEGF, and b) the modified heavy chain and modified light chain of a second full length antibody that specifically binds to ANG-2, in which the constant domains CL and CH1 are replaced by each other.

15. The antibody according to embodiment 14, comprising a) as heavy chain of the first full length antibody the amino acid sequence of SEQ ID NO: 102 and as light chain of the first full length antibody the amino acid sequence of SEQ ID NO: 36, and b) as modified heavy chain of the second full length antibody the amino acid sequence of SEQ ID NO: 103 and as modified light chain of the second full length antibody the amino acid sequence of SEQ ID NO: 37.

16. The antibody according to embodiment 14, comprising a) as heavy chain of the first full length antibody the amino acid sequence of SEQ ID NO: 104 and as light chain of the first full length antibody the amino acid sequence of SEQ ID NO: 40, and b) as modified heavy chain of the second full length antibody the amino acid sequence of SEQ ID NO: 105 and as modified light chain of the second full length antibody the amino acid sequence of SEQ ID NO: 41.

17. The antibody according to embodiment 14, comprising a) as heavy chain of the first full length antibody the amino acid sequence of SEQ ID NO: 106 and as light chain of the first full length antibody the amino acid sequence of SEQ ID NO: 44, and b) as modified heavy chain of the second full length antibody the amino acid sequence of SEQ ID NO: 107 and as modified light chain of the second full length antibody the amino acid sequence of SEQ ID NO: 45.

18. The antibody according to any one of embodiments 5 to 13, characterized in in comprising a) the heavy chain and the light chain of a first full length antibody that specifically binds to VEGF, and b) the heavy chain and the light chain of a second full length antibody that specifically binds to ANG-2, wherein the N-terminus of the heavy chain is connected to the C-terminus of the light chain via a peptidic linker.

19. The antibody according to embodiment 18, comprising a) as heavy chain of the first full length antibody the amino acid sequence of SEQ ID NO: 108 and as light chain of the first full length antibody the amino acid sequence of SEQ ID NO: 48, and b) as heavy chain of the second full length antibody connected to the light chain of the second full length antibody via a peptidic linker the amino acid sequence of SEQ ID NO: 109.

20. The antibody according to embodiment 18, comprising a) as heavy chain of the first full length antibody the amino acid sequence of SEQ ID NO: 110 and as light chain of the first full length antibody the amino acid sequence of SEQ ID NO: 51, and b) as heavy chain of the second full length antibody connected to the light chain of the second full length antibody via a peptidic linker the amino acid sequence of SEQ ID NO: 111.

21. The antibody according to any one of embodiments 18 to 20, wherein the antibody heavy chain variable domain (VH) and the antibody light chain variable domain (VL) of the heavy and light chain of the second full length antibody are disulfide stabilized by introduction of a disulfide bond between the heavy chain variable domain position 44 and light chain variable domain position 100 (numbering according to Kabat EU index numbering system).

22. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein the antibody comprises the amino acid sequence of SEQ ID NO: 34, 35, 36 and 37, or the antibody comprises the amino acid sequence of SEQ ID NO: 38, 39, 40, and 41, or the antibody comprises the amino acid sequence of SEQ ID NO: 42, 43, 44, and 45, or the antibody comprises the amino acid sequence of SEQ ID NO: 46, 47, and 48, or the antibody comprises the amino acid sequence of SEQ ID NO: 49, 50, and 51, and the bispecific antibody comprises an Fc-region of human IgG1 or human IgG4 subclass comprising the mutations I253A, H310A and H435A in both Fc-region polypeptides (numbering according to EU Index of Kabat).

23. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein the variable domains comprise SEQ ID NO: 20, 21, 28 and 29 with 0, 1, 2, or 3 mutations in each variable domain, and the bispecific antibody comprises an Fc-region of human IgG1 or human IgG4 subclass comprising the mutations I253A, H310A and H435A in both Fc-region polypeptides (numbering according to EU Index of Kabat).

24. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein the antibody comprises the amino acid sequence of SEQ ID NO: 20, 21, 28 and 29, and the bispecific antibody comprises an Fc-region of human IgG1 or human IgG4 subclass comprising the mutations I253A, H310A and H435A in both Fc-region polypeptides (numbering according to EU Index of Kabat).

25. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and ii) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and iii) the bispecific antibody comprises a constant heavy chain region of human IgG1 or human IgG4 subclass (derived from human origin) comprising the mutations I253A, H310A and H435A (numbering according to EU Index of Kabat), and wherein the variable domains comprise not more than 3 mutations with respect to SEQ ID NO: 20, 21, 28 and 29.

26. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein i) the first antigen-binding site specifically binding to VEGF comprises in the heavy chain variable domain a CDR3H region of SEQ ID NO: 14, a CDR2H region of SEQ ID NO: 15, and a CDR1H region of SEQ ID NO: 16, and in the light chain variable domain a CDR3L region of SEQ ID NO: 17, a CDR2L region of SEQ ID NO: 18, and a CDR1L region of SEQ ID NO: 19, and ii) the second antigen-binding site specifically binding to ANG-2 comprises in the heavy chain variable domain a CDR3H region of SEQ ID NO: 22, a CDR2H region of, SEQ ID NO: 23, and a CDR1H region of SEQ ID NO: 24, and in the light chain variable domain a CDR3L region of SEQ ID NO: 25, a CDR2L region of SEQ ID NO: 26, and a CDR1L region of SEQ ID NO: 27, and iii) the bispecific antibody comprises an Fc-region of human IgG1 or human IgG4 subclass comprising the mutations I253A, H310A and H435A in both Fc-region polypeptides (numbering according to EU Index of Kabat).

27. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2, wherein the bispecific antibody comprises an Fc-region of human IgG1 or human IgG4 subclass comprising the mutations I253A, H310A and H435A in both Fc-region polypeptides (numbering according to EU Index of Kabat).

28. The antibody according to any one of embodiments 1 to 21, wherein the antibody is not a bispecific, bivalent antibody comprising a first antigen-binding site that specifically binds to human VEGF and a second antigen-binding site that specifically binds to human ANG-2.

29. A bispecific, bivalent antibody comprising a first antigen-binding site that specifically binds to human VEGF and a second antigen-binding site that specifically binds to human ANG-2, comprising the amino acid sequences of SEQ ID NO: 102, of SEQ ID NO: 103, of SEQ ID NO: 36, and of SEQ ID NO: 37.

30. A bispecific, bivalent antibody comprising a first antigen-binding site that specifically binds to human VEGF and a second antigen-binding site that specifically binds to human ANG-2, comprising the amino acid sequences of SEQ ID NO: 104, of SEQ ID NO: 105, of SEQ ID NO: 40, and of SEQ ID NO: 41.

31. A bispecific, bivalent antibody comprising a first antigen-binding site that specifically binds to human VEGF and a second antigen-binding site that specifically binds to human ANG-2, comprising the amino acid sequences of SEQ ID NO:106, of SEQ ID NO: 107, of SEQ ID NO: 44, and of SEQ ID NO: 45.

32. A bispecific, bivalent antibody comprising a first antigen-binding site that specifically binds to human VEGF and a second antigen-binding site that specifically binds to human ANG-2, comprising the amino acid sequences of SEQ ID NO: 108, of SEQ ID NO: 109, and of SEQ ID NO: 48.

33. A bispecific, bivalent antibody comprising a first antigen-binding site that specifically binds to human VEGF and a second antigen-binding site that specifically binds to human ANG-2, comprising the amino acid sequences of SEQ ID NO: 110, of SEQ ID NO: 111, and of SEQ ID NO: 51.

34. An antibody according to any one of embodiments 1 to 33, wherein the antibody does not bind to human FcRn.

35. An antibody according to any one of embodiments 1 to 34, wherein the antibody does bind or does not bind to Staphylococcal protein A.

36. An antibody according to any one of embodiments 34 to 35, wherein the binding or not binding is determined by surface plasmon resonance.

37. An antibody according to any one of embodiments 1 to 36, wherein the antibody
  shows a lower serum concentration compared to corresponding bispecific antibody without the mutations in the Fc-region polypeptides (96 hours after intravitreal application in mice, which are mouse FcRn deficient, but hemizygous transgenic for human FcRn) (determined in assays as described in Example 6), and/or
  shows a similar (factor 0.8 to 1.2) concentration in whole right eye lysates compared to corresponding bispecific antibody without the mutations in the Fc-region polypeptides (in mice, which are mouse FcRn deficient, but hemizygous transgenic for human FcRn, 96 hours after intravitreal application in the right eye) (determined in assays as described in Example 6).

38. Use of an antibody according to any one of embodiments 1 to 37 for the transport of a soluble receptor ligand from the eye over the blood-ocular-barrier into the blood circulation.

39. An antibody according to any one of embodiments 1 to 37 for use as a medicament.

40. An antibody according to any one of embodiments 1 to 37 for use in the treatment of an ocular vascular disease.

41. Use of an antibody according to any one of embodiments 1 to 37 for the removal of one or more soluble receptor ligands from the eye.

42. An antibody according to any one of embodiments 1 to 37 for use in the removal of one or more soluble receptor ligands from the eye.

43. Use of an antibody according to any one of embodiments 1 to 37 for the treatment of eye diseases, especially of ocular vascular diseases.

44. Use of an antibody according to any one of embodiments 1 to 37 for the transport of one or more soluble receptor ligands from the intravitreal space to the blood circulation.

45. An antibody according to any one of embodiments 1 to 37 for use in the transport of one or more soluble receptor ligands from the intravitreal space to the blood circulation.

46. An antibody according to any one of embodiments 1 to 37 for use in treating an eye disease.

47. An antibody according to any one of embodiments 1 to 37 for use in the transport of a soluble receptor ligand from the eye over the blood-ocular-barrier into the blood circulation.

48. An antibody according to any one of embodiments 1 to 37 for use in the removal of one or more soluble receptor ligands from the eye.

49. An antibody according to any one of embodiments 1 to 37 for use in treating eye diseases, especially ocular vascular diseases.

50. An antibody according to any one of embodiments 1 to 37 for use in the transport of one or more soluble receptor ligands from the intravitreal space to the blood circulation.

51. A method of treating an individual having an ocular vascular disease comprising administering to the individual an effective amount of an antibody according to any one of embodiments 1 to 37.

52. A method for transporting a soluble receptor ligand from the eye over the blood-ocular-barrier into the blood circulation in an individual comprising administering to the individual an effective amount of an antibody according to any one of embodiments 1 to 37 to transport a soluble receptor ligand from the eye over the blood-ocular-barrier into the blood circulation.

53. A method for the removal of one or more soluble receptor ligands from the eye in an individual comprising administering to the individual an effective amount of an antibody according to any one of embodiments 1 to 37 to remove one or more soluble receptor ligands from the eye.

54. A method for the transport of one or more soluble receptor ligands from the intravitreal space to the blood circulation in an individual comprising administering to the individual an effective amount of an antibody according to any one of embodiments 1 to 37 to transport one or more soluble receptor ligands from the intravitreal space to the blood circulation.

55. A method for transporting a soluble receptor ligand from the intravitreal space or the eye over the blood-ocular-barrier into the blood circulation in an individual comprising administering to the individual an effective amount of an antibody according to any one of embodiments 1 to 37 to transport a soluble receptor ligand from the intravitreal space or the eye over the blood-ocular-barrier into the blood circulation.

56. A pharmaceutical formulation comprising the antibody according to any one of embodiments 1 to 37.

57. A pharmaceutical formulation comprising the antibody according to any one of embodiments 1 to 37 for use in the treatment of ocular vascular diseases.

58. Use of the antibody according to any one of embodiments 1 to 37 for the manufacture of a medicament for the treatment of ocular vascular diseases.

59. A method of treatment of patient suffering from ocular vascular diseases by administering the antibody according to any one of embodiments 1 to 37 to a patient in the need of such treatment.

60. The pharmaceutical formulation according to any one of embodiments 55 to 56, wherein the antibody is administered via intravitreal application.

61. The administering according to any one of embodiments 51 to 55 and 59, wherein the administering is an intravitreal application.

V. Examples

The following are examples of methods and formulations as reported herein. It is understood that various other embodiments may be practiced, given the general description provided above.

Although the foregoing invention has been described in some detail by way of illustration and example for purposes of clarity of understanding, the descriptions and examples should not be construed as limiting the scope as reported herein. The disclosures of all patent and scientific literature cited herein are expressly incorporated in their entirety by reference.

Methods

Electrospray Ionization Mass Spectrometry (ESI-MS)

Protein aliquots (50 µg) were deglycosylated by adding 0.5 µL N-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 M TCEP (Pierce) in 4 M guanidine*HCl (Pierce) and 50 µL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and, thus, the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween-20™ pH 6.0 (GE Healthcare Bioscience) as running and dilution buffer. 200 nM of antibody samples were injected at a flow rate of 50 µL/min at room temperature. Association time was 180 seconds, dissociation phase took 360 seconds. Regeneration of the chip surface was reached by a short injection of HBS-P, pH 8.0. Evaluation of SPR-data was performed by comparison of the biological response signal height at 180 seconds after injection and at 300 seconds after injection. The corresponding parameters are the RU max level (180 seconds after injection) and late stability (300 seconds after end of injection).

Protein A Surface Plasmon Resonance (SPR) Analysis

The assay is based on surface plasmon resonance spectroscopy. Protein A is immobilized onto the surface of a SPR biosensor. By injecting the sample into the flow cells of the SPR spectrometer it forms a complex with the immobilized protein A resulting in an increasing mass on the sensor chip surface, and therefore to a higher response (as 1 RU is defined as 1 pg/mm$^2$). Afterwards the sensor chip is regenerated by dissolving the sample-protein A-complex. The gained responses are then evaluated for the signal high in response units (RU) and the dissociation behavior.

Around 3,500 response units (RU) of protein A (20 µg/mL) were coupled onto a CMS chip (GE Healthcare) at pH 4.0 by using the amine coupling kit of GE Healthcare.

The sample and system buffer was HBS-P+ (0.01 M HEPES, 0.15 M NaCl, 0.005% Surfactant P20 Sterile-filtered, pH 7.4). Flow cell temperature was set to 25° C. and sample compartment temperature to 12° C. The system was primed with running buffer. Then, a 5 nM solutions of the sample constructs were injected for 120 seconds with a flow rate of 30 µL/min, followed by a 300 seconds dissociation phase. Then the sensor chip surface was regenerated by two 30 seconds long injections of Glycine-HCl pH 1.5 at a flow rate of 30 µL/min. Each sample was measured as a triplicate.

Bispecific Antibodies and Their Respective Sequences

| Description | Sequences |
| --- | --- |
| <VEGF-ANG-2> CrossMAb IgG1 with IHH-AAA mutations | SEQ ID NO: 34, SEQ ID NO: 35, SEQ ID NO: 36, SEQ ID NO: 37 |
| <VEGF-ANG-2> CrossMAb IgG1 wild type (without IHH-AAA mutations) | SEQ ID NO: 52, SEQ ID NO: 53, SEQ ID NO: 54, SEQ ID NO: 55 |
| <VEGF-ANG-2> CrossMAb IgG1 with IHH-AAA mutations and P329G LALA mutations | SEQ ID NO: 38, SEQ ID NO: 39, SEQ ID NO: 40, SEQ ID NO: 41 |
| <VEGF-ANG-2> CrossMAb IgG1 with P329G LALA mutations only (without IHH-AAA mutations) | SEQ ID NO: 56, SEQ ID NO: 57, SEQ ID NO: 58, SEQ ID NO: 59 |
| <VEGF-ANG-2> CrossMAb IgG4 with IHH-AAA mutations and with SPLE mutations | SEQ ID NO: 42, SEQ ID NO: 43, SEQ ID NO: 44, SEQ ID NO: 45 |

-continued

| Description | Sequences |
|---|---|
| <VEGF-ANG-2> OAscFab IgG1 with IHH-AAA mutations | SEQ ID NO: 46, SEQ ID NO: 47, SEQ ID NO: 48 |
| <VEGF-ANG-2> OAscFab IgG4 with IHH-AAA mutations and with SPLE mutations | SEQ ID NO: 49, SEQ ID NO: 50, SEQ ID NO: 51 |
| <VEGF/ANG2> CrossMab IgG1 with HHY-AAA mutations | SEQ ID NO: 102, SEQ ID NO: 103, SEQ ID NO: 36, SEQ ID NO: 37 |
| <VEGF/ANG2> CrossMab IgG1 with HHY-AAA mutations and P329G LALA mutations | SEQ ID NO: 104, SEQ ID NO: 105, SEQ ID NO: 40, SEQ ID NO: 41 |
| <VEGF/ANG2> CrossMab IgG4 with HHY-AAA mutations and with SPLE mutations | SEQ ID NO: 106, SEQ ID NO: 107, SEQ ID NO: 44, SEQ ID NO: 45 |
| <VEGF-ANG-2> OAscFab IgG1 with HHY-AAA mutations | SEQ ID NO: 108, SEQ ID NO: 109, SEQ ID NO: 48 |
| <VEGF-ANG-2> OAscFab IgG4 with HHY-AAA mutations and with SPLE mutations | SEQ ID NO: 110, SEQ ID NO: 111, SEQ ID NO: 51 |

The term "with (the) mutation IHH-AAA" as used herein refers to the combination of the mutations I253A (Ile253Ala), H310A (His310Ala), and H435A (His435Ala) in a constant heavy chain region of IgG1 or IgG4 subclass (numbering according to EU Index of Kabat), the term "with (the) mutation HHY-AAA" as used herein refers the combination of the mutations H310A (His310Ala), H433A (His433Ala) and Y436A (Tyr436Ala) in a constant heavy chain region of IgG1 or IgG4 subclass (numbering according to EU Index of Kabat), the term "with (the) mutation P329G LALA" as used herein refers to the combination of the mutations L234A (Leu234Ala), L235A (Leu235Ala) and P329G (Pro329Gly) in a constant heavy chain region of IgG1 subclass (numbering according to EU Index of Kabat), and the term "with (the) mutation SPLE" as used herein refers to the combination of the mutations S228P (Ser228Pro) and L235E (Leu235Glu) a constant heavy chain region of IgG4 subclass (numbering according to EU Index of Kabat).

| Description | Sequences |
|---|---|
| <IGF-1R> IgG1 wt | SEQ ID NO: 88<br>SEQ ID NO: 89 |
| <IGF-1R> IgG1 with I253A, H310A, H435A | SEQ ID NO: 88<br>SEQ ID NO: 90 |
| <IGF-1R> IgG1 with M252Y, S254T, T256E | SEQ ID NO: 88<br>SEQ ID NO: 91 |
| <IGF-1R> IgG1 wt, KiH | SEQ ID NO: 88<br>SEQ ID NO: 92<br>SEQ ID NO: 93 |
| <IGF-1R> IgG1 knob wt, hole I253A, H310A, H435A | SEQ ID NO: 88<br>SEQ ID NO: 94<br>SEQ ID NO: 95 |
| <IGF-1R> IgG1 knob wt, hole H310A, H433A, Y436A | SEQ ID NO: 88<br>SEQ ID NO: 96<br>SEQ ID NO: 97 |
| <IGF-1R> IgG1 knob wt, hole M252Y, S254T, T256E | SEQ ID NO: 88<br>SEQ ID NO: 98<br>SEQ ID NO: 99 |
| <IGF-1R> IgG1 knob wt, hole L251D, L314D, L432D | SEQ ID NO: 88<br>SEQ ID NO: 100<br>SEQ ID NO: 101 |
| <IGF-1R> IgG1 with H310A, H433A, Y436A | SEQ ID NO: 88<br>SEQ ID NO: 112 |

General

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acid residues of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, MD (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, New York (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wisconsin) software package version 10.2 and Infomax's Plasmid NT1 Advance suite version 8.0 was used for sequence creation, mapping, analysis, annotation and illustration.

Expression Plasmids

For the expression of the described antibodies expression plasmids for transient expression (e.g. in HEK293-F cells) based either on a cDNA organization with or without a CMV-Intron A promoter or on a genomic organization with a CMV promoter were used.

The transcription unit of the antibody gene was composed of the following elements:

unique restriction site(s) at the 5' end, the immediate early enhancer and promoter from the human cytomegalovirus, in the case of the cDNA organization the Intron A sequence, a 5'-untranslated region of a human immunoglobulin gene, a nucleic acid encoding an immunoglobulin heavy chain signal sequence, a nucleic acid encoding the human antibody chain (wild-type or with domain exchange) either as cDNA or in genomic organization with the immunoglobulin exon-intron organization, a 3' non-translated region with a polyadenylation signal sequence, and unique restriction site(s) at the 3' end.

Beside the antibody expression cassette the plasmids contained:

an origin of replication which allows replication of this plasmid in *E. coli,* a β-lactamase gene which confers ampicillin resistance in *E. coli.,* and the dihydrofolate reductase gene from *Mus musculus* as a selectable marker in eukaryotic cells.

The nucleic acids encoding the antibody chains were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression plasmids in in HEK293-F cells growing in suspension as described below.

Example 1

Expression and Purification

Transient Transfections in HEK293-F System

The monospecific and bispecific antibodies were generated by transient transfection with the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of approx. $1.5*10^6$ cells/mL with approx. 42 mL of a mixture of A) 20 mL Opti-MEM (Invitrogen) with 600 µg total plasmid DNA (1 µg/mL)

encoding the heavy or modified heavy chain, respectively and the corresponding light chain in an equimolar ratio and B) 20 ml Opti-MEM with 1.2 mL 293 fectin or fectin (2 µL/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MabSelect-Sure-Sepharose™ (for non-IHH-AAA mutants) (GE Healthcare, Sweden) or KappaSelect-Agarose (for IHH-AAA mutants) (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated (non-IHH-AAA mutations and wild-type antibodies) with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The IHH-AAA mutants were captured on a KappaSelect resin equilibrated with 25 mM Tris, 50 mM NaCl, pH 7.2, washed with equilibration buffer and eluted with 25 mM sodium citrate pH 2.9. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The (monospecific or bispecific) antibody containing fractions were pooled and further purified by size exclusion chromatography using a Superdex 200 26/60 GL (GE Healthcare, Sweden) column equilibrated with 20 mM histidine, 140 mM NaCl, pH 6.0. The (monospecific or bispecific) antibody containing fractions were pooled, concentrated to the required concentration using Vivaspin ultrafiltration devices (Sartorius Stedim Biotech S.A., France) and stored at −80° C.

TABLE

| Yields of bispecific <VEGF-ANG-2> antibodies | | | |
|---|---|---|---|
| | VEGFang2-0015 (without IHH-AAA mutation) | VEGFang2-0016 (with IHH-AAA mutation) | VEGF/ANG2-0121 (with HHY-AAA mutation) |
| titer supernatant | 64 µg/ml, (2 L = 128 mg) | n.a. (2 L scale) | 60.8 µg/ml (2 L = 121.60 mg) |
| protein A (MabSelectSure) | 118 mg (~70% monomer) | n.a. | 100.5 mg (pool1 + pool2) |
| Kappa Select | n.a. | 117 mg (~83% monomer) | n.a. |
| butyl Sepharose | 60 mg | 57 mg | 49 mg |
| SEC | 35 mg (>95% monomer) | 38 mg (>95% monomer) | 32.4 mg (>95% monomer) |

Purity and antibody integrity were analyzed after each purification step by CE-SDS using microfluidic Labchip technology (Caliper Life Science, USA). Five μL of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

TABLE

Removal of typical side products by different sequential purification steps determined by CE-SDS.

| Purifi-cation Step | VEGFang2-0015 | | | | | | VEGFang2-0016 | | | | | |
|---|---|---|---|---|---|---|---|---|---|---|---|---|
| | \% peak area* * analysis: CE-SDS (Caliper Labchip GXII) | | | | | | | | | | | |
| | mAb | ¾ Ab | (HC) 2 | ½ Ab | (LC) 2 | LC | mAb | ¾ Ab | (HC) 2 | ½ Ab | (LC) 2 | LC |
| Mab Select Sure | 55.7 | 19 | 10.6 | 9.8 | 3.5 | 0.9 | | | — | | | |
| Kappa Select | | | — | | | | 63 | 13.4 | 3.5 | 6.1 | 5.8 | 7.4 |
| butyl-Sepha-rose | 81.4 | 1.9 | 2.3 | 8.2 | 3.6 | 1.8 | 76.2 | 1.3 | 0.7 | 8.3 | 7.7 | 5.8 |
| Super-dex 200_SEC | 92.4 | 1.8 | 2.6 | 1.4 | 0.5 | 0.5 | 99 | 1.1 | n.d. | n.d. | n.d. | n.d |

The aggregate content of antibody samples was analyzed by high-performance SEC using a Superdex 200 analytical size-exclusion column (GE Healthcare, Sweden) in 2×PBS (20 mM $Na_2HPO_4$, 2 mM $KH_2PO_4$, 274 mM NaCl and 5.4 mM KCl, pH 7.4) running buffer at 25° C. 25 μg protein were injected on the column at a flow rate of 0.75 mL/min and eluted isocratic over 50 minutes.

Analogously the <VEGF-ANG-2> bispecific antibodies VEGFang2-0012 and VEGFang2-0201 were prepared and purified with the following yields:

| | VEGFang2-0012 (with IHH-AAA mutation) | VEGFang2-0201 (without IHH-AAA mutation) |
|---|---|---|
| titer //amount | — | 36 μg/mL / 72 mg |
| scale | 2.1 L | 2 L |
| protein A (MabSelectSure) | — | 66 mg (~95% monomer) |
| KappaSelect | 43 mg (~65% monomer) | — |
| butyl Sepharose | — | 45 mg |
| SEC | 14 mg | 21 mg (>98% monomer) |
| yield hydroxylapatite | 8.5 mg (>98% monomer) | |
| total yield (recovery) | 8.5 mg (20%) | 21 mg (30%) |

Also the <VEGF-ANG-2> bispecific antibodies <VEGF-ANG-2> CrossMAb IgG4 with IHH-AAA mutation and with SPLE mutation (SEQ ID NO: 42, SEQ ID NO: 43, SEQ ID NO: 44, SEQ ID NO: 45), <VEGF-ANG-2> OAscFab IgG1 with IHH-AAA mutation (SEQ ID NO: 46, SEQ ID NO: 47, SEQ ID NO: 48), <VEGF-ANG-2> OAscFab IgG4 with IHH-AAA mutation and with SPLE mutation (SEQ ID NO: 49, SEQ ID NO: 50, SEQ ID NO: 51), <VEGF-ANG-2> CrossMab IgG1 with HHY-AAA mutation and P329G LALA mutation (SEQ ID NO: 90, SEQ ID NO: 91, SEQ ID NO: 40, SEQ ID NO: 41), <VEGF-ANG-2> CrossMab IgG4 with HHY-AAA mutation and SPLE mutation (SEQ ID NO: 92, SEQ ID NO: 93, SEQ ID NO: 44, SEQ ID NO: 45), <VEGF-ANG-2> OAscFab IgG1 with HHY-AAA mutation (SEQ ID NO: 94, SEQ ID NO: 95, SEQ ID NO: 48), and <VEGF-ANG-2> OAscFab IgG4 with HHY-AAA mutation and SPLE mutation (SEQ ID NO: 96, SEQ ID NO: 97, SEQ ID NO: 51) and also the <IGF-1R> monospecific antibodies <IGF-1R> wild-type (SEQ ID NO: 88, SEQ ID NO: 89), <IGF-1R> IgG1 with IHH-AAA mutations (SEQ ID NO: 88, SEQ ID NO: 90), <IGF-1R> IgG1 with YTE mutations (SEQ ID NO: 88, SEQ ID NO: 91), <IGF-1R> IgG1 wild-type with KiH mutations (SEQ ID NO: 88, SEQ ID NO: 92, SEQ ID NO: 93), <IGF-1R> IgG1 with KiH mutations and the IHH-AAA mutation in the hole chain (SEQ ID NO: 88, SEQ ID NO: 94, SEQ ID NO: 95), <IGF-1R> IgG1 with KiH mutations and the HHY-AAA mutations in the hole chain (SEQ ID NO: 88, SEQ ID NO: 96, SEQ ID NO: 97), <IGF-1R> IgG1 with KiH mutation and the YTE mutation (SEQ ID NO: 88, SEQ ID NO: 98, SEQ ID NO: 99), <IGF-1R> IgG1 with KiH mutation and the DDD mutation (SEQ ID NO: 88, SEQ ID NO: 100, SEQ ID NO: 101), and <IGF-1R> IgG1 with HHY-AAA mutations (SEQ ID NO: 88, SEQ ID NO: 112) can be prepared and purified analogously.

Example 2

Analytics & Developability
Small-Scale DLS-Based Viscosity Measurement.

Viscosity measurement was essentially performed as described in (He, F. et al., Analytical Biochemistry 399 (2009) 141-143). Briefly, samples were concentrated to various protein concentrations in 200 mM arginine succinate, pH 5.5, before polystyrene latex beads (300 nm diameter) and Polysorbate 20 (0.02% v/v) were added. Samples were transferred into an optical 384-well plate by centrifugation through a 0.4 μm filter plate and covered with paraffin oil. The apparent diameter of the latex beads was determined by dynamic light scattering at 25° C. The viscosity of the solution can be calculated as $\eta=\eta 0(rh/rh,0)$ ($\eta$: viscosity; $\eta 0$: viscosity of water; rh: apparent hydrodynamic radius of the latex beads; rh,0: hydrodynamic radius of the latex beads in water).

To allow comparison of various samples at the same concentration, viscosity-concentration data were fitted with the Mooney equation (Equation 1) (Mooney, M., Colloid.

Sci., 6 (1951) 162-170; Monkos, K., Biochem. Biophys. Acta 304 (1997) 1339) and data interpolated accordingly.

$$\eta = \eta_0 \exp\left(\frac{S\Phi}{1 - K\Phi}\right)$$ Equation 1

(S: hydrodynamic interaction parameter of the protein; K: self-crowding factor; $\Phi$: volume fraction of the dissolved protein)

Figure 2:
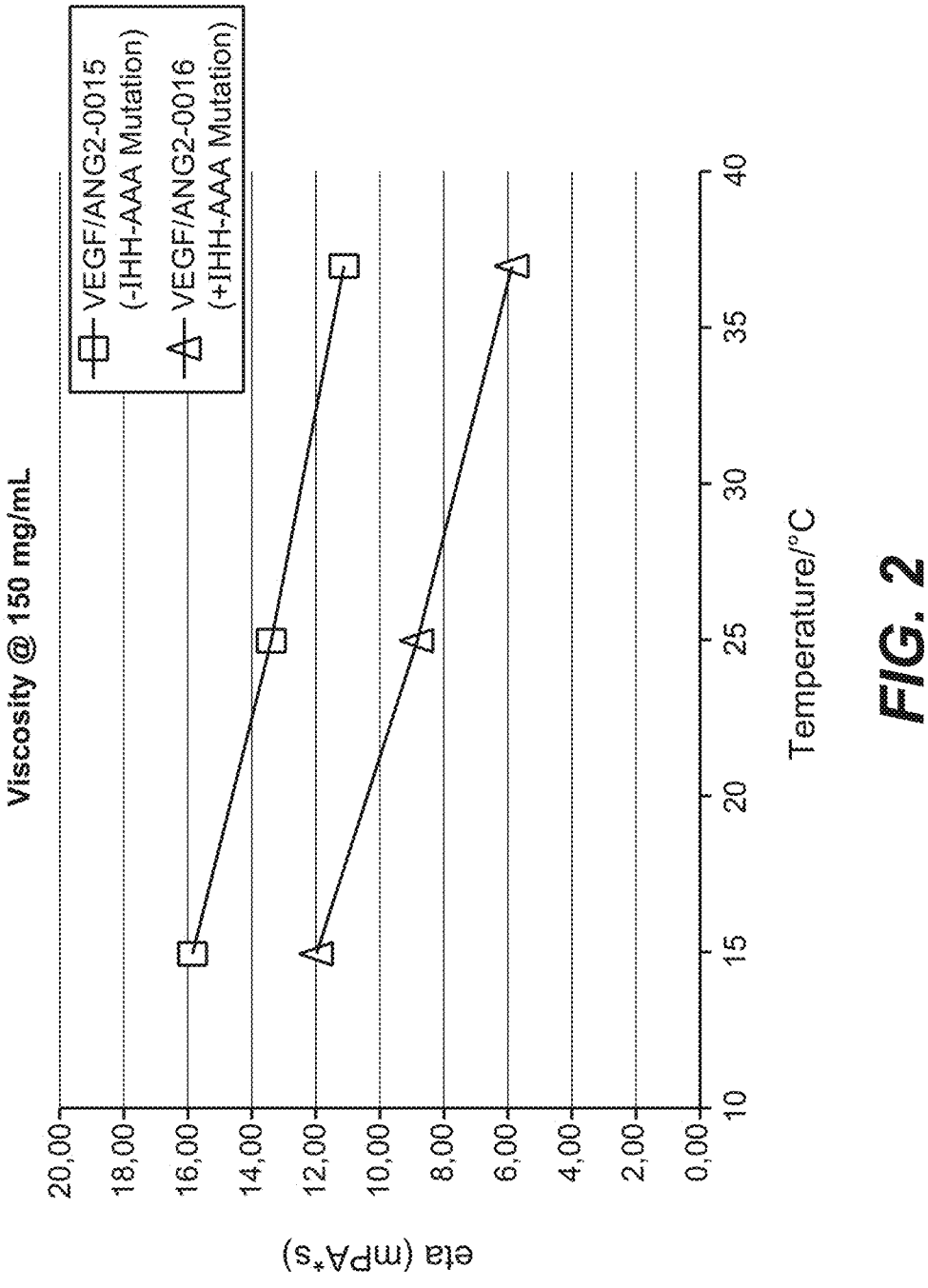
FIG. 2: Small-scale DLS-based viscosity measurement: Extrapolated viscosity at 150 mg/mL in 200 mM arginine/succinate, pH 5.5 (comparison of <VEGF-ANG-2> antibodies VEGFang2-0016 (with IHH-AAA mutation) with a reference antibody VEGFang2-0015 (without such IHH-AAA mutations)).

Results are shown in FIG. 2: VEGFang2-0016 with IHH-AAA mutation in the Fc-region shows a lower viscosity at all measured temperatures compared to VEGFang2-0015 without the IHH-AAA mutation in the Fc-region.

DLS Aggregation Onset Temperature

Figure 3:
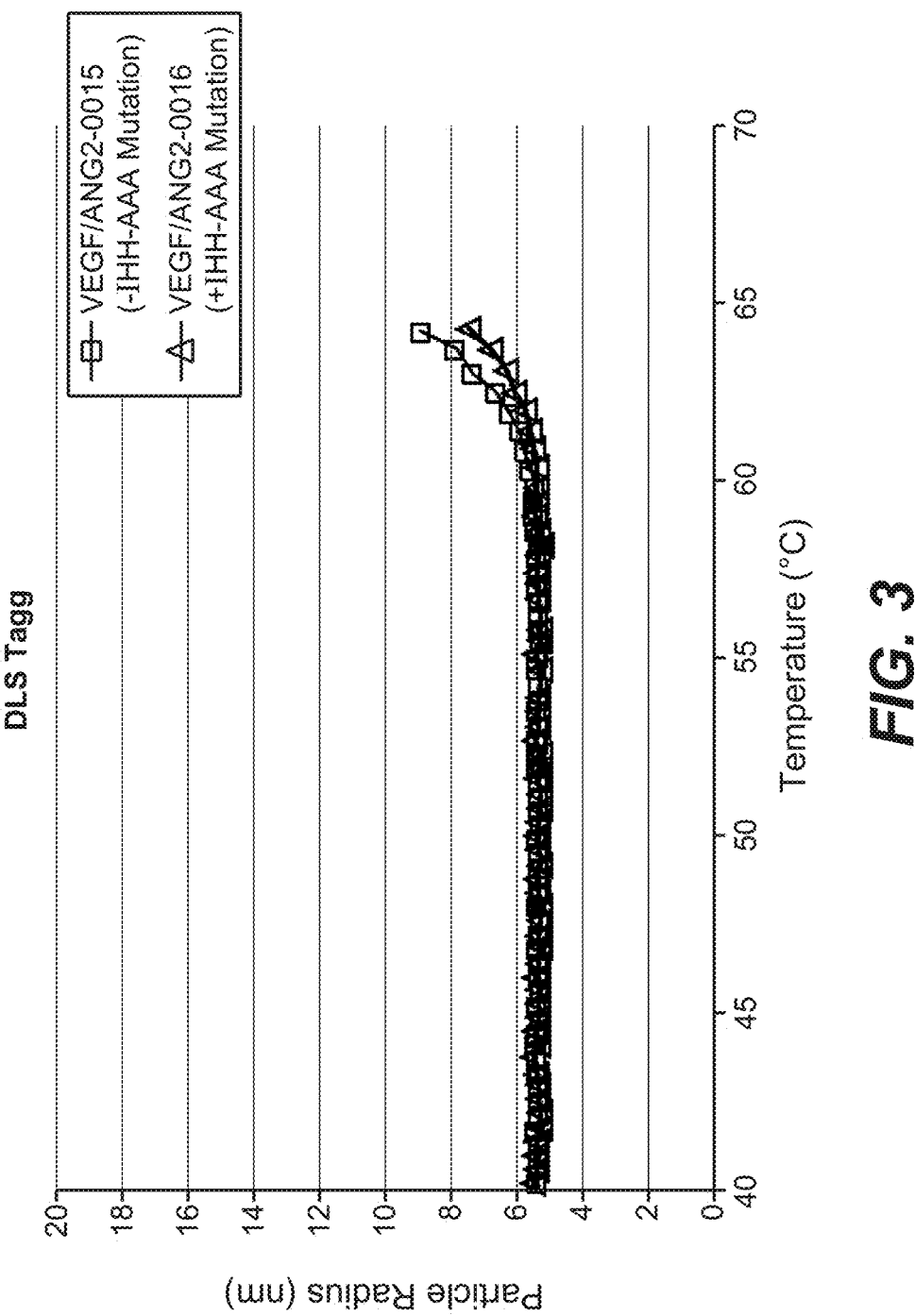
FIG. 3: DLS Aggregation depending on temperature (including DLS aggregation onset temperature) in 20 mM histidine buffer, 140 mM NaCl, pH 6.0 (comparison of <VEGF-ANG-2> antibodies as reported herein VEGFang2-0016 (with IHH-AAA mutation) with a reference antibody VEGFang2-0015 (without such IHH-AAA mutation)).

Samples were prepared at a concentration of 1 mg/mL in 20 mM Histidine/Histidine hydrochloride, 140 mM NaCl, pH 6.0, transferred into an optical 384-well plate by centrifugation through a 0.4 μm filter plate and covered with paraffin oil. The hydrodynamic radius was measured repeatedly by dynamic light scattering while the samples were heated with a rate of 0.05° C./min from 25° C. to 80° C. The aggregation onset temperature is defined as the temperature at which the hydrodynamic radius starts to increase. Results are shown in FIG. 3. In FIG. 3 the aggregation of VEGFang2-0015 without the IHH-AAA mutation versus VEGFang2-0016 with IHH-AAA mutation in the Fc-region is shown. VEGFang2-0016 showed an aggregation onset temperature of 61° C. whereas VEGFang2-0015 without the IHH-AAA mutation showed an onset temperature of 60° C.

DLS Time-Course

Samples were prepared at a concentration of 1 mg/mL in 20 mM Histidine/Histidine hydrochloride, 140 mM NaCl, pH 6.0, transferred into an optical 384-well plate by centrifugation through a 0.4 μm filter plate and covered with paraffin oil. The hydrodynamic radius was measured repeatedly by dynamic light scattering while the samples were kept at a constant temperature of 50° C. for up to 145 hours. In this experiment, aggregation tendencies of the native, unfolded protein at elevated temperature would lead to an increase of the average particle diameter over time. This DLS-based method is very sensitive for aggregates because these contribute over-proportionally to the scattered light intensity. Even after 145 hours at 50° C. (a temperature close to the aggregation-onset temperature, see above), an average particle diameter increase of only less than 0.5 nm was found for both VEGFang2-0015 and VEGFang2-0016.

Seven Day Storage at 40° C. at 100 mg/mL

Samples were concentrated to a final concentration of 100 mg/mL in 200 mM arginine succinate, pH 5.5, sterile filtered and quiescently stored at 40° C. for seven days. Before and after storage, the content of high and low molecular weight species (HMWs and LMWs, respectively) was determined by size-exclusion chromatography. The difference in HMW and LMW content between the stored sample and a sample measured immediately after preparation is reported as "HMW increase" and "LMW increase", respectively. Results are shown in the Table below and FIG. 4, which show that VEGFang2-0015 (without IHH-AAA mutation) shows a higher reduction of the main peak and a higher HMW increase compared to VEGFang2-0016 (with IHH-AAA mutation). Surprisingly VEGFang2-0016 (with IHH-AAA mutation) showed a lower aggregation tendency compared to VEGFang2-0015 (without IHH-AAA mutation).

TABLE

| Delta Main-, HMW and LMW peaks after seven days at 40° C. | | | |
|---|---|---|---|
| | delta_area % (40° C.-(−80° C.)) | | |
| | main peak | HMW | LMW |
| VEGFang2-0015 (−IHH-AAA mutation) | −3.56 | 2.89 | 0.67 |
| VEGFang2-0016 (+IHH-AAA mutation) | −1.74 | 1.49 | 0.25 |

The functional analysis of <VEGF-ANG-2> bispecific antibodies was assessed by Surface Plasmon Resonance (SPR) using a BIAcore® T100 or T200 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus the determination of the association rate constant (ka), the dissociation rate constant (kd), and of the equilibrium constant (KD).

Example 3

Binding to VEGF, ANG-2, FcgammaR and FcRn
VEGF Isoforms Kinetic Affinity Including Assessment of Species-Cross-Reactivity Around 12,000 resonance units (RU) of the capturing system (10 μg/mL goat anti human F(Ab)'$_2$; Order Code: 28958325; GE Healthcare Bio-Sciences AB, Sweden) were coupled on a CM5 chip (GE Healthcare BR-1005-30) at pH 5.0 by using an amine coupling kit supplied by GE Healthcare. The sample and system buffer was PBS-T (10 mM phosphate buffered saline including 0.05% Tween-20™) pH 7.4. The flow cell was set to 25° C.—and the sample block set to 12° C.—and primed with running buffer twice. The bispecific antibody was captured by injecting a 50 nM solution for 30 seconds at a flow of 5 μL/min. Association was measured by injection of human hVEGF121, mouse mVEGF120 or rat rVEGF164 in various concentrations in solution for 300 seconds at a flow of 30 μL/min starting with 300 nM in 1:3 dilutions. The dissociation phase was monitored for up to 1200 seconds and triggered by switching from the sample solution to running buffer. The surface was regenerated by 60 seconds washing with a Glycine pH 2.1 solution at a flow rate of 30 μL/min. Bulk refractive index differences were corrected by subtracting the response obtained from a goat anti human F(Ab')$_2$ surface. Blank injections were also subtracted (=double referencing). For calculation of apparent $K_D$ and other kinetic parameters the Langmuir 1:1 model was used. Results are shown below.

ANG-2 Solution Affinity Including Assessment of Species-Cross-Reactivity

Solution affinity measures the affinity of an interaction by determining the concentration of free interaction partners in an equilibrium mixture. The solution affinity assay involves the mixing of an <VEGF-ANG-2> bispecific antibody, kept at a constant concentration, with a ligand (=ANG-2) at varying concentrations. Maximum possible resonance units (e.g. 17,000 resonance units (RU)) of an antibody was immobilized on the CM5 chip (GE Healthcare BR-1005-30)

surface at pH 5.0 using an amine coupling kit supplied by GE Healthcare. The sample and system buffer was HBS-P pH 7.4. Flow cell was set to 25° C. and sample block to 12° C. and primed with running buffer twice. To generate a calibration curve increasing concentrations of ANG-2 were injected into a BIAcore flow-cell containing the immobilized <VEGF-ANG-2> bispecific antibody. The amount of bound ANG-2 was determined as resonance units (RU) and plotted against the concentration. Solutions of each ligand (11 concentrations from 0 to 200 nM for the <VEGF-ANG-2> bispecific antibody) were incubated with 10 nM ANG-2 and allowed to reach equilibrium at room temperature. Free ANG-2 concentrations were determined from calibration curve generated before and after measuring the response of solutions with known amounts of ANG-2. A 4-parameter fit was set with XLfit4 (IDBS Software) using Model 201 using free ANG-2 concentration as y-axis and used concentration of antibody for inhibition as x-axis. The affinity was calculated by determining the inflection point of this curve. The surface was regenerated by one time 30 seconds washing with a 0.85% $H_3PO_4$ solution at a flow rate of 30 μL/min. Bulk refractive index differences were corrected by subtracting the response obtained from a blank-coupled surface. Results are shown in below.

FcRn Steady State Affinity

Figure 5A:
FIGS. 5A and B:FcRn steady state affinity of A: VEGFang2-0015 (without IHH-AAA mutation) and B: VEGFang2-0016 (with IHH-AAA mutation).
Figure 5B:
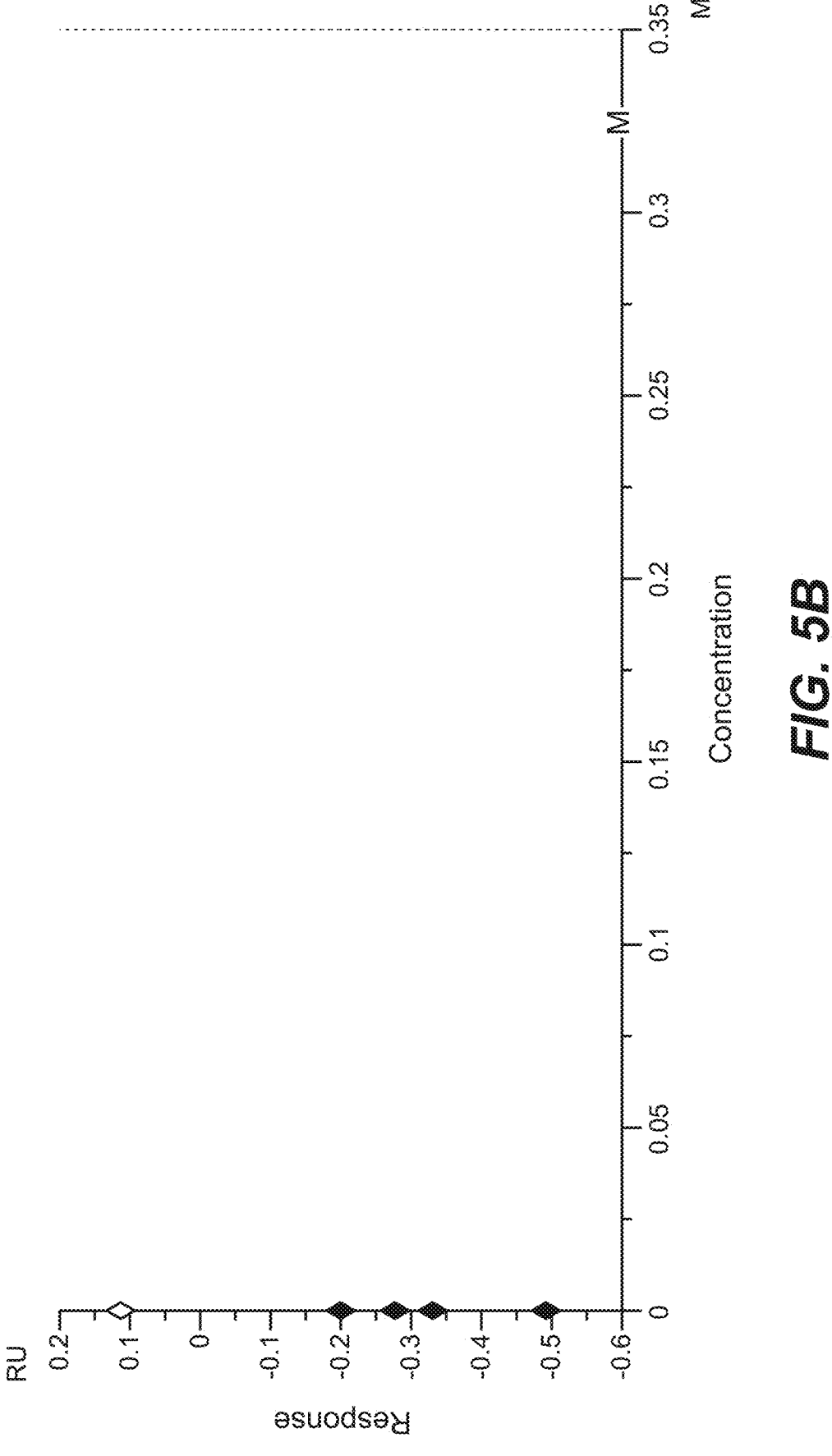

For FcRn measurement a steady state affinity was used to compare bispecific antibodies against each other. Human FcRn was diluted into coupling buffer (10 μg/mL, Na-Acetate pH 5.0) and immobilized on a C1-Chip (GE Healthcare BR-1005-35) by targeted immobilization procedure using a BIAcore wizard to a final response of 200 RU. Flow cell was set to 25° C. and sample block to 12° C. and primed with running buffer twice. The sample and system buffer was PBS-T (10 mM phosphate buffered saline including 0.05% Tween-20™) pH 6.0. To assess different IgG concentrations for each antibody, a concentration of 62.5 nM, 125 nM 250 nM, and 500 nM was prepared. Flow rate was set to 30 μL/min and the different samples were injected consecutively onto the chip surface choosing 180 seconds association time. The surface was regenerated by injected PBS-T pH 8 for 60 seconds at a flow rate of 30 μL/min. Bulk refractive index differences were corrected by subtracting the response obtained from a blank surface. Buffer injections were also subtracted (=double referencing). For calculation of steady state affinity the method from the BIA-Evaluation software was used. Briefly, the RU values were plotted against the analyzed concentrations, yielding a dose-response curve. Based on a 2-parametric fit, the upper asymptote was calculated, allowing the determination of the half-maximal RU value and hence the affinity. Results are shown in FIG. 5 and the Table below. Analogously the affinity to Cynomolgus, mouse and rabbit FcRn can be determined.

FcgammaRIIIa Measurement

Figure 6:
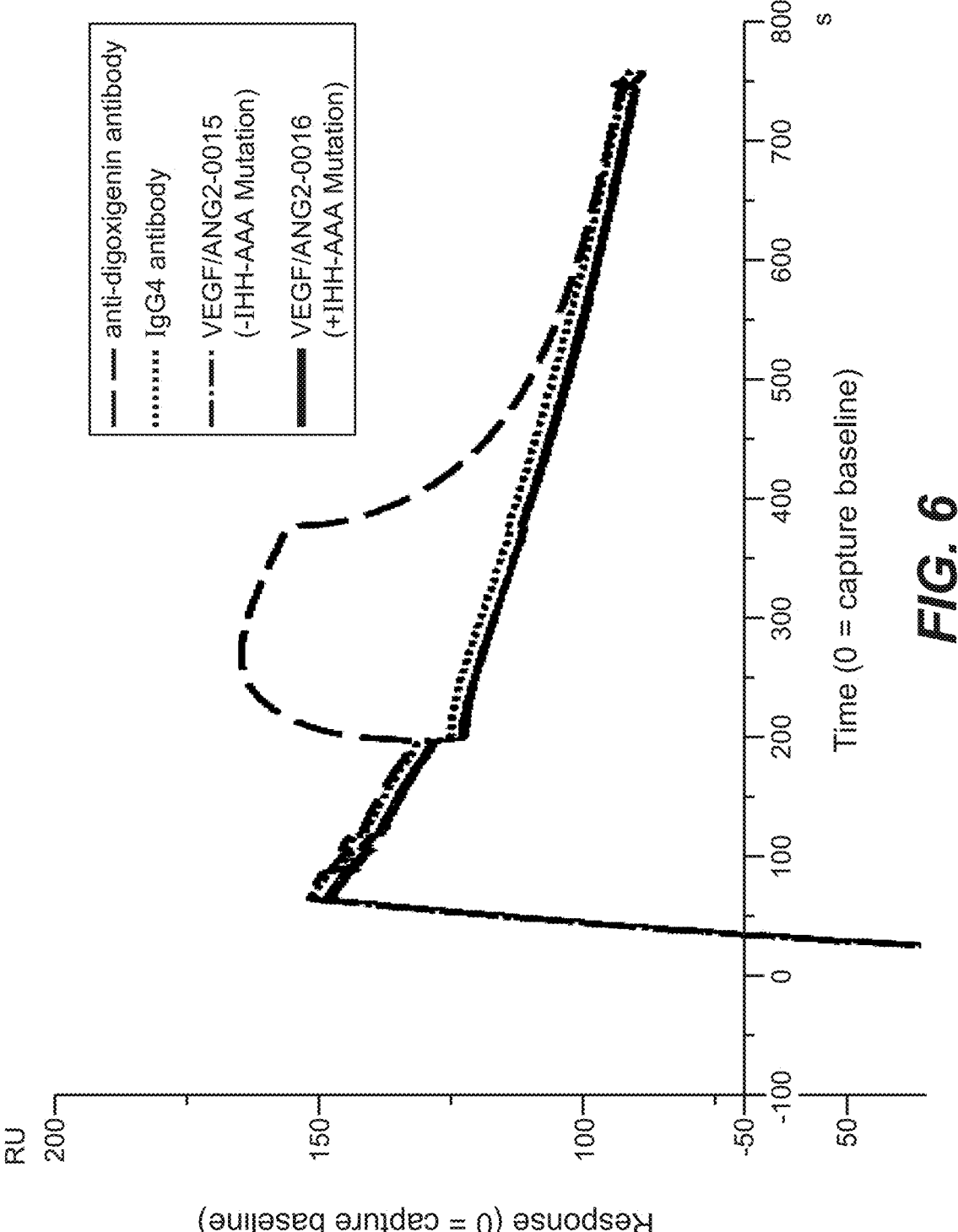
FIG. 6: FcgammaRIIIa interaction measurement of VEGFang2-0015 without IHH-AAA mutation and VEGFang2-0016 with IHH-AAA mutation (both are IgG1 subclass with P329G LALA mutations; as controls an anti-digoxigenin antibody (anti-Dig) of IgG1 subclass and an IgG4 based antibody were used).

For FcgammaRIIIa measurement a direct binding assay was used. Around 3,000 resonance units (RU) of the capturing system (1 μg/mL Penta-His; Qiagen) were coupled on a CM5 chip (GE Healthcare BR-1005-30) at pH 5.0 by using an amine coupling kit supplied by GE Healthcare. The sample and system buffer was HBS-P+ pH 7.4. The flow cell was set to 25° C.—and sample block to 12° C.—and primed with running buffer twice. The FcgammaRIIIa-His-receptor was captured by injecting a 100 nM solution for 60 seconds at a flow of 5 μL/min. Binding was measured by injection of 100 nM of bispecific antibody or monospecific control antibodies (anti-digoxigenin antibody (anti-Dig) for IgG1 subclass and an IgG4 subclass antibody) for 180 seconds at a flow of 30 μL/min. The surface was regenerated by 120 seconds washing with Glycine pH 2.5 solution at a flow rate of 30 μL/min. Because FcgammaRIIIa binding differs from the Langmuir 1:1 model, only binding/no binding was determined with this assay. In a similar manner Fcgamma-RIa and FcgammaRIIa binding can be determined. Results are shown in FIG. 6, where it follows that by introduction of the mutations P329G LALA no more binding to FcgammaRIIIa could be detected.

Assessment of Independent VEGF- and ANG-2-Binding to the <VEGF-ANG-2> Bispecific Antibodies Around 3,500 resonance units (RU) of the capturing system (10 μg/mL goat anti-human IgG; GE Healthcare Bio-Sciences AB, Sweden) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween-20™) pH 7.4. The temperature of the flow cell was set to 25° C. and of the sample block to 12° C. Before capturing, the flow cell was primed with running buffer twice.

The bispecific antibody was captured by injecting a 10 nM solution for 60 seconds at a flow of 5 μL/min. Independent binding of each ligand to the bispecific antibody was analyzed by determining the active binding capacity for each ligand, either added sequentially or simultaneously (flow of 30 μL/min):

1. Injection of human VEGF with a concentration of 200 nM for 180 seconds (identifies the single binding of the antigen).
2. Injection of human ANG-2 with a concentration of 100 nM for 180 seconds (identifies single binding of the antigen).
3. Injection of human VEGF with a concentration of 200 nM for 180 seconds followed by an additional injection of human ANG-2 with a concentration of 100 nM for 180 seconds (identifies binding of ANG-2 in the presence of VEGF).
4. Injection of human ANG-2 with a concentration of 100 nM for 180 seconds followed by an additional injection of human VEGF with a concentration of 200 nM (identifies binding of VEGF in the presence of ANG-2).
5. Co-injection of human VEGF with a concentration of 200 nM and of human ANG-2 with a concentration of 100 nM for 180 seconds (identifies the binding of VEGF and of ANG-2 at the same time).

The surface was regenerated by 60 seconds washing with a 3 M $MgCl_2$ solution at a flow rate of 30 μL/min. Bulk refractive index differences were corrected by subtracting the response obtained from a goat anti-human IgG surface.

The bispecific antibody was able to bind both antigens mutual independently if the resulting final signal of the approaches 3, 4 & 5 equals or is similar to the sum of the individual final signals of the approaches 1 and 2. Results are shown in the Table below, where both antibodies VEGFang2-0016, VEGFang2-0012 were shown to be able to bind mutual independently to VEGF and ANG-2.

Assessment of Simultaneous VEGF- and ANG-2-Binding to the <VEGF-ANG-2> Bispecific Antibodies First, around 1,600 resonance units (RU) of VEGF (20 μg/mL) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween-20™) pH 7.4. Flow cell was set to 25° C. and sample block to 12° C. and primed with running buffer twice. Second, 50 nM solution of the bispecific antibody was injected for 180 seconds at a flow of 30 μL/min. Third, hANG-2 was injected for 180 seconds at a flow of 30 μL/min. The binding response of hANG-2 depends from the amount of the bispecific antibody bound to VEGF and shows simultaneous binding. The surface was regenerated by 60 seconds washing with a 0.85% $H_3PO_4$ solution at a flow rate of 30 μL/min. Simultaneous binding is shown by an additional specific binding signal of hANG-2 to the previous VEGF bound <VEGF-ANG-2> bispecific antibodies. For both bispecific antibodies VEGFang2-0015 and VEGFang2-0016 simultaneous VEGF- and ANG-2-binding to the <VEGF-ANG-2> bispecific antibodies could be detected (data not shown).

TABLE

Results: Kinetic affinities to VEGF isoforms from different species

|  | VEGFang2-0015-apparent affinity | VEGFang2-0016-apparent affinity | VEGFang2-0012-apparent affinity | VEGFang2-0201-apparent affinity |
|---|---|---|---|---|
| human VEGF 121 | ≤1 pM (out of BIAcore specification) | ≤1 pM (out of BIAcore specification) | ≤1 pM (out of BIAcore specification) | ≤1 pM (out of BIAcore specification) |
| mouse VEGF 120 | no binding | no binding | no binding | no binding |
| rat VEGF 164 | 13 nM | 14 nM | 24 nM | 35 nM |

TABLE

Results: Solution affinities to ANG-2

|  | VEGFang2-0015 KD [nM] | VEGFang2-0016 KD [nM] | VEGFang2-0012 KD [nM] | VEGFang2-0201 KD [nM] |
|---|---|---|---|---|
| human ANG-2 | 8 | 20 | 20 | tbd |
| Cynomolgus ANG-2 | 5 | 13 | 10 | tbd |
| mouse ANG-2 | 8 | 13 | 8 | tbd |
| rabbit ANG-2 | 4 | 11 | 8 | tbd |

TABLE

Results: Affinity to FcRn of <VEGF-ANG-2> bispecific antibodies

|  | VEGFang2-0015 [affinity] | VEGFang2-0016 [affinity] | VEGFang2-0012 [affinity] | VEGFang2-0201 [affinity] |
|---|---|---|---|---|
| human FcRn | 0.8 μM | no binding | no binding | 0.8 μM |
| Cynomolgus FcRn | 0.9 μM | no binding | no binding | 1.0 μM |
| mouse FcRn | 0.2 μM | no binding | no binding | 0.2 μM |

TABLE

Results Binding to FcgammaRI-IIIa

|  | VEGFang2-0015 | VEGFang2-0016 | VEGFang2-0012 | VEGFang2-0201 |
|---|---|---|---|---|
| FcΓRIa | no binding | no binding | binding | binding |
| FcΓRIIa | no binding | no binding | no binding | binding |
| FcΓRIIIa | no binding | no binding | no binding | binding |

TABLE

Results: Independent binding of VEGF- and ANG-2 to <VEGF-ANG-2> bispecific antibodies

|  | 1) ANG-2 [RUmax] | 2) VEGF [RUmax] | 3) first VEGF then ANG-2 [RUmax] | 4) first ANG-2 then VEGF [RUmax] | 5) Co-injection ANG-2 + VEGF [RUmax] |
|---|---|---|---|---|---|
| VEGFang2-0016 | 174 | 50 | 211 | 211 | 211 |
| VEGFang2-0012 | 143 | 43 | 178 | 177 | 178 |

Example 4

Mass Spectrometry

This section describes the characterization of <VEGF-ANG-2> bispecific antibodies with emphasis on the correct assembly. The expected primary structures were confirmed by electrospray ionization mass spectrometry (ESI-MS) of the deglycosylated, and intact or IdeS-digested (IgG-degrading enzyme of *S. pyogenes*) <VEGF-ANG-2> bispecific antibodies. The IdeS-digestion was performed with 100 μg purified antibody incubated with 2 μg IdeS protease (Fabricator) in 100 mmol/L $NaH_2PO_4/Na_2HPO_4$, pH 7.1 at 37° C. for 5 h. Subsequently, the antibodies were deglycosylated with N-Glycosidase F, Neuraminidase and O-glycosidase (Roche) in 100 mmol/L $NaH_2PO_4/Na_2HPO_4$, pH 7.1 at 37° C. for up to 16 hours at a protein concentration of 1 mg/mL and subsequently desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

The masses obtained for the IdeS-digested, deglycosylated (Table below), or intact, deglycosylated (Table below) molecules correspond to the predicted masses deduced from the amino acid sequences for the <VEGF-ANG-2> bispecific antibodies consisting of two different light chains LCANG-2 and LCLucentis, and two different heavy chains HCANG-2 and HCLucentis.

TABLE

Masses of the deglycosylated and IdeS-digested bispecific <VEGF/ANG2> antibodies VEGFang2-0201 (without IHH-AAA mutation) and VEGFang2-0012 (with IHH-AAA mutation)

|  | F(Ab')2 of the <VEGF-ANG-2> bispecific antibody | | Deglycosylated Fc-region of the <VEGF-ANG-2> bispecific antibody | |
|---|---|---|---|---|
| sample | predicted average mass [Da] | observed average mass [Da] | predicted average mass [Da] | observed average mass [Da] |
| VEGFang2-0201 | 99360.8 | 99360.7 | 47439.2 | 47430.1 |
| VEGFang2-0012 | 99360.8 | 99361.1 | 47087.7 | 47082.0 |

TABLE

Masses of the deglycosylated <VEGF/ANG2> antibodies
VEGFang2-0016 (with IHH-AAA mutation) and
VEGFang2-0015 (without IHH-AAA mutation)

| | deglycosylated <VEGF-ANG-2> bispecific antibody | |
|---|---|---|
| | predicted average mass [Da] | observed average mass [Da] |
| VEGFang2-0016 | 146156.9 | 146161.2 |
| VEGFang2-0015 | 146505.3 | 146509.4 |

Example 5

FcRn Chromatography
Coupling to Streptavidin Sepharose:

One gram streptavidin sepharose (GE Healthcare) was added to the biotinylated and dialyzed receptor and incubated for two hours with shaking. The receptor derivatized sepharose was filled in a 1 mL XK column (GE Healthcare).
Chromatography Using the FcRn Affinity Column:
Conditions:
column dimensions: 50 mm×5 mm
bed height: 5 cm
loading: 50 µg sample
equilibration buffer: 20 mM MES, with 150 mM NaCl, adjusted to pH 5.5
elution buffer: 20 mM Tris/HCl, with 150 mM NaCl, adjusted to pH 8.8
elution: 7.5 CV equilibration buffer, in 30 CV to 100% elution buffer, 10 CV elution buffer
Human FcRn Affinity Column Chromatography In the following Table retention times of <VEGF-ANG-2> bispecific antibodies on affinity columns comprising human FcRn are given. Data were obtained using the conditions above.

TABLE

Results: retention times of <VEGF-ANG-2> bispecific antibodies

| antibody | retention time [min] |
|---|---|
| VEGFAng2-0015 (without IHH-AAA mutation) | 78.5 |
| VEGFAng2-0201 (without IHH-AAA mutation) | 78.9 |
| VEGFAng2-0012 (with IHH-AAA mutation) | 2.7 (Void-peak) |
| VEGFAng2-0016 (with IHH-AAA mutation) | 2.7 (Void-peak) |

Example 6

Pharmacokinetic (PK) Properties of Antibodies with IHH-AAA Mutation
PK Data with FcRn Mice Transgenic for Human FcRn
In Life Phase:

The study included female C57BL/6J mice (background); mouse FcRn deficient, but hemizygous transgenic for human FcRn (huFcRn, line 276-/tg)
Part 1:

All mice were injected once intravitreally into the right eye with 2 µL/animal of the appropriate solution (i.e. 21 µg compound/animal (VEGFAng2-0015 (without IHH-AAA mutation)) or 23.6 µg compound/animal (VEGFAng2-0016 (with IHH-AAA mutation)).

Mice were allocated to 2 groups with 6 animals each. Blood samples were taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 µL of the compound were injected using a 35-gauge needle.

Blood was collected via the retrobulbar venous plexus of the contralateral eye from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.
Part 2:

All mice were injected once intravenously via the tail vein with 200 µL/animal of the appropriate solution (i.e. 21 µg compound/animal (VEGFAng2-0015 (without IHH-AAA mutation)) or 23.6 µg compound/animal (VEGFAng2-0016 (with IHH-AAA mutation)).

Mice were allocated to 2 groups with 5 animals each. Blood samples were taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 µL were obtained from blood after 1 hour at RT by centrifugation (9,300×g) at 4° C. for 3 min. Serum samples were frozen directly after centrifugation and stored frozen at −80° C. until analysis.
Preparation of Whole Eye Lysates (Mice)

The eye lysates were gained by physico-chemical disintegration of the whole eye from laboratory animals. For mechanical disruption, each eye was transferred into a 1.5 mL micro vial with conical bottom. After freeze and thawing, the eyes were washed with 1 mL cell washing buffer once (Bio-Rad, Bio-Plex Cell Lysis Kit, Cat. No. 171-304011). In the following step, 500 µL of freshly prepared cell lysis buffer were added and the eyes were grinded using a 1.5 mL tissue grinding pestle (Kimble Chase, 1.5 mL pestle, Art. No. 749521-1500). The mixture was then frozen and thawed five times and grinded again. To separate lysate from remaining tissue the samples were centrifuged for 4 min at 4,500 g. After centrifuging the supernatant was collected and stored at −20° C. until further analysis in the quantification ELISA.
Analysis The concentrations of the <VEGF-ANG-2> antibodies in mice serum and eye lysates were determined with an enzyme linked immunosorbent assay (ELISA).

For quantification of <VEGF-ANG-2> antibodies in mouse serum samples and eye lysates, a standard solid-phase serial sandwich immunoassay with biotinylated and digoxigenylated monoclonal antibodies used as capture and detection antibodies was performed. To verify the integrity of the bispecificity of the analyte the biotinylated capture antibody recognizes the VEGF-binding site whereas the digoxigenylated detection antibody will bind to the ANG-2 binding site of the analyte. The bound immune complex of capture antibody, analyte and detection antibody on the solid phase of the streptavidin coated micro titer plate (SA-MTP)

was then detected with a horseradish-peroxidase coupled to an anti-digoxigenin antibody. After washing unbound material from the SA-MTP and addition of ABTS-substrate, the gained signal was proportional to the amount of analyte bound on the solid phase of the SA-MTP. Quantification was then done by converting the measured signals of the samples into concentrations referring to calibrators analyzed in parallel.

In a first step the SA-MTP was coated with 100 µL/well of biotinylated capture antibody solution (anti-idiotypic antibody mAb<Id<VEGF>>M-2.45.51-IgG-Bi(DDS)) with a concentration of 1 µg/mL for one hour at 500 rpm on a MTP-shaker. Meanwhile calibrators, QC-samples and samples were prepared. Calibrators and QC-samples were diluted to 2% serum matrix; samples were diluted until the signals were within the linear range of the calibrators.

After coating the SA-MTP with capture antibody, the plate was washed three times with washing buffer and 300 µL/well. Subsequently 100 µL/well of the calibrators, QC-samples and samples were pipetted on the SA-MTP and incubated again for one hour at 500 rpm. The analyte was now bound with its anti-VEGF binding site via the capture antibody to the solid phase of the SA-MTP. After incubation and removal of unbound analyte by washing the plate 100 µL/well of the first detection antibody (anti-idiotypic antibody mAb<Id-<ANG-2>>M-2.6.81-IgG-Dig(XOSu)) with a concentration of 250 ng/mL was added to the SA-MTP. Again, the plate was incubated for one hour at 500 rpm on a shaker. After washing, 100 µL/well of the second detection antibody (pAb<Digoxigenin>S-Fab-POD (poly)) at a concentration of 50 mU/mL was added to the wells of the SA-MTP and the plate was incubated again for one hour at 500 rpm. After a final washing step to remove excess of detection antibody, 100 µL/well substrate (ABTS) was added. The antibody-enzyme conjugate catalyzes the color reaction of the ABTS® substrate. The signal was then measured by an ELISA reader at 405 nm wavelength (reference wavelength: 490 nm ([405/490] nm)).

Pharmacokinetic Evaluation

The pharmacokinetic parameters were calculated by non-compartmental analysis, using the pharmacokinetic evaluation program WinNonlin™ (Pharsight), version 5.2.1.

Results:

A) Serum Concentrations

Figure 7A:
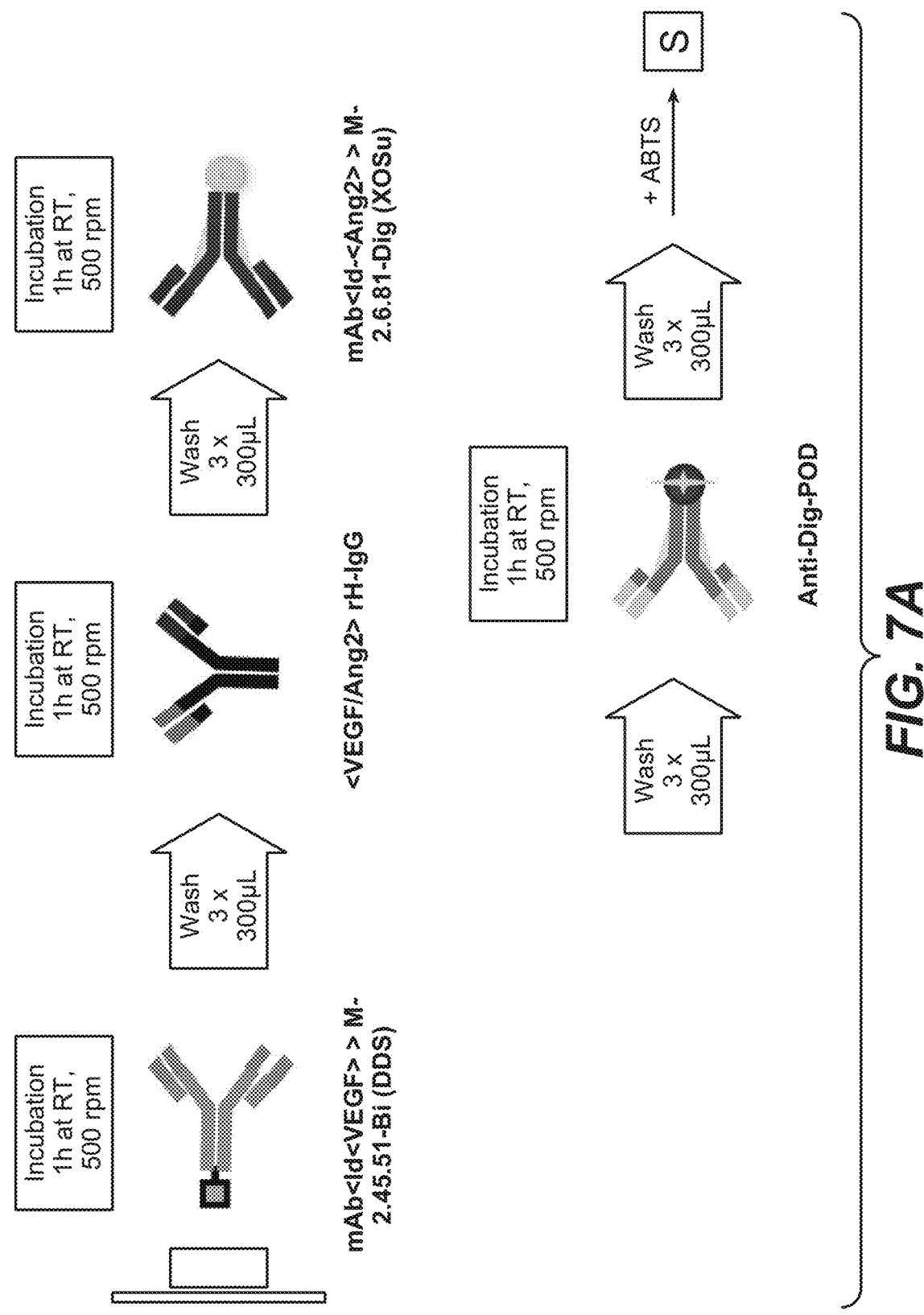
FIG. 7A: Schematic pharmacokinetic (PK)-ELISA assay principle for determination of concentrations of <VEGF-ANG-2> bispecific antibodies in serum and whole eye lysates.
Figure 7B:
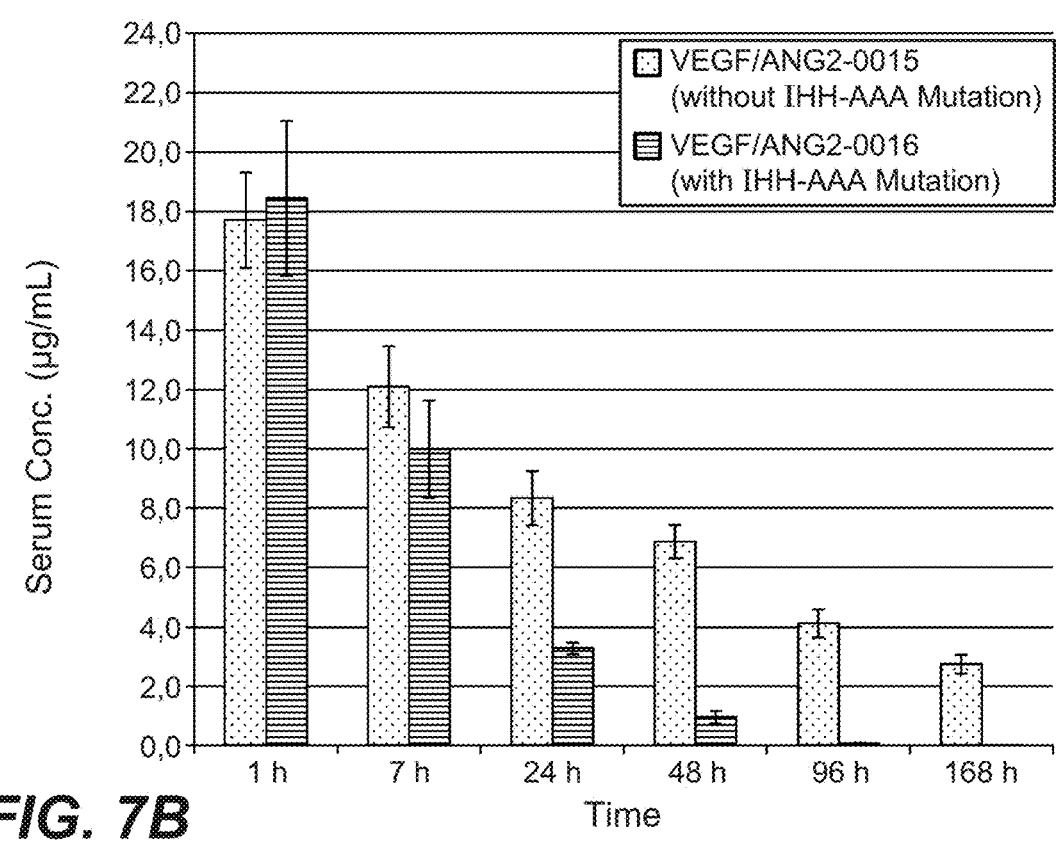
FIG. 7B: Serum concentration after intravenous (i.v.) application: comparison of VEGFang2-0015 without IHH-AAA mutation and VEGFang2-0016 with IHH-AAA mutation.
Figure 7C:
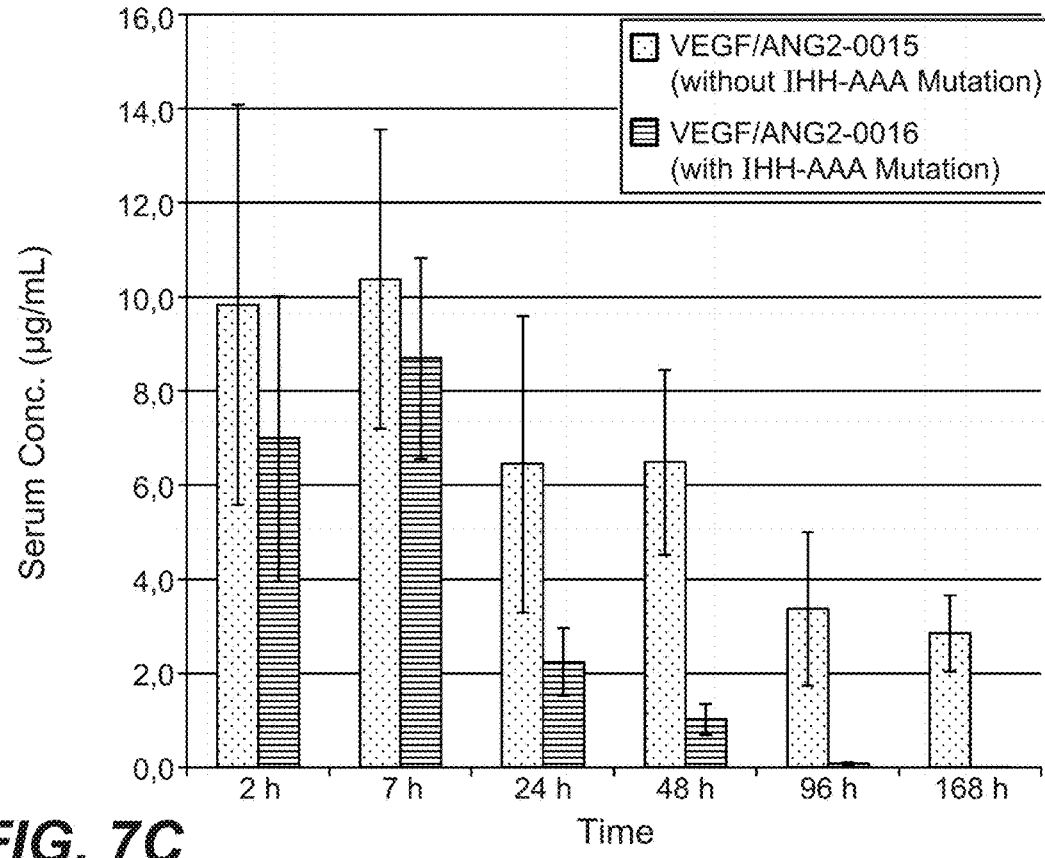
FIG. 7C: Serum concentration after intravitreal application: comparison of VEGFang2-0015 without IHH-AAA mutation and VEGFang2-0016 with IHH-AAA mutation.

Results for serum concentrations are shown in the following Tables and FIGS. 7B to 7C.

TABLE

VEGFAng2-0015 (without IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | | 17.7 |
| 2 h | 9.8 | |
| 7 h | 10.4 | 12.1 |
| 24 h | 6.4 | 8.3 |
| 48 h | 6.5 | 6.9 |
| 96 h | 3.4 | 4.1 |
| 168 h | 2.9 | 2.7 |

TABLE

VEGFAng2-0016 (with IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | | 18.4 |
| 2 h | 7.0 | |
| 7 h | 8.7 | 10.0 |
| 24 h | 2.2 | 3.3 |
| 48 h | 1.0 | 1.0 |
| 96 h | 0.1 | 0.1 |
| 168 h | 0.0 | 0.0 |

TABLE

VEGFang2-0015 (without IHH-AAA mutation) and VEGFang2-0016 (with IHH-AAA mutation): Comparison of serum concentrations after intravitreal application

| ID | VEGFang2-0015 (without IHH-AAA mutation) average conc. [µg/mL] | VEGFang2-0016 (with IHH-AAA mutation) average conc. [µg/mL] |
|---|---|---|
| 2 h | 9.8 | 7.0 |
| 7 h | 10.4 | 8.7 |
| 24 h | 6.4 | 2.2 |
| 48 h | 6.5 | 1.0 |
| 96 h | 3.4 | 0.1 |
| 168 h | 2.9 | 0.0 |

TABLE

VEGFang2-0015 (without IHH-AAA mutation) and VEGFang2-0016 (with IHH-AAA mutation): Comparison of serum concentrations after intravenous application

| ID | VEGFang2-0015 (without IHH-AAA mutation) average conc. [µg/mL] | VEGFang2-0016 (with IHH-AAA mutation) average conc. [µg/mL] |
|---|---|---|
| 1 h | 17.7 | 18.4 |
| 7 h | 12.1 | 10.0 |
| 24 h | 8.3 | 3.3 |
| 48 h | 6.9 | 1.0 |
| 96 h | 4.1 | 0.1 |
| 168 h | 2.7 | 0.0 |

Results:

B) Concentrations in Eye-Lysates of Left and Right Eyes

Figure 7D:
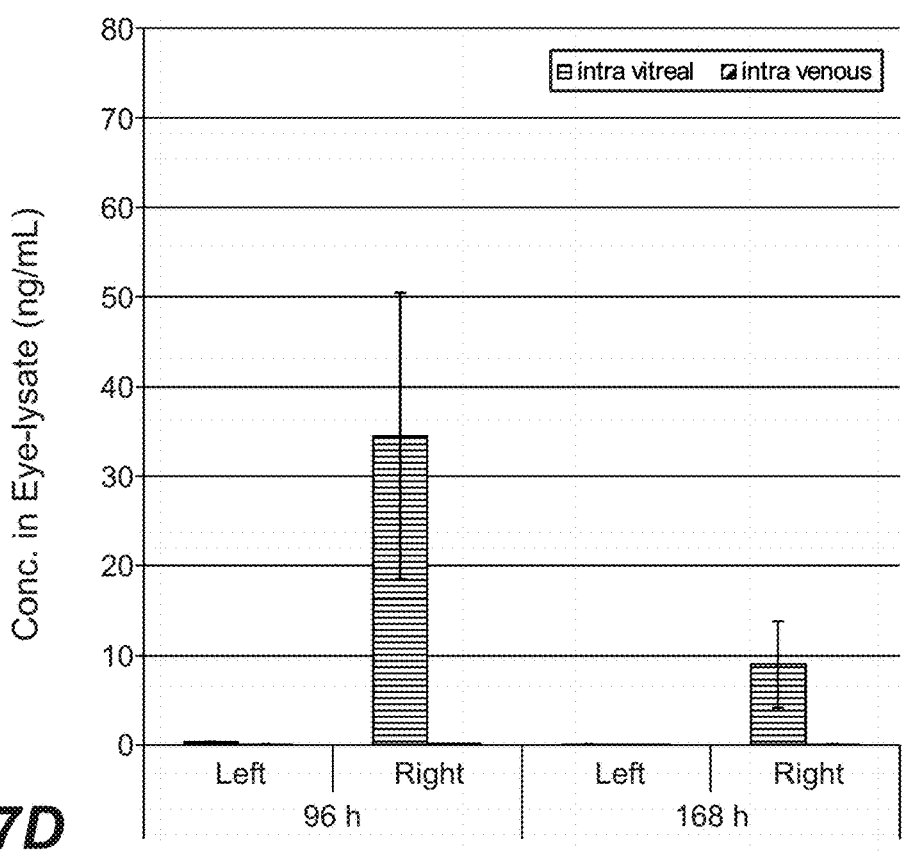
FIG. 7D: Eye lysates concentration of VEGFang2-0016 (with IHH-AAA mutation) in right and left eye (after intravitreal application only into the right eye in comparison to intravenous application): significant concentrations could be detected only in the right eye after intravitreal application; after intravenous application no concentration in eye lysates could be detected due to the low serum half-life of VEGFang2-0016 (with IHH-AAA mutation).
Figure 7E:
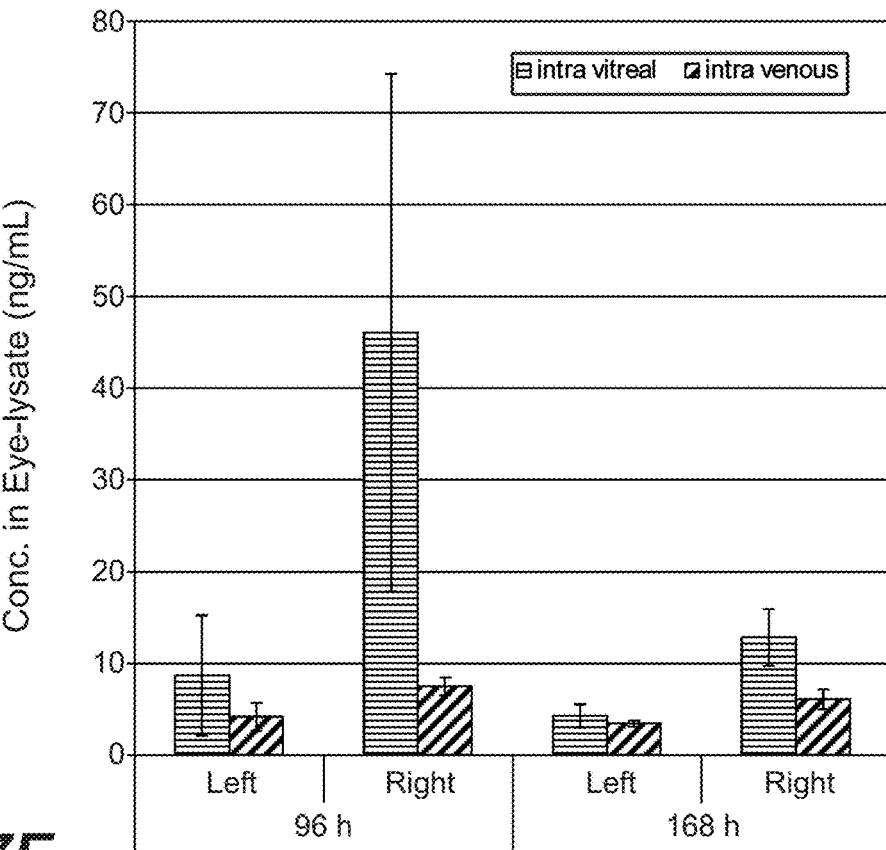
FIG. 7E: Eye lysates concentration of VEGFang2-0015 (without IHH-AAA mutation) in right and left eye (after intravitreal application only into the right eye in comparison to intravenous application): in the right eye (and to some extent in the left eye) after intravitreal application concentrations of VEGFang2-0015 could be detected; this indicates the diffusion from the right eye into serum and from there into the left eye, which can be explained by the long half-life of VEGFang2-0015 (without IHH-AAA mutation); after intravenous application also significant concentrations in eye lysates of both eyes could be detected due to diffusion into the eyes of the serum-stable VEGFang2-0015 (without IHH-AAA mutation).
Figure 8A:
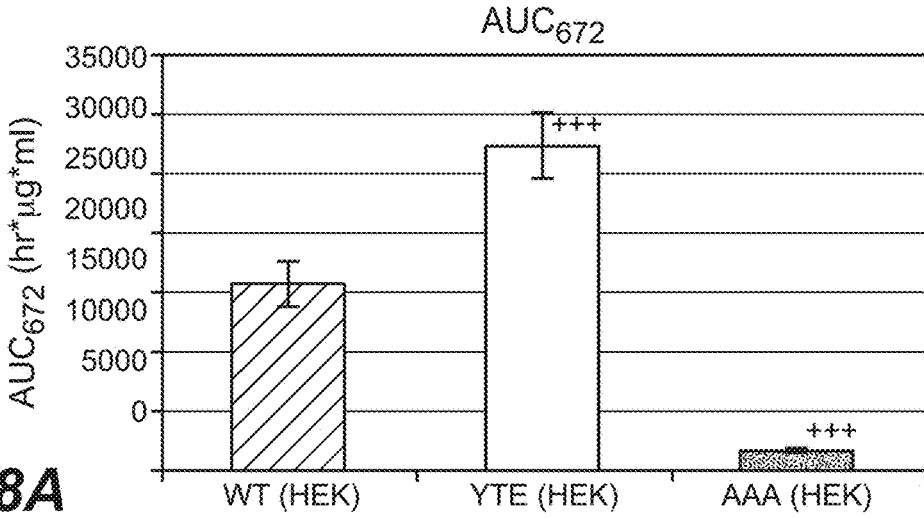
FIGS. 8A-8C: Antibodies engineered with respect to their ability to bind FcRn display prolonged (YTE mutation) or shortened (IHH-AAA mutation) in vivo half-lives, enhanced (YTE mutation) or reduced binding (IHH-AAA mutation) compared to the reference wild-type (wt) antibody in SPR analysis as well as enhanced or reduced retention time in FcRn column chromatography.
Figure 8B:
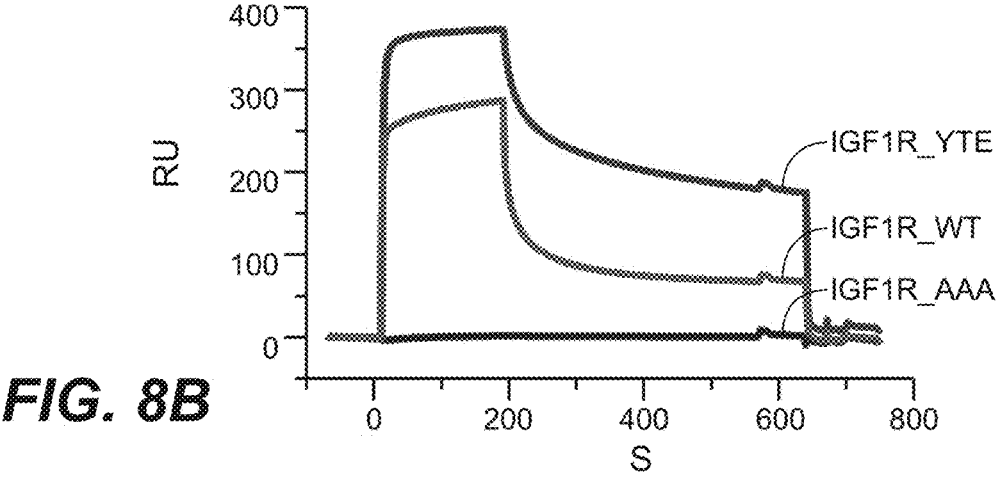
Figure 8C:
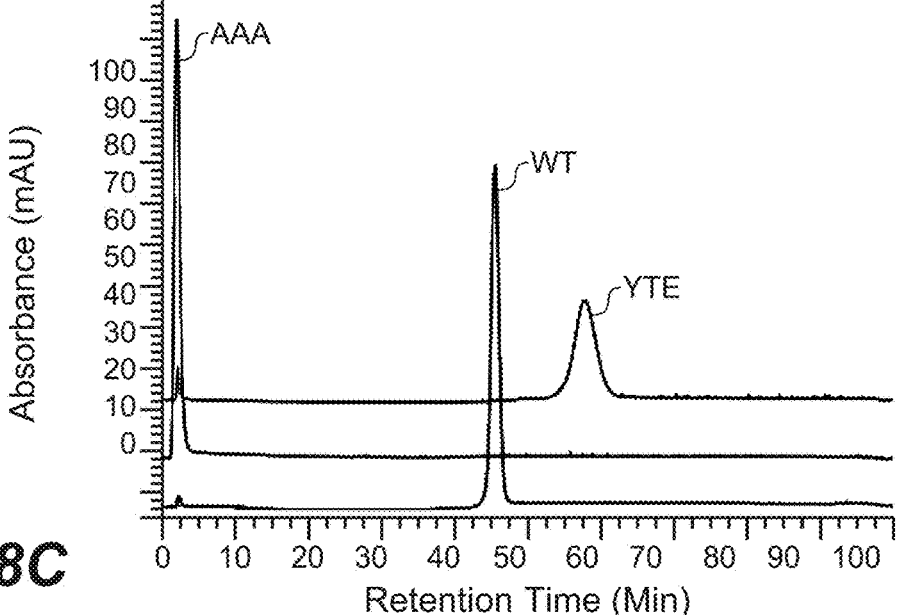

Results for concentrations in eye lysates are shown in the following Tables and FIGS. 7D to 7E.

TABLE

Concentrations of VEGFang2-0015 (without IHH-AAA mutation) in eye lysates after intra vitreal application into right eye mean conc. values from n = 6 mice

| ID | | mean conc. [ng/mL] |
|---|---|---|
| 96 h | left eye | 8.7 |
| | right eye | 46.1 |
| 168 h | left eye | 4.3 |
| | right eye | 12.9 |

TABLE

Concentrations of VEGFang2-0015 (without IHH-AAA mutation)
in eye lysates after intravenous application
mean conc. values from n = 5 mice

| ID | | mean conc. [ng/mL] |
|---|---|---|
| 96 h | left eye | 4.2 |
| | right eye | 7.5 |
| 168 h | left eye | 3.4 |
| | right eye | 6.1 |

TABLE

Concentrations of VEGFang2-0016 (with IHH-AAA mutation)
in eye lysates after intra vitreal application into right eye
mean conc. values from n = 5 mice

| ID | | mean conc. [ng/mL] |
|---|---|---|
| 96 h | left eye | 0.3 |
| | right eye | 34.5 |
| 168 h | left eye | 0.1 |
| | right eye | 9.0 |

TABLE

Concentrations of VEGFang2-0016 (with IHH-AAA
mutation) in eye lysates after intravenous application mean conc. values from n = 5 mice

| ID | | mean conc. [ng/mL] |
|---|---|---|
| 96 h | left eye | 0.0 |
| | right eye | 0.1 |
| 168 h | left eye | 0.0 |
| | right eye | 0.1 |

Summary of Results:

After intravitreal application the bispecific <VEGF-ANG-2> antibody as reported herein VEGFang2-0016 (with IHH-AAA mutation) shows similar concentrations (after 96 and 168 hours) in the eye lysates as compared to the bispecific <VEGF-ANG-2> antibody without IHH-AAA mutation VEGFang2-0015.

Also after intravitreal application the bispecific <VEGF-ANG-2> antibody as reported herein VEGFang2-0016 (with IHH-AAA mutation) shows in addition a faster clearance and shorter half-life in the serum as compared to the bispecific <VEGF-ANG-2> antibody without IHH-AAA mutation VEGFang2-0015.

Example 7

Mouse Cornea Micropocket Angiogenesis Assay

To test the anti-angiogenic effect bispecific <VEGF-ANG-2> antibody with the respective VEGF binding VH and VL of SEQ ID NO: 20 and 21 and the ANG-2 binding VH and VL of SEQ ID NO: 28 and 29 on VEGF-induced angiogenesis in vivo, a mouse cornea micropocket angiogenesis assay was performed. In this assay a VEGF soaked Nylaflo disc was implanted into a pocket of the avascular cornea at a fixed distance to the limbal vessels. Vessels immediately grow into the cornea towards the developing VEGF gradient. 8 to 10 weeks old female Balb/c mice were purchased from Charles River, Sulzfeld, Germany. The protocol was modified according to the method described by Rogers, M. S., et al., Nat. Protoc. 2 (2007) 2545-2550.

Briefly, micropockets with a width of about 500 μm were prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm was implanted and the surface of the implantation area was smoothened. Discs were incubated in corresponding growth factor or in vehicle for at least 30 min. After 3, 5 and 7 days (or alternatively only after 3, 5 or 7 days) eyes were photographed and vascular response was measured. The assay was quantified by calculating the percentage of the area of new vessels per total area of the cornea.

The discs were loaded with 300 ng VEGF or with PBS as a control and implanted for 7 days. The outgrowth of vessels from the limbus to the disc was monitored over time on day 3, 5 and/or 7. One day prior to disc implantation the antibodies were administered intravenously at a dose of 10 mg/kg (due to the intravenous application the serum-stable VEGFang2-0015 (without IHH-AAA mutation) which only differs from VEGFang2-0016 by the IHH-AAA mutation and has the same anti-VEGF and anti-ANG-2 VHs and VLs to mediate efficacy, was used as surrogate) for testing the anti-angiogenic effect on VEGF-induced angiogenesis in vivo. Animals in the control group receive vehicle. The application volume was 10 mL/kg.

Example 8

Pharmacokinetic (PK) Properties of Antibodies with HHY-AAA Mutation
PK Data with FcRn Mice Transgenic for Human FcRn
In Life Phase:

The study included female C57BL/6J mice (background); mouse FcRn deficient, but hemizygous transgenic for human FcRn (huFcRn, line 276-/tg)
Part 1:

All mice were injected once intravitreally into the right eye with the appropriate solution of IGF-1R 0033, IGF-1R 0035, IGF-1R 0045 (i.e. 22.2 μg compound/animal of IGF-1R 0033, 24.4 μg compound/animal IGF-1R 0035, 32.0 μg compound/animal IGF-1R and 32.0 μg compound/animal of IGF-1R 0045).

Thirteen mice were allocated to 2 groups with 6 and 7, respectively, animals each. Blood samples are taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 μL of the compound were injected using a 35-gauge needle.

Blood was collected via the retrobulbar venous plexus of the contralateral eye from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:

All mice were injected once intravenously via the tail vein with the appropriate solution of IGF-1R 0033, IGF-1R 0035, IGF-1R 0045 (i.e. 22.2 μg compound/animal of IGF-1R 0033, 24.4 μg compound/animal IGF-1R 0035, 32.0 μg compound/animal IGF-1R and 32.0 μg compound/animal of IGF-1R 0045).

Twelve mice were allocated to 2 groups with 6 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis.

Preparation of Cell Lysis Buffer

Carefully mix 100 μL factor 1, 50 μL factor 2 and 24.73 mL Cell Lysis buffer (all from Bio-Rad, Bio-Plex Cell Lysis Kit, Cat. No. 171-304011) and add 125 μL PMSF-solution (174.4 mg phenylmethylsulfonylfluoride diluted in 2.0 mL DMSO).

Preparation of Whole Eye Lysates (Mice)

The eye lysates were gained by physico-chemical disintegration of the whole eye from laboratory animals. For mechanical disruption each eye was transferred into a 1.5 mL micro vial with conical bottom. After thawing, the eyes were washed with 1 mL cell washing buffer once (Bio-Rad, Bio-Plex Cell Lysis Kit, Cat. No. 171-304011). In the following step 500 μL of freshly prepared cell lysis buffer were added and the eyes were grinded using a 1.5 mL tissue grinding pestle (VWR Int., Art. No. 431-0098). The mixture was then frozen and thawed five times and grinded again. To separate lysate from remaining tissue the samples were centrifuged for 4 min. at 4500×g. After centrifuging the supernatant was collected and stored at −20° C. until further analysis in the quantification ELISA Analysis (Serum)

For quantification of antibodies in mouse serum sample, a standard solid-phase serial sandwich immunoassay with biotinylated and digoxigenated monoclonal antibodies used as capture and detection antibodies is performed. Serum accounts for about 50% of the full blood sample volume.

More detailed, concentrations of the antibodies in mouse serum samples were determined by a human-IgG (Fab) specific enzyme linked immunosorbent assay. Streptavidin coated microtiter plates were incubated with the biotinylated anti-human Fab(kappa) monoclonal antibody M-1.7.10-IgG as capture antibody diluted in assay buffer for one hour at room temperature with agitation. After washing three times with phosphate-buffered saline-polysorbate 20 (Tween20), serum samples at various dilutions were added followed by second incubation for one hour at room temperature. After three repeated washings bound antibody was detected by subsequent incubation with the anti-human Fab(CH1) monoclonal antibody M-1.19.31-IgG conjugated to digoxigenin, followed by an anti-digoxigenin antibody conjugated to horseradish peroxidase (HRP). ABTS (2,2'-azino-bis(3-ethylbenzothiazoline-6-sulphonic acid); Roche Diagnostics GmbH, Mannheim, Germany) was used as HRP substrate to form a colored reaction product. Absorbance of the resulting reaction product was read at 405 nm (ABTS; reference wavelength: 490 nm).

All samples, positive and negative control samples were analyzed in replicates and calibrated against an antibody standard provided.

Analysis (Eye Lysate)

The concentrations of the analytes in mouse eye lysate samples were determined using a qualified electro-chemiluminescence immunoassay (ECLIA) method based on the ELECSYS® instrument platform (Roche Diagnostics GmbH, Mannheim, Germany) under non-GLP conditions.

The undiluted supernatant (eye lysates) was incubated with capture and detection molecules for 9 min. at 37° C. Biotinylated anti-human-Fab(kappa) monoclonal antibody M-1.7.10-IgG was used as capture molecule and a ruthenium(II)tris(bispyridyl)$_3^{2+}$ labeled anti-human-Fab(CH1) monoclonal antibody M-1.19.31-IgG was used for detection. Streptavidin-coated magnetic microparticles were added and incubated for additional 9 min. at 37° C. to allow binding of preformed immune complexes due to biotin-streptavidin interactions. The microparticles were magnetically captured on an electrode and a chemiluminescent signal generated using the co-reactant tripropyl amine (TPA). The gained signal was measured by a photomultiplier detector.

TABLE

Standard chart IGF-1R 0033

| | concen-tration [ng/mL] | signal mean counts | standard deviation signal counts | serum-conc. [ng/mL] | re-covery [%] |
|---|---|---|---|---|---|
| standard sample 9 | 0 | 1038 | 46 | — | — |
| standard sample 8 | 0.686 | 2682 | 105 | 0.675 | 98 |
| standard sample 7 | 2.06 | 6275 | 791 | 2.06 | 100 |
| standard sample 6 | 6.17 | 15907 | 316 | 6.23 | 101 |
| standard sample 5 | 18.5 | 45455 | 1238 | 18.8 | 102 |
| standard sample 4 | 55.6 | 133940 | 949 | 55.7 | 100 |
| standard sample 3 | 167 | 388069 | 2929 | 165 | 99 |
| standard sample 2 | 500 | 1129804 | 16777 | 503 | 101 |
| standard sample 1 | 1500 | 2956965 | 60287 | 1499 | 100 |

TABLE

Standard chart IGF-1R 0035

| | concen-tration [ng/mL] | signal mean counts | standard deviation signal counts | serum-conc. [ng/mL] | re-covery [%] |
|---|---|---|---|---|---|
| standard sample 9 | 0 | 1024 | 63 | — | — |
| standard sample 8 | 0.686 | 2817 | 38 | 0.681 | 99 |
| standard sample 7 | 2.06 | 6451 | 39 | 2.08 | 101 |
| standard sample 6 | 6.17 | 17100 | 319 | 6.13 | 99 |
| standard sample 5 | 18.5 | 49693 | 713 | 18.6 | 100 |
| standard sample 4 | 55.6 | 146746 | 2575 | 56.1 | 101 |
| standard sample 3 | 167 | 423597 | 5068 | 165 | 99 |
| standard sample 2 | 500 | 1224244 | 11655 | 502 | 100 |
| standard sample 1 | 1500 | 3144901 | 44536 | 1499 | 100 |

TABLE

Standard chart IGF-1R 0045

| | concen-tration [ng/mL] | signal mean counts | standard deviation signal counts | serum-conc. [ng/mL] | re-covery [%] |
|---|---|---|---|---|---|
| standard sample 9 | 0 | 1339 | 545 | — | — |
| standard sample 8 | 0.686 | 3108 | 61 | 0.622 | 91 |
| standard sample 7 | 2.06 | 7032 | 189 | 1.93 | 94 |
| standard sample 6 | 6.17 | 19175 | 750 | 6.10 | 99 |
| standard sample 5 | 18.5 | 55526 | 823 | 18.7 | 101 |

TABLE-continued

Standard chart IGF-1R 0045

| | concentration [ng/mL] | signal mean counts | standard deviation signal counts | serum-conc. [ng/mL] | recovery [%] |
|---|---|---|---|---|---|
| standard sample 4 | 55.6 | 158591 | 5412 | 55.7 | 100 |
| standard sample 3 | 167 | 456316 | 28759 | 167 | 100 |
| standard sample 2 | 500 | 1274801 | 47532 | 499 | 100 |
| standard sample 1 | 1500 | 3280452 | 239523 | 1501 | 100 |

Results:

A) Serum Concentrations

Figure 17:
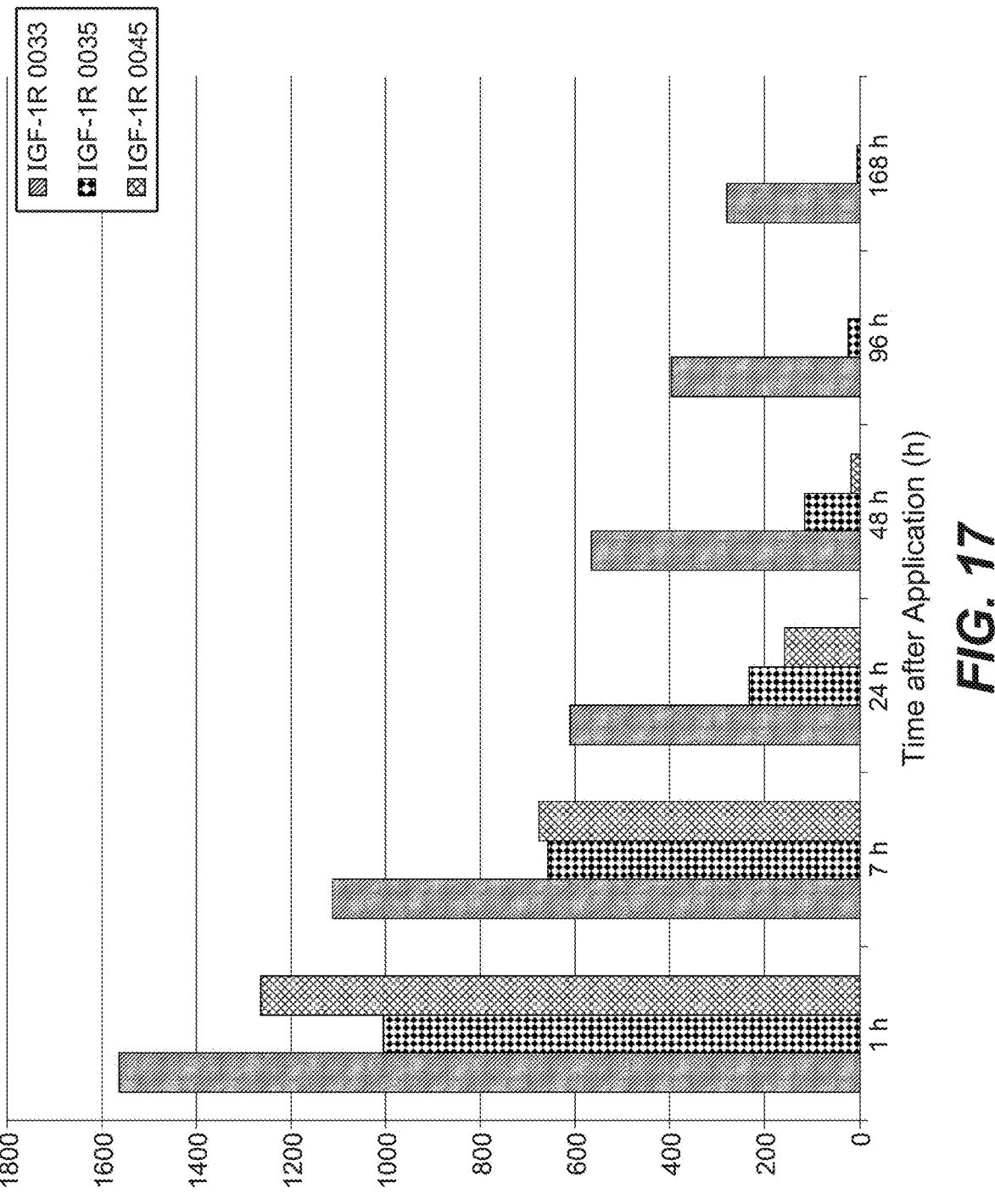
FIG. 17: Comparison of serum concentrations after intravenous application of antibodies IGF-1R 0033, 0035 and 0045.

Results for serum concentrations are shown in the following Tables and FIG. 17.

TABLE

IGF-1R 0033 (without HHY-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | n.d. | 34.7 |
| 2 h | 5.9 | n.d. |
| 7 h | 11.1 | 24.7 |
| 24 h | 4.4 | 13.6 |
| 48 h | 7.8 | 12.6 |
| 96 h | 2.1 | 8.9 |
| 168 h | 2.9 | 6.2 |

(n.d. = not determined)

TABLE

IGF-1R 0035 (with HHY-AAA mutation in one Fc-region polypeptide): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | n.d. | 24.5 |
| 2 h | 7.3 | n.d. |
| 7 h | 7.9 | 16.1 |
| 24 h | 2.3 | 5.7 |
| 48 h | 1.7 | 2.9 |
| 96 h | 0.3 | 0.6 |
| 168 h | 0.1 | 0.2 |

TABLE

IGF-1R 0045 (with HHY-AAA mutation in both Fc-region polypeptides): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | n.d. | 40.5 |
| 2 h | 13.2 | n.d. |
| 7 h | 9.6 | 21.7 |
| 24 h | 2.2 | 5.1 |

TABLE-continued

IGF-1R 0045 (with HHY-AAA mutation in both Fc-region polypeptides): Comparison of serum concentrations after intravitreal and intravenous application

| ID | serum concentration after intravitreal application average conc. [µg/mL] | serum concentration after intravenous application average conc. [µg/mL] |
|---|---|---|
| 48 h | 0.9 | 0.7 |
| 96 h | 0.05 | 0.03 |
| 168 h | 0.01 | BLQ |

(BLQ = below limit of quantitation)

TABLE

Comparison of serum concentrations after intravenous application of antibodies IGF-1R 0033, 0035 and 0045 normalized to 1 µg applied antibody

| ID | IGF-1R 0033 | IGF-1R 0035 | IGF-1R 0045 |
|---|---|---|---|
| | average conc. [ng/mL/µg applied antibody] | | |
| 1 h | 1564 | 1006 | 1266 |
| 7 h | 1114 | 659 | 679 |
| 24 h | 613 | 234 | 160 |
| 48 h | 569 | 118 | 21 |
| 96 h | 399 | 26 | 1 |
| 168 h | 280 | 7 | 0 |

Results:

B) Concentrations in Eye-Lysates of Left and Right Eyes

Figure 18:
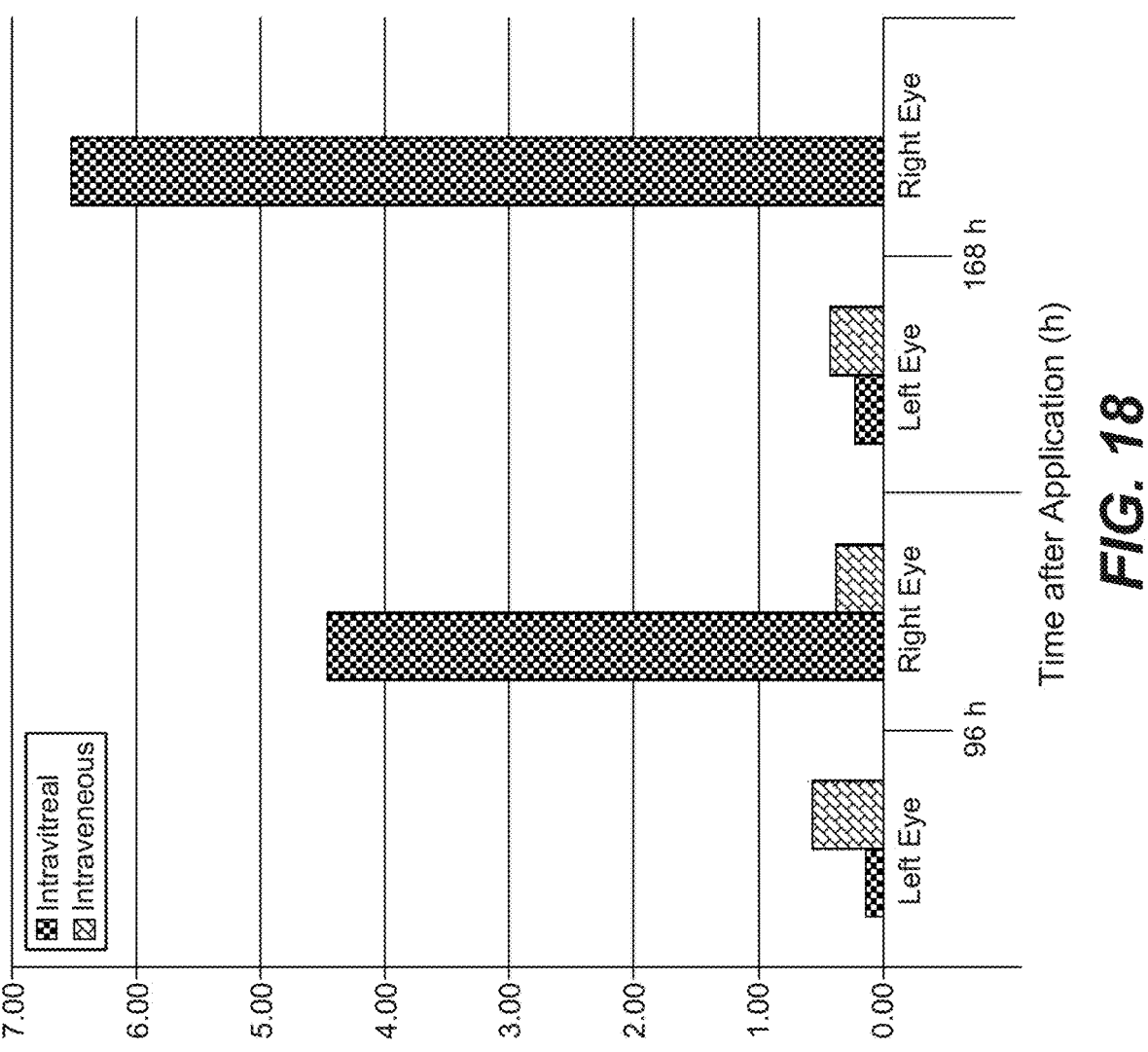
FIG. 18: Comparison of eye lysate concentration after intravitreal and intravenous application of antibody IGF-1R 0033.
Figure 19:
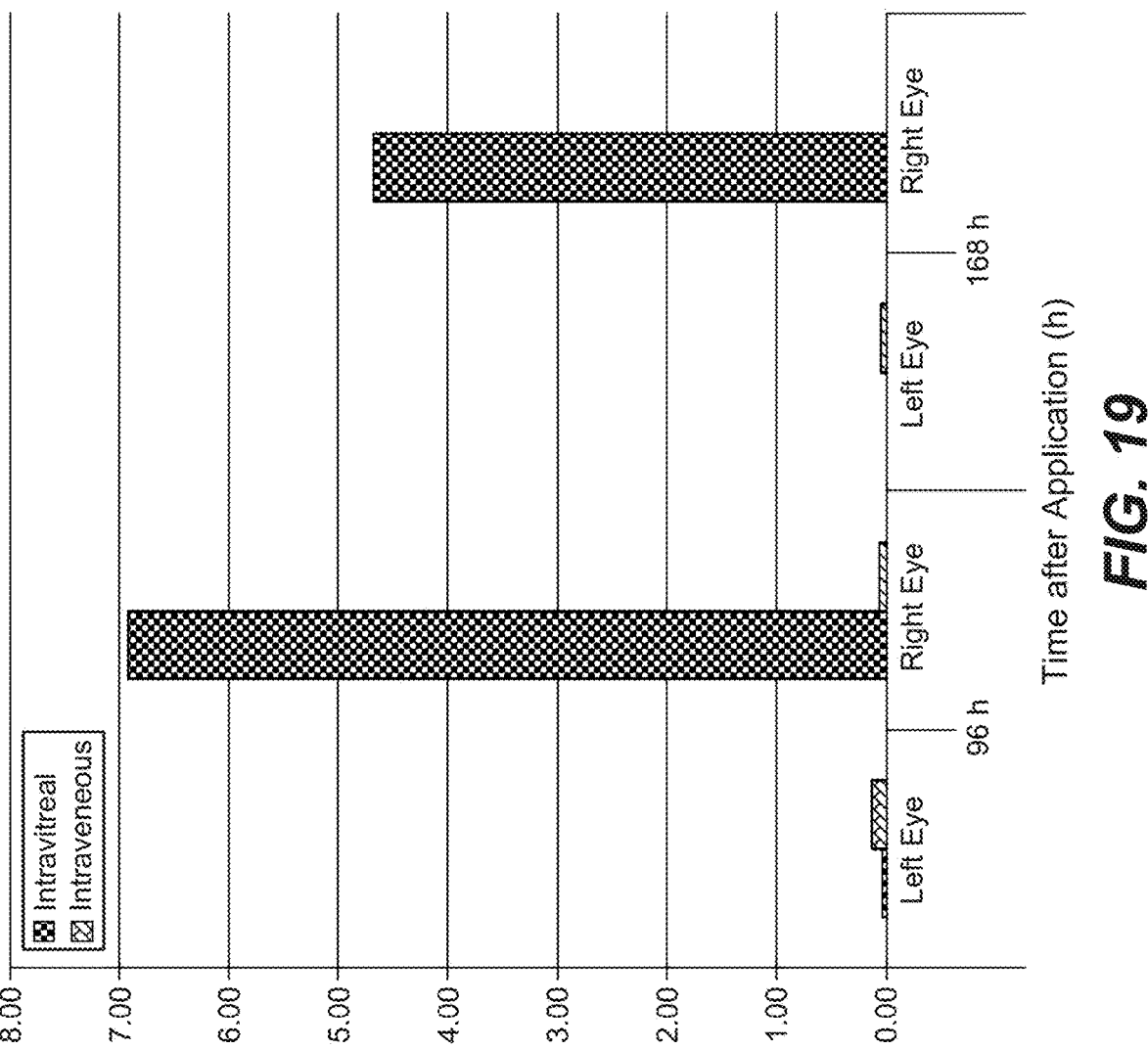
FIG. 19: Comparison of eye lysate concentration after intravitreal and intravenous application of antibody IGF-1R 0035.
Figure 20:
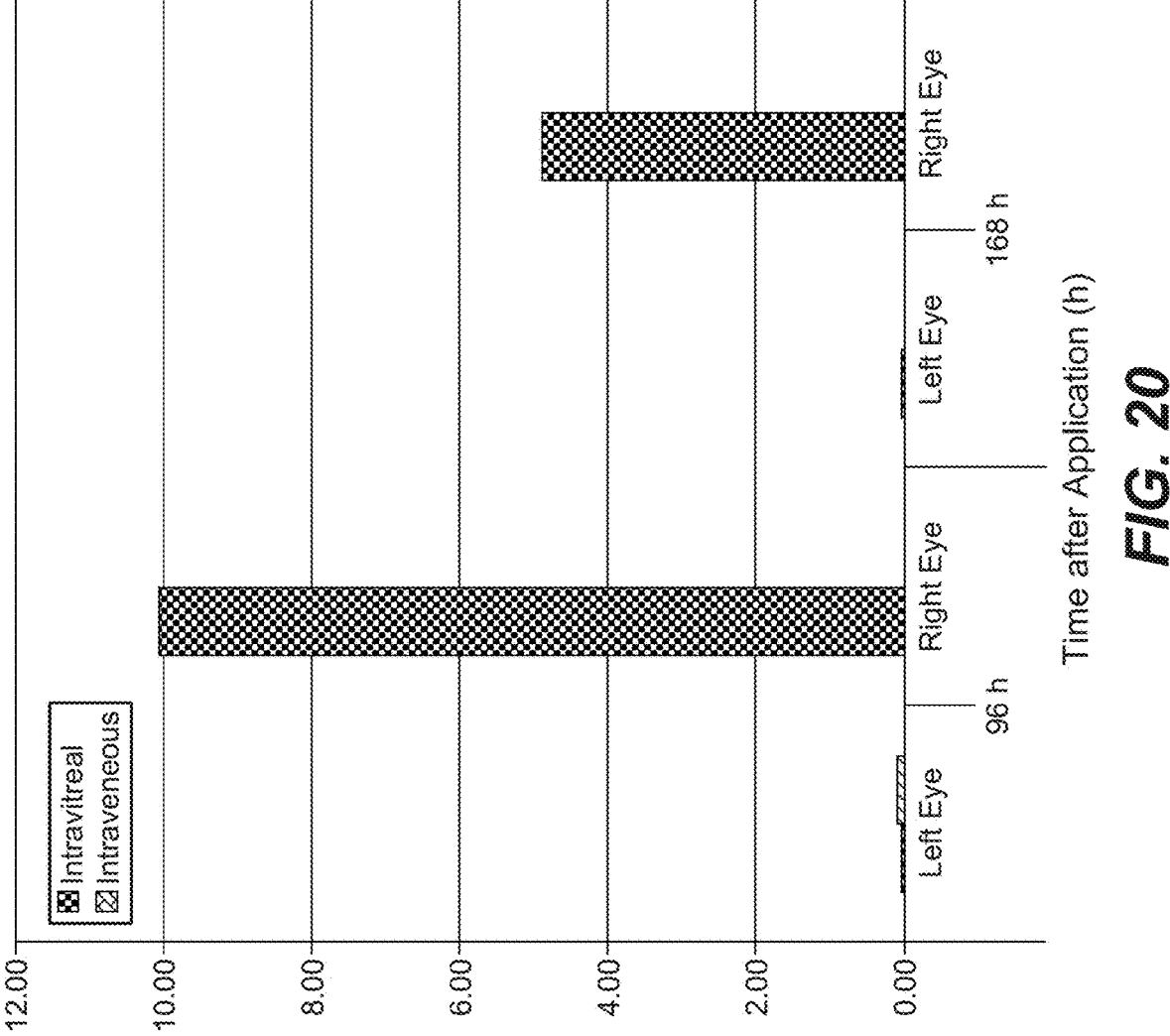
FIG. 20: Comparison of eye lysate concentration after intravitreal and intravenous application of antibody IGF-1R 0045.

Results for concentrations in eye lysates are shown in the following Tables and FIGS. 18 to 20.

TABLE

Concentrations of IGF-1R 0033 (without HHY-AAA mutation) in eye lysates after intravitreal application into the right eye mean conc. values from n = 7 (96 h) and n = 6 (196 h) mice

| ID | | mean conc. [ng/mL] |
|---|---|---|
| 96 h | left eye | 3.3 |
| | right eye | 99.5 |
| 168 h | left eye | 5.2 |
| | right eye | 144.9 |

TABLE

Concentrations of IGF-1R 0033 (without HHY-AAA mutation) in eye lysates after intravenous application mean conc. values from n = 5 (96 h) and n = 6 (196 h) mice

| ID | | mean conc. [ng/mL] |
|---|---|---|
| 96 h | left eye | 12.7 |
| | right eye | 8.5 |
| 168 h | left eye | 9.7 |
| | right eye | BLQ |

(BLQ = below limit of quantitation)

TABLE

Concentrations of IGF-1R 0035 (with the HHY-AAA
mutation in one Fc-region polypeptide) in eye lysates
after intravitreal application into the right eye mean conc. values from n = 6 mice

| ID | | mean conc. [ng/mL] |
|---|---|---|
| 96 h | left eye | 1.1 |
| | right eye | 169.2 |
| 168 h | left eye | 0.3 |
| | right eye | 114.7 |

TABLE

Concentrations of IGF-1R 0035 (with the HHY-AAA
mutation in one Fc-region polypeptide) in eye
lysates after intravenous application mean conc. values from n = 6 mice

| ID | | mean conc. [ng/mL] |
|---|---|---|
| 96 h | left eye | 3.7 |
| | right eye | 1.7 |
| 168 h | left eye | 1.4 |
| | right eye | 0.3 |

(BLQ = below limit of quantitation)

TABLE

Concentrations of IGF-1R 0045 (with the HHY-AAA
mutation in both Fc-region polypeptides) in eye lysates
after intravitreal application into the right eye mean conc. values from n = 6 mice

| ID | | mean conc. [ng/mL] |
|---|---|---|
| 96 h | left eye | 1.4 |
| | right eye | 322.6 |
| 168 h | left eye | 1.4 |
| | right eye | 156.8 |

TABLE

Concentrations of IGF-1R 0045 (with the HHY-AAA
mutation in both Fc-region polypeptides) in eye lysates
after intravenous application mean conc. values from n = 6 (96 h) and
n = 5 (196 h) mice

| ID | | mean conc. [ng/mL] |
|---|---|---|
| 96 h | left eye | 3.6 |
| | right eye | 1.3 |
| | left eye | 0.8 |
| 168 h | right eye | 0.4 |

(BLQ = below limit of quantitation)

TABLE

Concentrations of IGF-1R 0033, 0035 and 0045 in eye lysates
after intravitreal application into the right eye normalized to 1 μg
applied antibody

| ID | | IGF-1R 0033 | IGF-1R 0035 | IGF-1R 0045 |
|---|---|---|---|---|
| | | | mean conc. [ng/mL] | |
| 96 h | left eye | 0.15 | 0.05 | 0.04 |
| | right eye | 4.48 | 6.93 | 10.08 |
| 168 h | left eye | 0.24 | 0.01 | 0.04 |
| | right eye | 6.53 | 4.70 | 4.90 |

Summary of Results:

After intravitreal application the anti-IGF-1R antibodies 0035 and 0045 as reported herein (with one sided or both sided HHY-AAA mutation) shows similar concentrations (after 96 and 168 hours) in the eye lysates as compared to the anti-IGF-1R antibody without HHY-AAA mutation (IGF-1R 0033).

Also after intravitreal application the anti-IGF-1R antibodies 0035 and 0045 as reported herein (with one sided or both sided HHY-AAA mutation) shows in addition a faster clearance and shorter half-life in the serum as compared to the anti-IGF-1R antibody without HHY-AAA mutation (IGF-1R 0033).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody, comprising a first Fc-region polypeptide and a second Fc-region polypeptide, wherein the first and the second Fc-region polypeptide are both of human IgG1 of SEQ ID NO: 60 or human IgG4 subclass and comprise one or two of the mutations selected from the group H310A, H433A, and Y436A in the first Fc-region polypeptide and one or two of the mutations selected from the group consisting of the mutations H310A, H433A, and Y436A in the second Fc-region polypeptide so that all of the mutations in the first and the second Fc-region polypeptide when taken together result in that the mutations H310A, H433A, and Y436A are comprised in the Fc-region, wherein the numbering is according to the EU numbering of Kabat.

2. The antibody according to claim 1, wherein the antibody is a monoclonal antibody.

3. The antibody according to claim 1, wherein the antibody is a human, humanized or chimeric antibody.

4. The antibody according to claim 1, wherein the antibody is a bispecific antibody.

5. The antibody according to claim 1, wherein the antibody is a bivalent antibody.

6. The antibody according to claim 1, wherein the combination of mutations in the Fe-region maintains binding to Staphylococcus protein A.

7. A pharmaceutical formulation, comprising the antibody according to claim 1 and a pharmaceutically acceptable carrier.

\* \* \* \* \*